US012655135B2

(12) United States Patent
Li et al.

(10) Patent No.: US 12,655,135 B2
(45) Date of Patent: Jun. 16, 2026

(54) BENZO SEVEN-MEMBERED RING BIFUNCTIONAL COMPOUND AND APPLICATION THEREOF

(71) Applicants: CHIA TAI TIANQING PHARMACEUTICAL GROUP CO., LTD., Lianyungang (CN); MEDSHINE DISCOVERY INC., Nanjing (CN)

(72) Inventors: Zhengwei Li, Shanghai (CN); Wenyuan Qian, Shanghai (CN); Shuhui Chen, Shanghai (CN)

(73) Assignees: CHIA TAI TIANQING PHARMACEUTICAL GROUP CO., LTD., Lianyungang (CN); MEDSHINE DISCOVERY INC., Nanjing (CN)

( * ) Notice: Subject to any disclaimer, the term of this patent is extended or adjusted under 35 U.S.C. 154(b) by 402 days.

(21) Appl. No.: 18/274,674

(22) PCT Filed: Jan. 29, 2022

(86) PCT No.: PCT/CN2022/074965

§ 371 (c)(1),
(2) Date: Jul. 27, 2023

(87) PCT Pub. No.: WO2022/166879

PCT Pub. Date: Aug. 11, 2022

(65) Prior Publication Data

US 2024/0132482 A1 Apr. 25, 2024

(30) Foreign Application Priority Data

| | | | |
|---|---|---|---|
| Feb. 4, 2021 | (CN) | ......................... | 202110171911.0 |
| Apr. 13, 2021 | (CN) | ......................... | 202110396485.0 |
| Nov. 26, 2021 | (CN) | ......................... | 202111424605.X |
| Dec. 30, 2021 | (CN) | ......................... | 202111658629.1 |
| Jan. 14, 2022 | (CN) | ......................... | 202210045146.2 |

(51) Int. Cl.
*C07D 405/14* (2006.01)
*C07D 401/14* (2006.01)

(52) U.S. Cl.
CPC ......... *C07D 405/14* (2013.01); *C07D 401/14* (2013.01)

(58) Field of Classification Search
CPC ............................ C07D 405/14; C07D 401/14
USPC ....................................................... 514/253.1
See application file for complete search history.

(56) References Cited

U.S. PATENT DOCUMENTS

| | | | |
|---|---|---|---|
| 9,714,221 | B1 | 7/2017 | Bouaboula et al. |
| 10,800,770 | B1 | 10/2020 | Fan et al. |
| 10,899,742 | B1 | 1/2021 | Crew et al. |
| 2018/0079720 | A1 | 3/2018 | Bouaboula et al. |
| 2018/0155322 | A1 | 6/2018 | Crew et al. |
| 2018/0215731 | A1 | 8/2018 | Crew et al. |
| 2020/0392081 | A1 | 12/2020 | Bouaboula et al. |
| 2021/0139458 | A1 | 5/2021 | Crew et al. |
| 2021/0323916 | A1 | 10/2021 | Bouaboula et al. |
| 2022/0073460 | A1 | 3/2022 | Bouaboula et al. |

FOREIGN PATENT DOCUMENTS

| | | | |
|---|---|---|---|
| CN | 108884079 | A | 11/2018 |
| CN | 110291087 | A | 9/2019 |
| CN | 110612294 | A | 12/2019 |
| CN | 112262134 | A | 1/2021 |

OTHER PUBLICATIONS

Apr. 27, 2022 International Search Report issued in International Patent Application No. PCT/CN2022/074965.

*Primary Examiner* — Kahsay Habte
(74) *Attorney, Agent, or Firm* — Oliff PLC

(57) ABSTRACT

The present invention relates to a benzo seven-membered ring bifunctional compound and an application thereof, and in particular to a compound represented by formula (IV) and a pharmaceutically acceptable salt thereof. The compound can be used for preparing a drug for treating diseases related to an estrogen receptor protein degradation targeting chimera.

(IV)

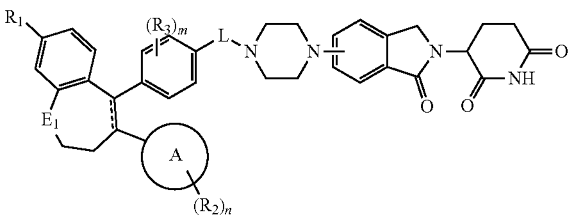

19 Claims, No Drawings

BENZO SEVEN-MEMBERED RING BIFUNCTIONAL COMPOUND AND APPLICATION THEREOF

CROSS-REFERENCE TO RELATED APPLICATIONS

The present application claims the priority and benefit to the Chinese Patent Application No. 202110171911.0 filed with China National Intellectual Property Administration on Feb. 4, 2021, the Chinese Patent Application No. 202110396485.0 filed with China National Intellectual Property Administration on Apr. 13, 2021, the Chinese Invention Patent Application No. 202111424605.X filed with China National Intellectual Property Administration on Nov. 26, 2021, the Chinese Patent Application No. 202111658629.1 filed with China National Intellectual Property Administration on Dec. 30, 2021, the Chinese Patent Application No. 202210045146.2 filed with China National Intellectual Property Administration on Jan. 14, 2022, which are incorporated herein by reference in their entireties.

TECHNICAL FIELD

The present application relates to a bifunctional benzo 7-membered cyclic compound and use thereof, and in particular to a compound of formula (IV) and a pharmaceutically acceptable salt thereof.

BACKGROUND

Estrogen receptors (ERs) are members of the nuclear hormone receptor family. They act as ligand-activated transcription factors, and are involved in the up- and down-regulation of gene expression. The natural ligand of ER, estrogen, plays an important role in female sexual development, maintaining bone density and regulating blood lipid level. Reduced estrogen production in postmenopausal females is associated with a number of diseases such as osteoporosis, atherosclerosis, depression, and cognitive disorders. In contrast, certain types of proliferative diseases such as breast cancer, uterine cancer and endometriosis are stimulated by estrogen, and thus antiestrogens (i.e., estrogen antagonists) are helpful in the prevention and treatment of such conditions.

Endocrine therapy for the estrogen-estrogen receptor signaling pathway in breast cancer cells has become the first choice for ER-positive breast cancer due to its minimal harm and remarkable efficacy. Endocrine therapies mainly include the following three: ovarian suppression, aromatase inhibitor, and selective estrogen receptor antagonist. The estrogen receptor antagonist is divided into two groups. Selective estrogen receptor modulators (SERM) directly act on estrogen receptors to block the signaling pathway, and have remarkable efficacy and a long history of use. Of these, tamoxifen is the most representative SERM. As a recommended first-line therapy, tamoxifen has shown significant clinical efficacy in the prevention and treatment of ER-positive breast cancer, but the patients may develop increasing drug resistance after long-term use. In the other group, selective estrogen receptor downregulators (SERDs), only fulvestrant is currently approved for marketing. Fulvestrant only antagonizes ERs without agonism, and may also cause degradation of ER protein. It can be used for treating ER-positive breast cancer (including patients who have developed drug resistance to tamoxifen or aromatase inhibitors), but exhibits poor PK properties, thus having seriously compromised efficacy. Therefore, the development of medications targeting ER-resistant breast cancer with better PK properties remains an unmet medical need.

PROTAC is a bifunctional heterodimer molecule comprising two micromolecular binding moieties joined together by a linker. One of the micromolecular ligands is designed to bind with high affinity to a target protein in the cell, while the other ligand is able to bind with high affinity to an E3 ubiquitin ligase. In the cell, PROTAC seeks out and selectively binds to a target protein of interest. After that, PROTAC recruits a specific E3 ubiquitin ligase to the target protein to form a ternary complex, with the target protein and the E3 ubiquitin ligase held in close proximity. The E3 ubiquitin ligase then recruits an E2 conjugating enzyme to the ternary complex. E2 enzyme ubiquitinates the target protein and labels the protein with an available lysine residue, and is then dissociated from the ternary complex. E3 then recruits additional E2 molecules, resulting in poly ubiquitination of the target protein, which labels the target protein for potential degradation by the cell's proteasome machinery. Finally, PROTAC detaches from the target protein and initiates another catalytic cycle.

Based on this principle, ER PROTACs are designed to comprise an ER ligand moiety at one end of the linker and an E3 ubiquitin ligase (such as cereblon, CRBN) ligand at the other end. In the cell, ER PROTAC selectively recruits the CRBN E3 ubiquitin ligase to ER and causes systemic degradation of ER, thus achieving regulation of the ER and treatment of estrogen-related disease.

SUMMARY

The present application provides a compound of formula (IV), an isomer thereof, or a pharmaceutically acceptable salt thereof, (IV)

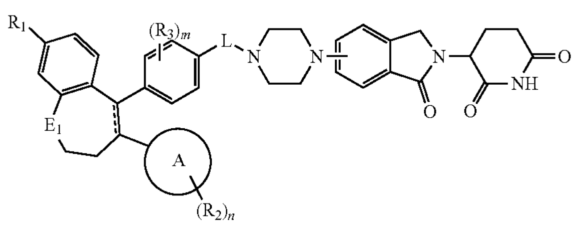

wherein, $R_1$ is selected from the group consisting of OH, $C_{1-3}$ alkoxy, and COOH;

each $R_2$ is independently selected from the group consisting of halogen, OH, CN, $NH_2$, $C_{1-3}$ alkyl, $C_{1-3}$ alkoxy, $C_{3-6}$ cycloalkyl, and —O—$C_{3-6}$ cycloalkyl, wherein the $C_{1-3}$ alkyl, $C_{1-3}$ alkoxy, $C_{3-6}$ cycloalkyl, and —O—$C_{3-6}$ cycloalkyl are optionally independently substituted with 1, 2, or 3 $R_a$;

each $R_a$ is independently selected from the group consisting of halogen, CN, and OH;

each $R_3$ is independently selected from halogen;

m and n are each independently selected from the group consisting of 0, 1, 2, and 3;

$E_1$ is selected from the group consisting of O and $CH_2$;

L is selected from $C_{1-6}$ alkylene, wherein 1 to 3 methylenes are optionally substituted by O, NH, $C_{3-6}$ cycloalkyl, or 4- to 6-membered heterocycloalkyl;

 is selected from the group consisting of a single bond and a double bond;

ring A is selected from the group consisting of phenyl and 5- to 6-membered heteroaryl.

In some embodiments of the present application, for the compound of formula (IV), the isomer thereof, or the pharmaceutically acceptable salt thereof, $R_1$ is selected from the group consisting of OH, $C_{1-3}$ alkoxy, and COOH;

each $R_2$ is independently selected from the group consisting of halogen, OH, CN, $NH_2$, $C_{1-3}$ alkyl, $C_{1-3}$ alkoxy, and $C_{3-6}$ cycloalkyl, wherein the $C_{1-3}$ alkyl, $C_{1-3}$ alkoxy, and $C_{3-6}$ cycloalkyl are optionally substituted with 1, 2, or 3 halogens;

each $R_3$ is independently selected from halogen;

m and n are each independently selected from the group consisting of 0, 1, 2, and 3;

$E_1$ is selected from the group consisting of O and $CH_2$;

L is selected from $C_{1-6}$ alkylene, wherein 1 to 3 methylenes are optionally substituted by O, NH, $C_{3-6}$ cycloalkyl, or 4- to 6-membered heterocycloalkyl;

 is selected from the group consisting of a single bond and a double bond;

ring A is selected from the group consisting of phenyl and 5- to 6-membered heterocycloalkyl.

In some embodiments of the present application, $R_1$ is selected from the group consisting of OH, $CH_3O$—, and COOH, and the other variables are as defined herein.

In some embodiments of the present application, $R_1$ is selected from OH, and the other variables are as defined herein.

In some embodiments of the present application, $R_2$ is independently selected from the group consisting of F, Cl, Br, I, OH, CN, $NH_2$, $CH_3$, ethyl, isopropyl, methoxy, ethoxy, isopropoxy, cyclopropyl, cyclobutyl, —O-cyclopropyl, and —O-cyclobutyl, wherein the $CH_3$, ethyl, isopropyl, methoxy, ethoxy, isopropoxy, cyclopropyl, cyclobutyl, —O-cyclopropyl, and —O-cyclobutyl are optionally independently substituted with 1, 2, or 3 $R_a$, and the other variables are as defined herein.

In some embodiments of the present application, $R_2$ is independently selected from the group consisting of F, Cl, Br, I, OH, CN, $NH_2$, $CH_3$, ethyl, isopropyl, methoxy, ethoxy, isopropoxy, cyclopropyl, and —O-cyclopropyl, wherein the $CH_3$, ethyl, isopropyl, methoxy, ethoxy, isopropoxy, cyclopropyl, and —O-cyclopropyl are optionally independently substituted with 1, 2, or 3 $R_a$, and the other variables are as defined herein.

In some embodiments of the present application, $R_a$ is independently selected from the group consisting of F, Cl, Br, I, and OH, and the other variables are as defined herein.

In some embodiments of the present application, $R_a$ is independently selected from the group consisting of F and OH, and the other variables are as defined herein.

In some embodiments of the present application, $R_2$ is independently selected from the group consisting of F, Cl, Br, I, OH, CN, $NH_2$, $CH_3$, ethyl, isopropyl, methoxy, ethoxy, isopropoxy, cyclopropyl, and —O-cyclopropyl, wherein the $CH_3$, ethyl, isopropyl, methoxy, ethoxy, isopropoxy, cyclopropyl, and —O-cyclopropyl are optionally independently substituted with 1, 2, or 3 $R_a$, each $R_a$ is independently selected from the group consisting of F, Cl, Br, I, and OH, and the other variables are as defined herein.

In some embodiments of the present application, $R_2$ is independently selected from the group consisting of F, Cl, OH, $CH_3$, isopropyl, methoxy, cyclopropyl, and —O-cyclopropyl, wherein the $CH_3$, isopropyl, methoxy, cyclopropyl, and —O-cyclopropyl are optionally independently substituted with 1, 2, or 3 $R_a$, each $R_a$ is independently selected from the group consisting of F and OH, and the other variables are as defined herein.

In some embodiments of the present application $R_2$ is independently selected from the group consisting of F, Cl, Br, I, OH, CN, $NH_2$, $CH_3$, $CF_3$, cyclopropyl,

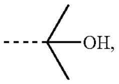

—$OCHF_2$, —$OCF_3$, and —O-cyclopropyl, and the other variables are as defined herein.

In some embodiments of the present application, $R_2$ is independently selected from the group consisting of F, Cl, OH, $CH_3$, $CF_3$, cyclopropyl,

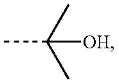

—$OCHF_2$, —$OCF_3$, and —O-cyclopropyl, and the other variables are as defined herein.

In some embodiments of the present application, $R_2$ is independently selected from the group consisting of F, Cl, Br, I, OH, CN, $NH_2$, $CH_3$, $CF_3$, and cyclopropyl, and the other variables are as defined herein.

In some embodiments of the present application, $R_2$ is independently selected from the group consisting of F, Cl, OH, $CH_3$, $CF_3$, and cyclopropyl, and the other variables are as defined herein.

In some embodiments of the present application, $R_3$ is independently selected from the group consisting of F and Cl, and the other variables are as defined herein.

In some embodiments of the present application, L is selected from the group consisting of $C_{1-6}$ alkylene, —O—$C_{1-5}$ alkylene, —$C_{3-6}$ cycloalkyl-, —$C_{3-6}$ cycloalkyl-$C_{1-3}$ alkylene, -4- to -6-membered heterocycloalkyl-, and -4- to -6-membered heterocycloalkyl-$C_{1-3}$ alkylene, and the other variables are as defined herein.

In some embodiments of the present application, L is selected from the group consisting of $C_{4-6}$ alkylene, —O—$C_{3-5}$ alkylene, -cyclohexyl, -cyclohexyl-$C_{1-3}$ alkylene, -6-membered heterocycloalkyl-, and -6-membered heterocycloalkyl-$C_{1-3}$ alkylene, and the other variables are as defined herein.

In some embodiments of the present application, L is selected from the group consisting of —O—$C_{3-5}$ alkylene and -piperidinyl-$C_{1-3}$ alkylene, and the other variables are as defined herein.

In some embodiments of the present application, L is selected from the group consisting of —O—$C_{3-5}$ alkylene and

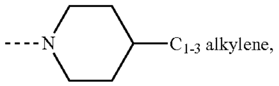

and the other variables are as defined herein.

In some embodiments of the present application, L is selected from $C_{1-6}$ alkylene, wherein 1 to 3 methylenes are optionally substituted by O, NH, cyclohexyl, or 6-membered heterocycloalkyl, and the other variables are as defined herein.

In some embodiments of the present application, L is selected from $C_{1-6}$ alkylene, wherein 1 to 3 methylenes are optionally substituted by O, NH, cyclohexyl, or piperidinyl, and the other variables are as defined herein.

In some embodiments of the present application, L is selected from the group consisting of

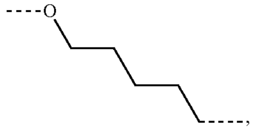, 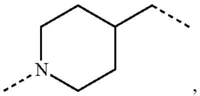, and 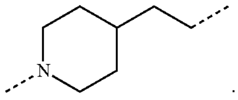.

and the other variables are as defined herein.

In some embodiments of the present application, L is selected from the group consisting of

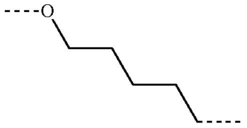 and 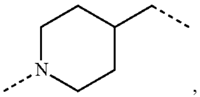, and the other variables are as defined herein.

In some embodiments of the present application, L is selected from

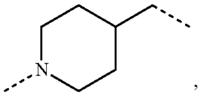, and the other variables are as defined herein.

In some embodiments of the present application, 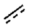 is selected from a double bond, and the other variables are as defined herein.

In some embodiments of the present application, ring A is selected from the group consisting of phenyl, pyridinyl, and pyrazolyl, and the other variables are as defined herein.

In some embodiments of the present application, ring A is selected from the group consisting of phenyl,

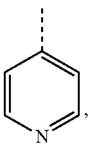, 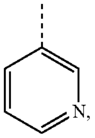, 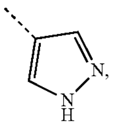, and the other variables are as defined herein.

In some embodiments of the present application, ring A is selected from phenyl, and the other variables are as defined herein.

In some embodiments of the present application, the structural unit

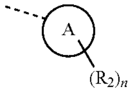

is selected from the group consisting of

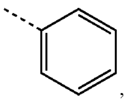, 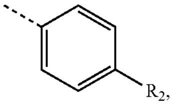, 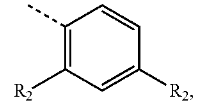, 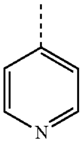, 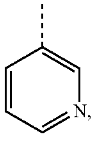, 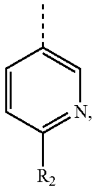, 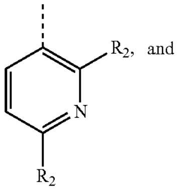, and 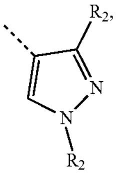, wherein each $R_2$ is independently selected from the group consisting of F, Cl, Br, I, OH, CN, $NH_2$, $CH_3$, ethyl, isopropyl, methoxy, ethoxy, isopropoxy, cyclopropyl, and —O-cyclopropyl, wherein the $CH_3$, ethyl, isopropyl, methoxy, ethoxy, isopropoxy, cyclopropyl, and —O-cyclopropyl are optionally independently substituted with 1, 2, or 3 $R_a$, each $R_a$ is independently selected from the group consisting of F, Cl, Br, I, and OH, and the other variables are as defined herein.

In some embodiments of the present application, the structural unit

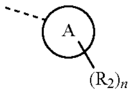

is selected from the group consisting of

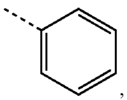, 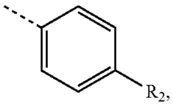, 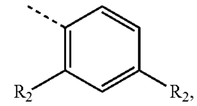, 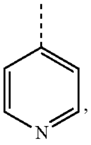, 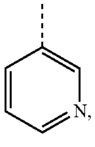, 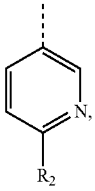, 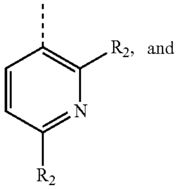, and -continued

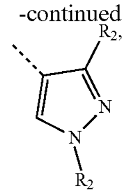

wherein each $R_2$ is independently selected from the group consisting of F, Cl, OH, $CH_3$, isopropyl, methoxy, cyclopropyl, and —O-cyclopropyl, wherein the $CH_3$, isopropyl, methoxy, cyclopropyl, and —O-cyclopropyl are optionally independently substituted with 1, 2, or 3 $R_a$, each $R_a$ is independently selected from the group consisting of F and OH, and the other variables are as defined herein.

In some embodiments of the present application, the structural unit

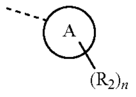

is selected from the group consisting of

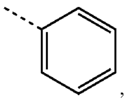
,
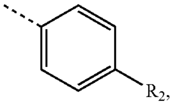
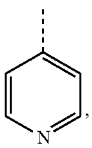
,
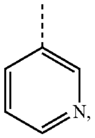
and
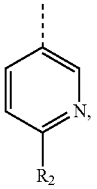

wherein each $R_2$ is independently selected from the group consisting of F, Cl, OH, $CH_3$, isopropyl, methoxy, cyclopropyl, and —O-cyclopropyl, wherein the $CH_3$, isopropyl, methoxy, cyclopropyl, and —O-cyclopropyl are optionally independently substituted with 1, 2, or 3 $R_a$, each $R_a$ is independently selected from the group consisting of F and OH, and the other variables are as defined herein.

In some embodiments of the present application, the structural unit

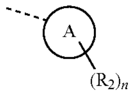

is selected from the group consisting of

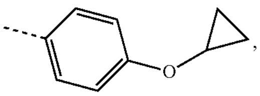
,
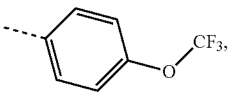

-continued

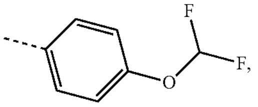
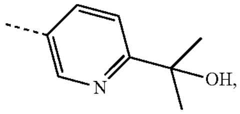
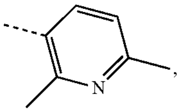
,
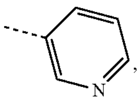
,
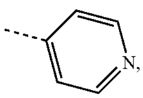
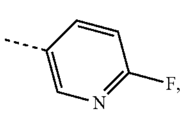
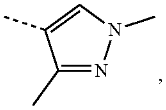
,
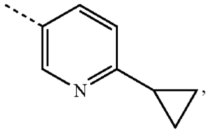
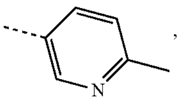
,
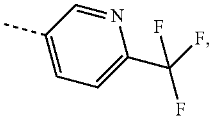
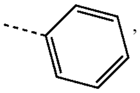
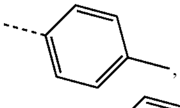
,
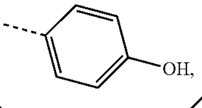
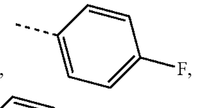
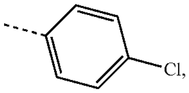
and
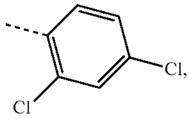

and the other variables are as defined herein.

In some embodiments of the present application, m is selected from the group consisting of 0 and 1, and the other variables are as defined herein.

In some embodiments of the present application, n is selected from the group consisting of 0, 1, and 2, and the other variables are as defined herein.

In some embodiments of the present application, $E_1$ is selected from $CH_2$, and the other variables are as defined herein.

The present application further provides a compound of formula (I), an isomer thereof, or a pharmaceutically acceptable salt thereof, (I)

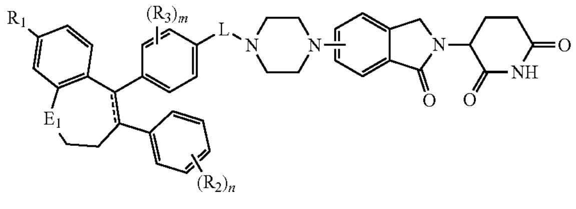

wherein, $R_1$ is selected from the group consisting of OH, $C_{1-3}$ alkoxy, and COOH;

each $R_2$ is independently selected from the group consisting of halogen, OH, CN, $NH_2$, $C_{1-3}$ alkyl, and $C_{1-3}$ alkoxy, wherein the $C_{1-3}$ alkyl and $C_{1-3}$ alkoxy are optionally substituted with 1, 2, or 3 halogens; each $R_3$ is independently selected from halogen;

m and n are each independently selected from the group consisting of 0, 1, 2, and 3;

$E_1$ is selected from the group consisting of O and $CH_2$;

L is selected from $C_{1-6}$ alkylene, wherein 1 to 3 methylenes are optionally substituted by O, NH, $C_{3-6}$ cycloalkyl, or 4- to 6-membered heterocycloalkyl;

⫽ is selected from the group consisting of a single bond and a double bond;

the "hetero" of the "4- to 6-membered heterocycloalkyl" includes 1, 2, or 3 heteroatoms or heteroatom groups independently selected from the group consisting of O, S, NH, and N.

In some embodiments of the present application, for the compound of formula (I), the isomer thereof, or the pharmaceutically acceptable salt thereof, $R_1$ is selected from the group consisting of OH and COOH;

each $R_2$ is independently selected from the group consisting of halogen, CN, $NH_2$, $C_{1-3}$ alkyl, and $C_{1-3}$ alkoxy, wherein the $C_{1-3}$ alkyl and $C_{1-3}$ alkoxy are optionally substituted with 1, 2, or 3 halogens;

each $R_3$ is independently selected from halogen;

m and n are each independently selected from the group consisting of 0, 1, 2, and 3;

$E_1$ is selected from the group consisting of O and $CH_2$;

L is selected from $C_{1-6}$ alkylene, wherein 1 to 3 methylenes are optionally substituted by O, NH, $C_{3-6}$ cycloalkyl, or 4- to 6-membered heterocycloalkyl;

⫽ is selected from the group consisting of a single bond and a double bond;

the "hetero" of the "4- to 6-membered heterocycloalkyl" includes 1, 2, or 3 heteroatoms or heteroatom groups independently selected from the group consisting of O, S, NH, and N.

In some embodiments of the present application, $R_1$ is selected from the group consisting of OH, $CH_3O$—, and COOH, and the other variables are as defined herein.

In some embodiments of the present application, $R_1$ is selected from OH, and the other variables are as defined herein.

In some embodiments of the present application, $R_2$ is independently selected from the group consisting of F, Cl, Br, I, OH, CN, $NH_2$, and $CH_3$, and the other variables are as defined herein.

In some embodiments of the present application, $R_2$ is independently selected from the group consisting of F, Cl, Br, I, CN, and $NH_2$, and the other variables are as defined herein.

In some embodiments of the present application, $R_2$ is independently selected from the group consisting of F, Cl, OH, and $CH_3$, and the other variables are as defined herein.

In some embodiments of the present application, $R_2$ is independently selected from the group consisting of F and Cl, and the other variables are as defined herein.

In some embodiments of the present application, $R_3$ is independently selected from the group consisting of F and Cl, and the other variables are as defined herein.

In some embodiments of the present application, m is selected from the group consisting of 0 and 1, and the other variables are as defined herein.

In some embodiments of the present application, n is selected from the group consisting of 0, 1, and 2, and the other variables are as defined herein.

In some embodiments of the present application, L is selected from $C_{1-6}$ alkylene, wherein 1 to 3 methylenes are optionally substituted by O, NH, cyclohexyl, or 6-membered heterocycloalkyl, and the other variables are as defined herein.

In some embodiments of the present application, L is selected from $C_{1-6}$ alkylene, wherein 1 to 3 methylenes are optionally substituted by O, NH, cyclohexyl, or piperidinyl, and the other variables are as defined herein.

In some embodiments of the present application, L is selected from the group consisting of

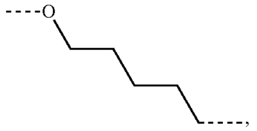,
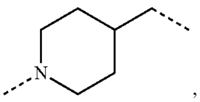, and
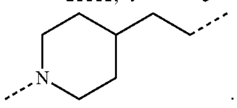.

and the other variables are as defined herein.

In some embodiments of the present application, L is selected from the group consisting of

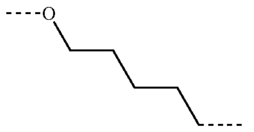 and 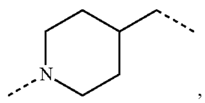, and the other variables are as defined herein.

In some embodiments of the present application, L is selected from

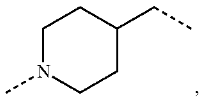, and the other variables are as defined herein.

In some embodiments of the present application, $E_1$ is selected from $CH_2$, and the other variables are as defined herein.

In some embodiments of the present application, ⫽ is selected from a double bond, and the other variables are as defined herein.

In some embodiments of the present application, the compound of formula (I), the isomer thereof, or the pharmaceutically acceptable salt thereof is selected from a compound of formula (I-1), (I-1)

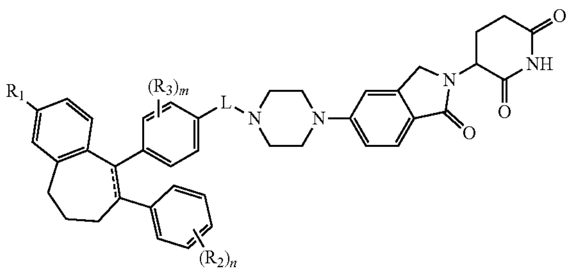

wherein, $R_1$, $R_2$, $R_3$, L, m, and n are defined as for the compound of formula (I).

In some embodiments of the present application, the compound of formula (I), the isomer thereof, or the pharmaceutically acceptable salt thereof is selected from a compound of formula (I-2), (I-2)

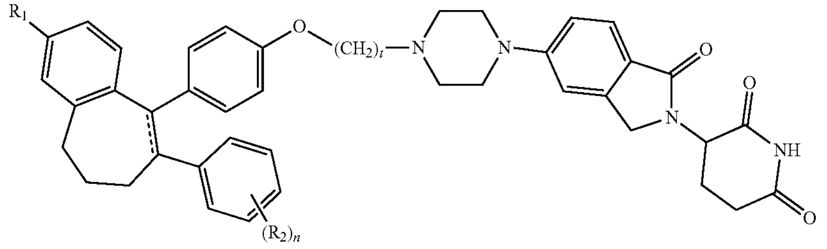

wherein, t is selected from the group consisting of 1, 2, 3, 4, and 5;

$R_1$, $R_2$, and n are defined as for the compound of formula (I).

In some embodiments of the present application, the compound of formula (I), the isomer thereof, or the pharmaceutically acceptable salt thereof is selected from a compound of formula (I-3), (I-3)

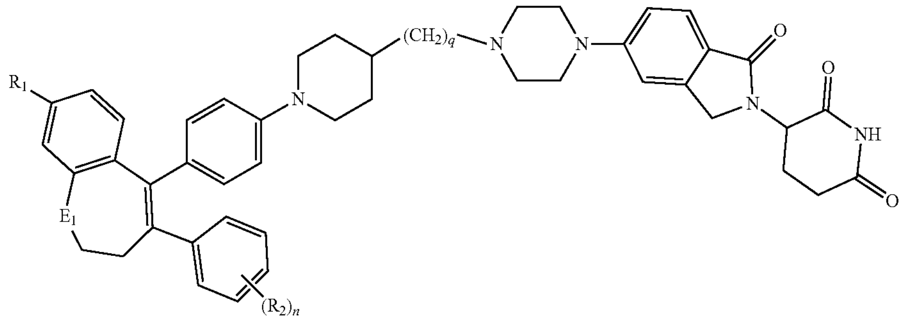

wherein, q is selected from the group consisting of 1 and 2;

$R_1$, $R_2$, $E_1$, and n are defined as for the compound of formula (I).

In some embodiments of the present application, the compound of formula (I), the isomer thereof, or the pharmaceutically acceptable salt thereof is selected from a compound of formula (I-3'), (I-3')

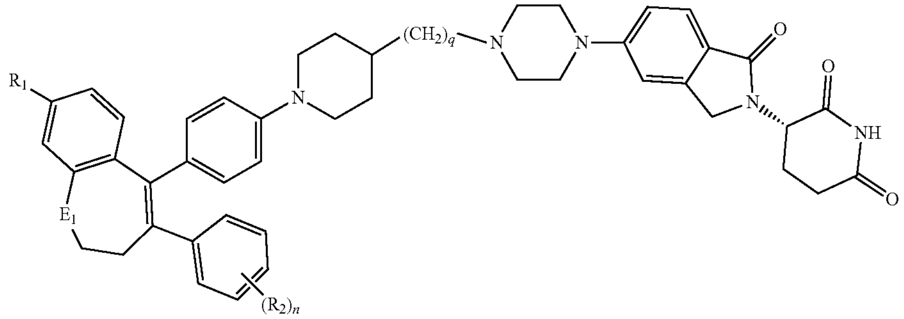

wherein, q is selected from the group consisting of 1 and 2;

$R_1$, $R_2$, $E_1$, and n are defined as for the compound of formula (I).

In some embodiments of the present application, the compound of formula (I), the isomer thereof, or the pharmaceutically acceptable salt thereof is selected from a compound of formula (I-3"), wherein, (I-3")

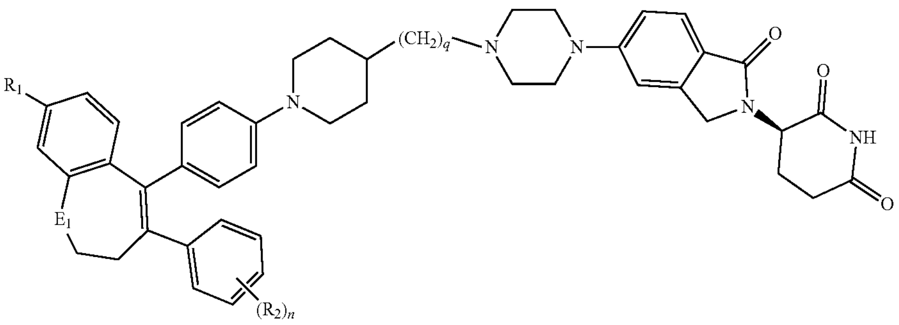

q is selected from the group consisting of 1 and 2;

$R_1$, $R_2$, $E_1$, and n are defined as for the compound of formula (I).

In some embodiments of the present application, the compound of formula (IV), the isomer thereof, or the pharmaceutically acceptable salt thereof is selected from a compound of formula (IV-1), (IV-1)

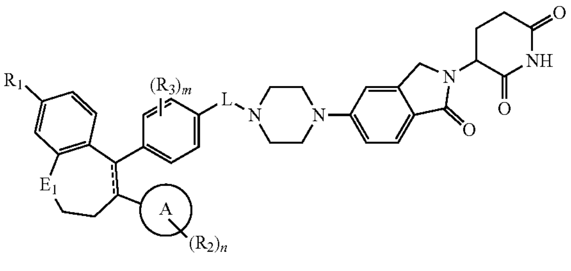

wherein, $R_1$, $R_2$, $R_3$, L, $E_1$, ring A, , m, and n are defined as for the compound of formula (IV).

In some embodiments of the present application, the compound of formula (IV), the isomer thereof, or the pharmaceutically acceptable salt thereof is selected from a compound of formula (IV-2), (IV-2)

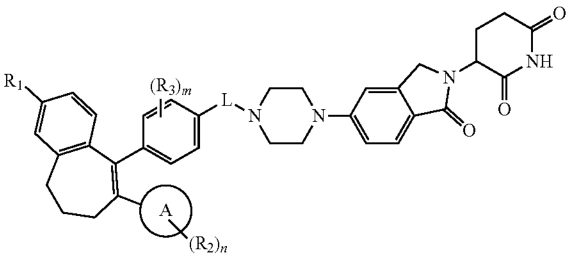

wherein, $R_1$, $R_2$, $R_3$, L, ring A, m, and n are defined as for the compound of formula (IV).

In some embodiments of the present application, the compound of formula (IV), the isomer thereof, or the pharmaceutically acceptable salt thereof is selected from a compound of formula (IV-3), (IV-3)

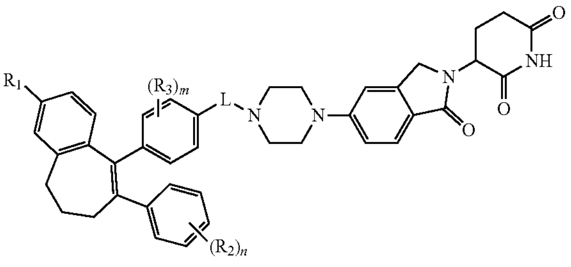

wherein, $R_1$, $R_2$, $R_3$, L, m, and n are defined as for the compound of formula (IV).

In some embodiments of the present application, the compound of formula (IV), the isomer thereof, or the pharmaceutically acceptable salt thereof is selected from a compound of formula (IV-4), (IV-4)

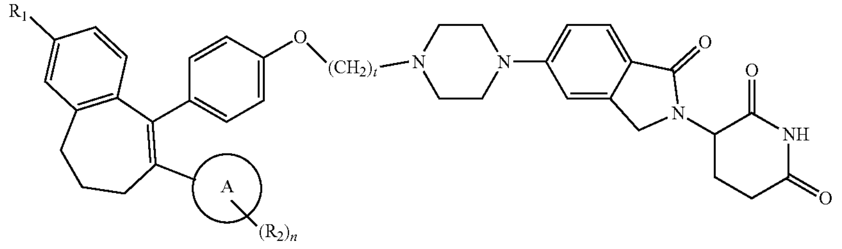

wherein, t is selected from the group consisting of 1, 2, 3, 4, and 5;

$R_1$, $R_2$, ring A, and n are defined as for the compound of formula (IV).

In some embodiments of the present application, the compound of formula (IV), the isomer thereof, or the pharmaceutically acceptable salt thereof is selected from a compound of formula (IV-5), (IV-5)

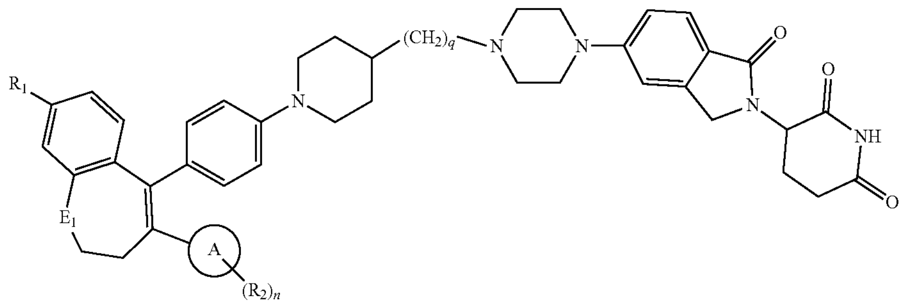

wherein, q is selected from the group consisting of 1 and 2;

$R_1$, $R_2$, $E_1$, ring A, and n are defined as for the compound of formula (IV).

In some embodiments of the present application, the compound of formula (IV), the isomer thereof, or the pharmaceutically acceptable salt thereof is selected from a compound of formula (IV-6), (IV-6)

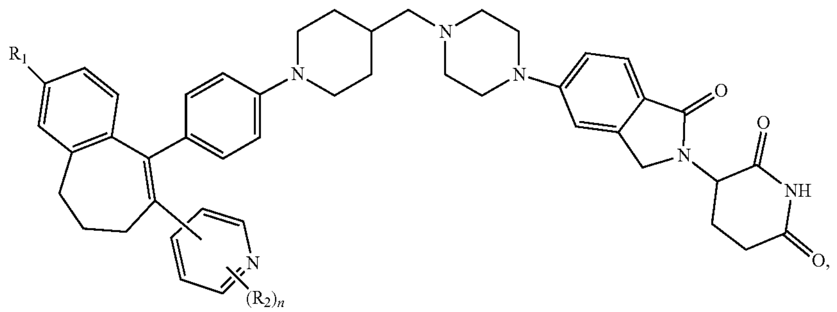

wherein, $R_1$, $R_2$, and n are defined as for the compound of formula (IV).

In some embodiments of the present application, the compound of formula (IV), the isomer thereof, or the pharmaceutically acceptable salt thereof is selected from a compound of formula (IV-5')

(IV-5')

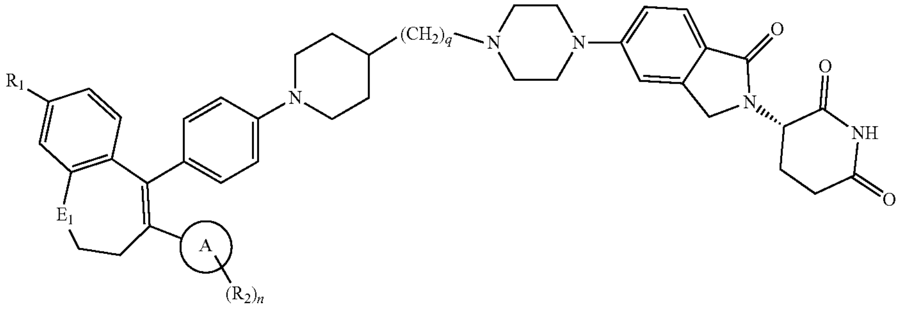

wherein, q is selected from the group consisting of 1 and 2;

$R_1$, $R_2$, $E_1$, ring A, and n are defined as for the compound of formula (IV).

In some embodiments of the present application, the compound of formula (IV), the isomer thereof, or the pharmaceutically acceptable salt thereof is selected from a compound of formula (IV-5"), (IV-5")

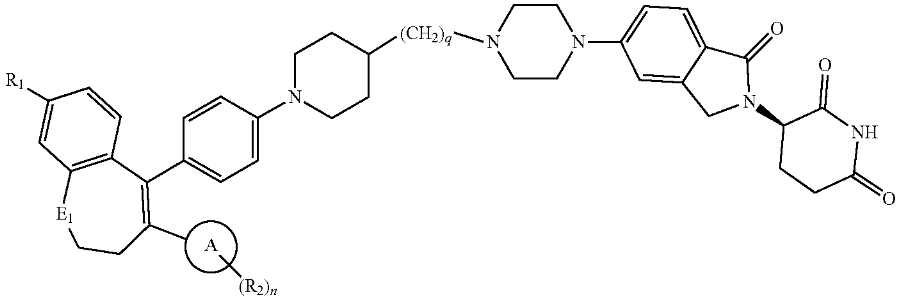

wherein, q is selected from the group consisting of 1 and 2;

$R_1$, $R_2$, $E_1$, ring A, and n are defined as for the compound of formula (IV).

In some embodiments of the present application, the compound of formula (IV), the isomer thereof, or the pharmaceutically acceptable salt thereof is selected from a compound of formula (IV-6')

(IV-6')

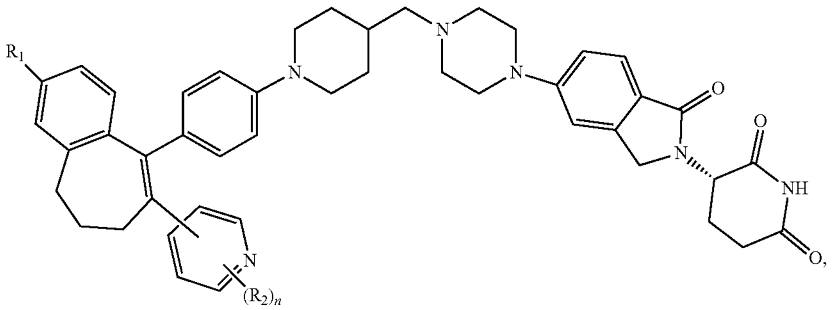

wherein, $R_1$, $R_2$, and n are defined as for the compound of formula (IV).

In some embodiments of the present application, the compound of formula (IV), the isomer thereof, or the pharmaceutically acceptable salt thereof is selected from a compound of formula (IV-6"), (IV-6")

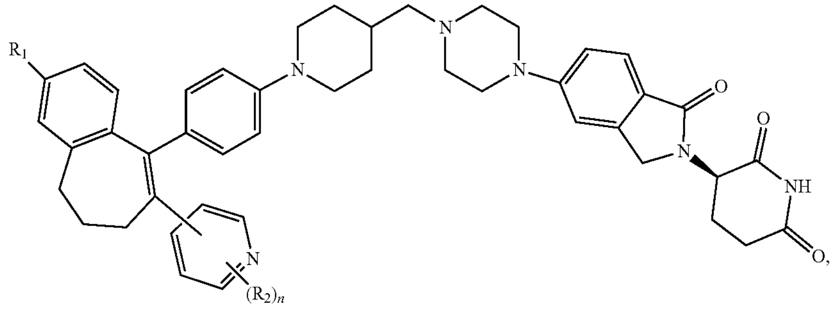

wherein, $R_1$, $R_2$, and n are defined as for the compound of formula (IV).

Some other embodiments of the present application are derived from any combination of the variables as described above.

The present application further provides a compound of a formula selected from the group consisting of the following, an isomer thereof, or a pharmaceutically acceptable salt thereof,

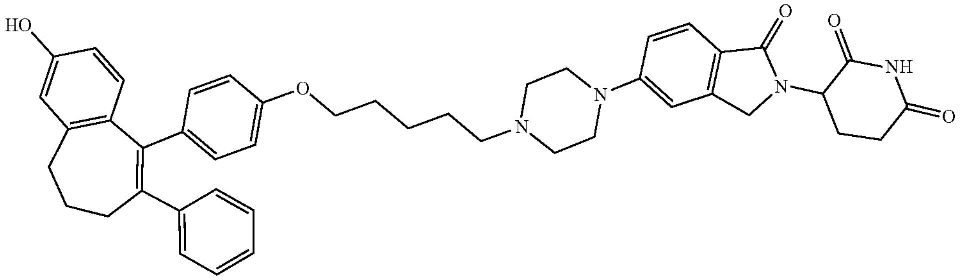

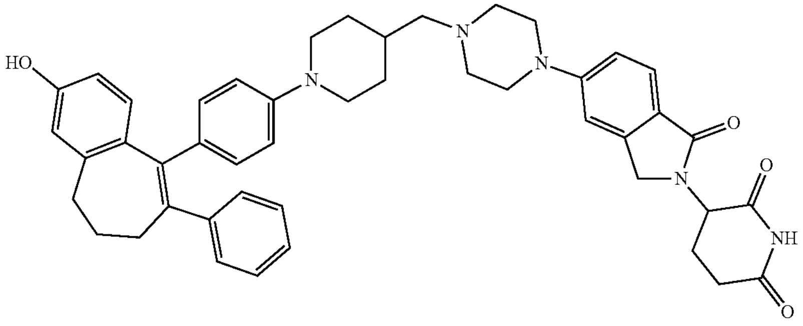

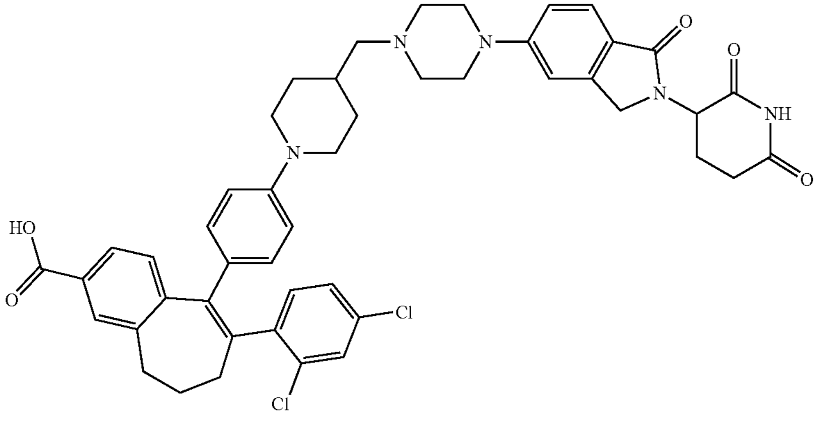

-continued
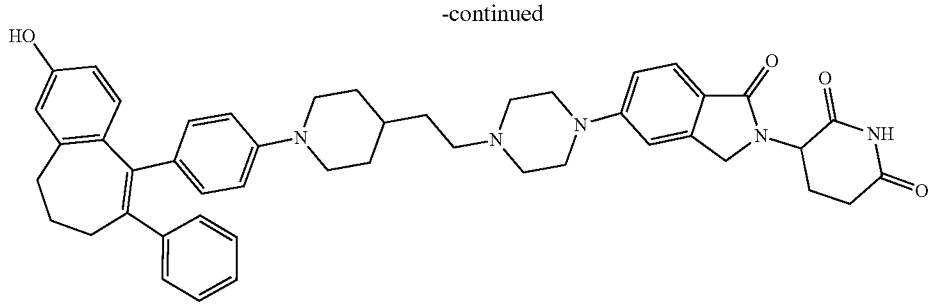
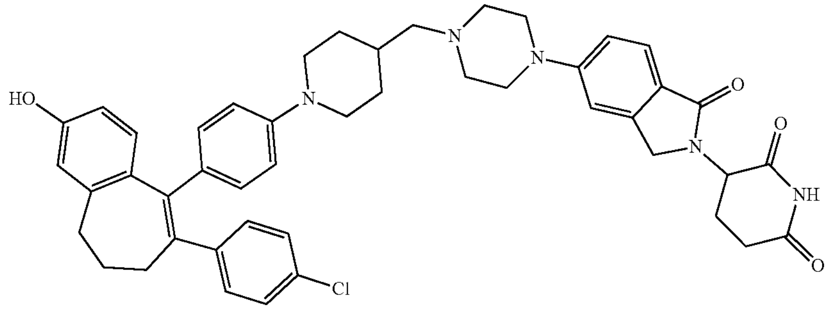
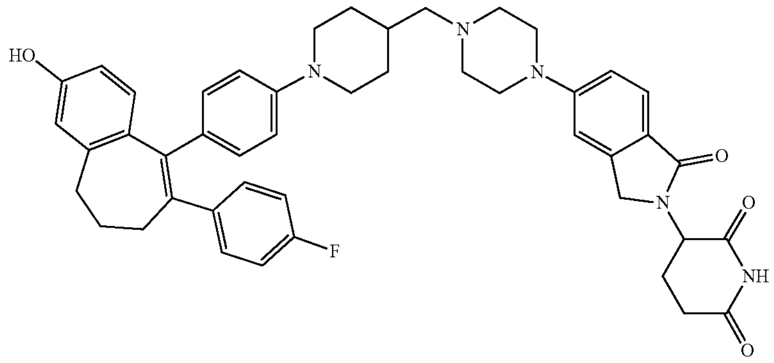
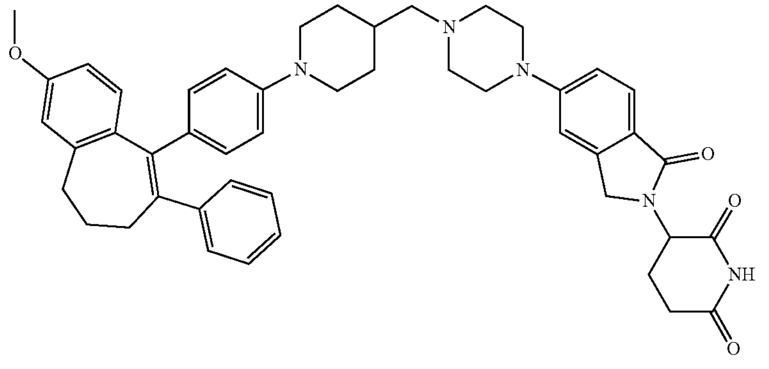
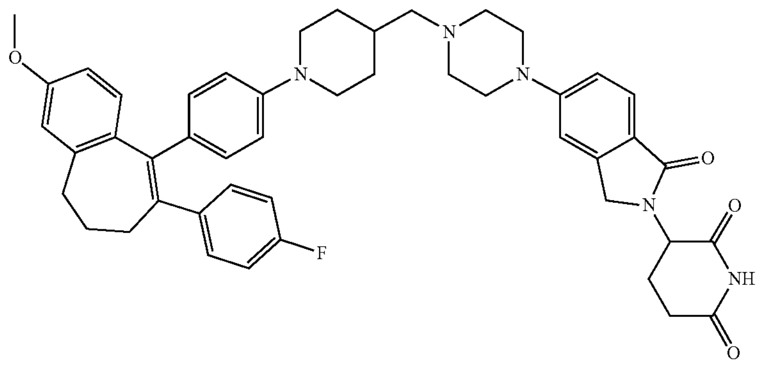

-continued
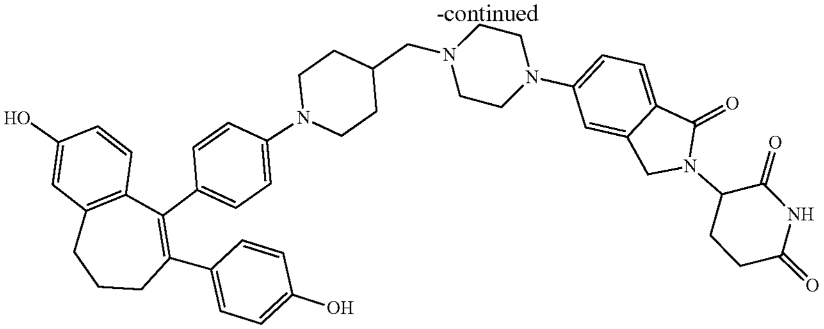
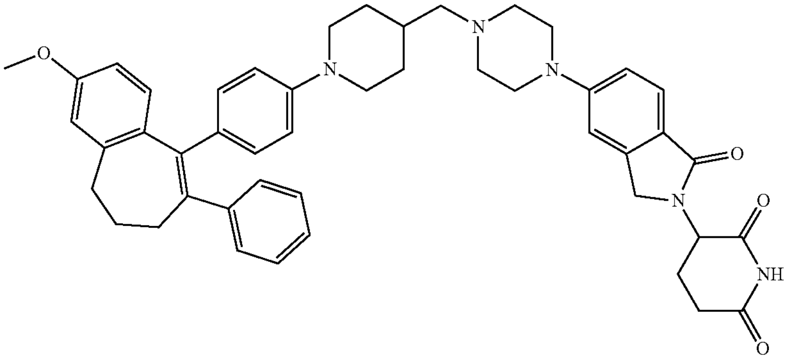
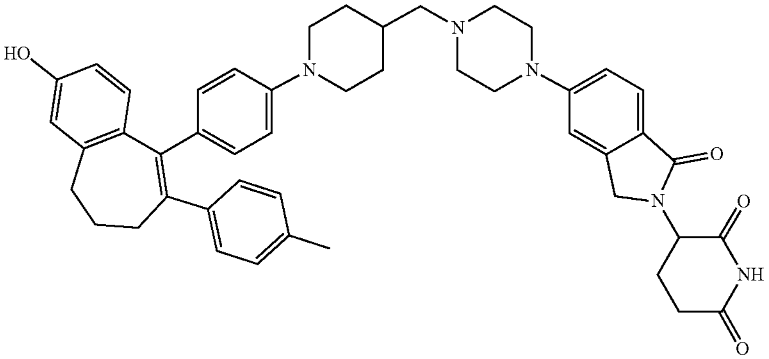
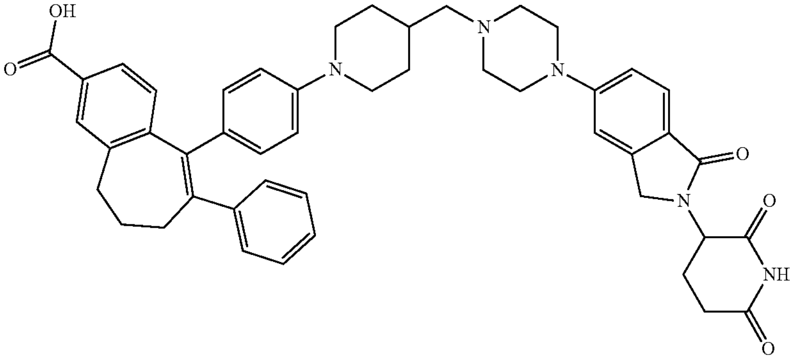
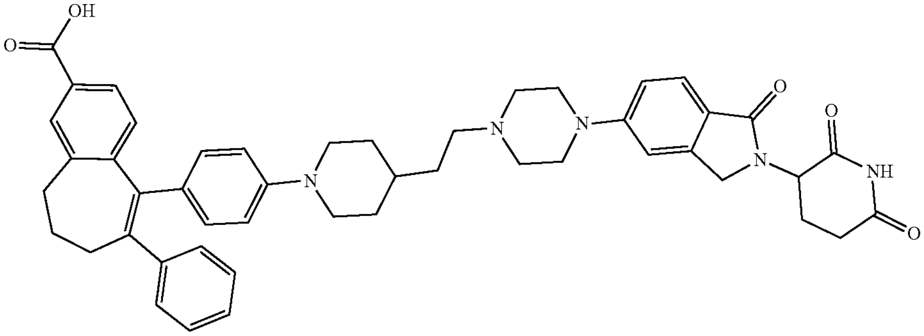

-continued
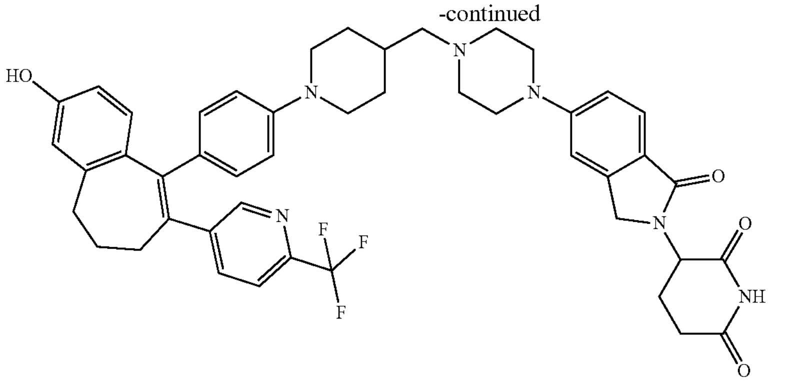
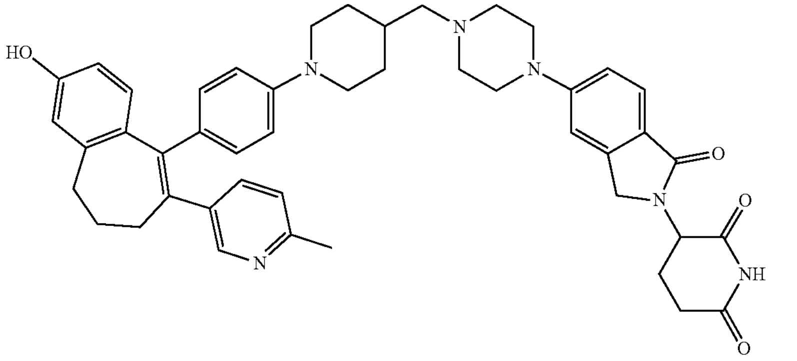
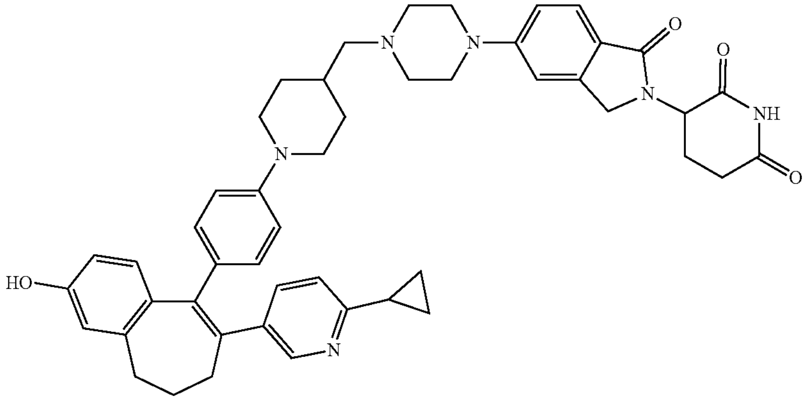
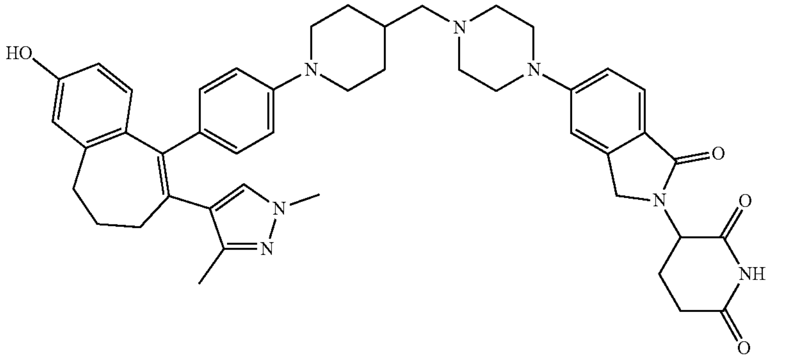

-continued
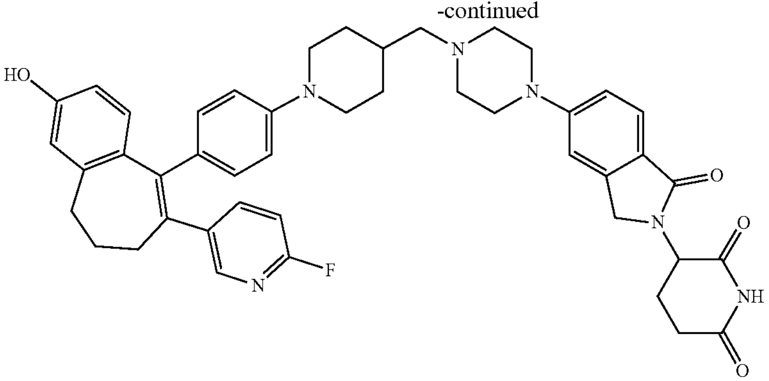
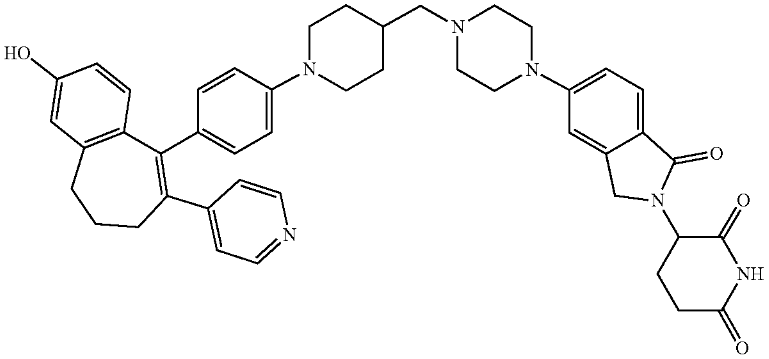
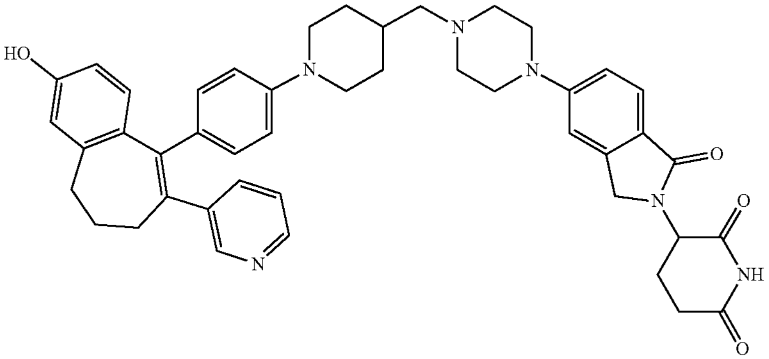
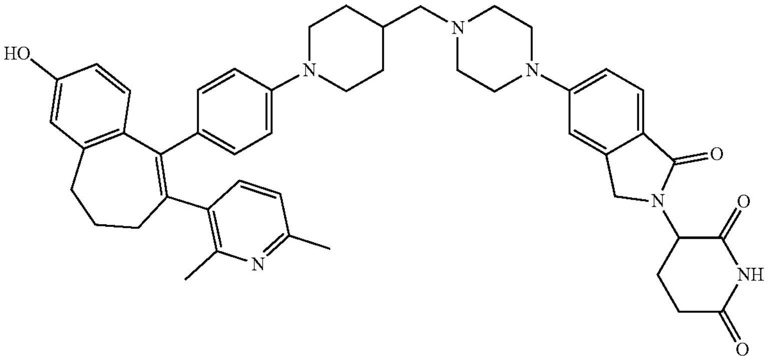

-continued
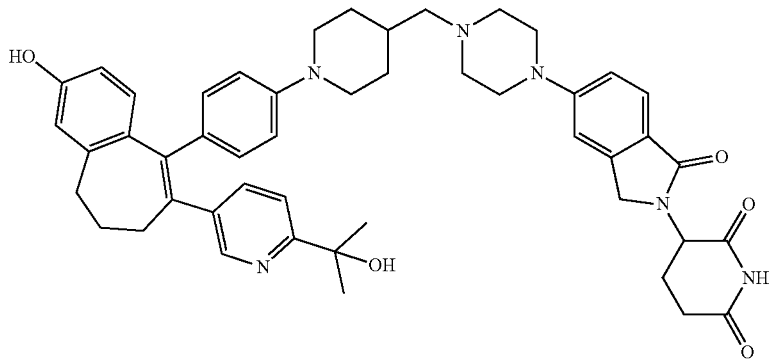
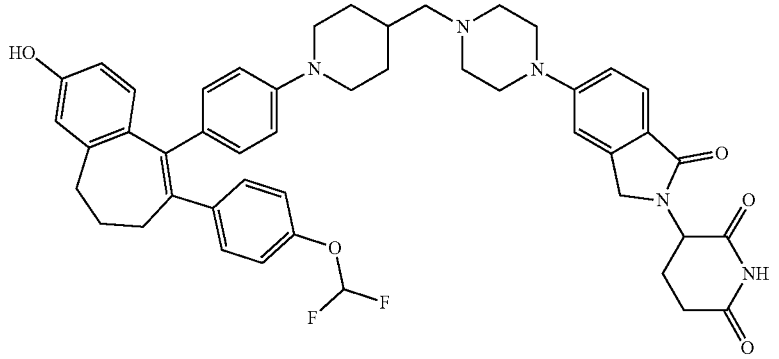
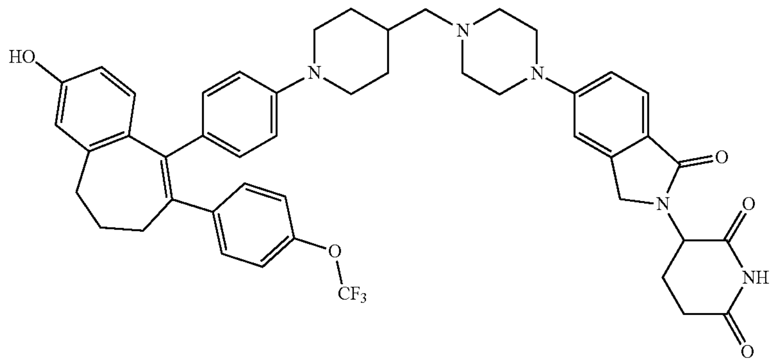
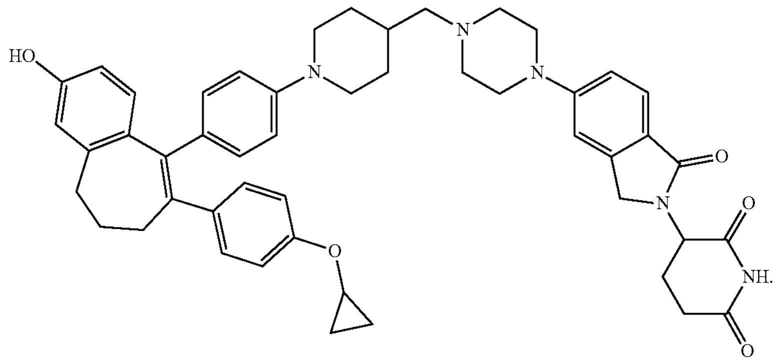

In some embodiments of the present application, the compound is selected from the group consisting of,
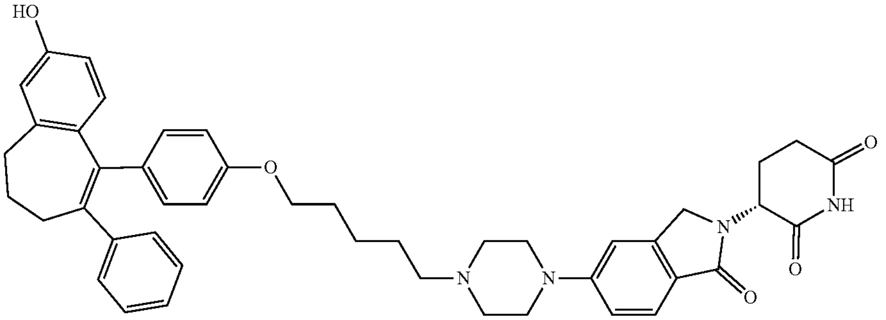
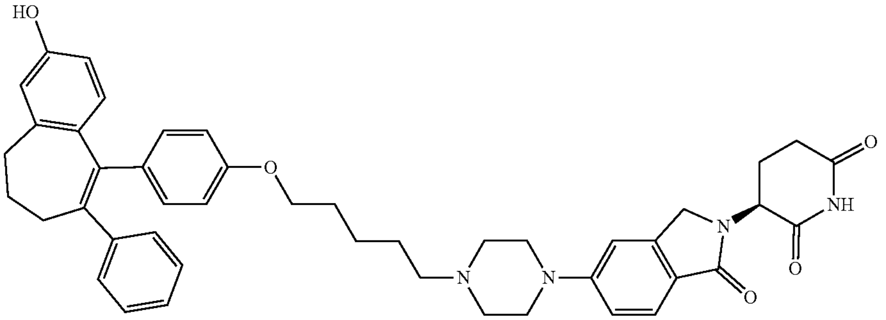
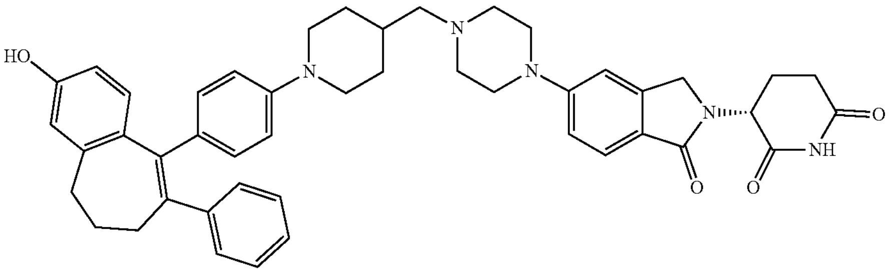
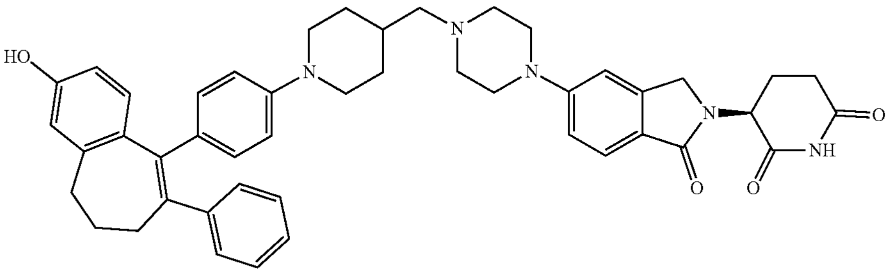
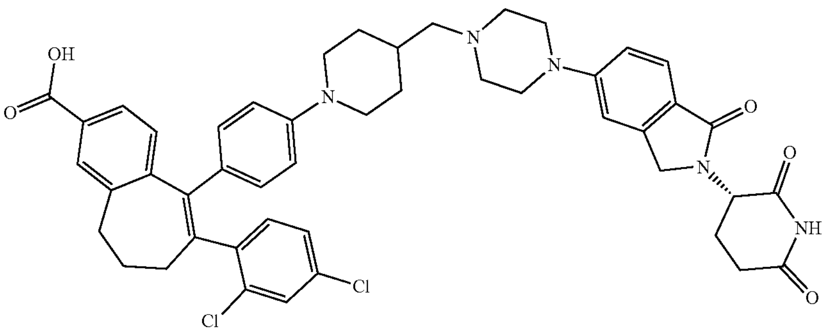

-continued
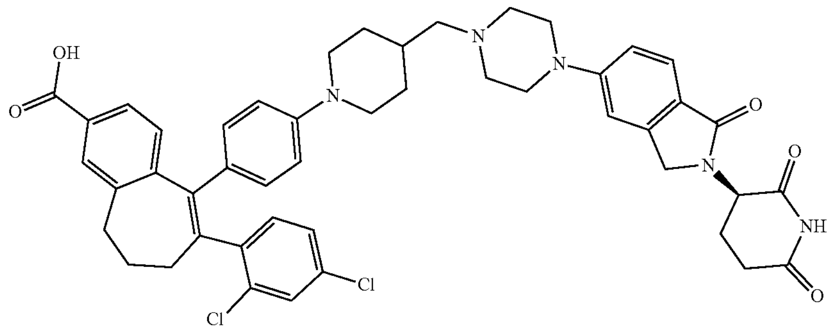
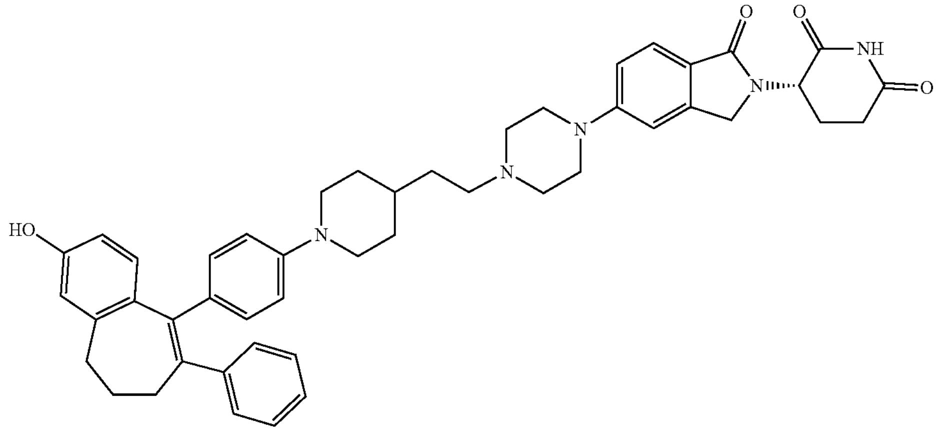
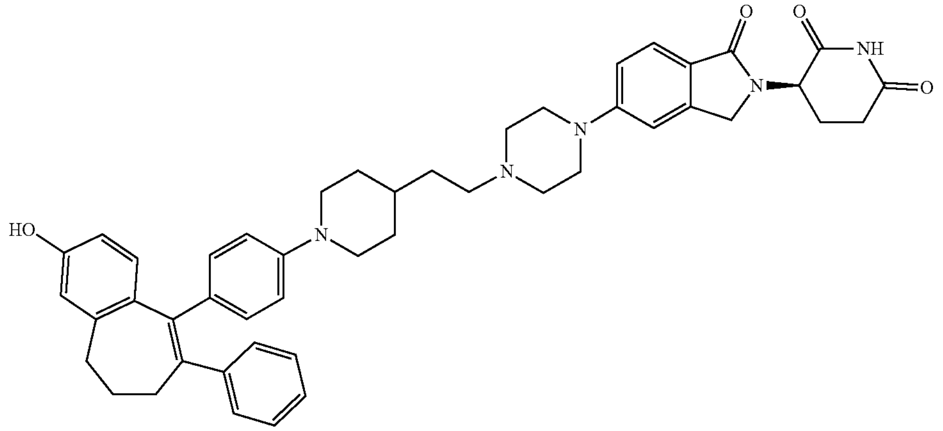
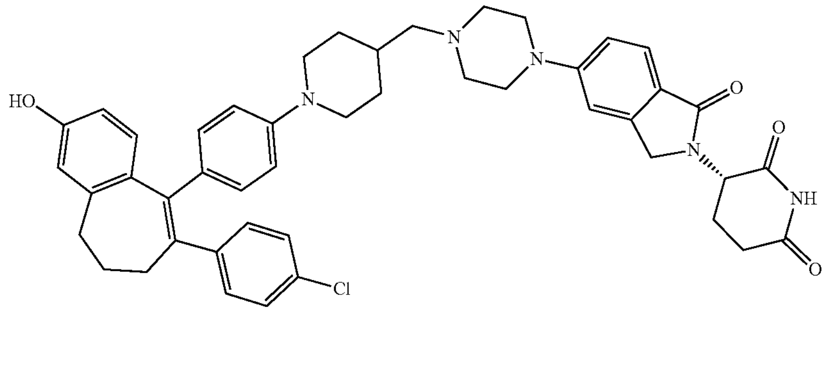

-continued
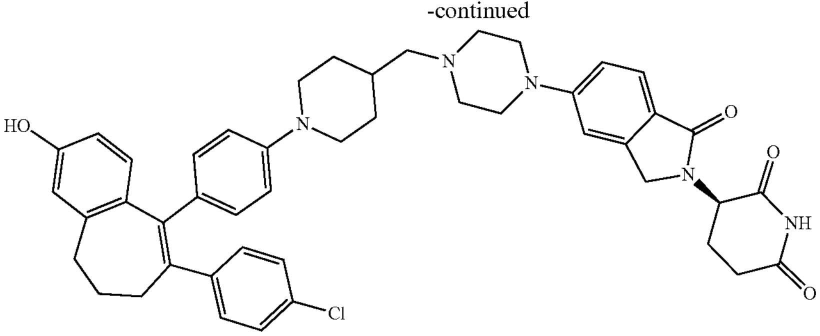
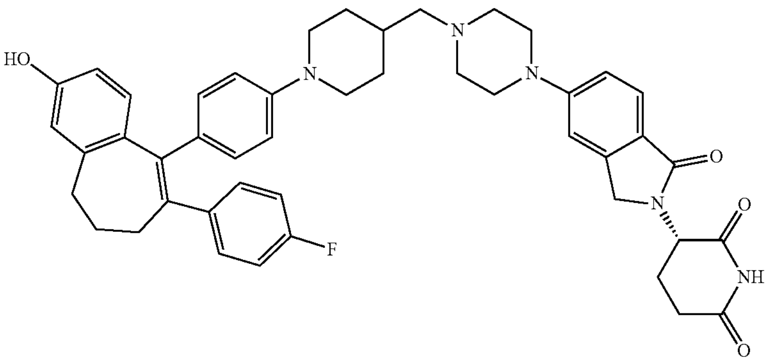
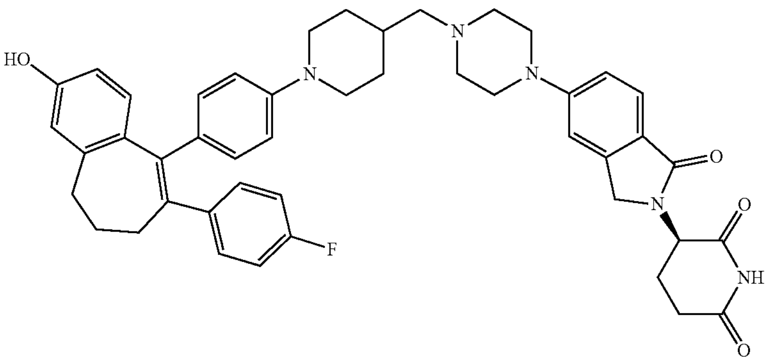
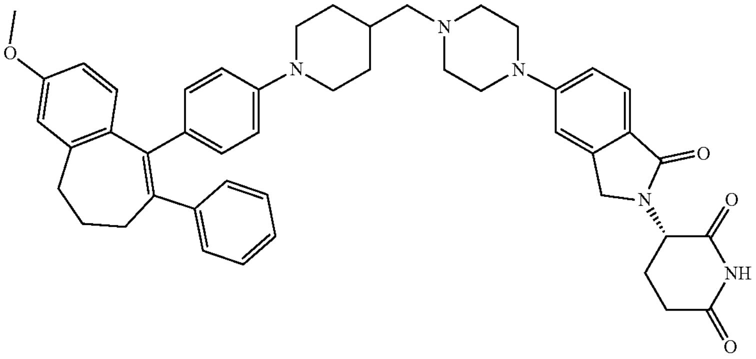

-continued
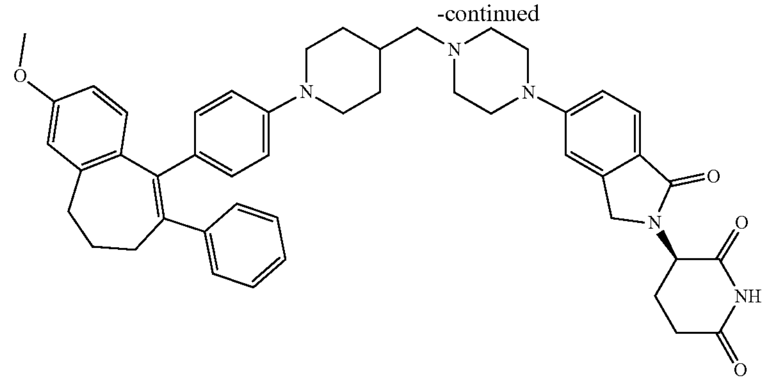
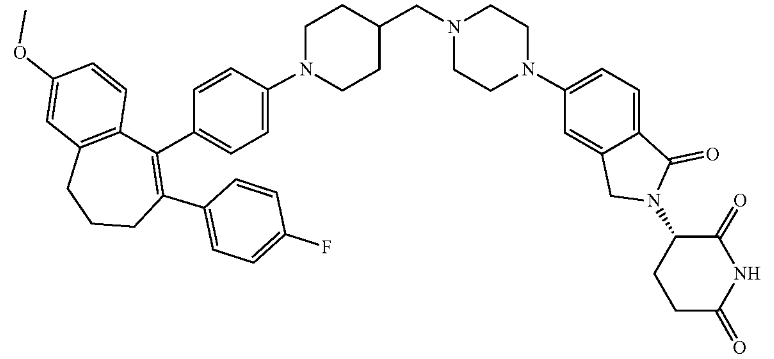
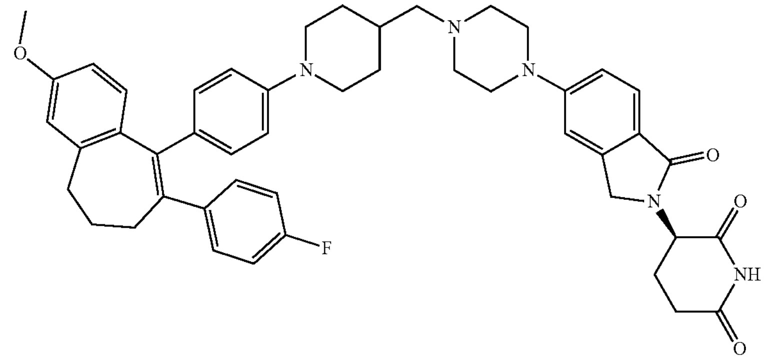
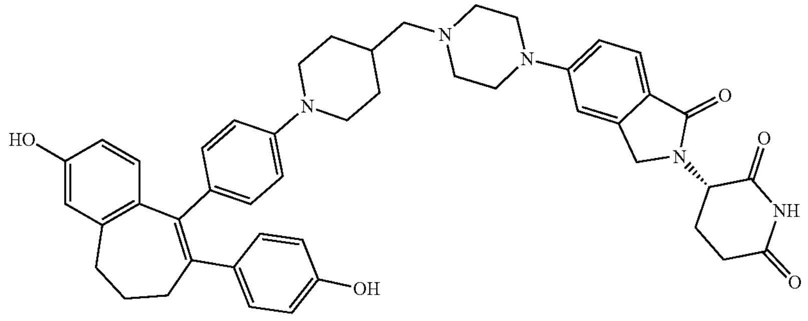
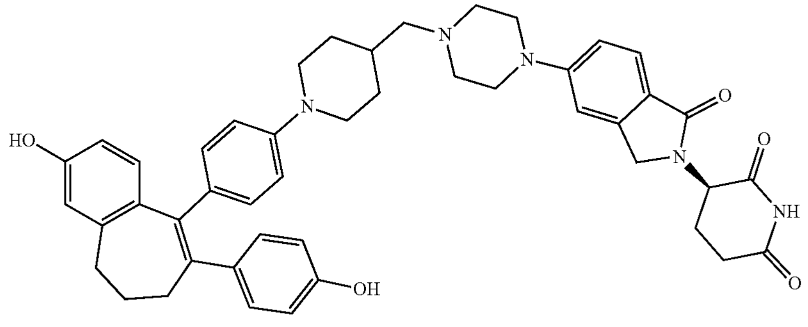

-continued
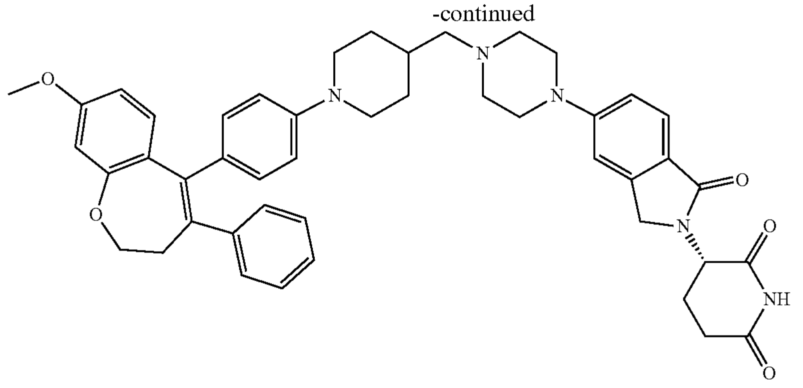
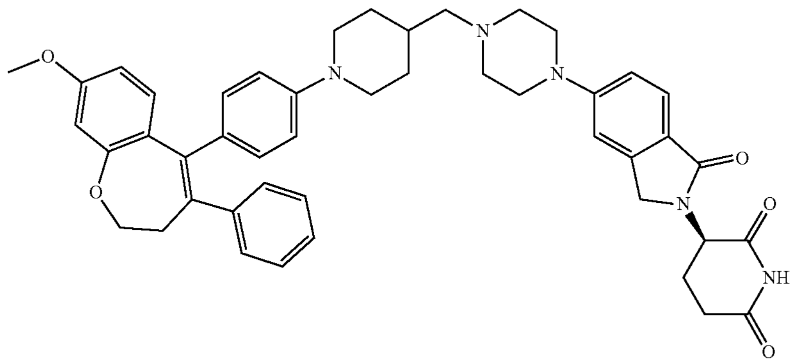
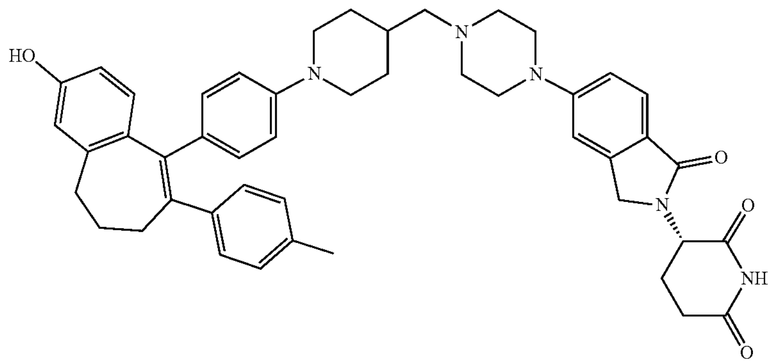
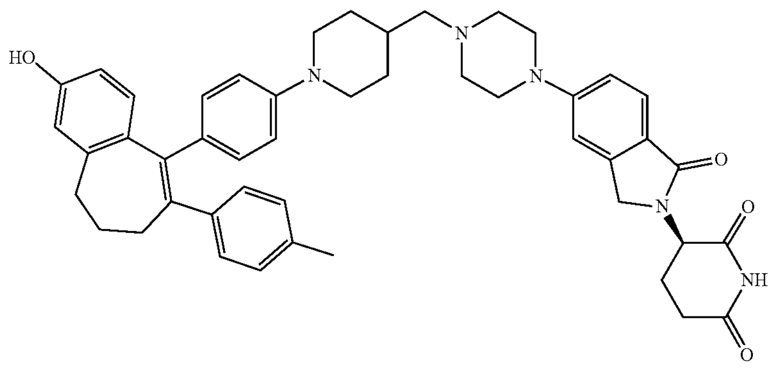

-continued
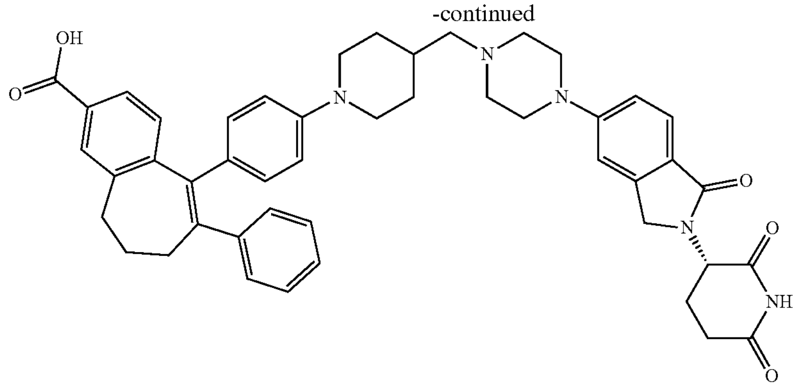
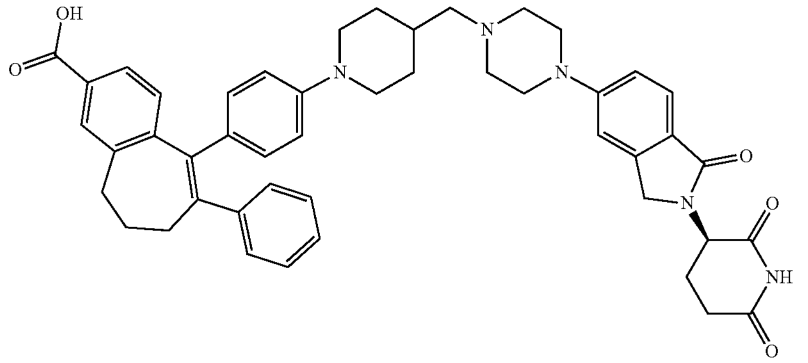
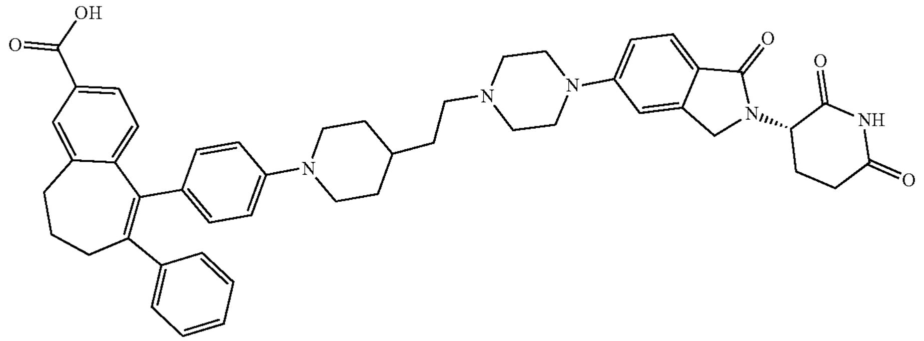
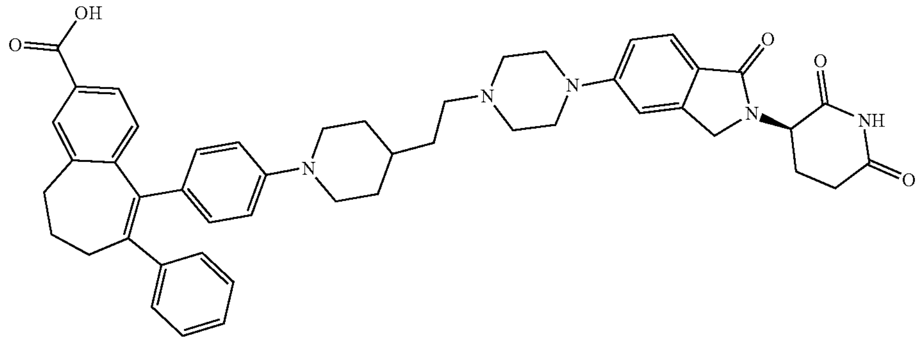

-continued
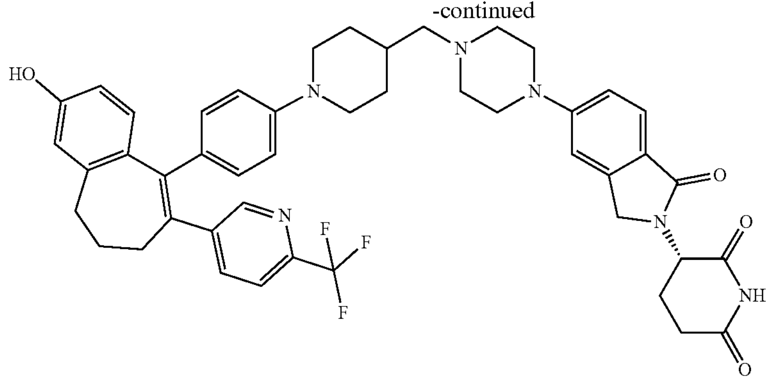
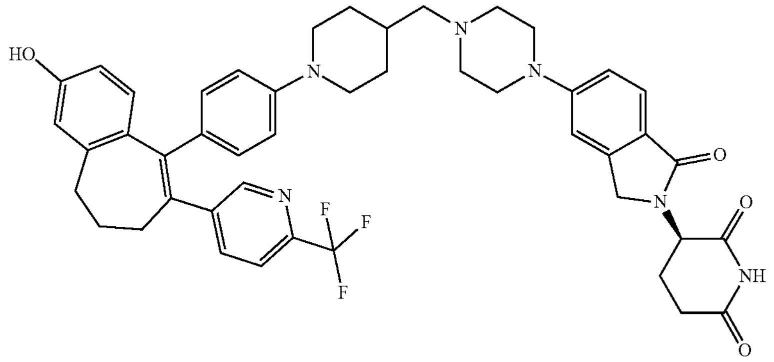
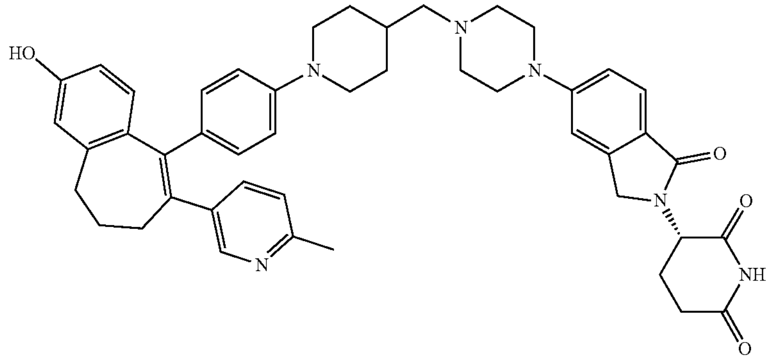
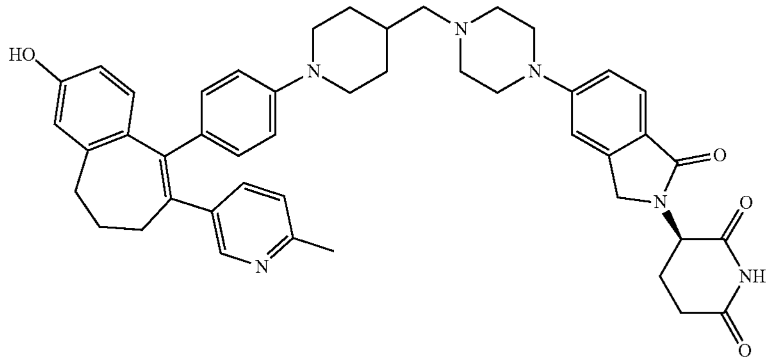

-continued
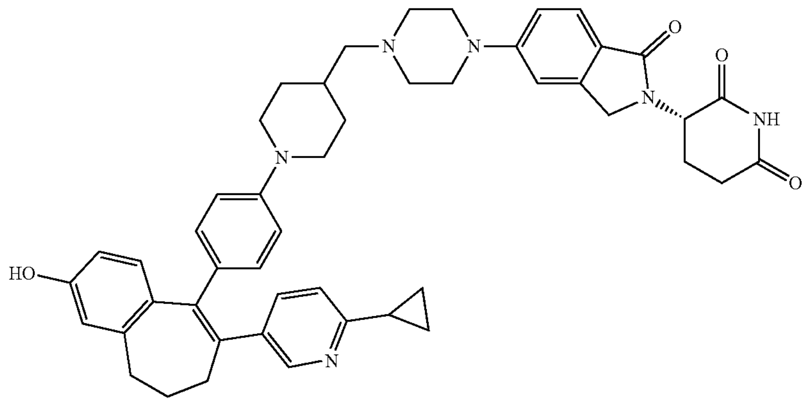
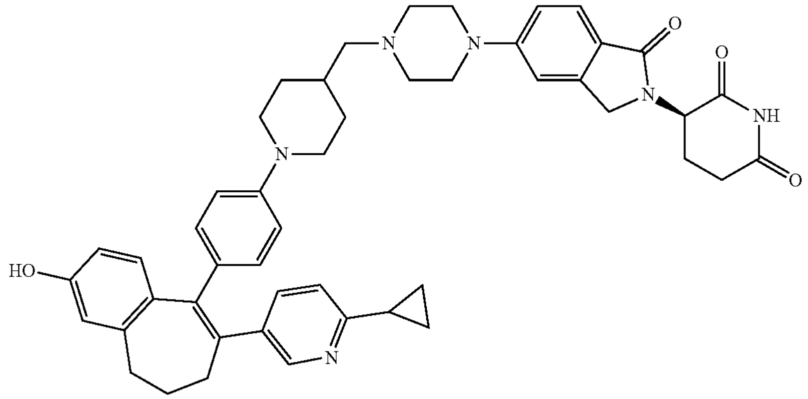
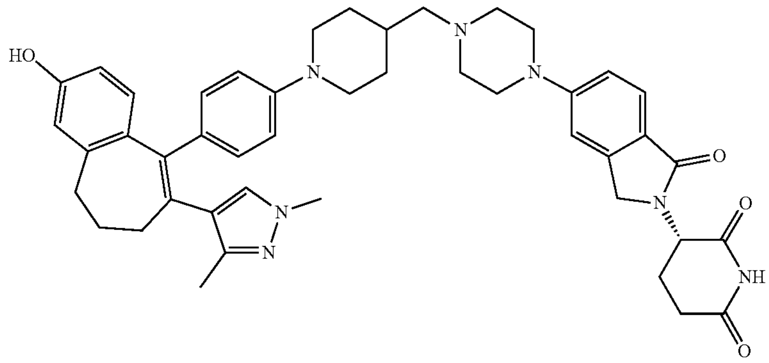
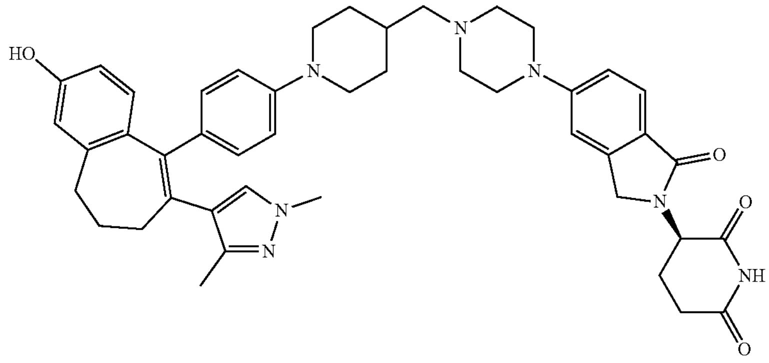

-continued
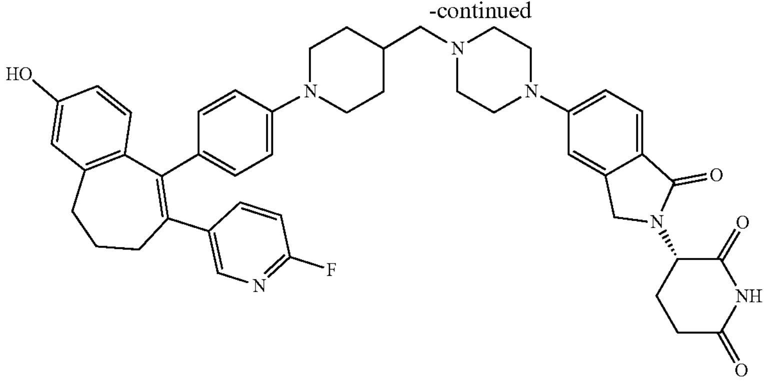
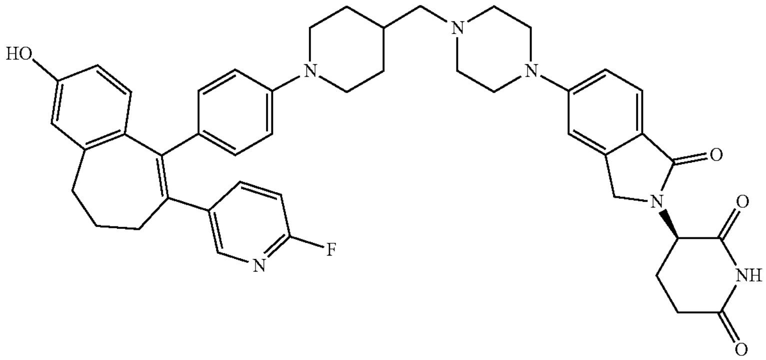
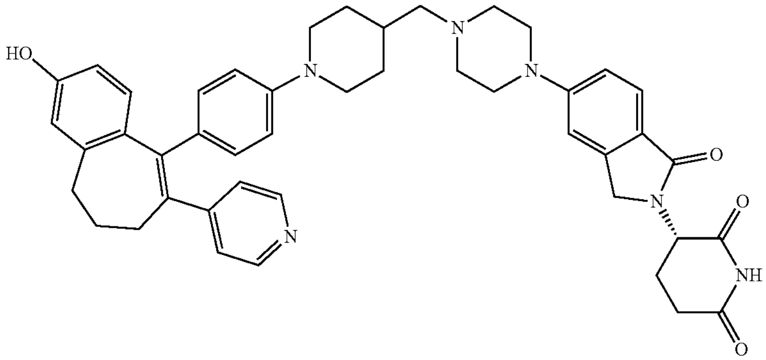
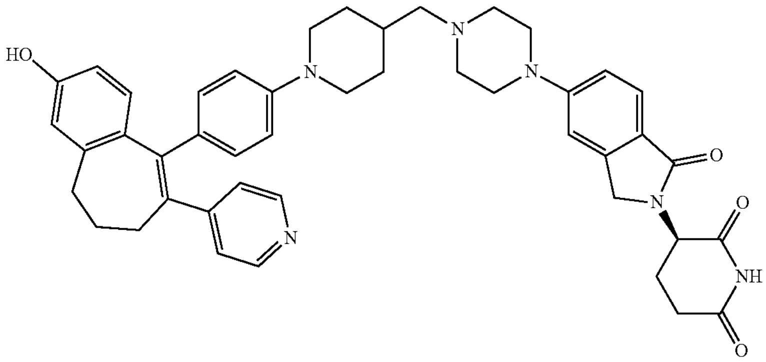

-continued
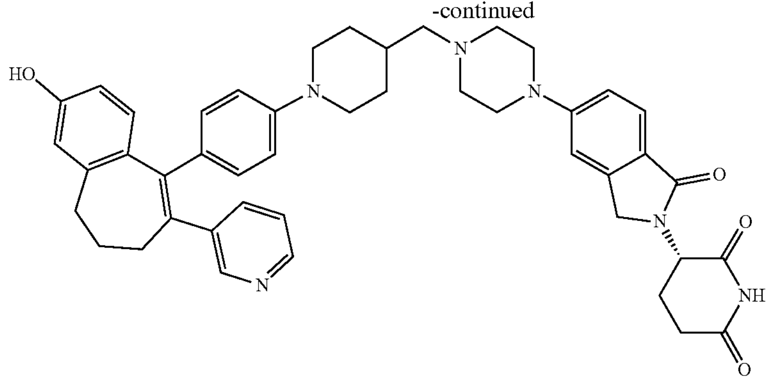
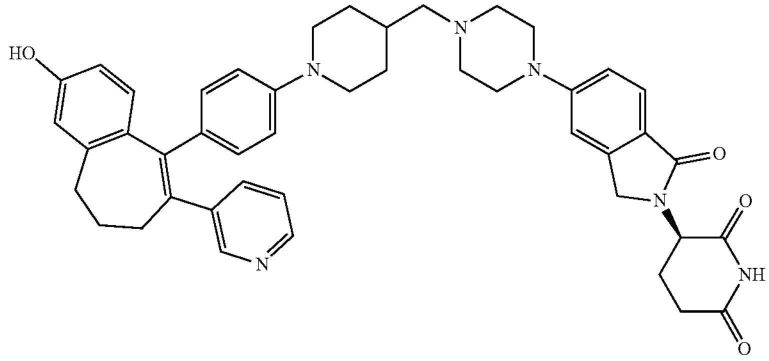
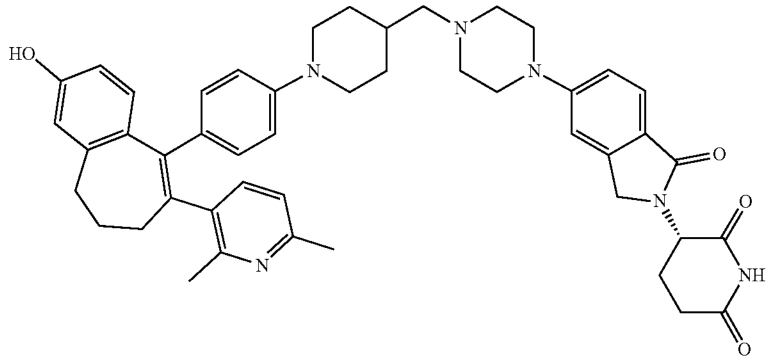
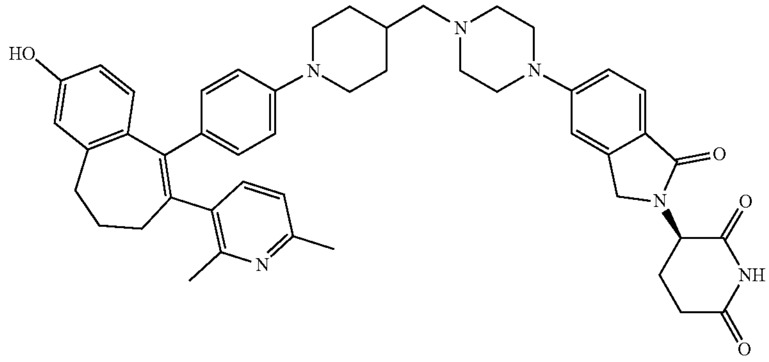

-continued
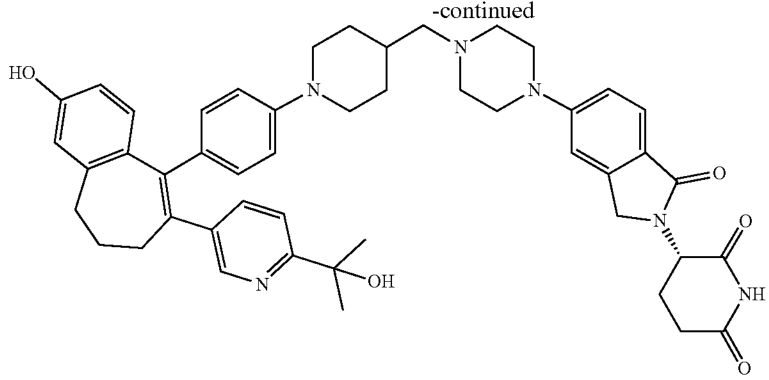
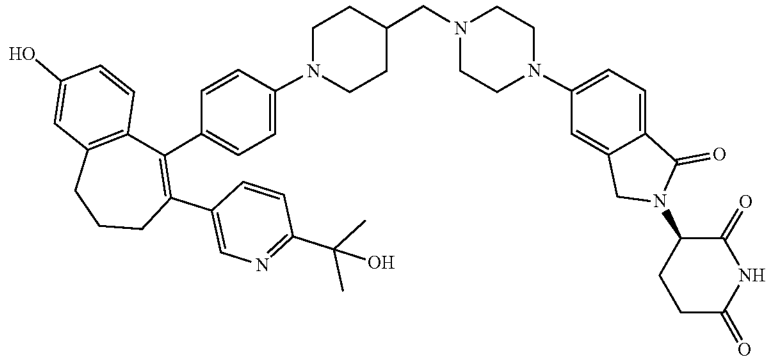
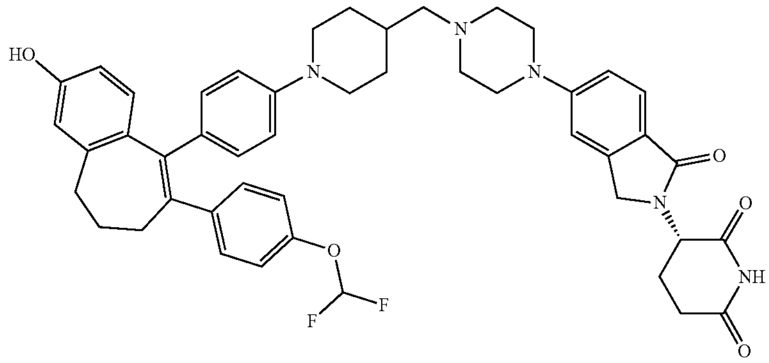
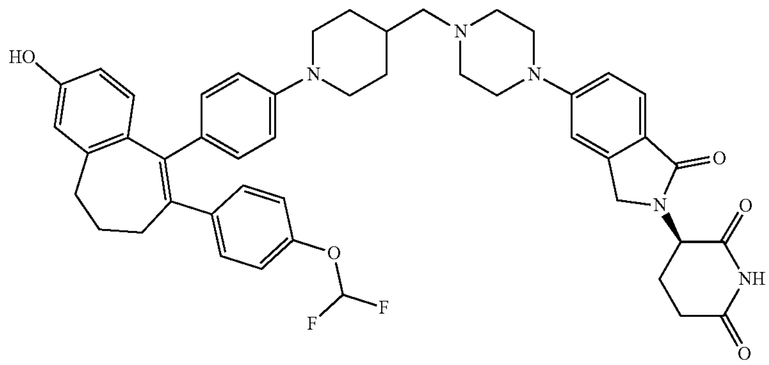

-continued

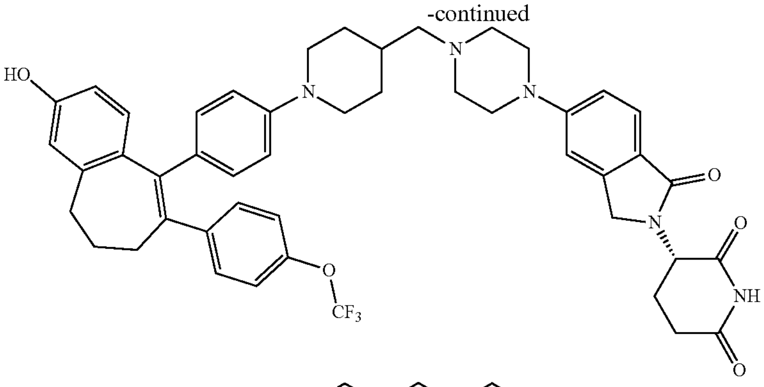

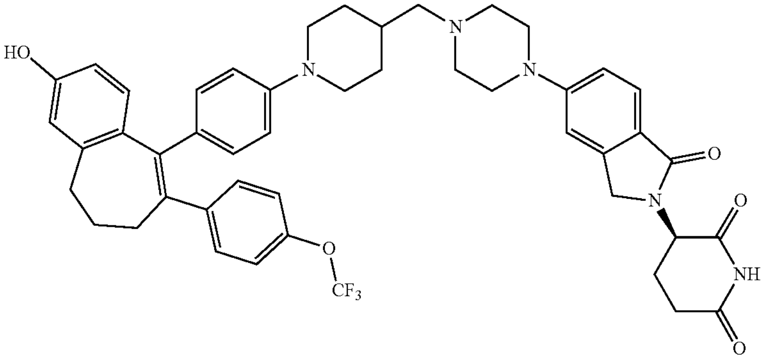

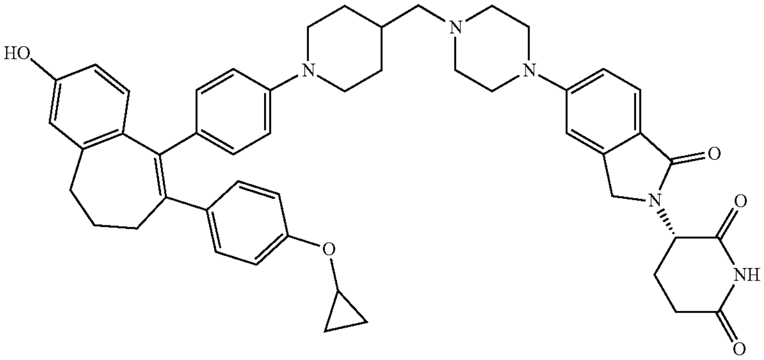

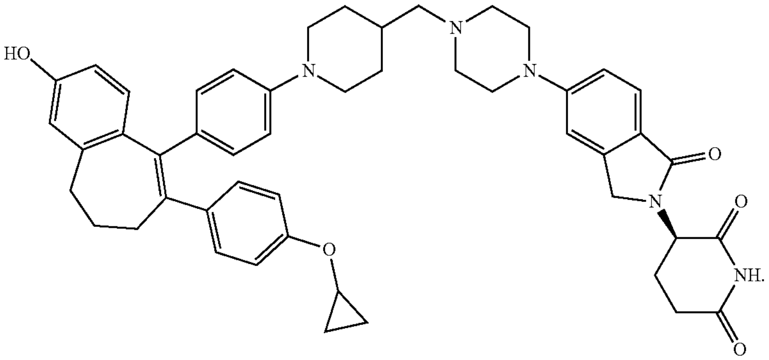

The present application further provides a pharmaceutical composition comprising a therapeutically effective amount of the compound, the isomer thereof or the pharmaceutically acceptable salt thereof disclosed herein, and a pharmaceutically acceptable carrier.

The present application further provides use of the compound, the isomer thereof, or the pharmaceutically acceptable salt thereof disclosed herein in preparing a medicament for use in treating a disease related to estrogen receptor proteolysis-targeting chimera.

The present application further provides a method for treating a disease related to estrogen receptor proteolysis-targeting chimera, comprising administering to a mammal, preferably a human, in need of such treatment a therapeutically effective amount of the compound, the isomer thereof, or the pharmaceutically acceptable salt thereof disclosed herein.

The present application further provides use of the compound, the isomer thereof, or the pharmaceutically acceptable salt thereof disclosed herein in preparing a medicament for treating a disease related to estrogen receptor proteolysis-targeting chimera.

The present application further provides the compound of formula (IV), the isomer thereof, or the pharmaceutically acceptable salt thereof disclosed herein in preparing a medicament for use in treating a disease related to estrogen receptor proteolysis-targeting chimera.

The present application further provides the compound of formula (I), the isomer thereof, or the pharmaceutically acceptable salt thereof disclosed herein in preparing a medicament for use in treating a disease related to estrogen receptor proteolysis-targeting chimera.

In some embodiments of the present application, the disease related to estrogen receptor proteolysis-targeting chimera is selected from the group consisting of a tumor and a cancer.

In some embodiments of the present application, the disease related to the estrogen receptor proteolysis-targeting chimera is selected from the group consisting of breast cancer, endometrial cancer, ovarian cancer, uterine cancer, prostate cancer, endometriosis, lung cancer, and esophageal cancer.

In some embodiments of the present application, the disease related to the estrogen receptor proteolysis-targeting chimera is selected from breast cancer.

Technical Effects

The compound in the present application, as a bifunctional ER PROTAC molecule with a novel structure, not only exhibits good inhibitory effects on estrogen-induced signaling, but also induces degradation of ERα. The bifunctional compound has good properties such as pharmacokinetics, bioavailability, and in-vivo efficacy, and can be formulated into novel estrogen receptor degrading agents.

Definitions

Unless otherwise stated, the following terms and phrases used herein are intended to have the following meanings. A particular term or phrase, unless otherwise specifically defined, should not be considered indefinite or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms that are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound of the present application, which is prepared from the compound having particular substituents discovered by the present application and a relatively non-toxic acid or base. When the compound of the present application contains a relatively acidic functional group, a base addition salt can be obtained by making such a compound in contact with a sufficient amount of a base in a pure solution or a suitable inert solvent. When the compound of the present application contains a relatively basic functional group, an acid addition salt can be obtained by making such a compound in contact with a sufficient amount of an acid in a pure solution or a suitable inert solvent. Certain specific compounds disclosed herein contain both basic and acidic functional groups that allow the compounds to be converted into either base or acid addition salts.

The pharmaceutically acceptable salts of the present application can be synthesized from a parent compound having an acidic or basic group using conventional chemical methods. In general, such salts are prepared by subjecting the free acid or base form of the compound to a reaction with a stoichiometric amount of the appropriate base or acid in water or an organic solvent or a mixture thereof.

The compounds described herein can be in the form of a geometric isomer or stereoisomer. All such compounds are contemplated herein, including cis- and trans-isomers, (−)- and (+)-enantiomers, (R)- and (S)-enantiomers, diastereomers, (D)-isomers, (L)-isomers, and racemic mixtures and other mixtures thereof, such as an enantiomer or diastereomer-enriched mixture, all of which are encompassed within the scope of the present application. The substituents such as alkyl may have an additional asymmetric carbon atom. All these isomers and mixtures thereof are encompassed within the scope of the present application.

The compounds and intermediates disclosed herein may also exist in different tautomeric forms, and all such forms are included within the scope of the present application. The term "tautomer" or "tautomeric form" refers to structural isomers of different energies that can interconvert via a low-energy barrier. For example, proton tautomerism (also referred to as prototropic tautomerism) involves interconversion via proton transfer, such as keto-enol isomerism and imine-enamine isomerism. A specific example of proton tautomerism is an imidazole moiety where a proton can transfer between two ring nitrogens. Valence tautomerism involves the interconversion via the recombination of some bonding electrons.

The compounds disclosed herein may contain an unnatural proportion of atomic isotope at one or more of the atoms that constitute the compound. For example, the compound may be labeled with a radioisotope, such as tritium ($^3H$), iodine-125 ($^{125}I$), or C-14 ($^{14}C$). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced adverse effects, increased stability, enhanced efficacy, prolonged biological half-life, and the like. All isotopic variations of the compounds described herein, whether radioactive or not, are encompassed within the scope of the present application.

The term "optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituents, wherein the substituents may include deuterium and hydrogen variants, as long as the valence of the specific atom is normal and the substituted compound is stable. When the substituent is oxygen (i.e., =O), it means that two hydrogen atoms are substituted. Substitution with oxygen does not occur in aromatic groups. The term "optionally substituted" means that an atom may or may not be substituted with a substituent. Unless otherwise specified, the type and number of the substituent may be arbitrary as long as being chemically achievable.

The term "substituted" means that a particular atom or group can be substituted by another atom or group as specified. For example, 1 or 2 or 3 of the $—CH_2—$ in $—CH_2CH_2CH_2—$ may be substituted by O, S, or NH to give $—O—CH_2—CH_2—$, $—O—CH_2—$, $—CH_2—O—CH_2—$, $—CH_2—O—$, $—CH_2—CH_2—O—$, $—O—$, or the like. For another example, 1 or 2 or 3 of the $—CH_2—$ in $—CH_2CH_2CH_2—$ may be substituted by cyclohexyl or piperidinyl to give

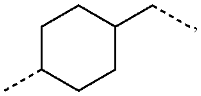
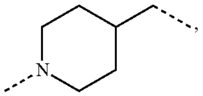
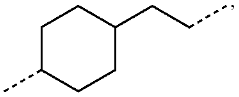
or
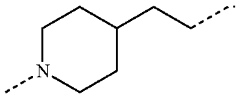

When any variable (e.g., R) occurs more than once in the composition or structure of a compound, the variable is independently defined in each case. Thus, for example, if a group is substituted with 0-2 R, the group can be optionally substituted with up to two R, and the definition of R in each case is independent. Furthermore, a combination of the substituent and/or the variant thereof is permissible only if the combination can result in a stable compound.

When one of the variables is selected from a single bond, it means that the two groups which it connects are connected directly. For example, in A-L-Z, when L represents a single bond, it means that the structure is actually A-Z.

When the direction for connection of the listed connecting group is not specified, the direction for connection is arbitrary. For example, when the connecting group L contained in

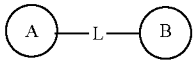

is -M-W—, -M-W— can either connect ring A and ring B in a direction same as left-to-right reading order to form

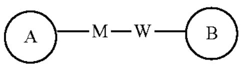, or connect ring A and ring B in a direction opposite to the left-to-right reading order to form

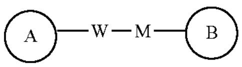.

A combination of the connecting group, the substituent, and/or the variant thereof is permissible only if the combination can result in a stable compound.

Unless otherwise specified, when a group has one or more connectable sites, any one or more of the sites of the group may be connected to other groups by chemical bonds. When there is no designated connecting mode for a chemical bond and H atoms are present at a connectable site, the number of the H atoms at the connectable site is correspondingly reduced based on the number of the connected chemical bonds, and a number of groups corresponding to the valence number are thus formed. The chemical bond that connects the site and another group may be represented by a straight solid line (  ), a straight dashed line (  ), or a wavy line (  ).

For example, the straight solid line in $—OCH_3$ refers to a connection with another group via the oxygen atom in the group; the straight dashed lines in

refer to connections with other groups via two ends of the nitrogen atom in the group; the wavy lines in

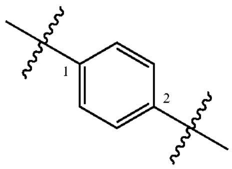 [SMILES: *c1ccc(*)cc1]

refer to connections with other groups via the carbon atoms at positions 1 and 2 in the phenyl group;

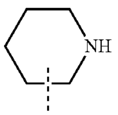
or
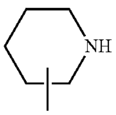

or means that any connectable site on the piperidinyl can be connected to another group via 1 bond in at least 4 connecting modes:

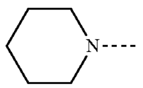,
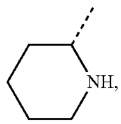,
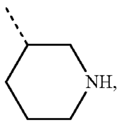,

-continued

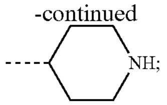

even if —N— is connected with an H atom,

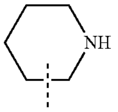

includes the connection mode of

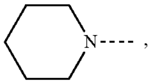

but when 1 bond is connected to a site, the number of H at that site is correspondingly reduced by 1 and the valence number of the piperidinyl is thus increased by one.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc., and may be monovalent (e.g., methyl), divalent (e.g., methylene) or polyvalent (e.g., methenyl). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like.

Unless otherwise specified, the term "$C_{1-3}$ alkyl" refers to a linear or branched saturated hydrocarbon group consisting of 1 to 3 carbon atoms. The $C_{1-3}$ alkyl includes, but is not limited to, $C_{1-2}$ and $C_{2-3}$ alkyl, and the like, and may be monovalent (e.g., methyl), divalent (e.g., methylene) or polyvalent (e.g., methenyl). Examples of $C_{1-3}$ alkyl include, but are not limited to, methyl (Me), ethyl (Et), propyl (including n-propyl and isopropyl), and the like.

Unless otherwise specified, the term "$C_{1-3}$ alkoxy" refers to those alkyl groups that each contain 1 to 3 carbon atoms and are linked to the rest part of the molecule via an oxygen atom. The $C_{1-3}$ alkoxy includes, but is not limited to, $C_{1-2}$, $C_{2-3}$, $C_3$, and $C_2$ alkoxy, and the like. Examples of $C_{1-3}$ alkoxy include, but are not limited to, methoxy, ethoxy, propoxy (including n-propoxy and isopropoxy), and the like.

Unless otherwise specified, the term "$C_{1-6}$ alkylene" refers to a saturated straight or branched or cyclic hydrocarbyl consisting of 1 to 6 carbon atoms, having 2 residues derived from the parent alkane by removal of two hydrogen atoms from the same carbon atom or two different carbon atoms. Nonrestrictive instances of alkylene include, but are not limited to, methylene ($—CH_2—$), 1,1-ethylene ($—CH(CH_3)—$), 1,2-ethylene ($—CH_2CH_2—$), 1,1-propylene ($—CH(CH_2CH_3—$), (1,2C propylene (propyl $2_2CH(CH_3)$, (1,3C propylene (propyl $3_2CH_2CH_2—$), 1,4C butylene (butyl $4_2CH_2CH_2CH_2—$), and the like.

Unless otherwise specified, the term "halogen" or "halogens", by itself or as part of another substituent, refers to a fluorine, chlorine, bromine, or iodine atom.

Unless otherwise specified, $C_{n-n+m}$ or $C_n$-$C_{n+m}$ includes any one of the specific cases of n to n+m carbon atoms. For example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$. Also, any range within n to n+m may be included. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc. Similarly, n- to n+m-membered represents that the number of atoms on the ring is n to n+m. For example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring. n- to n+m-membered also represents any range within n to n+m. For example, 3- to 12-membered ring includes 3- to 6-membered ring, 3- to 9-membered ring, 5- to 6-membered ring, 5- to 7-membered ring, 6- to 7-membered ring, 6- to 8-membered ring, 6- to 10-membered ring, and the like.

Unless otherwise specified, "$C_{3-6}$ cycloalkyl" refers to a saturated cyclic hydrocarbon group consisting of 3 to 6 carbon atoms, including monocyclic and bicyclic ring systems. The $C_{3-6}$ cycloalkyl includes $C_{3-5}$ cycloalkyl, $C_{4-5}$ cycloalkyl, $C_{5-6}$ cycloalkyl, and the like, and may be monovalent, divalent, or polyvalent. Examples of $C_{3-6}$ cycloalkyl include, but are not limited to, cyclopropyl, cyclobutyl, cyclopentyl, cyclohexyl, and the like.

Unless otherwise specified, the term "4- to 6-membered heterocycloalkyl", by itself or in combination with other terms, refers to a saturated cyclic group consisting of 4 to 6 ring atoms, of which 1, 2, 3, or 4 are heteroatoms independently selected from the group consisting of O, S, and N, and the rest are carbon atoms, wherein the nitrogen atom is optionally quaternized, and the nitrogen and sulfur heteroatoms can be optionally oxidized (i.e., NO and $S(O)_p$, wherein p is 1 or 2). It includes monocyclic and bicyclic systems, wherein the bicyclic system includes spirocyclic, fused, and bridged rings. Furthermore, with respect to the "4- to 6-membered heterocycloalkyl", a heteroatom may occupy the position where the heterocycloalkyl is connected to the rest of the molecule. The 4- to 6-membered heterocycloalkyl includes 5- to 6-membered heterocycloalkyl, 4-membered heterocycloalkyl, 5-membered heterocycloalkyl, 6-membered heterocycloalkyl, and the like. Examples of 4- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, and the like), tetrahydrofuranyl (including tetrahydrofuran-2-yl, and the like), tetrahydropyranyl, piperidinyl (including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl, 1,2-oxazinyl, 1,2-thiazinyl, hexahydropyridazinyl, hyperpiperazinyl, hyperpiperidinyl, and the like.

Unless otherwise specified, the term "5- to 6-membered heteroaryl" herein refers to a cyclic group consisting of 5 to 6 ring atoms and having a conjugated π-electron system, of which 1, 2, or 3 ring atoms are heteroatoms independently selected from the group consisting of O, S, and N, with the remaining being carbon atoms. The nitrogen atom is optionally quaternized, and the carbon, nitrogen and sulfur heteroatoms may optionally be oxidized (i.e., C=O, NO and $S(O)_p$, wherein p is 1 or 2). The 5- to 6-membered heteroaryl can be connected to the rest of the molecule through a heteroatom or a carbon atom. The 5- to 6-membered heteroaryl includes 5-membered heteroaryl and 6-membered heteroaryl. Examples of the 5- to 6-membered heteroaryl include, but are not limited to, pyrrolyl (including N-pyrrolyl, 2-pyrrolyl, 3-pyrrolyl, and the like), pyrazolyl (including 2-pyrazolyl, 3-pyrazolyl, and the like), imidazolyl (including N-imidazolyl, 2-imidazolyl, 4-imidazolyl, 5-imidazolyl, and the like), oxazolyl (including 2-oxazolyl, 4-oxazolyl, 5-oxazolyl, and the like), triazolyl (including 1H-1,2,3-triazolyl, 2H-1,2,3-triazolyl, 1H-1,2,4-triazolyl, 4H-1,2,4-triazolyl, and the like), tetrazolyl, isoxazolyl (including 3-isoxazolyl, 4-isoxazolyl, 5-isoxazolyl, and the like), thiazolyl (including 2-thiazolyl, 4-thiazolyl, 5-thiazolyl, and the like), furanyl (including 2-furanyl, 3-furanyl, and the like), thienyl (including 2-thienyl, 3-thienyl, and the like), pyridinyl (including 2-pyridinyl, 3-pyridinyl, 4-pyridinyl, and the like), pyrazinyl, or pyrimidinyl (including 2-pyrimidinyl, 4-pyrimidinyl, and the like).

The term "pharmaceutical composition" refers to a composition comprising one or more of the compound, the isomer thereof, or the pharmaceutically acceptable salt thereof disclosed herein, as well as other components such as a physiologically/pharmaceutically acceptable carrier and excipient. The pharmaceutical composition is intended to promote the administration to organisms, facilitate the absorption of the active ingredients and thus exert biological activity.

The term "ubiquitin ligase" refers to a family of proteins that facilitate the transfer of ubiquitin to a specific substrate protein for targeting and degrading the substrate protein. For example, IAP, E3 ubiquitin ligase protein, alone or in combination with E2 ubiquitin conjugating enzyme, causes the attachment of ubiquitin to lysine on a target protein, and subsequently targets the specific protein substrate for degradation by a proteasome. Thus, E3 ubiquitin ligase, either alone or in complex with E2 ubiquitin conjugating enzyme, is responsible for the transfer of ubiquitin to the target protein. In general, ubiquitin ligases are involved in poly ubiquitination, making a second ubiquitin attach to a first ubiquitin, a third ubiquitin attach to the second ubiquitin, and so on. Poly ubiquitination labels a protein for use in the degradation by the proteasome. However, there are some ubiquitination events that are limited to mono ubiquitination, wherein only a single ubiquitin is added to the substrate molecule by the ubiquitin ligase. Mono-ubiquitinated proteins are not used in the degradation by the proteasome, but may be altered in their location or function in cells, for example, via binding to other proteins with domains capable of binding to ubiquitin. More complicatedly, different lysines of ubiquitin can be targeted by E3 to prepare a chain. The most common site on ubiquitin is Lys48. This is the lysine recognized by proteasome for poly ubiquitination.

The term "-targeting chimera" refers to a bifunctional molecule comprising two micromolecule ligands, one with high affinity for the target protein, and the other for use in recruiting E3 ligase that ubiquitinates and targets the protein for proteolysis by a 26S proteasome.

The compounds disclosed herein can be prepared using a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The compound of the present application may be structurally confirmed by conventional methods well known to those skilled in the art; if the present application relates to the absolute configuration of the compound, this absolute configuration may be confirmed by means of conventional techniques in the art. For example, in single crystal X-ray diffraction (SXRD), intensity data of diffraction of the single crystal grown are collected with a Bruker D8 venture diffractometer, with the light source being Cu-Kα radiation and the scanning mode being p/o scanning; after related data are collected, a direct method (Shelxs97) is further employed to analyze the crystal structure, and thus the absolute configuration can be confirmed.

The solvents used in the present application are commercially available.

Compounds are named according to conventional nomenclature rules in the art or using ChemDraw® software, and supplier's catalog names are given for commercially available compounds.

DETAILED DESCRIPTION

The present application is described in detail below by way of examples, which, however, are not intended to disadvantageously limit the scope of the present application in any way. Although the present application has been described in detail herein and specific embodiments have also been disclosed, it will be apparent to those skilled in the art that various changes and modifications can be made to the specific embodiments without departing from the spirit and scope of the present application.

Reference Example 1

7-H

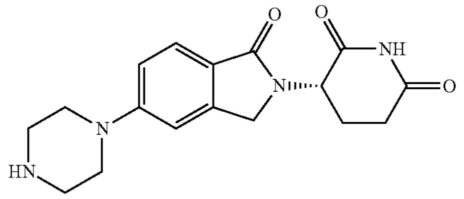

Synthetic Route:

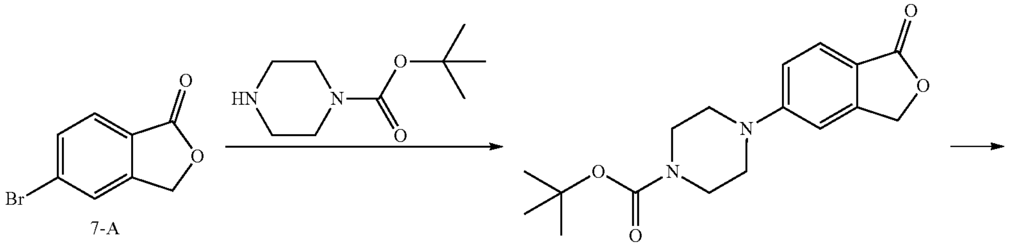

7-A

7-B

-continued

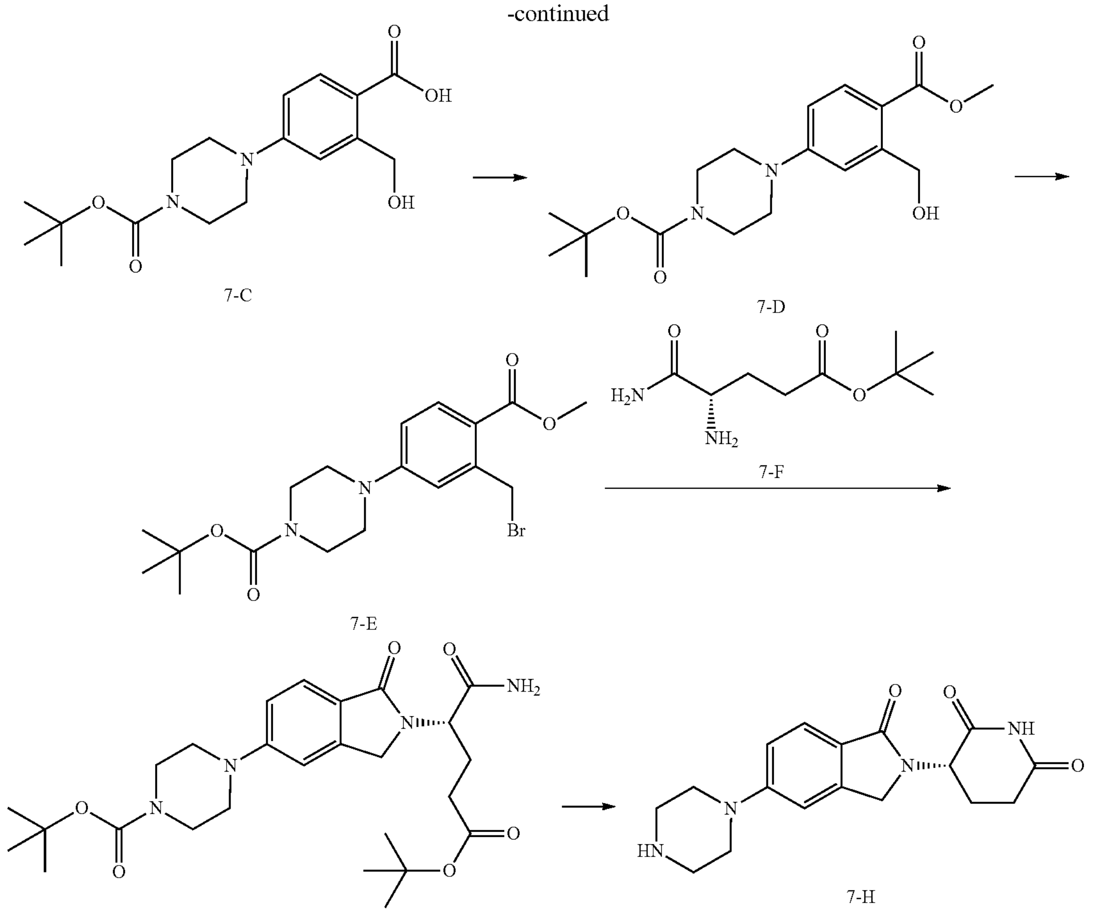

7-C 7-D 7-E 7-F 7-G 7-H

Step 1: Synthesis of Compound 7-B

7-A (37 g) and N-Boc piperazine (32.34 g) were dissolved in dioxane (450 mL), and tris(dibenzylideneacetone)dipalladium (15.90 g), 4,5-bis(diphenylphosphino)-9,9-dimethylxanthene (10.05 g) and potassium phosphate (73.74 g) were added with stirring. The mixture was stirred at 90-100° C. for 17 h under nitrogen atmosphere. After the completion of the reaction, the reaction solution was cooled to room temperature, filtered, and concentrated to give a crude product. Ethyl acetate (200 mL) and n-heptane (200 mL) were added. The mixture was triturated with stirring at 15-20° C. for 1 h and filtered, and the filter cake was dried in vacuum to give compound 7-B.

$^1$H NMR (400 MHz, $CDCl_3$) δ=7.77-7.75 (m, 1H), 6.99 (br dd, J=2.0, 8.6 Hz, 1H), 6.80 (s, 1H), 5.21 (s, 2H), 3.62-3.59 (m, 4H), 3.40-3.35 (m, 4H), 1.49 (s, 9H).

Step 2: Synthesis of Compound 7-C

7-B (43 g) was dissolved in tetrahydrofuran (150 mL), methanol (150 mL), and water (150 mL), and sodium hydroxide (21.61 g) was added with stirring. The mixture was stirred at 15-25° C. for 16 h. After the completion of the reaction, a 1 M hydrochloric acid solution was added to adjust to pH 4-5. The mixture was extracted with ethyl acetate (200 mL×3), and the organic phases were combined, dried over anhydrous sodium sulfate, filtered, and concentrated to give a crude product. Ethyl acetate (125 mL) and n-heptane (250 mL) were added. The mixture was triturated with stirring at 15-20° C. for 2 h and filtered, and the filter cake was dried in vacuum to give compound 7-C.

$^1$H NMR (400 MHz, DMSO-$d_6$) δ=7.79-7.77 (m, 1H), 7.35 (br d, J=5.8 Hz, 1H), 7.21 (br s, 1H), 6.82 (br dd, J=2.4, 8.9 Hz, 1H), 4.79 (s, 2H), 3.45 (br s, 4H), 3.30-3.28 (m, 4H), 1.46-1.39 (m, 9H).

Step 3: Synthesis of Compound 7-D

7-C (15 g) was dissolved in methanol (90 mL) and ethyl acetate (90 mL), and trimethylsilyldiazomethane in n-hexane (2 M, 45 mL) was added at −10 to 0° C. The mixture was stirred for 1 h. Trimethylsilyldiazomethane in n-hexane (2 M, 10 mL) was added at −10 to 0° C., and the mixture was stirred at 0 to 5° C. for 3 h. A small amount of acetic acid was added to quench the reaction, and water (450 mL) was added. The phases were separated, and the aqueous phase was extracted with ethyl acetate (120 mL). The organic phases were combined, washed with saturated sodium carbonate solution (140 mL) and saturated brine (140 mL), dried over anhydrous sodium sulfate, filtered, and concentrated to give compound 7-D.

Step 4: Synthesis of Compound 7-E

7-D (15 g) was dissolved in tetrahydrofuran (85 mL), and triphenylphosphine (16.84 g) and carbon tetrabromide (21.29 g) were added. The mixture was stirred at 15-25° C. for 12 h. 65 mL of petroleum ether/ethyl acetate (3/1) was added. The mixture was stirred and filtered, and the resulting filtrate was concentrated. 320 mL of petroleum ether/ethyl acetate (3/1) was added. The mixture was stirred and filtered, and the resulting filtrate was concentrated. 320 mL of petroleum ether/ethyl acetate (3/1) was added. The mixture was stirred, filtered, and concentrated to give compound 7-E.

$^1$H NMR (400 MHz, DMSO-$d_6$) δ=7.81 (d, J=8.8 Hz, 1H), 7.10 (d, J=2.8 Hz, 1H), 6.92 (dd, J=2.6, 8.9 Hz, 1H), 5.00 (s, 2H), 3.78 (s, 3H), 3.46-3.43 (m, 4H), 3.35-3.29 (m, 4H), 1.41 (s, 9H).

Step 5: Synthesis of Compound 7-G

7-E (19.2 g) was dissolved in acetonitrile (385 mL) and 7-F (16.63 g) and N,N-diisopropylethylamine (30.02 g) were added. The mixture was stirred at 75 to 80° C. for 24 hours. Water (260 mL) was added. The mixture was extracted with ethyl acetate (2×195 mL), washed with saturated brine (195 mL), dried over anhydrous sodium sulfate, filtered, and concentrated to give a crude product of compound 7-G. MS m/z: 525.3 [M+Na]+.

Step 6: Synthesis of Compound 7-H Trifluoroacetate

7-G (25 g) was dissolved in acetonitrile (375 mL), and benzenesulfonic acid (15.74 g) was added. The mixture was stirred at 75 to 80° C. for 16 h. A large amount of solid was generated. The mixture was filtered, and the filter cake was purified by preparative high-performance liquid chromatography (column: Phenomenex luna C18 250×80 mm×10 M; mobile phase: [water (trifluoroacetic acid)-acetonitrile]; acetonitrile: 0%-15.5%, duration: 18.5 min) to give compound 7-H trifluoroacetate.

$^1$H NMR (400 MHz, DMSO-$d_6$) δ=10.96 (s, 1H), 8.92-8.75 (m, 2H), 7.63-7.53 (m, 1H), 7.18-7.08 (m, 2H), 5.05 (dd, J=5.0, 13.3 Hz, 1H), 4.38-4.23 (m, 2H), 3.55-3.44 (m, 4H), 3.25 (br s, 4H), 2.96-2.84 (m, 1H), 2.64-2.54 (m, 1H), 2.41-2.31 (m, 1H), 2.02-1.91 (m, 1H).

Example 1

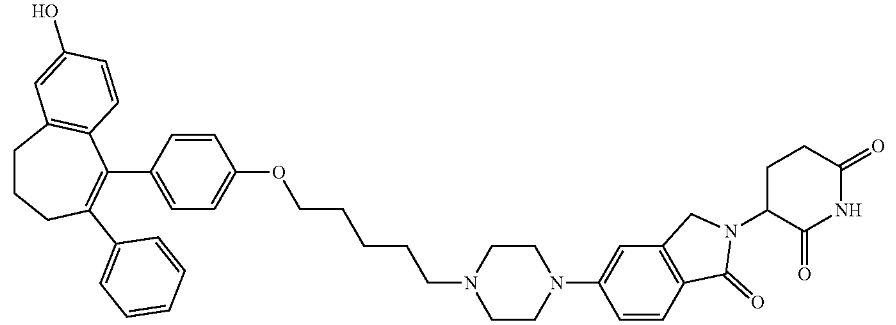

1

Synthetic Route:

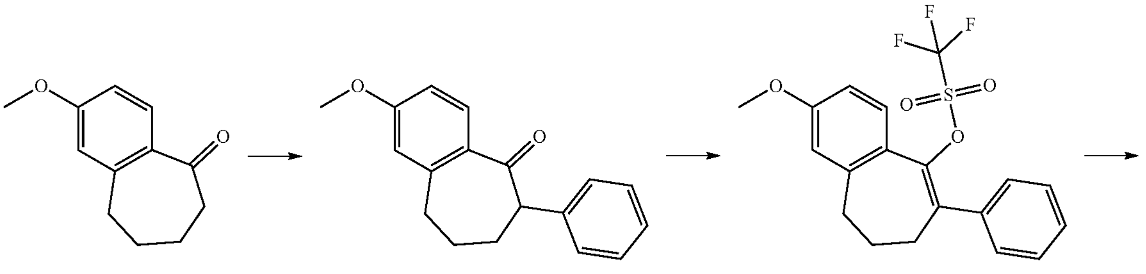

1-A

1-B

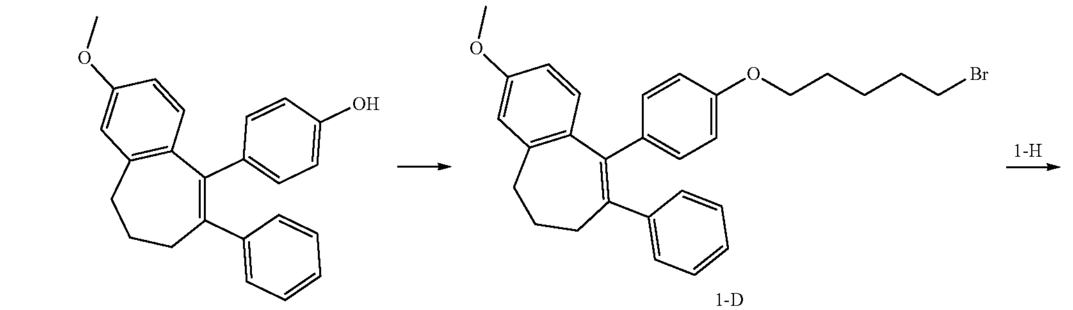

1-C

1-D

-continued

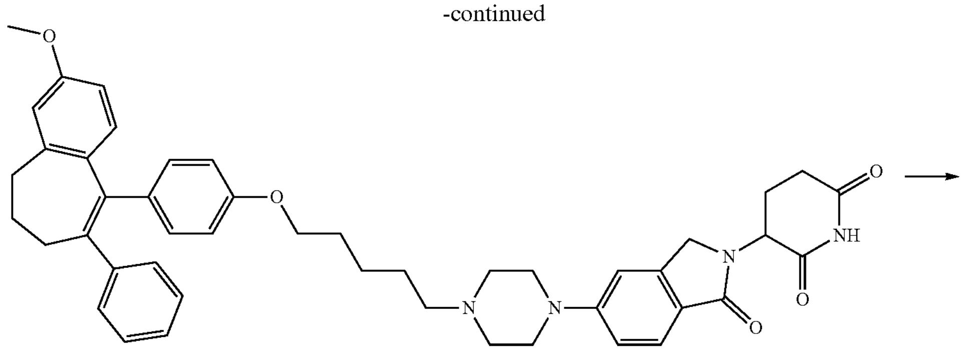

1-I

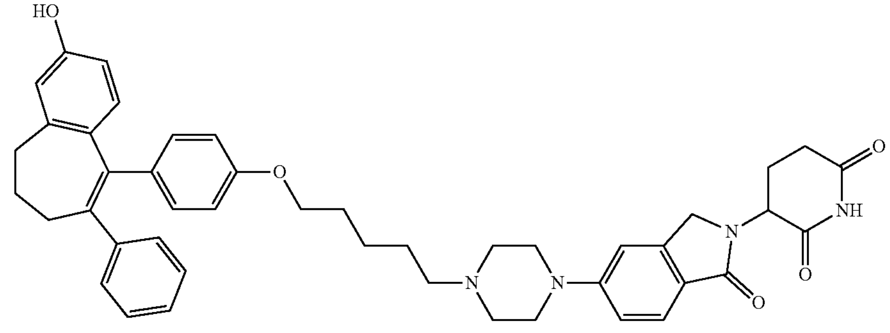

1

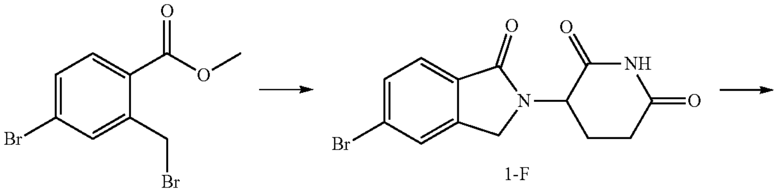

1-E 1-F

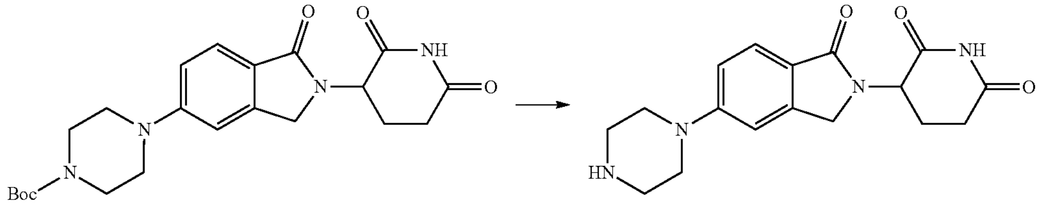

1-G 1-H

Step 1: Synthesis of Compound 1-A

2-Methoxy-6,7,8,9-tetrahydro-5H-benzo[7]annulen-5-one (2 g) was dissolved in 1,4-dioxane (30 mL), and dichlorobis[di-t-butyl-(4-dimethylaminophenyl)phosphino] palladium(II) (744.41 mg) and potassium t-butoxide (1.77 g) were added. After the reaction solution was purged with nitrogen three times, iodobenzene (4.72 g) was added, and the reaction solution was stirred at an external temperature of 100° C. under nitrogen atmosphere for 16 h. The reaction solution was filtered through diatomite, and the resultant filtrate was subjected to rotary evaporation to remove the solvent at reduced pressure to give a crude product. The crude product was separated by column chromatography (petroleum ether/ethyl acetate=1:0 to 20:1) to give compound 1-A. MS m/z: 266.9 $[M+H]^+$.

$^1$H NMR (400 MHz, $CDCl_3$) δ=7.72 (d, J=8.5 Hz, 1H), 7.38-7.33 (m, 2H), 7.29-7.26 (m, 3H), 6.83 (dd, J=2.5, 8.5 Hz, 1H), 6.77 (d, J=2.3 Hz, 1H), 4.05 (dd, J=4.8, 10.8 Hz, 1H), 3.87 (s, 3H), 3.19-3.08 (m, 1H), 3.00-2.91 (m, 1H), 2.23-2.14 (m, 2H), 1.91-1.80 (m, 1H), 1.57 (s, 1H).

Step 2: Synthesis of Compound 1-B

Compound 1-A (220 mg) was dissolved in dichloromethane (10 mL), and pyridine (130.68 mg) was added. The reaction solution was purged with nitrogen three times, and trifluoromethanesulfonic anhydride (582.64 mg) was added dropwise. After the completion of the addition, the reaction solution was stirred at an external temperature of 30° C. under nitrogen atmosphere for 1 h. Water (20 mL) and dichloromethane (20 mL) were added to the reaction solution, and the phases were separated. The aqueous phase was extracted with dichloromethane (10 mL×2), and the organic phases were combined, washed with saturated brine (30 mL), and dried over anhydrous sodium sulfate. The solvent was removed by rotary evaporation at reduced pressure to give a crude product. The crude product was separated by column chromatography (petroleum ether/ethyl acetate=1:0 to 20:1) to give compound 1-B.

$^1$H NMR (400 MHz, DMSO-$d_6$) δ=7.48-7.41 (m, 5H), 7.39-7.34 (m, 1H), 7.00-6.95 (m, 2H), 3.82 (s, 3H), 2.78 (t, J=7.0 Hz, 2H), 2.43-2.30 (m, 2H), 2.23-2.12 (m, 2H).

Step 3: Synthesis of Compound 1-C

Compound 1-B (1.67 g) was dissolved in 1,4-dioxane (20 mL) and water (2 mL), and p-hydroxyphenylboronic acid (693.81 mg), [1,1-bis(diphenylphosphino)ferrocene]palladium(II) dichloride dichloromethane complex (342.32 mg), and potassium carbonate (1.16 g) were added. The reaction solution was purged with nitrogen three times, and stirred at an external temperature of 90° C. under nitrogen atmosphere for 16 h. The reaction solution was filtered through diatomite, and the resultant filtrate was subjected to rotary evaporation to remove the solvent at reduced pressure to give a crude product. The crude product was separated by column chromatography (petroleum ether/ethyl acetate=1:0 to 20:1) to give compound 1-C.

$^1$H NMR (400 MHz, DMSO-$d_6$) δ=9.23 (s, 1H), 7.19-7.07 (m, 5H), 6.87 (br s, 1H), 6.73-6.68 (m, 2H), 6.62 (br d, J=8.3 Hz, 2H), 6.47 (br d, J=8.3 Hz, 2H), 3.76 (s, 3H), 2.73 (br t, J=6.1 Hz, 2H), 2.25 (br t, J=6.3 Hz, 2H), 2.10-2.03 (m, 2H).

Step 4: Synthesis of Compound 1-D

Compound 1-C (35 mg) was dissolved in acetone (5 mL), and 1,5-dibromopentane (70.51 mg) and potassium carbonate (42.38 mg) were added. The reaction solution was stirred at an external temperature of 70° C. under nitrogen atmosphere for 16 h. The reaction solution was filtered through diatomite and subjected to rotary evaporation to remove the solvent at reduced pressure to give a crude product. The crude product was purified by thin-layer chromatography (petroleum ether/ethyl acetate=15:1) to give compound 1-D.

$^1$H NMR (400 MHz, DMSO-$d_6$) δ=7.26-7.07 (m, 5H), 6.88 (br d, J=2.0 Hz, 1H), 6.80-6.57 (m, 6H), 3.89-3.82 (m, 2H), 3.76 (br s, 3H), 3.56-3.49 (m, 2H), 2.74 (br s, 2H), 2.27 (br d, J=5.5 Hz, 2H), 2.07 (br d, J=6.3 Hz, 2H), 1.87-1.79 (m, 2H), 1.68 (br d, J=6.0 Hz, 2H), 1.49 (br d, J=7.3 Hz, 2H).

Step 5: Synthesis of Compound 1-F

Compound 1-E (5 g) was dissolved in N,N-dimethylformamide (50 mL), and 3-amino-2,6-piperidinedione hydrochloride (2.94 g) and potassium carbonate (6.73 g) were added. The reaction solution was stirred at an external temperature of 75 to 80° C. under nitrogen atmosphere for 15 h. The reaction solution was added to water (250 mL), stirred for 2 h, and then filtered in vacuum to give a filter cake, which was rinsed with water (20 mL×3). Petroleum ether (25 mL) and ethyl acetate (5 mL) were added to the resulting cake, and after stirring for 0.5 hours, the mixture was filtered in vacuum e to give compound 1-F. MS m/z: 323.8 [M+H]$^+$.

Step 6: Synthesis of Compound 1-G

Compound 1-F (3.6 g) was dissolved in anhydrous N,N-dimethylformamide (50 mL), and 1-Boc-piperazine (4.15 g), potassium phosphate (9.46 g), (dibenzylideneacetone) dipalladium (1.02 g), and 2-dicyclohexylphosphine-2,4,6-triisopropylbiphenyl (531.09 mg) were added. The mixture was purged with nitrogen three times, and was stirred at 100° C. for 1.5 h. After the reaction solution was cooled, 50 mL of water was added. The mixture was extracted with 200 mL of ethyl acetate (50 mL×4), and the organic phase was washed with saturated brine (90 mL), dried over anhydrous sodium sulfate, filtered, concentrated, and purified by flash chromatography (petroleum ether/tetrahydrofuran=3/7 to 55/45) to give compound 1-G. MS m/z: 429.1 [M+H]$^+$.

Step 7: Synthesis of Compound 1-H Hydrochloride

Compound 1-G (0.68 g) was dissolved in dichloromethane (7 mL), and hydrogen chloride/dioxane (4 M, 396.75 L) was added. The mixture was stirred at 20° C. for 0.5 h, and concentrated to give 1-H hydrochloride. MS m/z: 328.8 [M+H]$^+$.

Step 8: Synthesis of Compound 1-I

Compound 1-D (30 mg) was dissolved in 1-methyl-2-pyrrolidone (2 mL), and compound 1-H hydrochloride (26.72 mg) and N,N-diisopropylethylamine (39.45 mg) was added. The reaction solution was subjected to a microwave reaction at 140° C. for 2 h. Ethyl acetate (15 mL) and water (20 mL) were added to the reaction solution. The phases were separated, and the organic phase was washed with water (20 mL×3), washed with saturated brine (10 mL), and dried over anhydrous sodium sulfate. The solvent was removed by rotary evaporation at reduced pressure to give a crude product. The crude product was separated by column chromatography (dichloromethane/methanol=1:0 to 50:1) to give compound 1-I.

$^1$H NMR (400 MHz, DMSO-$d_6$) δ=10.94 (s, 1H), 7.51 (br d, J=8.5 Hz, 1H), 7.20-7.02 (m, 7H), 6.88 (br s, 1H), 6.77-6.59 (m, 6H), 5.08-5.00 (m, 1H), 4.36-4.14 (m, 2H), 3.86 (br s, 2H), 3.76 (s, 3H), 3.26 (br s, 8H), 2.95-2.82 (m, 2H), 2.74 (br s, 2H), 2.38-2.21 (m, 6H), 2.06 (br s, 2H), 1.68 (br s, 2H), 1.50 (br s, 2H), 1.39 (br s, 2H).

Step 9: Synthesis of Compound 1

Compound 1-I (50 mg) was dissolved in dichloromethane (2 mL), boron tribromide (67.81 mg) was added at −70 to −60° C. under nitrogen atmosphere, and the mixture was stirred at −70 to −60° C. for 6 h. The reaction solution was adjusted to about pH 7 to 8 with a saturated sodium bicarbonate solution at 0 to 5° C. The reaction solution was extracted with dichloromethane (20 mL×3), and the organic phases were combined and washed once with saturated brine (20 mL), dried over anhydrous sodium sulfate, filtered, and concentrated by a rotary evaporator to give a crude product. The crude product was purified by a thin-layer chromatography (dichloromethane/methanol=10:1), followed by another TLC (dichloromethane/methanol=10:1, Rf=0.4) and then preparative liquid chromatography (neutral, column: Welch Xtimate C18 150×25 mm×5 μm; mobile phase: [water (10 mM $NH_4HCO_3$)-acetonitrile]; acetonitrile %: 55%-85%, 9 min) to give compound 1. MS m/z: 725.3 [M+H]$^+$.

$^1$H NMR (400 MHz, $CDCl_3$) δ=7.73 (d, J=8.5 Hz, 1H), 7.17-7.13 (m, 4H), 7.12-7.06 (m, 1H), 6.98 (m, 1H), 6.87 (s, 1H), 6.82-6.73 (m, 4H), 6.62-6.56 (m, 3H), 5.35 (s, 1H), 5.20 (dd, J=5.1, 13.2 Hz, 1H), 4.44-4.38 (m, 1H), 4.28-4.22 (m, 1H), 3.87 (t, J=6.4 Hz, 2H), 3.34 (m, 4H), 2.95-2.80 (m, 2H), 2.75 (t, J=7.0 Hz, 2H), 2.68-2.58 (m, 4H), 2.44 (m, 2H), 2.40-2.35 (m, 2H), 2.21 (m, 2H), 2.17-2.12 (m, 2H), 1.77 (m, 2H), 1.64-1.59 (m, 2H), 1.49 (m, 2H).

Example 2

2

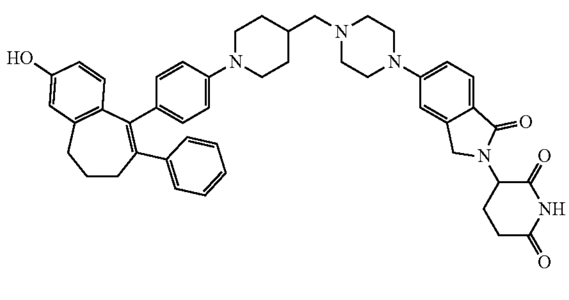

Synthetic Route:
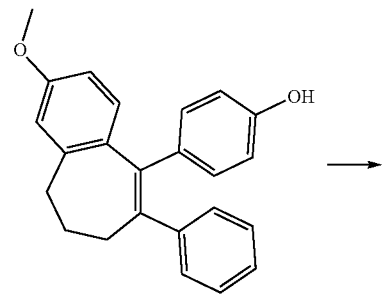
1-C
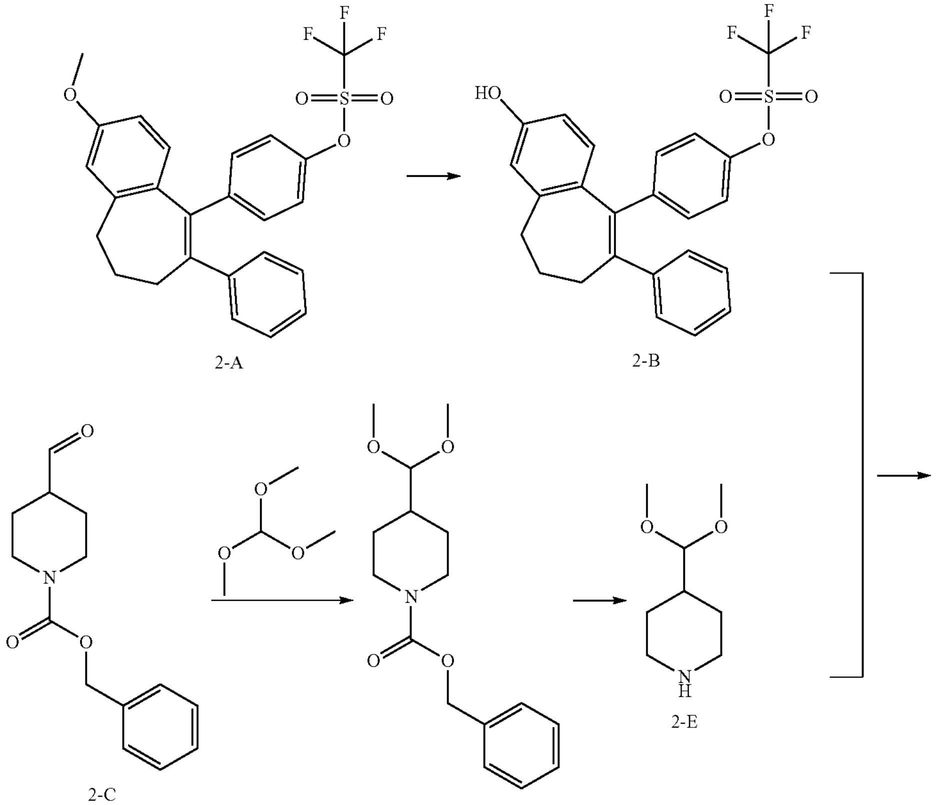
2-A 2-B 2-C 2-D 2-E
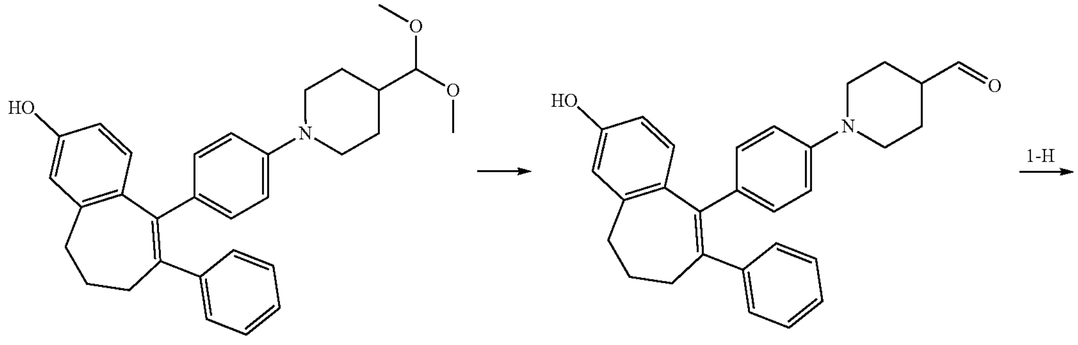
2-F 2-G -continued

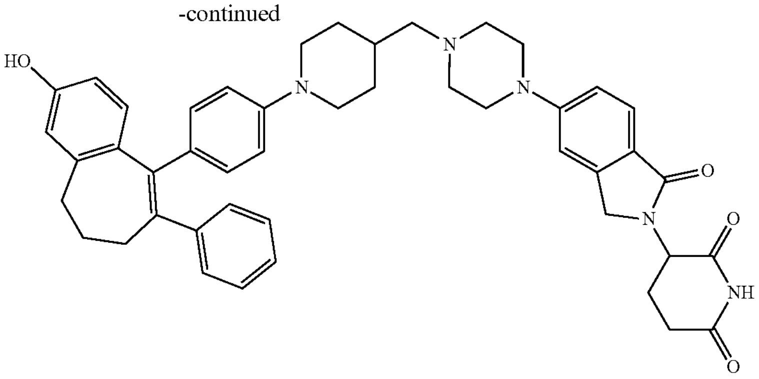

2

Step 1: Synthesis of Compound 2-A

Pyridine (339.56 mg) was added to compound 1-C (0.98 g) in anhydrous dichloromethane (10 mL), and trifluoromethanesulfonic anhydride (1.21 g) was slowly added dropwise at 0° C. The mixture was stirred at 20° C. for 12 h. After the completion of the reaction, the reaction solution was poured into 30 mL of water and extracted with dichloromethane (20 mL×3), and the organic phase was washed with saturated brine (10 mL×2), dried over anhydrous sodium sulfate, filtered, and concentrated to give a crude product. The crude product was purified by column chromatography (0-5%, ethyl acetate/petroleum ether) to give compound 2-A. MS m/z: 474.8 $[M+H]^+$.

Step 2: Synthesis of Compound 2-B

At −65° C., under nitrogen atmosphere, boron tribromide (2.03 g) was slowly added dropwise into compound 2-A (0.64 g) in anhydrous dichloromethane (3 mL), and the reaction solution was stirred at −65 to 20° C. for 1 h. After the completion of the reaction, the reaction solution was slowly added to 30 mL of water. The mixture was adjusted to pH 7-8 with saturated sodium bicarbonate solution (20 mL), extracted with ethyl acetate (20 mL×3), and the organic phase was washed with saturated brine (10 mL×2), dried over anhydrous sodium sulfate, filtered, and concentrated to give compound 2-B.

Step 3: Synthesis of Compound 2-D

Compound 2-C (10 g) and trimethyl orthoformate (21.46 g) were dissolved in absolute methanol (100 mL), and p-toluenesulfonic acid monohydrate (769.21 mg) was added. The mixture was stirred at 15° C. for 12 h under nitrogen atmosphere. The mixture was adjusted to pH 7-8 with saturated sodium carbonate solution and extracted with dichloromethane (100 mL), and the organic phase was washed once with saturated brine (50 mL), dried over anhydrous sodium sulfate, filtered, and concentrated by a rotary evaporator to give compound 2-D.

$^1H$ NMR (400 MHz, DMSO-$d_6$) δ=7.40-7.28 (m, 5H), 5.06 (s, 2H), 4.05-3.98 (m, 3H), 3.25 (s, 6H), 2.75 (s, 2H), 1.83-1.67 (m, 1H), 1.67-1.56 (m, 2H), 1.09 (dq, J=4.4, 12.5 Hz, 2H).

Step 4: Synthesis of Compound 2-E

Compound 2-D (26 g) was dissolved in methanol (500 mL), wet palladium on carbon (3 g, purity: 10%) was added, and the mixture was stirred under hydrogen atmosphere at 50 psi, 25° C. for 12 h. The reaction solution was filtered through diatomite, and the filtrate was concentrated by a rotary evaporator to give 2-E.

$^1H$ NMR (400 MHz, DMSO-$d_6$) δ=5.20 (s, 1H), 4.01 (d, J=6.8 Hz, 1H), 3.24 (s, 6H), 3.01 (d, J=11.8 Hz, 2H), 2.56-2.51 (m, 2H), 1.74-1.64 (m, 1H), 1.60 (d, J=13.1 Hz, 2H), 1.23-1.12 (m, 2H).

Step 5: Synthesis of Compound 2-F

Potassium tert-butoxide (0.35 g), 2-dicyclohexylphosphino-2,4,6-triisopropylbiphenyl (115.95 mg), and palladium acetate (27.3 mg) were added to a solution of compound 2-B (0.56 g) and compound 2-E (0.29 g) in toluene (5 mL). The reaction solution was stirred under nitrogen atmosphere at 90° C. for 12 h, and concentrated by a rotary evaporator. The crude product was purified by column chromatography (tetrahydrofuran 0-10%, tetrahydrofuran/petroleum ether system) to give compound 2-F. MS m/z: 470.1 $[M+H]^+$.

Step 6: Synthesis of Compound 2-G

Trifluoroacetic acid (616 mg) was added to compound 2-F (80 mg) in dichloromethane (5 mL), and the reaction solution was stirred at 20° C. for 1 h, and concentrated at reduced pressure to give a crude product of compound 2-G. MS m/z: 423.9 $[M+H]^+$.

Step 7: Synthesis of Compound 2

Sodium acetate (27.11 mg) was added to a solution of compound 2-G (70 mg) and compound 1-H hydrochloride (72.35 mg) in methanol (5 mL), and the reaction solution was stirred at 20° C. for 12 min. Sodium cyanoborohydride (20.77 mg) was added to the reaction solution, and the reaction solution was stirred at 20° C. for another 5 h. The reaction was quenched by adding saturated ammonium chloride (30 mL), and the mixture was extracted with dichloromethane (10 mL×3). The organic phase was washed with saturated brine (20 mL), dried over anhydrous sodium sulfate, filtered, and concentrated to give a crude product. The crude product was purified by column chromatography (methanol 0-5%, methanol/dichloromethane system) to give compound 2. MS m/z: 735.9 $[M+H]^+$.

$^1H$ NMR (400 MHz, DMSO-$d_6$) δ=10.95 (s, 1H), 9.36 (s, 1H), 7.52 (d, J=8.8 Hz, 1H), 7.19-7.02 (m, 7H), 6.70-6.54 (m, 7H), 5.05 (dd, J=5.0, 13.3 Hz, 1H), 4.39-4.13 (m, 2H), 3.59 (br d, J=11.5 Hz, 2H), 3.27 (br s, 4H), 2.99-2.81 (m, 1H), 2.66 (br s, 2H), 2.56 (br s, 2H), 2.5 (s, 4H), 2.41-2.30 (m, 2H) 2.28-2.16 (m, 4H), 2.08-1.92 (m, 4H), 1.77 (br d, J=12.3 Hz, 2H), 1.19-1.07 (m, 2H).

Example 3
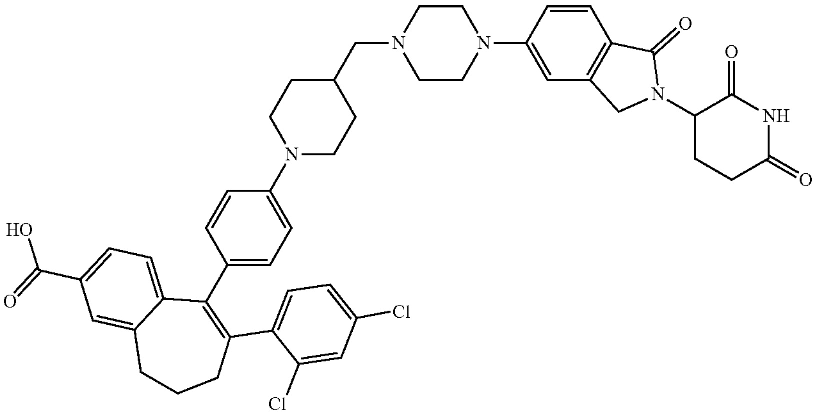
3
Synthetic Route:
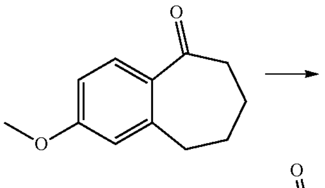
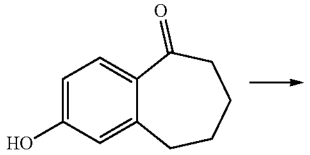
3-A
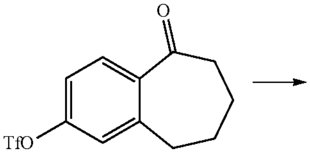
3-B
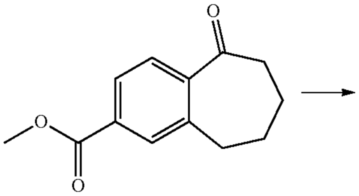
3-C
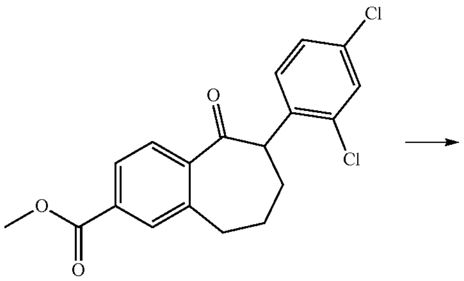
3-D
-continued
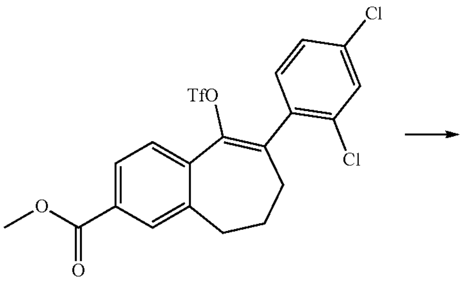
3-E
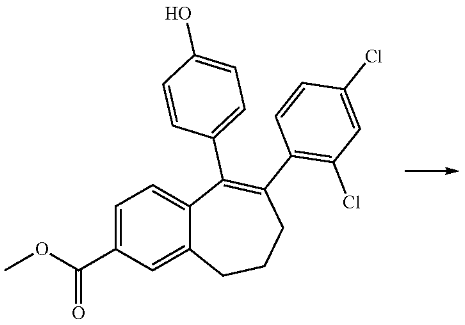
3-F
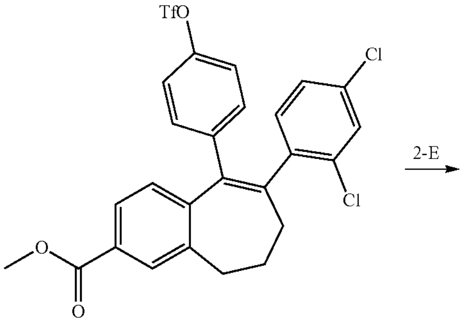
3-G -continued

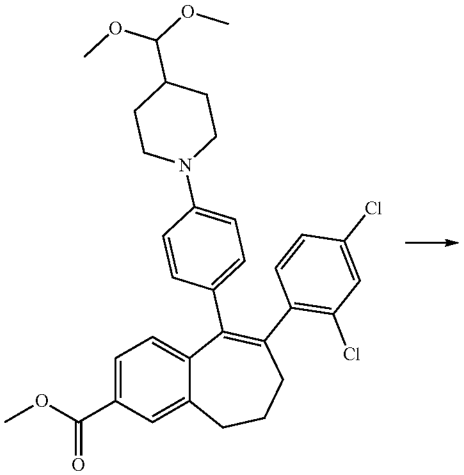

3-H

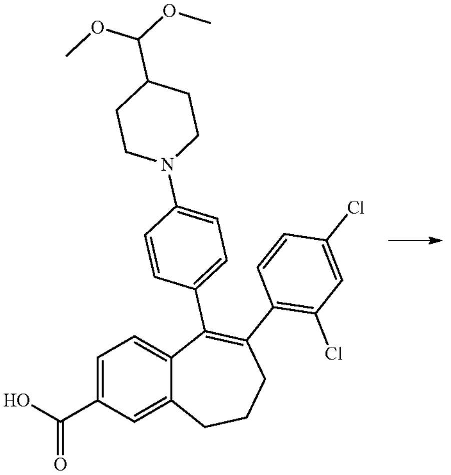

3-I

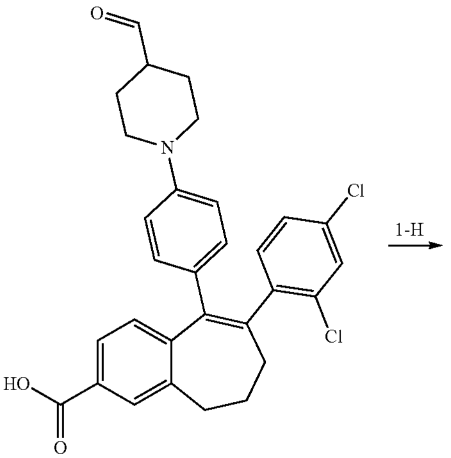

3-J

-continued

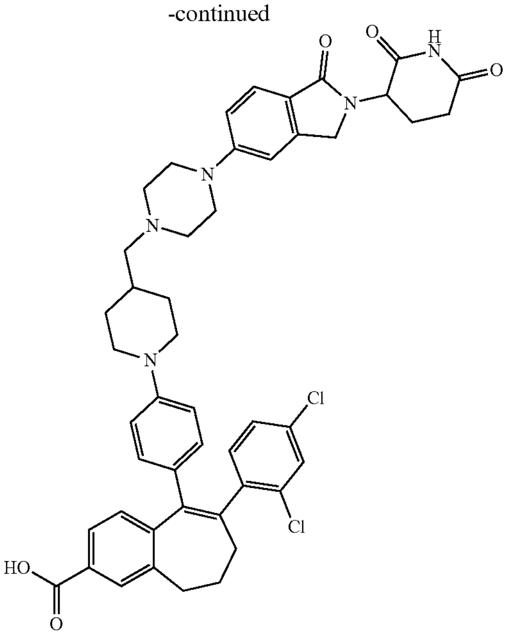

3

Step 1: Synthesis of Compound 3-A

Anhydrous toluene (30 mL) was added to a three-necked flask, and aluminum trichloride (1.68 g) was slowly added with stirring, followed by the addition of 2-methoxybenzcycloheptan-5-one (1 g, 1 eq.). The mixture was stirred at 90° C. for 1 h. The reaction solution was cooled to room temperature, poured into crushed ice (60 g) slowly, stirred for 20 min, and filtered. The filter cake was rinsed with water (15 mL) and isopropyl ether (15 mL), and concentrated by a rotary evaporator to give compound 3-A. MS m/z: 177.1 $[M+H]^+$.

Step 2: Synthesis of Compound 3-B

Compound 3-A (953 mgl) was dissolved in anhydrous dichloromethane (20 mL), and 2,6-dimethylpyridine (1.16 g) was added. Under nitrogen atmosphere, trifluoromethanesulfonic anhydride (3.05 g) was added at 0° C. and the mixture was stirred at 0° C. for 1 h. The mixture was stirred at 20° C. for 48 h. The reaction solution was concentrated by a rotary evaporator to give a crude product. The crude product was separated by column chromatography (petroleum ether/ethyl acetate=3:1) and then separated by TLC (petroleum ether/ethyl acetate=3:1) to give compound 3-B. MS m/z: 308.8 $[M+H]^+$.

Step 3: Synthesis of Compound 3-C

Compound 3-B (460 mg) was dissolved in anhydrous N,N-dimethylformamide (20 mL), and methanol (20 mL), N,N-diisopropylethylamine (742.00 mg) and [1,1-bis(triphenylphosphino)ferrocene]palladium dichloride (54.59 mg) were added. The mixture was stirred under carbon monoxide atmosphere at 45 PSI, 75° C. for 48 h. The reaction solution was filtered through diatomite, and the filtrate was concentrated by a rotary evaporator to give a crude product. The crude product was separated by column chromatography (petroleum ether/ethyl acetate=3:1) to give compound 3-C. MS m/z: 218.8 $[M+H]^+$.

$^1$H NMR (400 MHz, $CDCl_3$) δ=7.93 (dd, J=1.4, 7.9 Hz, 1H), 7.88 (s, 1H), 7.73 (d, J=8.0 Hz, 1H), 3.93 (s, 3H), 3.01-2.93 (m, 2H), 2.78-2.71 (m, 2H), 1.93-1.86 (m, 2H), 1.85-1.78 (m, 2H).

Step 4: Synthesis of Compound 3-D

Compound 3-C (500 mg) and 2,4-dichloroiodobenzene (1.56 g) were dissolved in anhydrous toluene (9 mL) and water (1 mL), and cesium carbonate (1.12 g), 4,5-bis(diphenylphosphino)-9,9-dimethylxanthene (265.12 mg), and palladium acetate (51.43 mg) were added. The mixture was stirred under nitrogen atmosphere at 110° C. for 22 h. Water (20 mL) was added, and the mixture was extracted with ethyl acetate (20 mL×3). The organic phases were combined, washed once with saturated brine (20 mL), dried over anhydrous sodium sulfate, filtered, and concentrated by a rotary evaporator to give a crude product. The crude product was separated by column chromatography (petroleum ether/ethyl acetate=3:1) to give compound 3-D. MS m/z: 363.0 $[M+H]^+$.

Step 5: Synthesis of Compound 3-E

Sodium hydride (145.35 mg, purity: 60%) was dissolved in 2-methyltetrahydrofuran (10 mL), and 1,8-diazabicyclo[5.4.0]undec-7-ene (75.44 mg) was added. A solution of 3-D (600 mg) and N-phenylbis(trifluoromethanesulfonyl)imide (1.18 g) in 2-methyltetrahydrofuran (5 mL) was slowly added dropwise under nitrogen atmosphere at 20° C., and the mixture was stirred under nitrogen atmosphere at 20° C. for 12 h. The reaction solution was cooled to 0° C., and 1 M diluted hydrochloric acid (5 mL) was slowly added dropwise. The phases were separated, and the organic phase was washed once with saturated brine (10 mL), dried over anhydrous sodium sulfate, filtered, and concentrated by a rotary evaporator to give a crude product. The crude product was separated by column chromatography (petroleum ether/ethyl acetate=5:1) to give compound 3-E. MS m/z: 494.9 $[M+H]^+$.

Step 6: Synthesis of Compound 3-F

Compound 3-E (1.1 g) and p-hydroxyphenylboronic acid (459.49 mg) were dissolved in 1,4-dioxane (20 mL), and sodium carbonate (470.78 mg) and water (2 mL) were added. [1,1-Bis(triphenylphosphino)ferrocene]palladium dichloride dichloromethane complex (181.37 mg) was added under nitrogen atmosphere, and the mixture was stirred under nitrogen atmosphere at 90° C. for 12 h. The reaction solution was filtered through diatomite, and water (20 mL) was added to the filtrate. The mixture was extracted with ethyl acetate (20 mL×3), and the organic phases were combined, washed once with saturated brine (20 mL), dried over anhydrous sodium sulfate, filtered, and concentrated by a rotary evaporator to give a crude product. The crude product was separated by column chromatography (petroleum ether/ethyl acetate=3:1) to give compound 3-F. MS m/z: 439.0 $[M+H]^+$.

Step 7: Synthesis of Compound 3-G

Compound 3-F (360 mg) was dissolved in anhydrous dichloromethane (10 mL), and pyridine (129.63 mg) was added. Under nitrogen atmosphere, trifluoromethanesulfonic anhydride (462.39 mg) was added and the mixture was stirred at 15° C. for 12 h. Water (20 mL) was added to the reaction solution, and the mixture was extracted with dichloromethane (20 mL×3). The organic phases were combined and washed once with saturated brine (20 mL), dried over anhydrous sodium sulfate, filtered, and concentrated by a rotary evaporator to give a crude product. The crude product was separated by column chromatography (petroleum ether/ethyl acetate=10:1) to give compound 3-G. MS m/z: 571.4 $[M+H]^+$.

Step 8: Synthesis of Compound 3-H

Compounds 3-G (240 mg) and 2-E (100.32 mg) were dissolved in anhydrous toluene (10 mL), and 2-di-t-butylphosphine-2',4',6'-triisopropylbiphenyl (40.05 mg) and sodium tert-butoxide (121.10 mg) were added. Under nitrogen atmosphere, palladium acetate (9.43 mg) was added, and the mixture was stirred under nitrogen atmosphere at 90° C. for 4 h. The reaction solution was filtered through diatomite. The filter cake was rinsed with ethyl acetate (20 mL), and water (20 mL) was added to the filtrate. The mixture was extracted with ethyl acetate (20 mL×3), and the organic phases were combined, washed once with saturated brine (20 mL), dried over anhydrous sodium sulfate, filtered, and concentrated by a rotary evaporator to give a crude product. The crude product was separated by column chromatography (petroleum ether/ethyl acetate=3:1) to give compound 3-H. MS m/z: 580.1 $[M+H]^+$.

Step 9: Synthesis of Compound 3-I

Compound 3-H (180 mg) was dissolved in methanol (10 mL), and an aqueous solution (5 mL) of sodium hydroxide (24.80 mg) was added. The mixture was stirred at 65° C. for 1 h, and adjusted to pH 6-7 with 2 M diluted hydrochloric acid. The reaction solution was extracted with dichloromethane (20 mL×3), and the organic phases were combined and washed once with saturated brine (20 mL), dried over anhydrous sodium sulfate, filtered, and concentrated by a rotary evaporator to give compound 3-I. MS m/z: 566.0 $[M+H]^+$.

Step 10: Synthesis of Compound 3-J

Compound 3-I (180 mg) was dissolved in anhydrous dichloromethane (10 mL), and trifluoroacetic acid (7.70 g) was added. The mixture was stirred at 20° C. for 12 h. The reaction solution was directly concentrated by a rotary evaporator to give a crude product of compound 3-J, which was directly used in the next step. MS m/z: 520.0 $[M+H]^+$.

Step 11: Synthesis of Compound 3 Hydrochloride

Compound 1-H (157.72 mg, hydrochloride salt) was dissolved in methanol (10 mL), and sodium acetate (70.93 mg) was added. The mixture was stirred under nitrogen atmosphere at 15° C. for 10 min before the addition of 3-J (150 mg), stirred under nitrogen atmosphere at 15° C. for 10 min before the addition of sodium triacetoxyborohydride (183.25 mg), and stirred under nitrogen atmosphere at 15° C. for 12 h. The mixture was then adjusted to pH 4-5 with 2 M diluted hydrochloric acid. The reaction solution was extracted with dichloromethane (30 mL×3), and the organic phases were combined and washed once with saturated brine (30 mL), dried over anhydrous sodium sulfate, and concentrated by a rotary evaporator to give a crude product. The crude product was separated by preparative liquid chromatography (hydrochloric acid system; column: Xtimate C18 150×40 mm×5 μm, mobile phase: [water (0.05% hydrochloric acid)-acetonitrile], acetonitrile %: 30%-50%, 10 min) to give compound 3 hydrochloride. MS m/z: 832.3 $[M+H]^+$.

$^1H$ NMR (400 MHz, DMSO-$d_6$) δ=10.96 (m, 2H), 7.93 (s, 1H), 7.77 (d, J=7.9 Hz, 1H), 7.63-7.56 (m, 2H), 7.43 (s, 1H), 7.32-7.23 (m, 4H), 7.18-7.13 (m, 2H), 6.91-6.86 (m, 2H), 5.06 (dd, J=4.8, 13.2 Hz, 1H), 4.42-4.19 (m, 2H), 3.98 (d, J=12.6 Hz, 2H), 3.67-3.59 (m, 8H), 3.13 (m, 3H), 2.98-2.89 (m, 3H), 2.75-2.66 (m, 1H), 2.59 (d, J=16.4 Hz, 2H), 2.46-2.31 (m, 2H), 2.17 (m, 4H), 2.12-1.93 (m, 4H).

Example 4
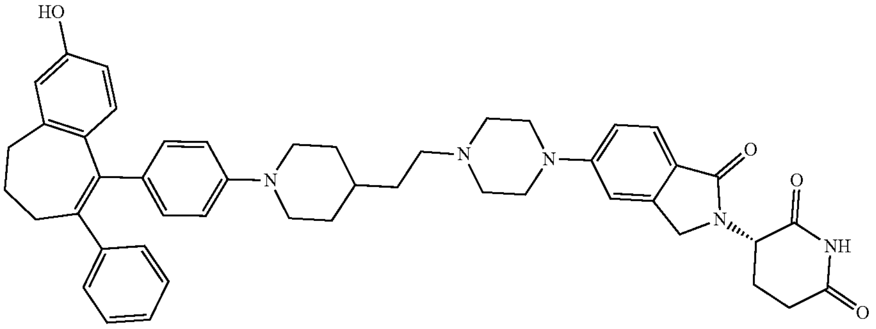
4
Synthetic Route:
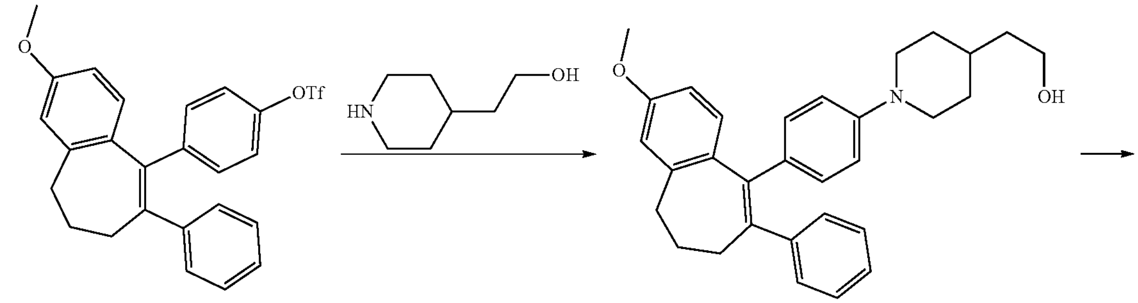
2-B
4-A
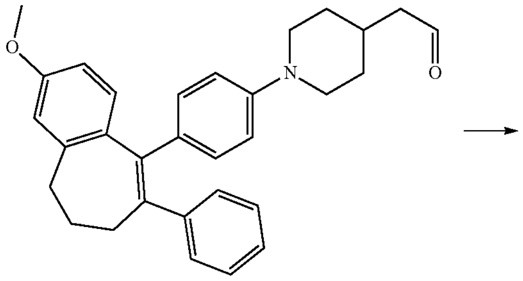
4-B
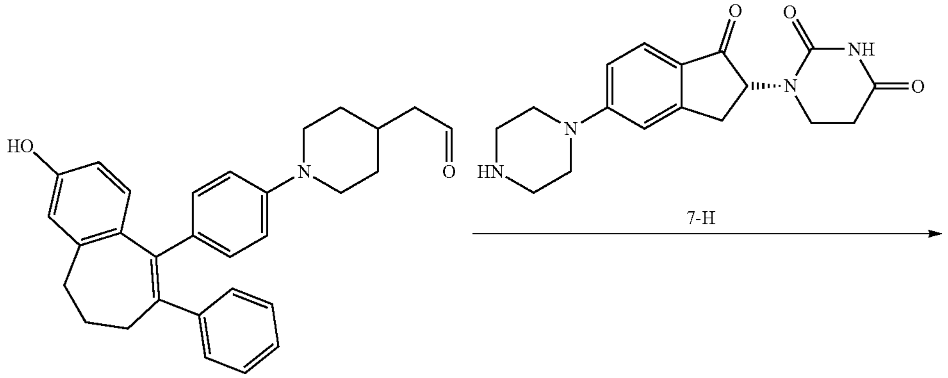
4-C -continued

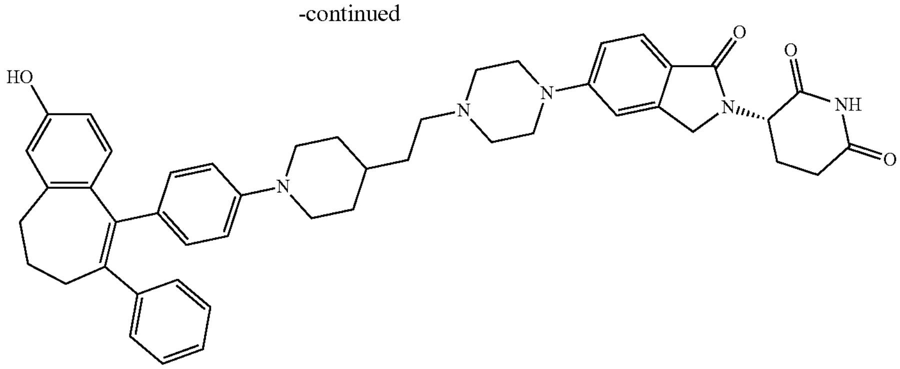

4

Step 1: Synthesis of Compound 4-A

Sodium tert-butoxide (0.57 g), 2-dicyclohexylphosphino-2,4,6-triisopropylbiphenyl (188.88 mg), and palladium acetate (44.48 mg) were added to a solution of compound 2-B (0.94 g) and compound 4-piperidineethanol (0.38 g) in toluene (5 mL). The reaction solution was stirred under nitrogen atmosphere at 90° C. for 12 h, and concentrated by a rotary evaporator. The crude product was purified by column chromatography (ethyl acetate %: 0-20%, ethyl acetate/petroleum ether) to give compound 4-A.

$^1$H NMR (400 MHz, $CDCl_3$) δ=7.20-7.07 (m, 5H), 6.87-6.76 (m, 4H), 6.74-6.60 (m, 3H), 3.84 (s, 3H), 3.77-3.70 (m, 2H), 3.60 (br d, J=12.3 Hz, 2H), 2.78 (t, J=7.0 Hz, 2H), 2.63 (br t, J=11.3 Hz, 2H), 2.42-2.32 (m, 2H), 2.22-2.10 (m, 2H), 1.79 (br d, J=12.8 Hz, 2H), 1.61-1.55 (m, 3H), 1.35 (br d, J=8.8 Hz, 2H).

Step 2: Synthesis of Compound 4-B

Dess-Martin reagent (112.2 mg) was added to compound 4-A (80 mg) in dichloromethane (5 mL), and the reaction solution was stirred at 20° C. for 1 h, The reaction solution was filtered, and the filtrate was concentrated by a rotary evaporator. The crude product was purified by column chromatography (ethyl acetate: 0-5%, ethyl acetate/petroleum ether) to give compound 4-B.

$^1$H NMR (400 MHz, $CDCl_3$) δ=9.81 (s, 1H), 7.21-7.06 (m, 5H), 6.88-6.60 (m, 7H), 3.84 (s, 3H), 3.60 (br d, J=12.5 Hz, 2H), 2.79 (br t, J=6.9 Hz, 2H), 2.68 (br t, J=11.5 Hz, 2H), 2.47-2.32 (m, 4H), 2.16 (quin, J=6.9 Hz, 2H), 2.05-1.96 (m, 1H), 1.80 (br d, J=12.5 Hz, 2H), 1.41 (br d, J=10.3 Hz, 2H).

Step 3: Synthesis of Compound 4-C

At −60° C., under nitrogen atmosphere, boron tribromide (222.76 mg) was slowly added dropwise into compound 4-B (40 mg) in anhydrous dichloromethane (50 mL), and the reaction solution was stirred at −60 to 20° C. for 3.5 h. After the completion of the reaction, the reaction solution was added slowly to 100 mL of water and extracted with dichloromethane (30 mL×3). The organic phase was washed with saturated brine (20 mL), dried over anhydrous sodium sulfate, filtered, and concentrated to give compound 4-C. MS m/z: 438.0 [M+H]+

Step 4: Synthesis of Compound 4

Trifluoroacetate of 7-H (333.63 mg), sodium acetate (123.73 mg), and magnesium sulfate (453.89 mg) were added in sequence to a solution of compound 4-C (330 mgl) in dichloromethane (10 mL) and methanol (2 mL). After the reaction solution was stirred at 20° C. for 30 min, sodium triacetoxyborohydride (479.51 mg) was added, and the mixture was stirred at 20° C. for another 3.5 h. After the completion of the reaction, diluted hydrochloric acid (1 M, 1 mL) was added dropwise to the reaction solution. After being stirred for 10 min, the mixture was adjusted to pH 7 to 8 with saturated sodium bicarbonate (10 mL), extracted with dichloromethane (20 mL×3), washed with saturated brine (10 mL), dried over anhydrous sodium sulfate, filtered, and subjected to rotary evaporation at reduced pressure to give a crude product, which was purified by column chromatography (methanol: 0-2%, methanol/dichloromethane) to give compound 4. MS m/z: 750.4 $[M+H]^+$ $^1$H NMR (400 MHz, DMSO-$d_6$) δ=10.94 (s, 1H), 9.35 (s, 1H), 7.51 (br d, J=8.5 Hz, 1H), 7.18-7.11 (m, 4H), 7.06 (br s, 3H), 6.69-6.55 (m, 7H), 5.04 (br d, J=8.8 Hz, 1H), 4.38-4.15 (m, 2H), 3.57 (br d, J=11.3 Hz, 2H), 3.27 (br s, 6H), 2.88 (br d, J=12.3 Hz, 1H), 2.70-2.52 (m, 8H), 2.38 (br s, 4H), 2.24 (br s, 2H), 2.02 (br s, 3H), 1.72 (br d, J=10.3 Hz, 2H), 1.41 (br s, 3H).

Example 5

5

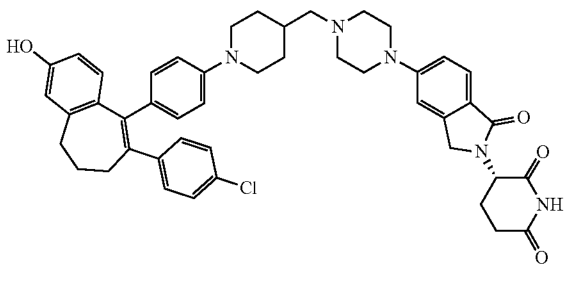

Synthetic Route:
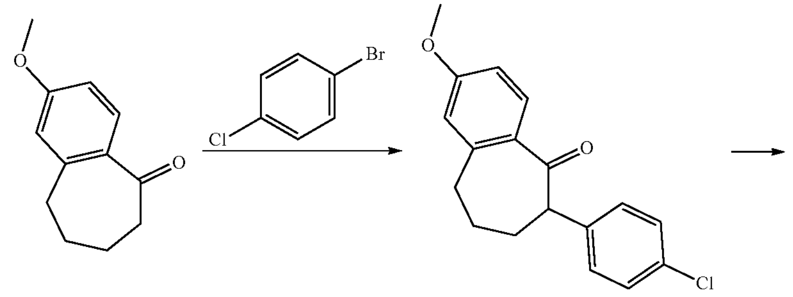
5-A
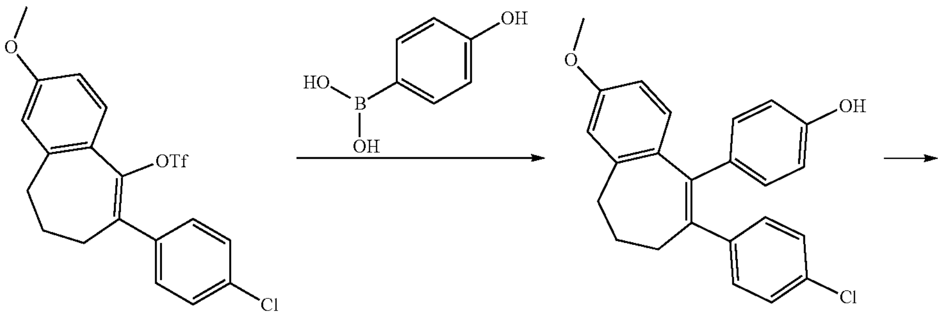
5-B 5-C
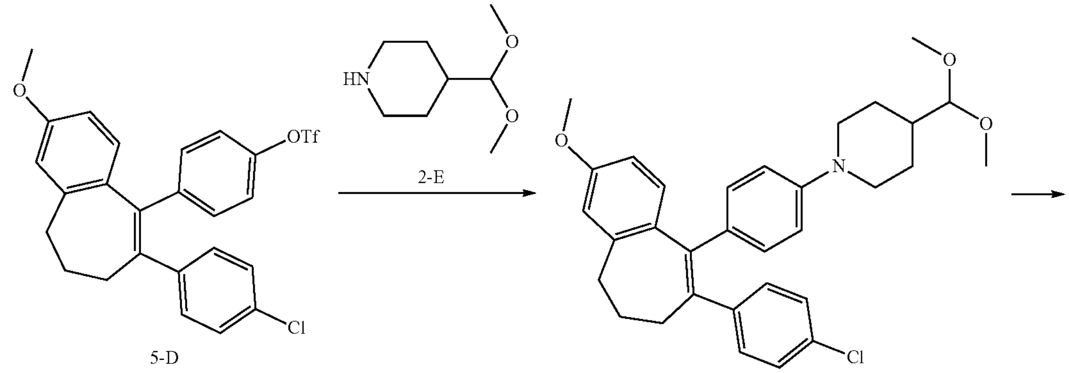
5-D 5-E
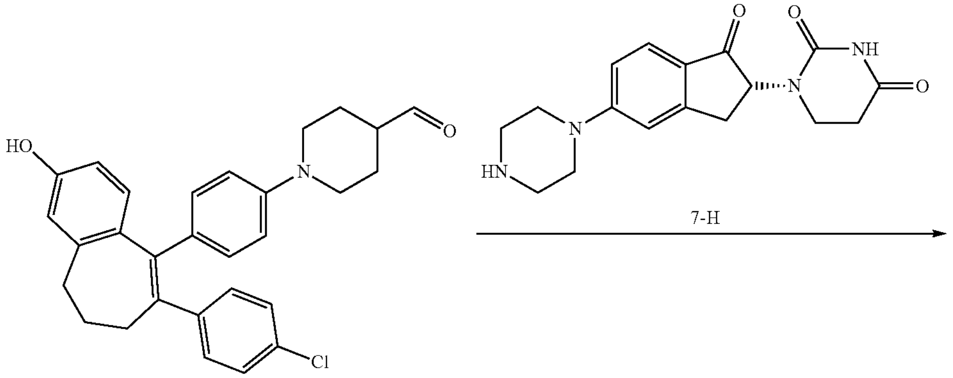
5-F -continued

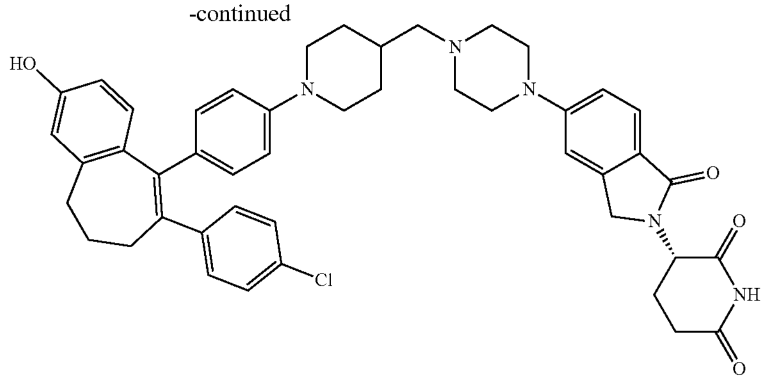

5

Step 1: Synthesis of Compound 5-A p-Bromochlorobenzene (1.31 g), sodium tert-butoxide (656.70 mg), 2-dicyclohexylphosphine-2,4,6-triisopropylbiphenyl (501.18 mg), and palladium acetate (118.02 mg) were added to a solution of compound 2-methoxy-6,7,8,9-tetrahydro-5H-benzo[7]annulen-5-one (1.00 g) in toluene (10 mL), and the mixture was purged with nitrogen for 1 min and subjected to a microwave reaction at 120° C. for 1 h. After the completion of the reaction, the reaction solution was filtered through diatomite, the filter cake was washed with ethyl acetate (10 mL×3), and the organic phase was concentrated at reduced pressure to give a crude product. The crude product was purified by column chromatography (ethyl acetate: 0-4%, ethyl acetate/petroleum ether) to give compound 5-A. MS m/z: 300.9 $[M+H]^+$ $^1H$ NMR (400 MHz, $CDCl_3$) δ=7.70 (d, J=8.5 Hz, 1H), 7.30 (d, J=8.5 Hz, 2H), 7.24-7.17 (m, 2H), 6.82 (dd, J=2.5, 8.5 Hz, 1H), 6.76 (d, J=2.0 Hz, 1H), 4.03 (dd, J=5.0, 11.0 Hz, 1H), 3.85 (s, 3H), 3.19-3.05 (m, 1H), 3.01-2.88 (m, 1H), 2.23-2.06 (m, 3H), 1.93-1.75 (m, 1H).

Step 2: Synthesis of Compound 5-B Pyridine (2.29 g) was added to a solution of compound 5-A (5.80 g) in anhydrous dichloromethane (120 mL), and trifluoromethanesulfonic anhydride (13.60 g) was slowly added dropwise at 0° C. The mixture was stirred at 20° C. for 12 h. After the completion of the reaction, the reaction solution was poured into 100 mL of water and extracted with dichloromethane (30 mL×3). The organic phase was washed with saturated sodium bicarbonate (50 mL×1), dried over anhydrous sodium sulfate, filtered, and concentrated to give a crude product of compound 5-B.

Step 3: Synthesis of Compound 5-C p-Hydroxyphenylboronic acid (3.42 g), potassium carbonate (5.72 g), and [1,1-bis(diphenylphosphino)ferrocene] dichloropalladium dichloromethane (1.69 g) were added to a solution of compound 5-B (8.95 g) in 1,4-dioxane (100 mL) and water (10 mL), and the mixture was purged with nitrogen for 3 times and reacted at 90° C. for 5 h. After the completion of the reaction, the reaction solution was cooled to room temperature and filtered through diatomite, the filter cake was washed with ethyl acetate (10 mL×3), and the organic phase was concentrated at reduced pressure to give a crude product. The crude product was purified by column chromatography (0-10%, ethyl acetate/petroleum ether) to give compound 5-C. MS m/z: 377.0 $[M+H]^+$ $^1H$ NMR (400 MHz, DMSO-$d_6$) δ=9.32 (s, 1H), 7.24-7.20 (m, 2H), 7.16-7.12 (m, 2H), 6.88 (d, J=2.5 Hz, 1H), 6.76-6.71 (m, 1H), 6.70-6.67 (m, 1H), 6.63 (d, J=8.5 Hz, 2H), 6.51 (d, J=8.8 Hz, 2H), 3.77 (s, 3H), 2.73 (br t, J=6.8 Hz, 2H), 2.28-2.20 (m, 2H), 2.12-2.03 (m, 2H).

Step 4: Synthesis of Compound 5-D

Pyridine (1.11 g) was added to a solution of compound 5-C (3.53 g) in anhydrous dichloromethane (80 mL), and trifluoromethanesulfonic anhydride (6.61 g) was slowly added dropwise at 0° C. The mixture was stirred at 20° C. for 12 h. After the completion of the reaction, the reaction solution was poured into 100 mL of water and extracted with dichloromethane (30 mL×3). The organic phase was dried over anhydrous sodium sulfate, filtered, and concentrated to give crude product 5-D.

Step 5: Synthesis of Compound 5-E

2-E (234.64 mg), sodium tert-butoxide (188.83 mg), 2-dicyclohexylphosphine-2,4,6-triisopropylbiphenyl (93.67 mg), and palladium acetate (22.06 mg) were added to a solution of compound 5-D (0.50 g) in toluene (10 mL). The mixture was purged with nitrogen for 3 times and reacted at 90° C. for 4 h. After the completion of the reaction, the reaction solution was cooled to room temperature and filtered through diatomite, the filter cake was washed with ethyl acetate (10 mL×3), and the organic phase was concentrated at reduced pressure to give a crude product. The crude product was purified by column chromatography (ethyl acetate: 0-10%, ethyl acetate/petroleum ether) to give compound 5-E. MS m/z: 518.3 $[M+H]^+$.

$^1H$ NMR (400 MHz, $CDCl_3$) δ=7.13-7.07 (m, 4H), 6.83 (d, J=8.3 Hz, 1H), 6.80 (d, J=2.5 Hz, 1H), 6.77-6.72 (m, 2H), 6.68 (dd, J=2.8, 8.5 Hz, 1H), 6.66-6.62 (m, 2H), 4.07 (d, J=7.3 Hz, 1H), 3.83 (s, 3H), 3.64 (br d, J=12.3 Hz, 2H), 3.36 (s, 6H), 2.75 (br t, J=7.0 Hz, 2H), 2.60 (dt, J=2.1, 12.2 Hz, 2H), 2.38-2.27 (m, 2H), 2.17-2.09 (m, 2H), 1.82 (br d, J=12.3 Hz, 2H), 1.50-1.34 (m, 3H).

Step 6: Synthesis of Compound 5-F

Boron tribromide (676.98 mg) was added to a solution of compound 5-E (140 mg) in dichloromethane (28 mL) at 0° C., and the reaction solution was stirred at 20° C. for 2 h. After the completion of the reaction, 50 mL of water was added to the reaction solution, and the mixture was extracted with dichloromethane (20 mL×3). The organic phase was dried over anhydrous sodium sulfate, filtered, and concentrated at reduced pressure to give crude compound 5-F. MS m/z: 476.2 $[M+H+H_2O]^+$ Step 7: Synthesis of Compound 5

Sodium acetate (47.29 mg) and magnesium sulfate (173.46 mg) were added to a solution of compound 5-F (132 mg) and trifluoroacetate of compound 7-H (191.25 mg) in dichloromethane (5 mL) and methanol (1 mL), and the reaction solution was stirred at 20° C. for 30 min. Sodium triacetoxyborohydride (183.25 mg) was added to the reaction solution, and the mixture was stirred at 20° C. for another 12 h. Water (20 mL) was added to the reaction solution for quenching, and the mixture was extracted with dichloromethane (20 mL×3). The organic phase was dried over anhydrous sodium sulfate, filtered, and concentrated to give a crude product, which was purified by column chromatography (methanol: 0-10%, methanol/dichloromethane) to give compound 5.

$^1$H NMR (400 MHz, DMSO-$d_6$) δ=10.96 (s, 1H), 9.41 (s, 1H), 7.52 (br d, J=8.8 Hz, 1H), 7.26-7.19 (m, 2H), 7.19-7.12 (m, 2H), 7.10-7.03 (m, 2H), 6.72-6.62 (m, 5H), 6.60-6.52 (m, 2H), 5.05 (br dd, J=4.9, 13.3 Hz, 1H), 4.39-4.28 (m, 1H), 4.25-4.16 (m, 1H), 3.63 (br d, J=12.0 Hz, 2H), 3.34-3.23 (m, 6H), 2.97-2.84 (m, 1H), 2.69-2.54 (m, 8H), 2.40-2.32 (m, 2H), 2.25-2.16 (m, 4H), 2.12-1.93 (m, 3H), 1.78 (br d, J=11.6 Hz, 2H), 1.67 (br s, 1H).

Example 6

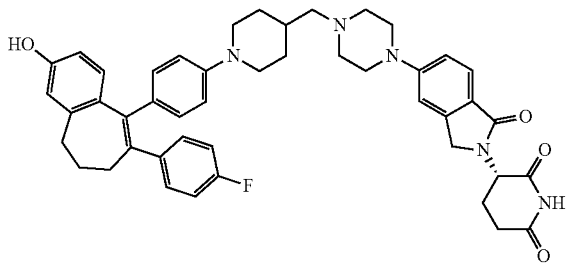

6

Synthetic Route:

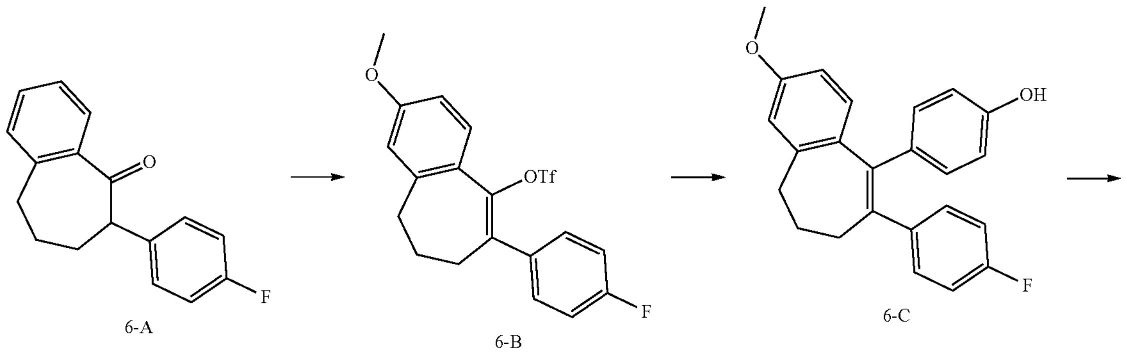

6-A 6-B 6-C

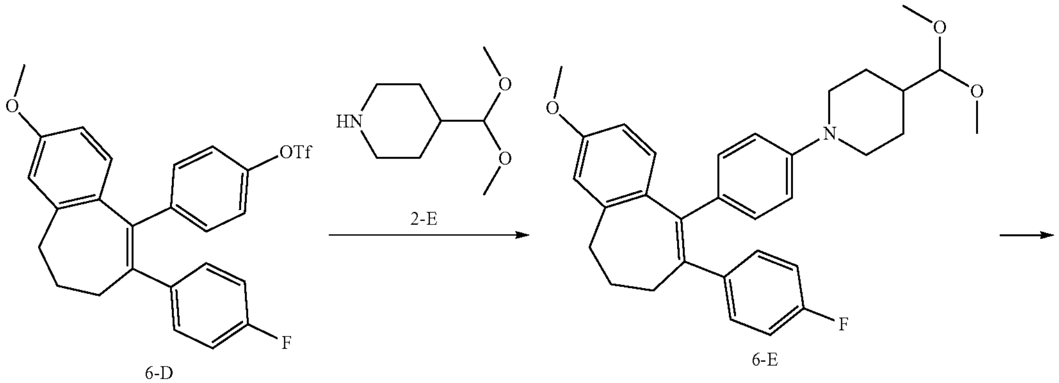

2-E

6-D 6-E

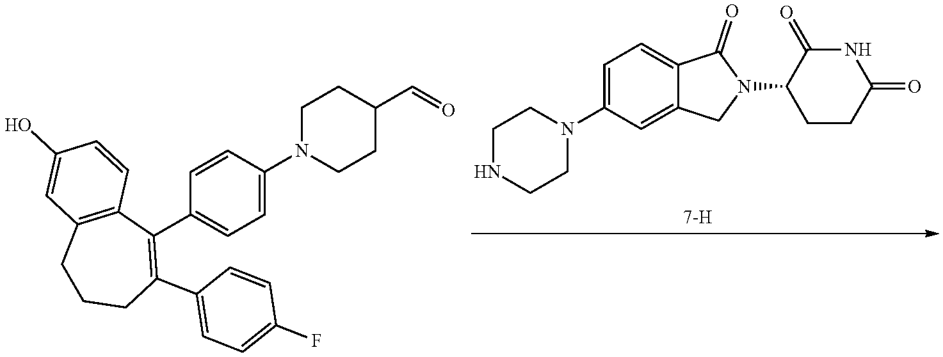

7-H

6-F

-continued

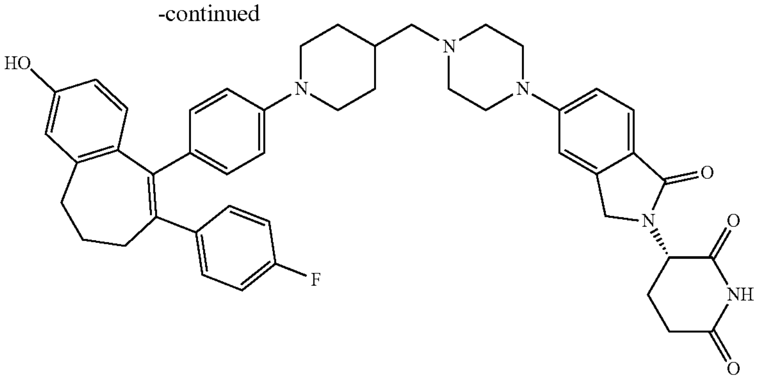

6

Step 1: Synthesis of Compound 6-B

Anhydrous dichloromethane (100 mL) was added to compound 6-A (5.25 g), trifluoromethanesulfonic anhydride (13.02 g) was added at 0° C., and pyridine (2.19 g) was slowly added dropwise. The mixture was stirred at 25° C. for 12 h. After the completion of the reaction, the reaction solution was poured into 30 mL of water and extracted with dichloromethane (20 mL×2). The organic layer was washed with saturated sodium bicarbonate solution (20×2 mL), and the organic phase was left. The organic phase was dried over 2.5 g of anhydrous sodium sulfate, left to stand for 10 min, and then filtered. The filtrate was concentrated at reduced pressure to give 6-B.

Step 2: Synthesis of Compound 6-C 40 mL of 1,4-dioxane and 5 mL of water were added to compound 6-B (8.56 g), followed by the addition of 4-hydroxyphenylboronic acid (3.40 g). The mixture was dissolved and stirred, and then [1,1-bis(diphenylphosphino) ferrocene]dichloropalladium dichloromethane (1.68 g) and potassium carbonate (5.68 g) were added. The mixture was purged with nitrogen for 3 times, heated to 90° C., and stirred for 4 h. After the completion of the reaction, 20 mL of ethanol was added to the system, and the mixture was concentrated at reduced pressure to give a crude product, which was washed with water (20 mL×2) and extracted with ethyl acetate (30 mL×2). The organic phase was concentrated to give 6-C.

$^1$H NMR (400 MHz, $CDCl_3$) δ=7.18-7.07 (m, 2H), 6.91-6.81 (m, 4H), 6.81-6.75 (m, 2H), 6.75-6.69 (m, 1H), 6.61-6.55 (m, 2H), 3.85 (s, 3H), 2.79 (t, J=7.0 Hz, 2H), 2.41-2.34 (m, 2H), 2.20-2.11 (m, 2H); MS m/z: 361.1 $[M+H]^+$.

Step 3: Synthesis of Compound 6-D

Dichloromethane (100 mL) was added to compound 6-C (7.12 g), and trifluoromethanesulfonic anhydride (13.93 g) and pyridine (2.34 g) were added at 0° C. The mixture was reacted at 25° C. for 12 h. After the completion of the reaction, water (40 mL) was added to the system, and the mixture was extracted with dichloromethane (20 mL×2). The organic layer was washed with saturated sodium bicarbonate solution (15 mL×2). The organic phase was dried over 2 g of anhydrous sodium sulfate, left to stand for 10 min, and then filtered. The filtrate was concentrated at reduced pressure to give 6-D.

Step 4: Synthesis of Compound 6-E 10 mL of toluene, 2-E (242.48 mg), sodium tert-butoxide (292.70 mg), palladium acetate (22.79 mg), and 2-di-tert-butylphosphine-2',4',6'-triisopropylbiphenyl (96.80 mg) were added to compound 6-D (641.03 mg) under nitrogen atmosphere. The mixture was reacted at 90° C. for 6 h. After the completion of the reaction, the system was filtered through diatomite with a sand core funnel. The filtrate was washed with water (20 mL×2) and extracted with ethyl acetate (20 mL×2). The organic phase was concentrated at reduced pressure to give 6-E. MS m/z: 502.4 $[M+H]^+$.

Step 5: Synthesis of Compound 6-F

Compound 6-E (0.1541 g) was added to DCM (10 mL), and boron tribromide (772.67 mg) was added at −60° C. The mixture was stirred for 30 min, the dry ice was removed, and the mixture was reacted at 20° C. for 5 h. After the completion of the reaction, water (20 mL) was added to the system, and the mixture was extracted with dichloromethane (10 mL×2). The organic phase was dried over 1 g of anhydrous sodium sulfate, filtered, and then concentrated at reduced pressure to give 6-F. MS m/z: 442.2 $[M+H]^+$.

Step 6: Synthesis of Compound 6

Anhydrous dichloromethane (10 mL), methanol (2 mL), and trifluoroacetate of 7-H (137.82 mg) were added to compound 6-F (0.0917 g), followed by the addition of anhydrous magnesium sulfate (124.99 mg) and sodium acetate (34.07 mg). The mixture was stirred at 20° C. for 0.5 h, and then sodium triacetoxyborohydride (132.05 mg) was added. The mixture was reacted at 20° C. for 11.5 h. After the completion of the reaction, the crude product was purified by column chromatography (0-8%, dichloromethane/methanol) to give compound 6.

$^1$H NMR (400 MHz, DMSO-$d_6$) δ=10.96 (s, 1H), 9.39 (s, 1H), 7.52 (d, J=8.3 Hz, 1H), 7.15 (br d, J=5.8 Hz, 2H), 7.11-6.91 (m, 4H), 6.65 (s, 5H), 6.57 (s, 2H), 5.15-4.96 (m, 1H), 4.40-4.26 (m, 1H), 4.23 (s, 1H), 3.73-3.53 (m, 4H), 3.29 (br dd, J=2.4, 4.9 Hz, 4H), 3.31-3.24 (m, 1H), 3.17 (d, J=5.3 Hz, 2H), 2.69-2.61 (m, 6H), 2.37-2.31 (m, 2H), 2.27-2.16 (m, 4H), 2.04 (br d, J=6.5 Hz, 2H), 1.76 (br s, 2H), 1.16 (br d, J=9.0 Hz, 2H); MS m/z: 754.3 $[M+H]^+$.

Example 7
7
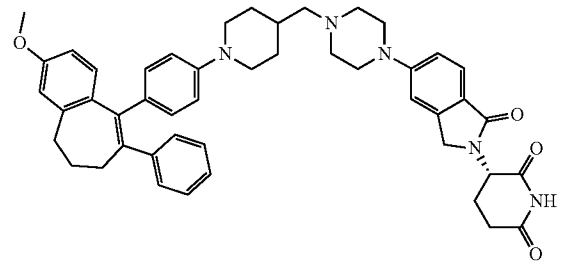
Synthetic Route:
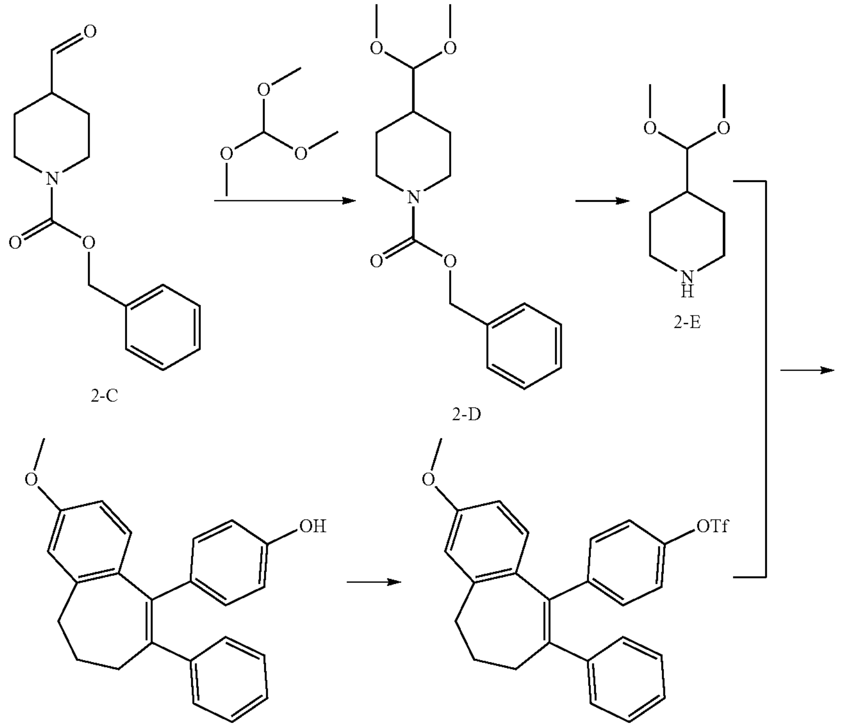
2-C
2-D
2-E
7-I
7-J
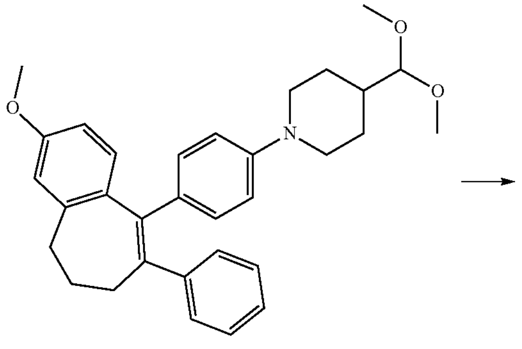
7-K -continued

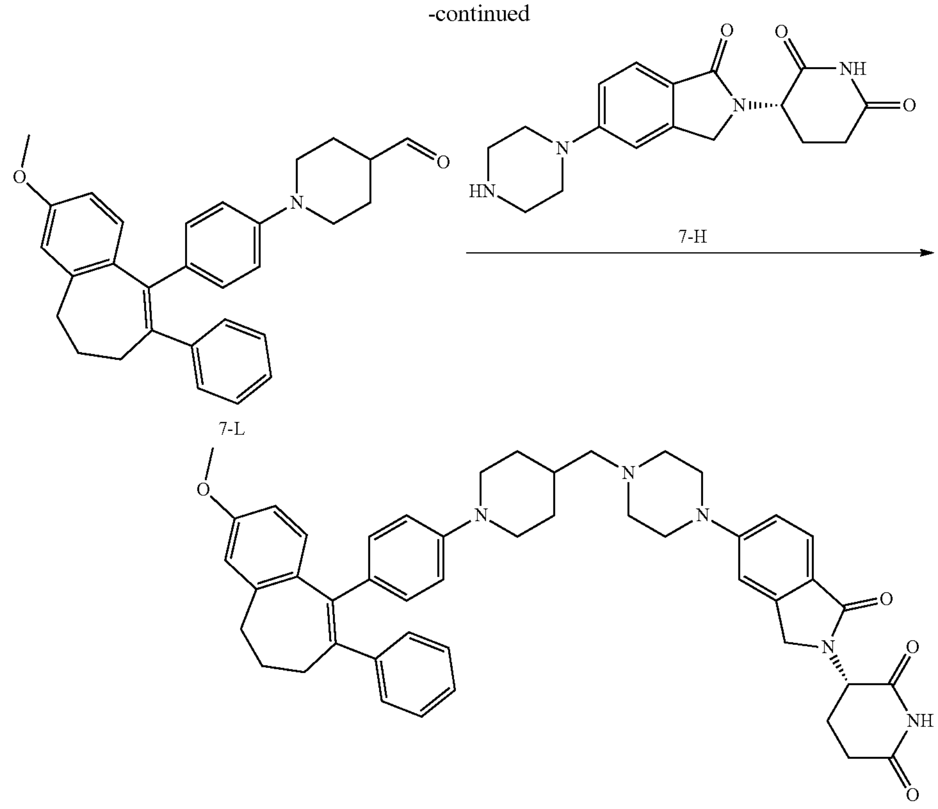

7-L

7-H

7

Step 1: Synthesis of Compound 2-D

Compound 2-C (10 g, 40.44 mmol) and trimethyl orthoformate (21.46 g, 202.19 mmol, 22.17 mL) were dissolved in anhydrous methanol (100 mL), and p-toluenesulfonic acid monohydrate (769.21 mg, 4.04 mmol) was added. The mixture was stirred at 15° C. for 5 h under nitrogen atmosphere. The mixture was adjusted to pH 7-8 with saturated sodium carbonate solution, water (100 mL) and dichloromethane (100 mL) were added, and the phases were separated. The organic phase was washed once with saturated brine (50 mL), dried over anhydrous sodium sulfate, filtered, and concentrated by a rotary evaporator to give crude compound 2-D.

$^1$H NMR (400 MHz, DMSO-$d_6$) δ=7.37-7.31 (m, 5H), 5.05 (s, 2H), 4.05-3.99 (m, 3H), 3.24 (s, 6H), 2.75 (br, 2H), 1.74 (tdt, J=3.6, 7.6, 11.3 Hz, 1H), 1.62 (br d, J=12.4 Hz, 2H), 1.09 (dq, J=4.4, 12.5 Hz, 2H)

Step 2: Synthesis of Compound 2-E

Compound 2-D (50 g) was dissolved in methanol (1000 mL), wet palladium on carbon (7 g, purity: 10%) was added, and the mixture was stirred under hydrogen atmosphere at 50 PSI, 25° C. for 12 h. The reaction solution was filtered through diatomite, the filter cake was washed with methanol (200 mL×5), and the organic phase was concentrated at reduced pressure to give crude compound 2-E.

$^1$H NMR (400 MHz, DMSO-$d_6$) δ=4.00 (d, J=6.8 Hz, 1H), 3.27-3.21 (m, 6H), 2.94 (br d, J=11.5 Hz, 2H), 2.44 (dt, J=2.0, 12.2 Hz, 2H), 1.69-1.60 (m, 1H), 1.56 (br d, J=13.3 Hz, 2H), 1.10 (dq, J=3.9, 12.2 Hz, 2H)

Step 3: Synthesis of Compound 7-J

Pyridine (866.24 mg) was added to a solution of compound 7-I (2.5 g) in anhydrous dichloromethane (50 mL), and trifluoromethanesulfonic anhydride (5.15 g) was slowly added dropwise at 0° C. The mixture was stirred at 25° C. for 12 h. After the completion of the reaction, the reaction solution was poured into 50 mL of water and extracted with dichloromethane (30 mL×3). The organic phase was washed with saturated brine (20 mL×2), dried over anhydrous sodium sulfate, filtered, and concentrated to give crude compound 7-J.

Step 4: Synthesis of Compound 7-K

7-J (3 g) was dissolved in toluene (60 mL), and 2-E (1.62 g), sodium tert-butoxide (1.22 g), 2-dicyclohexylphosphine-2,4,6-triisopropylbiphenyl (602.82 mg), and palladium acetate (141.95 mg) were added thereto. The mixture was purged with $N_2$ for 3 times, heated to 90° C., and stirred for 12 h. The mixture was filtered and concentrated to give a crude product, which was purified by column chromatography (ethyl acetate: 0-20%, petroleum ether/ethyl acetate) to give compound 7-K.

$^1$H NMR (400 MHz, DMSO-$d_6$) δ=7.17-7.13 (m, 5H), 6.87 (d, J=2.5 Hz, 1H), 6.72-6.61 (m, 5H), 6.46 (d, J=8.8 Hz, 1H), 4.07-4.00 (m, 1H), 3.77 (s, 3H), 3.61 (br d, J=12.0 Hz, 1H), 3.42 (br s, 5H), 3.25 (s, 2H), 2.74 (br t, J=6.7 Hz, 2H), 2.27-2.24 (m, 2H), 2.06 (m, 2H), 1.76-1.56 (m, 3H), 1.25-1.23 (m, 2H), 1.19-1.16 (m, 2H).

Step 5: Synthesis of Compound 7-L

7-K (0.9 g) was dissolved in tetrahydrofuran (25 mL), and diluted sulfuric acid (1 M, 25 mL) was added. The mixture was stirred at 60° C. for 4 h. The mixture was adjusted to pH 7 with saturated sodium bicarbonate solution and extracted with ethyl acetate (50 mL×2). The organic phases were combined, washed with saturated brine (50 mL×2), dried over anhydrous sodium sulfate, filtered, and concentrated by a rotary evaporator to give crude compound 7-L. MS m/z: 438.2 [M+Na]$^+$.

Step 6: Synthesis of Compound 7

Compound 7-L (0.3 g) and trifluoroacetate of compound 7-H (454.95 mg) were dissolved in a solution of methanol (10 mL) and dichloromethane (2 mL), and sodium acetate (112.48 mg) and magnesium sulfate (412.63 mg) were added. The mixture was stirred at 20° C. for 30 min. Sodium triacetoxyborohydride (435.92 mg) was added to the reaction solution, and the mixture was stirred at 20° C. for another 11.5 h. 1 M diluted hydrochloric acid (30 mL) was added and stirred for 30 min to quench the reaction. The mixture was adjusted to pH 7 with saturated sodium bicarbonate solution and extracted with dichloromethane (50 mL×3). The organic phases were combined, washed with saturated brine (20 mL×2), dried over anhydrous sodium sulfate, filtered, and concentrated by a rotary evaporator to give crude compound 7.

$^1$H NMR (400 MHz, DMSO-$d_6$) δ=10.94 (s, 1H), 7.51 (d, J=8.3 Hz, 1H), 7.21-7.02 (m, 7H), 6.88 (d, J=2.3 Hz, 1H), 6.76-6.60 (m, 6H), 5.04 (dd, J=5.0, 13.3 Hz, 1H), 4.37-4.13 (m, 2H), 3.77 (s, 3H), 3.60 (br d, J=11.8 Hz, 2H), 3.32-3.23 (m, 6H), 2.96-2.83 (m, 1H), 2.78-2.69 (m, 2H), 2.56 (br t, J=11.7 Hz, 6H), 2.47-2.29 (m, 2H), 2.28-2.17 (m, 4H), 2.12-1.89 (m, 3H), 1.83-1.59 (m, 3H).

Example 8

8

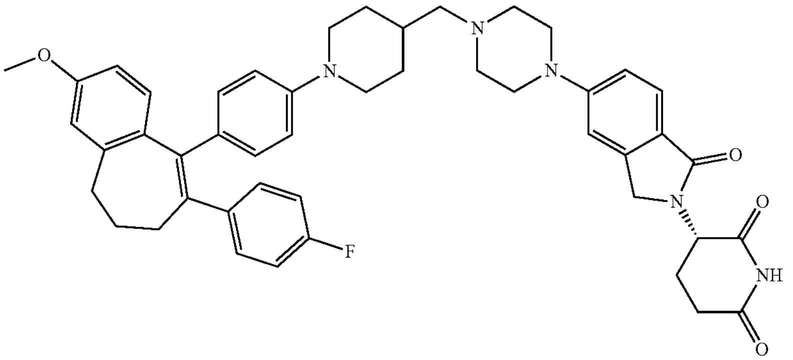

Synthetic Route:

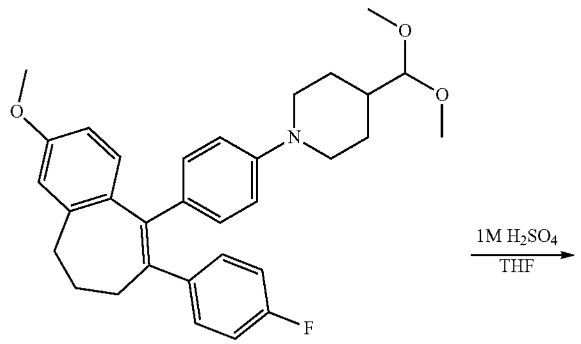

6-E

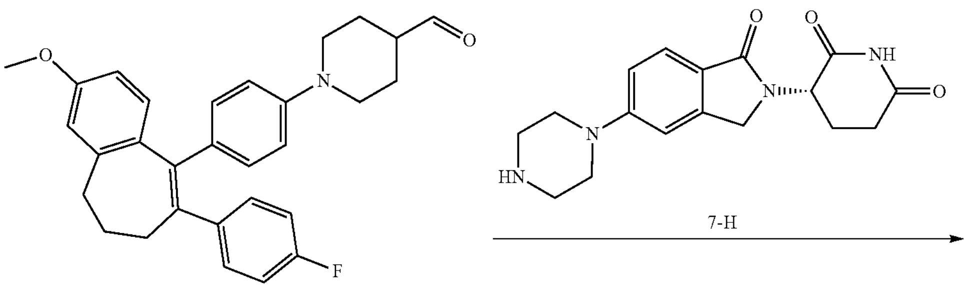

7-H

8-A

-continued

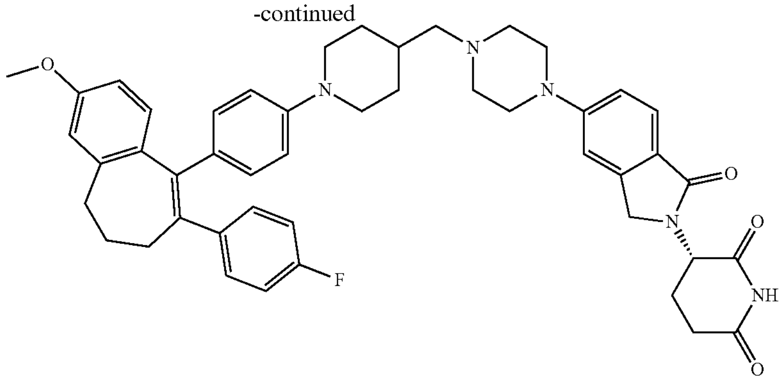

8

Step 1: Synthesis of Compound 8-A

Compound 6-E (0.227 g) was dissolved in 10 mL of tetrahydrofuran, and $H_2SO_4$ (1 M, 6.09 mL) was added. The mixture was reacted at 60° C. for 4 h under $N_2$ atmosphere. After the completion of the reaction, the system was washed with water (40 mL×2), and the aqueous phase was washed with saturated sodium bicarbonate solution until pH=7. The mixture was extracted with 20 mL of ethyl acetate, and the organic phase was dried over anhydrous sodium sulfate and concentrated at reduced pressure to give crude product 8-A. MS m/z: 456.2 $[M+H]^+$.

Step 2: Synthesis of Compound 8

Compound 8-A (0.244 g) and trifluoroacetate of compound 7-H (355.42 mg) were dissolved in 15 mL of dichloromethane and 3 mL of methanol, and anhydrous magnesium sulfate (322.35 mg) and anhydrous sodium acetate (87.87 mg) were added. The mixture was stirred for 30 min, and then sodium triacetoxyborohydride (340.55 mg) was added. The mixture was reacted at 25° C. for 6 h under $N_2$ atmosphere. After the completion of the reaction, the system was filtered through diatomite, and water (20 mL) was added to the filtrate. The mixture was extracted with dichloromethane (20 mL), and the organic phase was concentrated at reduced pressure to give a crude product, which was purified by column chromatography (methanol: 0-8%, dichloromethane/methanol) to give compound 8.

$^1H$ NMR (400 MHz, DMSO-$d_6$) δ=11.99 (br, 1H), 10.96 (s, 1H), 7.52 (d, J=8.8 Hz, 1H), 7.18 (dd, J=5.6, 8.7 Hz, 2H), 7.10-6.97 (m, 4H), 6.88 (d, J=2.5 Hz, 1H), 6.73 (br d, J=2.5 Hz, 1H), 6.70-6.65 (m, 4H), 5.05 (dd, J=4.9, 13.2 Hz, 1H), 4.37-4.29 (m, 1H), 4.25-4.16 (m, 1H), 4.03 (d, J=7.0 Hz, 1H), 3.77 (s, 3H), 3.66-3.58 (m, 2H), 3.28 (br s, 4H), 3.17 (d, J=5.3 Hz, 1H), 2.73 (br s, 2H), 2.57 (br s, 2H), 2.41-2.35 (m, 1H), 2.28-2.17 (m, 4H), 2.09 (s, 2H), 1.99 (s, 2H), 1.91 (s, 4H), 1.82-1.72 (m, 2H), 1.18 (s, 2H), MS m/z: 768.4 $[M+H]^+$.

Example 9

9

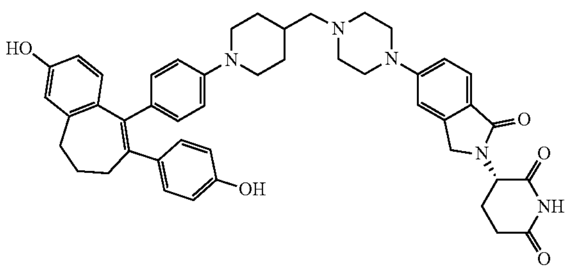

Synthetic Route:

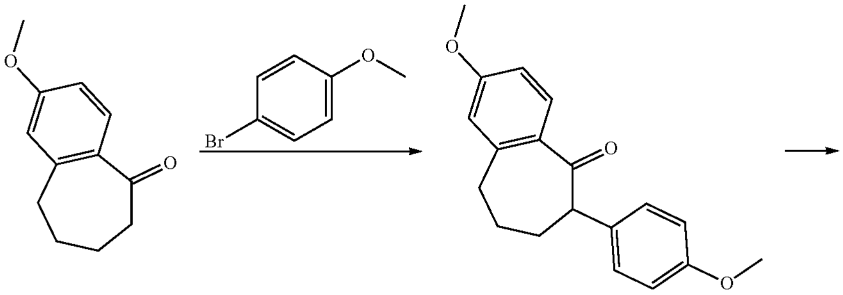

9-A

-continued

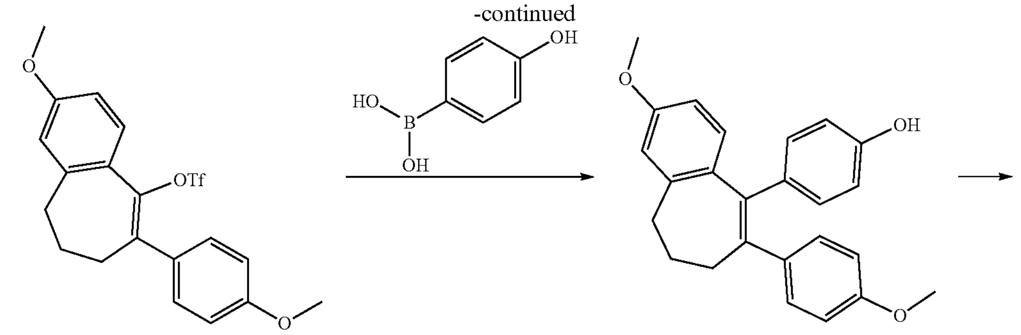

9-B 9-C

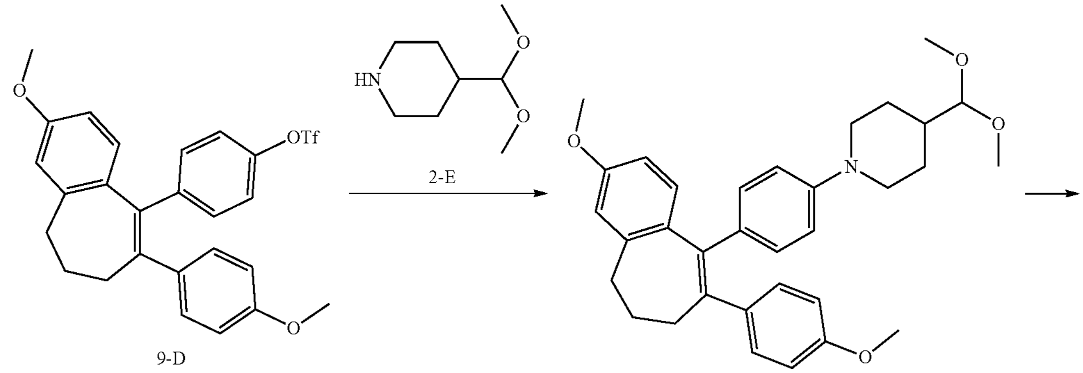

9-E

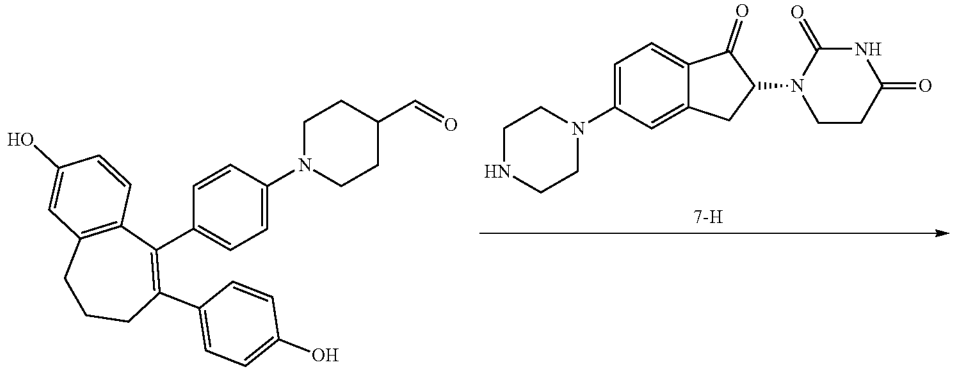

9-F

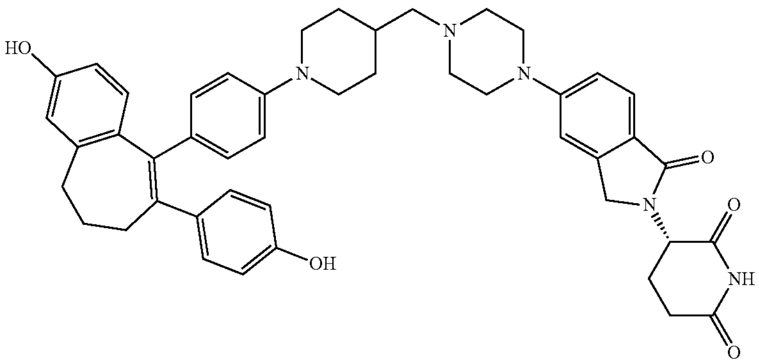

9

Step 1: Synthesis of Compound 9-A p-Methoxybromobenzene (1.28 g), sodium tert-butoxide (656.70 mg), 2-dicyclohexylphosphine-2,4,6-triisopropylbiphenyl (501.18 mg), and palladium acetate (118.02 mg) were added to a solution of compound 2-methoxy-6,7,8,9-tetrahydro-5H-benzo[7]annulen-5-one (1.00 g) in toluene (10 mL), and the mixture was purged with nitrogen for 1 min and subjected to a microwave reaction at 120° C. for 1 h. After the completion of the reaction, the reaction solution was filtered through diatomite, the filter cake was washed with ethyl acetate (10 mL×3), and the organic phase was concentrated at reduced pressure to give a crude product. The crude product was purified by column chromatography (ethyl acetate: 0-8%, ethyl acetate/petroleum ether) to give compound 9-A. MS m/z: 296.9 $[M+H]^+$ Step 2: Synthesis of Compound 9-B Pyridine (1.12 g) was added to a solution of compound 9-A (2.80 g) in anhydrous dichloromethane (60 mL), and trifluoromethanesulfonic anhydride (6.66 g) was slowly added dropwise at 0° C. The mixture was stirred at 20° C. for 12 h. After the completion of the reaction, the reaction solution was poured into 100 mL of water and extracted with dichloromethane (30 mL×3). The organic phase was washed with saturated sodium bicarbonate (50 mL×1), dried over anhydrous sodium sulfate, filtered, and concentrated to give crude product 9-B.

Step 3: Synthesis of Compound 9-C p-Hydroxyphenylboronic acid (1.70 g), potassium carbonate (2.84 g), and [1,1-bis(diphenylphosphino)ferrocene] dichloropalladium dichloromethane (838.71 mg) were added to a solution of compound 9-B (4.40 g) in 1,4-dioxane (50 mL) and water (5 mL), and the mixture was purged with nitrogen for 3 times and reacted at 90° C. for 5 h. After the completion of the reaction, the reaction solution was cooled to room temperature and filtered through diatomite, the filter cake was washed with ethyl acetate (10 mL×6), and the organic phase was concentrated at reduced pressure to give a crude product. The crude product was purified by column chromatography (ethyl acetate: 5%-12%, ethyl acetate/petroleum ether) to give compound 9-C. MS m/z: 373.0 $[M+H]^+$ $^1$H NMR (400 MHz, DMSO-$d_6$) δ=9.24 (s, 1H), 7.05 (d, J=8.5 Hz, 2H), 6.87 (d, J=2.5 Hz, 1H), 6.75-6.71 (m, 3H), 6.69-6.66 (m, 1H), 6.64 (d, J=8.5 Hz, 2H), 6.49 (d, J=8.5 Hz, 2H), 3.76 (s, 3H), 3.70 (s, 3H), 2.72 (br t, J=6.8 Hz, 2H), 2.28-2.19 (m, 2H), 2.11-2.02 (m, 2H).

Step 4: Synthesis of Compound 9-D

Pyridine (692.62 mg) was added to a solution of compound 9-C (2.20 g) in anhydrous dichloromethane (50 mL), and trifluoromethanesulfonic anhydride (4.12 g) was slowly added dropwise at 0° C. The mixture was stirred at 20° C. for 16 h. After the completion of the reaction, the reaction solution was poured into 100 mL of water and extracted with dichloromethane (30 mL×3). The organic phase was dried over anhydrous sodium sulfate, filtered, and concentrated to give crude product 9-D.

Step 5: Synthesis of Compound 9-E

2-E (236.70 mg), sodium tert-butoxide (190.48 mg), 2-dicyclohexylphosphine-2,4,6-triisopropylbiphenyl (94.49 mg), and palladium acetate (22.25 mg) were added to a solution of compound 9-D (0.50 g) in toluene (10 mL). The mixture was purged with nitrogen for 3 times and reacted at 90° C. for 2 h. After the completion of the reaction, the reaction solution was cooled to room temperature and filtered through diatomite, the filter cake was washed with ethyl acetate (15 mL×6), and the organic phase was concentrated at reduced pressure to give a crude product. The crude product was purified by column chromatography (ethyl acetate: 5%-8%, ethyl acetate/petroleum ether) to give compound 9-E. MS m/z: 514.3 $[M+H]^+$.

$^1$H NMR (400 MHz, DMSO-$d_6$) δ=7.07 (d, J=8.8 Hz, 2H), 6.87 (d, J=2.5 Hz, 1H), 6.74 (d, J=8.8 Hz, 3H), 6.68 (s, 1H), 6.65 (s, 4H), 4.07 (d, J=6.5 Hz, 1H), 3.76 (s, 3H), 3.70 (s, 3H), 3.62 (br d, J=11.8 Hz, 2H), 3.26 (s, 6H), 2.72 (br t, J=6.7 Hz, 2H), 2.56-2.53 (m, 2H), 2.28-2.18 (m, 2H), 2.10-2.01 (m, 2H), 1.68 (br d, J=10.3 Hz, 3H), 1.26 (br d, J=12.8 Hz, 2H).

Step 6: Synthesis of Compound 9-F

Boron tribromide (341.40 mg) was added to a solution of compound 9-E (70 mg) in dichloromethane (14 mL) at 0° C., and the reaction solution was stirred at 20° C. for 1 h. After the completion of the reaction, the reaction solution was added to 50 mL of water, and the mixture was extracted with dichloromethane (10 mL×3). The organic phase was dried over anhydrous sodium sulfate, filtered, and concentrated at reduced pressure to give crude compound 9-F. MS m/z: 440.2 $[M+H]^+$.

Step 7: Synthesis of Compound 9

Sodium acetate (14.93 mg) and magnesium sulfate (54.77 mg) were added to a solution of compound 9-F (40 mg) and trifluoroacetate of compound 7-H (60.39 mg) in dichloromethane (5 mL) and methanol (1 mL), and the reaction solution was stirred at 20° C. for 30 min. Sodium triacetoxyborohydride (57.86 mg) was added to the reaction solution, and the mixture was stirred at 20° C. for another 12 h. The reaction solution was concentrated at reduced pressure to give a crude product, which was purified by column chromatography (methanol: 0-5%, methanol/dichloromethane) to give compound 9. MS m/z: 752.4 $[M+H]^+$.

$^1$H NMR (400 MHz, DMSO-$d_6$) δ=10.96 (s, 1H), 9.33 (s, 1H), 9.24 (s, 1H), 7.53 (d, J=8.4 Hz, 1H), 7.13-7.03 (m, 2H), 6.93 (d, J=8.5 Hz, 2H), 6.65 (s, 5H), 6.59-6.48 (m, 4H), 5.05 (dd, J=5.1, 13.3 Hz, 1H), 4.38-4.16 (m, 2H), 3.61 (br d, J=10.5 Hz, 2H), 3.32-3.23 (m, 6H), 2.93-2.85 (m, 1H), 2.70-2.54 (m, 8H), 2.41-2.32 (m, 3H), 2.20 (br s, 3H), 2.06-1.95 (m, 3H), 1.85-1.59 (m, 3H).

Example 10

10

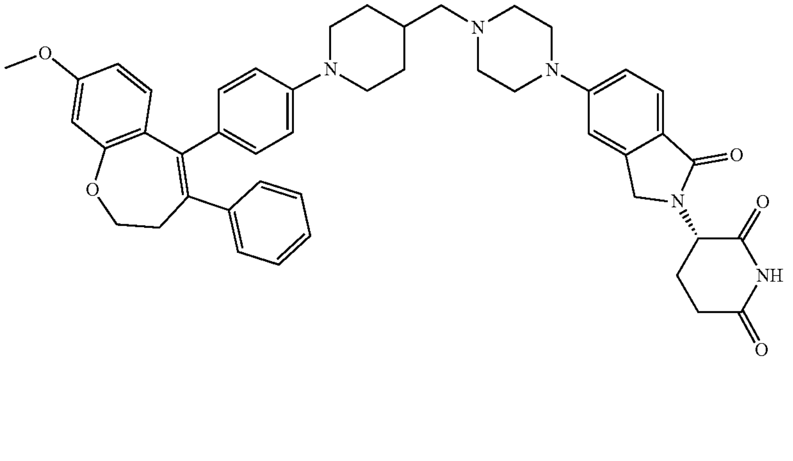

Synthetic Route:
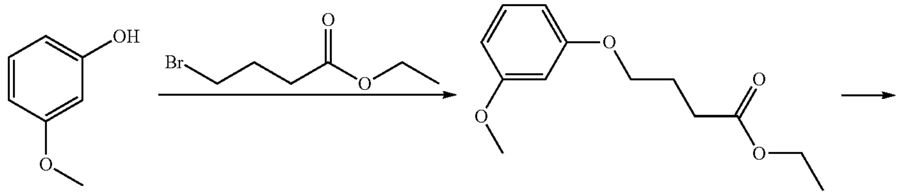
10-A
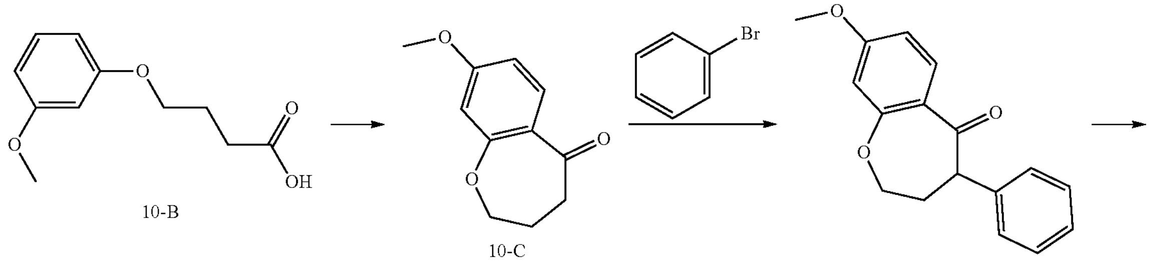
10-B 10-C 10-D
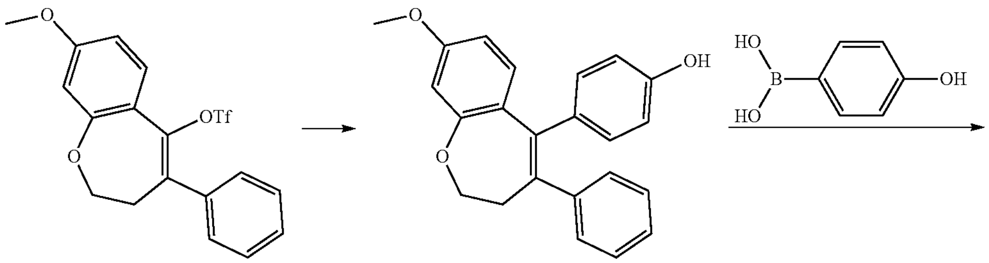
10-E 10-F
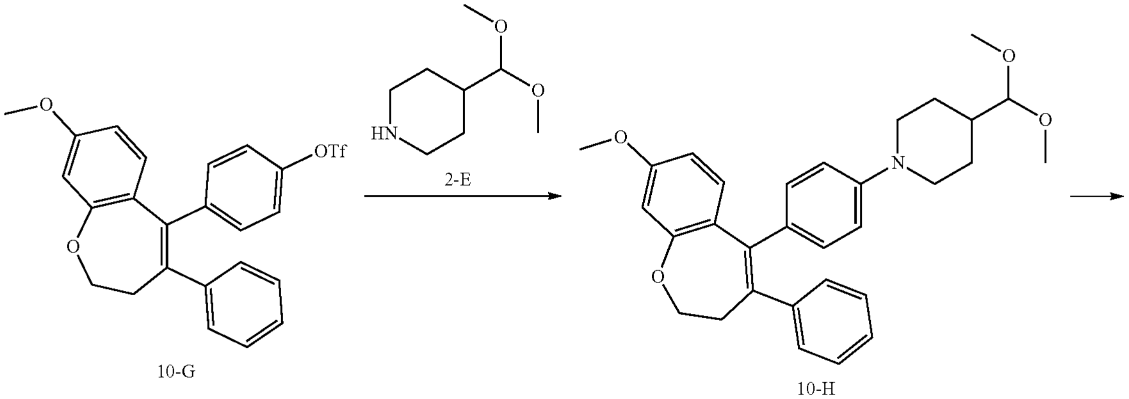
10-G 10-H
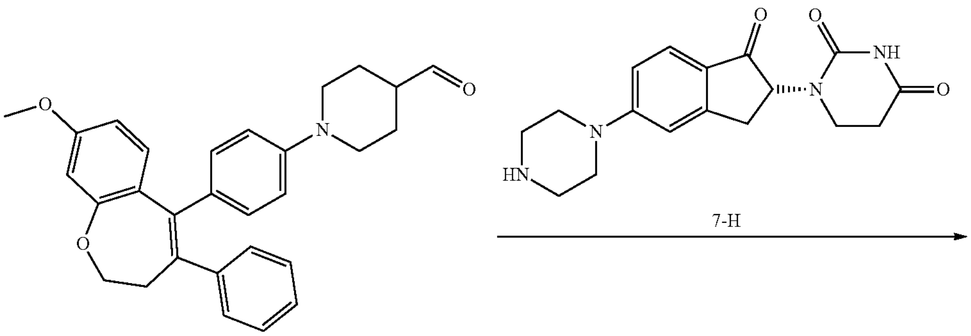
10-I -continued

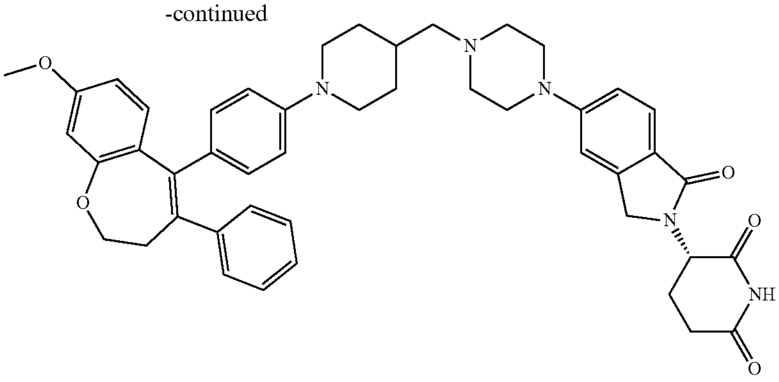

10

Step 1: Synthesis of Compound 10-A

Ethyl 4-bromobutyrate (15.87 g) and potassium carbonate (33.40 g) were added to a solution of m-methoxyphenol (10 g) in N,N-dimethylformamide (100 mL). The mixture was stirred at 20° C. for 12 h. After the completion of the reaction, the reaction solution was poured into 300 mL of water and extracted with ethyl acetate (50 mL×2). The organic phase was washed with saturated brine (50 mL×2), dried over anhydrous sodium sulfate, filtered, and concentrated to give crude compound 10-A. TLC: PE/EA=10/1, $R_f$=0.27.

Step 2: Synthesis of Compound 10-B

Potassium hydroxide (9.42 g) was added to a solution of compound 10-A (20 g) in anhydrous methanol (150 mL) and water (50 mL). The mixture was stirred at 40° C. for 1 h. The reaction solution was adjusted to pH 3 to 4 with 1 M diluted hydrochloric acid aqueous solution, stirred at room temperature for 30 min to precipitate a solid, filtered, and dried to give crude compound 10-B.

Step 3: Synthesis of Compound 10-C

Polyphosphoric acid (25 g) was added to a solution of compound 10-B (5 g) in chlorobenzene (100 mL). The mixture was stirred at 80° C. for 12 h. The hot reaction solution was poured slowly into ice water (200 mL), extracted with dichloromethane (100 mL×3), washed with saturated sodium bicarbonate (30 mL) and saturated brine (50 mL), dried over anhydrous sodium sulfate, filtered, and subjected to rotary evaporation at reduced pressure to give a crude product. The crude product was purified by column chromatography (0-15%, ethyl acetate/petroleum ether) to give compound 10-C.

$^1$H NMR (400 MHz, $CDCl_3$) δ=7.77 (d, J=8.8 Hz, 1H), 6.66 (dd, J=2.3, 8.8 Hz, 1H), 6.56 (d, J=2.3 Hz, 1H), 4.25 (t, J=6.7 Hz, 2H), 3.84 (s, 3H), 2.87 (t, J=7.0 Hz, 2H), 2.20 (quin, J=6.8 Hz, 2H).

Step 4: Synthesis of Compound 10-D

Compound 10-C (1 g), bromobenzene (1.06 g), sodium tert-butoxide (999.94 mg), 2-dicyclohexylphosphine-2,4,6-triisopropylbiphenyl (496.04 mg), and palladium acetate (116.80 mg) were mixed with toluene solution (10 mL) and stirred. The mixture was placed in a microwave tube, purged with nitrogen, and then subjected to a microwave reaction at 120° C. for 1 h. The reaction solution was filtered and subjected to rotary evaporation at reduced pressure to give a crude product. The crude product was purified by column chromatography (ethyl acetate: 0-5%, ethyl acetate/petroleum ether) to give compound 10-D. MS m/z: 268.9 $[M+H]^+$.

Step 5: Synthesis of Compound 10-E

Trifluoromethanesulfonic anhydride (17.72 g) and pyridine (2.98 g) were added to a solution of compound 10-D (6.74 g) in dichloromethane (120 mL) at 0-5° C. The mixture was heated to 33° C. and stirred for 12 h. After the completion of the reaction, the reaction solution was added to water (300 mL), extracted with dichloromethane (50 mL×2), washed with saturated brine (50 mL×2), dried over anhydrous sodium sulfate, filtered, and subjected to rotary evaporation at reduced pressure to give compound 10-E.

Step 6: Synthesis of Compound 10-F p-Hydroxyphenylboronic acid (1.34 g), potassium carbonate (2.24 g), and [1,1-bis(diphenylphosphino)ferrocene] dichloropalladium dichloromethane (660.87 mg) were added to a solution of compound 10-E (3.24 g) in dioxane (50 mL) and water (5 mL). The mixture was heated to 90° C. and stirred for 2 h under nitrogen atmosphere. After the completion of the reaction, the reaction solution was filtered and subjected to rotary evaporation at reduced pressure to give a crude product, which was purified by column chromatography (ethyl acetate: 0-10%, ethyl acetate/petroleum ether) to give compound 10-F.

$^1$H NMR (400 MHz, $CDCl_3$) δ=7.21-7.09 (m, 5H), 6.88-6.77 (m, 3H), 6.70 (d, J=2.8 Hz, 1H), 6.63-6.54 (m, 3H), 4.62 (t, J=6.1 Hz, 2H), 3.83 (s, 3H), 2.74 (t, J=6.0 Hz, 2H).

Step 7: Synthesis of Compound 10-G

Trifluoromethanesulfonic anhydride (5.63 g) and pyridine (947.40 mg) were added to a solution of compound 10-F (2.75 g) in dichloromethane (50 mL) at 0-5° C. The mixture was heated to 25° C. and stirred for 12 h. After the completion of the reaction, the reaction solution was added to water (300 mL), extracted with dichloromethane (50 mL×2), washed with saturated brine (50 mL×2), dried over anhydrous sodium sulfate, filtered, and subjected to rotary evaporation at reduced pressure to give a crude product, which was purified by column chromatography (ethyl acetate: 0-8%, ethyl acetate/petroleum ether) to give compound 10-G.

Step 8: Synthesis of Compound 10-H

Compound 2-E (1.25 g), sodium tert-butoxide (1.21 g), 2-dicyclohexylphosphine-2,4,6-triisopropylbiphenyl (400.21 mg), and palladium acetate (94.24 mg) were added to a solution of compound 10-G (2 g) in toluene (20 mL). The mixture was heated to 90° C. and stirred for 3 h under nitrogen atmosphere. After the completion of the reaction, the reaction solution was filtered and subjected to rotary evaporation at reduced pressure to give a crude product, which was purified by column chromatography (ethyl acetate: 0-25%, ethyl acetate/petroleum ether) to give compound 10-H. MS m/z: 486.3 $[M+H]^+$.

Step 9: Synthesis of Compound 10-I

Diluted hydrochloric acid (1 M, 20 mL) was added to a solution of compound 10-H (0.77 g) in tetrahydrofuran (20 mL). The mixture was heated to 60° C. and stirred for 12 h. After the completion of the reaction, the reaction solution was cooled and added to water (20 mL). The mixture was adjusted to pH 7 to 8 with saturated sodium bicarbonate (50 mL), extracted with ethyl acetate (50 mL×2), washed with saturated brine (30 mL), dried over anhydrous sodium sulfate, filtered, and subjected to rotary evaporation at reduced pressure to give compound 10-I. MS m/z: 440.1 $[M+H]^+$.

Step 10: Synthesis of Compound 10

Trifluoroacetate of 7-H (375.92 mg), sodium acetate (92.94 mg), and magnesium sulfate (340.95 mg) were added in sequence to a solution of compound 10-I (0.83 g) in dichloromethane (10 mL) and methanol (1 mL). After the reaction solution was stirred at 20° C. for 30 min, sodium triacetoxyborohydride (360.19 mg) was added, and the mixture was stirred at 20° C. for another 11.5 h. After the completion of the reaction, diluted hydrochloric acid (1 M, 1 mL) was added dropwise to the reaction solution. After being stirred for 10 min, the mixture was adjusted to pH 7 to 8 with saturated sodium bicarbonate (20 mL), extracted with dichloromethane (50 mL×3), washed with saturated brine (20 mL), dried over anhydrous sodium sulfate, filtered, and subjected to rotary evaporation at reduced pressure to give a crude product, which was purified by column chromatography (methanol: 0-2%, methanol/dichloromethane) to give compound 10. MS m/z: 752.4 $[M+H]^+$.

$^1H$ NMR (400 MHz, $CDCl_3$) δ=7.99 (s, 1H), 7.73 (d, J=8.5 Hz, 1H), 7.17 (d, J=4.3 Hz, 4H), 7.10 (qd, J=4.3, 8.5 Hz, 1H), 6.99 (dd, J=1.9, 8.7 Hz, 1H), 6.88 (s, 1H), 6.82 (dd, J=4.1, 8.7 Hz, 3H), 6.70-6.63 (m, 3H), 6.58 (dd, J=2.6, 8.7 Hz, 1H), 5.20 (dd, J=5.1, 13.2 Hz, 1H), 4.60 (t, J=6.0 Hz, 2H), 4.46-4.20 (m, 2H), 3.82 (s, 3H), 3.63 (br d, J=12.3 Hz, 2H), 3.32 (br s, 4H), 2.95-2.76 (m, 2H), 2.71 (t, J=5.9 Hz, 2H), 2.68-2.55 (m, 6H), 2.32 (dd, J=5.3, 13.1 Hz, 1H), 2.27 (br d, J=5.8 Hz, 2H), 2.29-2.24 (m, 1H), 2.23-2.19 (m, 1H), 1.86 (br d, J=12.5 Hz, 2H), 1.32 (br d, J=10.8 Hz, 2H).

Example 11

11

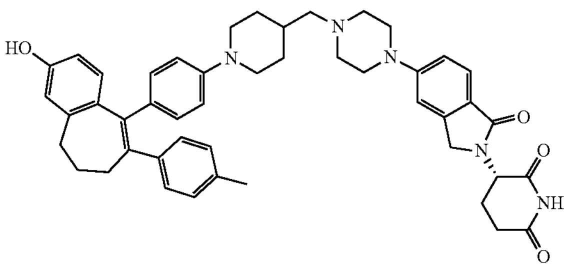

Synthetic Route:

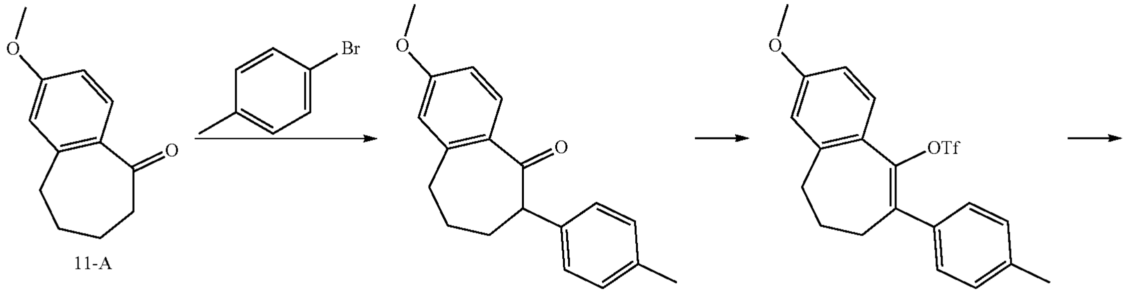

11-A

11-B

11-C

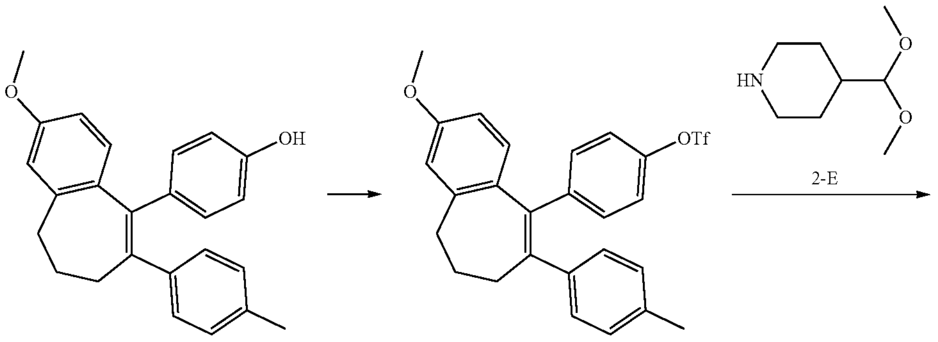

11-D

11-E

-continued

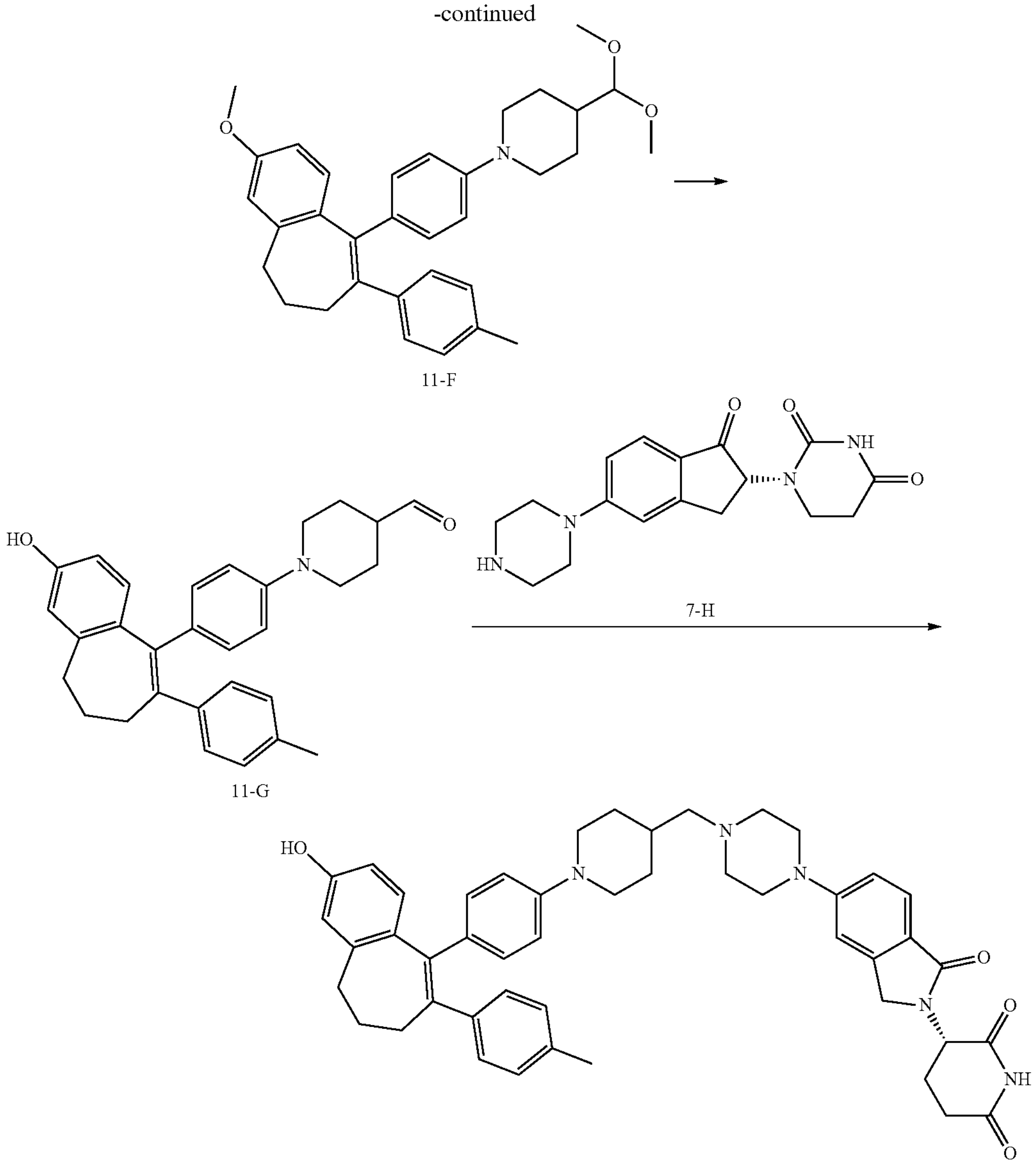

11-F

11-G

7-H

11

Step 1: Synthesis of Compound 11-B

11-A (1 g) and 4-bromotoluene (1.08 g) were dissolved in 10 mL of toluene, followed by the addition of palladium acetate (118.02 mg), 2-di-tert-butylphosphine-2',4',6'-triisopropylbiphenyl (501.18 mg), and sodium tert-butoxide (656.70 mg). The mixture was subjected to a microwave reaction at 120° C. for 1 h under $N_2$ atmosphere. After the completion of the reaction, the system was filtered through diatomite with a sand core funnel. The filtrate was washed with water (20 mL×2) and extracted with ethyl acetate (20 mL×2). The organic phase was concentrated at reduced pressure to give 11-B. MS m/z: 281.0 $[M+H]^+$.

Step 2: Synthesis of Compound 11-C

Compound 11-B (2.88 g) was dissolved in 30 mL of anhydrous dichloromethane, trifluoromethanesulfonic anhydride (7.25 g) was added at 0° C., and pyridine (1.22 g) was slowly added dropwise. The mixture was stirred at 25° C. for 12 h under $N_2$ atmosphere. After the completion of the reaction, the reaction solution was poured into water (30 mL) and extracted with dichloromethane (20 mL×2). The organic layer was washed with saturated sodium bicarbonate solution (20×2 mL), and the organic phase was left. The organic phase was dried over 2.5 g of anhydrous sodium sulfate, left to stand for 10 min, and then filtered. The filtrate was concentrated at reduced pressure to give 11-C.

Step 3: Synthesis of Compound 11-D

Compound 11-C (4.1 g) was dissolved in 1,4-dioxane (40 mL) and water (5 mL), followed by the addition of 4-hydroxyphenylboronic acid (1.65 g) and anhydrous potassium carbonate (2.75 g). After the mixture was stirred and dissolved, [1,1-bis(diphenylphosphino)ferrocene]dichloropalladium dichloromethane (811.84 mg) was added, and the mixture was purged with nitrogen for 3 times and reacted at 90° C. for 4 h. After the completion of the reaction, 20 mL of ethanol was added to the system, and the mixture was concentrated at reduced pressure to give a crude product, which was washed with water (20 mL×2) and extracted with ethyl acetate (20 mL×2). The organic phase was concentrated to give a crude product, which was purified by column chromatography (ethyl acetate: 0-10%, petroleum ether/ethyl acetate) to give compound 11-D.

$^1$H NMR (400 MHz, DMSO-$d_6$) δ=9.25 (s, 1H), 7.05-6.93 (m, 4H), 6.87 (d, J=2.5 Hz, 1H), 6.76-6.66 (m, 2H), 6.66-6.59 (m, 2H), 6.55-6.41 (m, 2H), 3.76 (s, 3H), 3.45 (dq, J=5.1, 7.0 Hz, 2H), 2.72 (br t, J=6.8 Hz, 2H), 2.22 (s, 3H), 2.12-1.96 (m, 2H). MS m/z: 357.1 [M+H]$^+$.

Step 4: Synthesis of Compound 11-E

Compound 11-D (2.6 g) was dissolved in 20 mL of anhydrous dichloromethane, trifluoromethanesulfonic anhydride (5.14 g) was added at 0° C., and pyridine (865.44 mg) was slowly added dropwise. The mixture was stirred at 25° C. for 6 h under $N_2$ atmosphere. After the completion of the reaction, the reaction solution was poured into water (30 mL) and extracted with dichloromethane (20 mL×2). The organic layer was washed with saturated sodium bicarbonate solution (20 mL×2), and the organic phase was left. The organic phase was dried over 2.5 g of anhydrous sodium sulfate, left to stand for 10 min, and then filtered. The filtrate was concentrated at reduced pressure to give 11-E. MS m/z: 489.1 [M+H]$^+$.

Step 5: Synthesis of Compound 11-F

Compounds 11-E (0.6 g) and 2-E (293.77 mg) were dissolved in 10 mL of toluene, followed by the addition of sodium tert-butoxide (354.61 mg), 2-di-tert-butylphosphine-2',4',6'-triisopropylbiphenyl (117.27 mg), and palladium acetate (27.61 mg). The mixture was reacted at 90° C. for 6 h under nitrogen atmosphere. After the completion of the reaction, the system was filtered through diatomite with a sand core funnel. The filtrate was washed with water (20 mL×2) and extracted with ethyl acetate (20 mL×2). The organic phase was concentrated at reduced pressure to give 11-F, MS m/z: 498.3 [M+H]$^+$.

Step 6: Synthesis of Compound 11-G

Compound 11-F (300 mg) was dissolved in DCM (10 mL), and boron tribromide (1.51 g) was slowly added dropwise at −60° C. under $N_2$ atmosphere. The mixture was reacted at 25° C. for 4 h. After the completion of the reaction, water (20 mL) was added to the system, and the mixture was extracted with dichloromethane (20 mL×2). The organic phase was dried over anhydrous magnesium sulfate and filtered, and the filtrate was concentrated at reduced pressure to give 11-G.

Step 7: Synthesis of Compound 11

11-G (0.299 g) and trifluoroacetate of 7-H (336.57 mg) were dissolved in 15 mL of dichloromethane, followed by the addition of anhydrous sodium acetate (112.10 mg) and anhydrous magnesium sulfate (411.25 mg). After the mixture was stirred for 30 min under nitrogen atmosphere, sodium triacetoxyborohydride (434.47 mg) was added, and the mixture was reacted at 25° C. for 6 h. After the completion of the reaction, the crude product was purified by column chromatography (methanol: 0-8%, dichloromethane/methanol) to give compound 11.

$^1$H NMR (400 MHz, DMSO-$d_6$) δ=10.96 (s, 1H), 9.35 (s, 1H), 7.52 (d, J=8.5 Hz, 1H), 7.11-7.01 (m, 4H), 7.00-6.94 (m, 2H), 6.72-6.48 (m, 7H), 5.05 (dd, J=5.1, 13.2 Hz, 1H), 4.40-4.28 (m, 1H), 4.26-4.15 (m, 1H), 3.61 (br d, J=12.0 Hz, 2H), 3.28 (br s, 4H), 2.97-2.84 (m, 1H), 2.65 (br s, 2H), 2.57 (br s, 3H), 2.43-2.30 (m, 2H), 2.22 (s, 8H), 2.06-1.87 (m, 4H), 1.78 (br d, J=11.3 Hz, 2H), 1.72-1.59 (m, 1H), 1.26-1.08 (m, 3H). MS m/z: 749.94 [M+H]$^+$.

Example 12

12

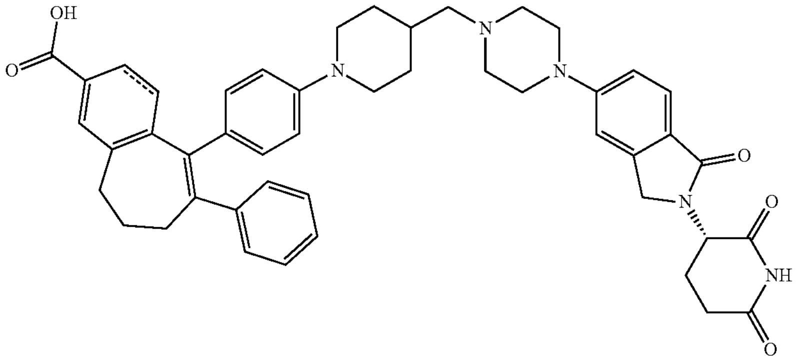

Synthetic Route:
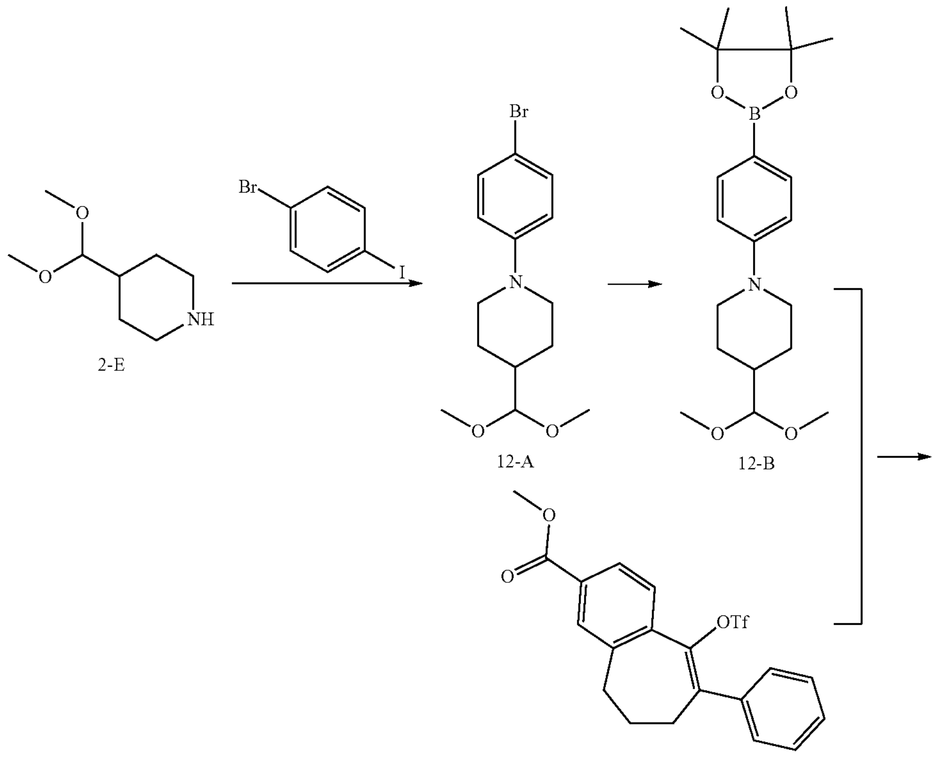
2-E 12-A 12-B 13-E
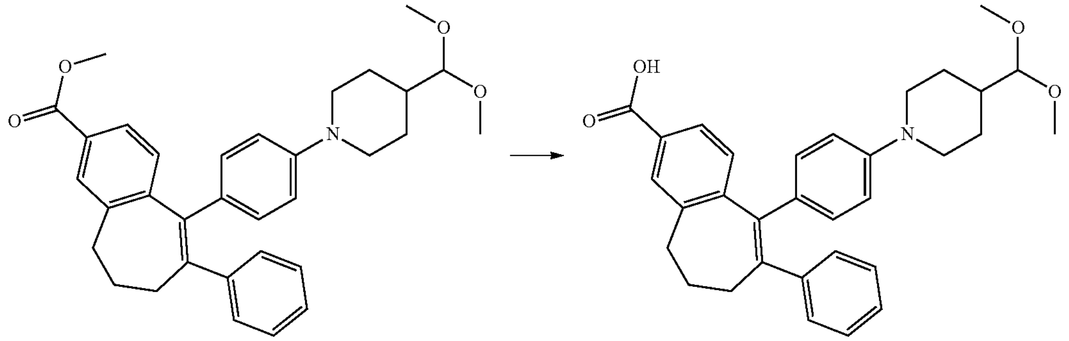
12-C 12-D
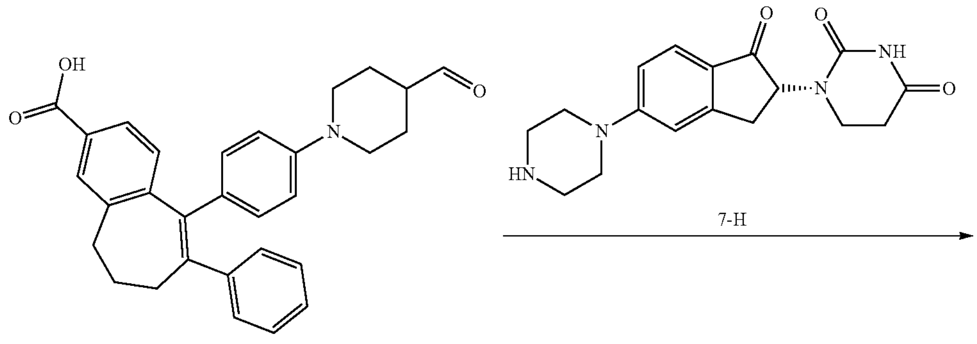
12-E 7-H -continued

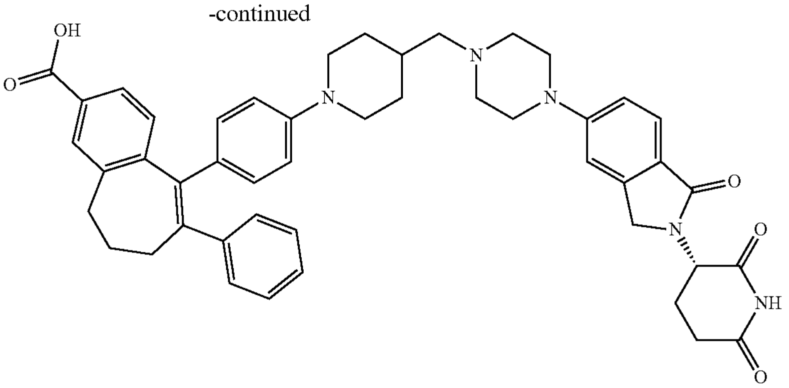

12

Step 1: Synthesis of Compound 12-A

4-Bromoiodobenzene (1 g), L-proline (162.78 mg), cuprous iodide (134.64 mg), and potassium carbonate (977.05 mg) were added to a solution of compound 2-E (562.83 mg) in DMSO (10 mL). The mixture was stirred at 90° C. for 12 h under $N_2$ atmosphere. After the completion of the reaction, the reaction solution was poured into 100 mL of water and extracted with ethyl acetate (100 mL×3), and the organic phase was washed with water (100 mL×2) and saturated brine (100 mL), dried over anhydrous sodium sulfate, filtered, and concentrated to give a crude product. The crude product was purified by column chromatography (0-10%, ethyl acetate/petroleum ether) to give compound 12-A. MS m/z: 313.9 [M+H]1.

Step 2: Synthesis of Compound 12-B

Compound 12-A (425 mg), bis(pinacolato)diboron (446.51 mg), 2-di-tert-butylphosphine-2',4',6'-triisopropylbiphenyl (322.40 mg), and potassium acetate (398.23 mg) were dissolved in dioxane (10 mL), and the mixture was stirred for 5 mi Tris(dibenzylideneacetone)dipalladium (371.57 mg) was added, and the mixture was stirred at 125° C. for 12 h under $N_2$ atmosphere. 15 mL of ethyl acetate was added for dilution, and the mixture was filtered through diatomite and distilled at reduced pressure to give a crude product. The crude product was purified by column chromatography (0-15%, ethyl acetate/petroleum ether) to give compound 12-B. MS m/z: 362.1 $[M+H]^+$ Step 3: Synthesis of Compound 12-C Compound 12-B (135 mg) and compound 13-E (114.38 mg) were dissolved in dioxane (4 mL) and water (1 mL), and [1,1-bis(diphenylphosphino)ferrocene]palladium chloride (23.17 mg) and $K_2CO_3$ (131.27 mg) were added. The mixture was stirred at 90° C. for 1 h under $N_2$ atmosphere. After the completion of the reaction, the reaction solution was added to 20 mL of water and extracted with ethyl acetate (10 mL×3). The organic phase was washed with saturated brine (10 mL), dried over anhydrous sodium sulfate, filtered, and concentrated to give compound 12-C. MS m/z: 512.1 $[M+H]^+$.

Step 4: Synthesis of Compound 12-D

Compound 12-C (120 mg) was dissolved in methanol (2 mL) and water (1 mL), and sodium hydroxide (37.52 mg) was added. The mixture was stirred at 65° C. for 1 h. After the completion of the reaction, 20 mL of petroleum ether was added, the mixture was slurried, and then the phases were separated to give an aqueous layer. The aqueous layer was adjusted to pH of about 6 with 1 M diluted hydrochloric acid and extracted with ethyl acetate (10 mL×3), and the organic layer was dried over anhydrous sodium sulfate and concentrated to give compound 12-D. MS m/z: 498.2 $[M+H]^+$.

Step 5: Synthesis of Compound 12-E

Compound 12-D (100 mg) was dissolved in 5 mL of tetrahydrofuran, and 2.53 mL of diluted sulfuric acid (1 M, 2.53 mL) was added. The mixture was stirred at 60° C. for 0.5 h. The reaction solution was added to 5 mL of $H_2O$, and the mixture was adjusted to pH 7-8 with saturated sodium bicarbonate and extracted with ethyl acetate (10 mL×3). The organic phase was washed with 20 mL of saturated brine, dried over anhydrous sodium sulfate, and concentrated to give compound 12-E. MS m/z: 470.2 $[M+H+H_2O]^+$.

Step 6: Synthesis of Compound 12

Compound 12-E (102 mg), trifluoroacetate of compound 7-H (99.93 mg), and sodium acetate (42.25 mg) were dissolved in 2 mL of dichloromethane and 1 mL of methanol. After the mixture was clear, magnesium sulfate (135.95 mg) was added. After the mixture was stirred at 20° C. for 30 min, sodium triacetoxyborohydride (143.62 mg) was added, and the mixture was stirred at 20° C. for 2 h. After the completion of the reaction, the reaction solution was added to 10 mL of water, 2 drops of 1 M diluted hydrochloric acid were added, and the mixture was extracted with dichloromethane (20 mL×3). The organic phases were combined, washed once with saturated brine (10 mL), dried over anhydrous sodium sulfate, and concentrated by a rotary evaporator to give a crude product. The crude product was purified by column chromatography (methanol: 0-4%, methanol/dichloromethane) to give compound 12.

$^1H$ NMR (400 MHz, CHLOROFORM-d) 6=7.89 (s, 1H), 7.78-7.64 (m, 2H), 7.14-7.02 (m, 5H), 6.92 (br d, J=8.0 Hz, 2H), 6.81 (br s, 1H), 6.69-6.51 (m, 4H), 5.14 (br dd, J=4.5, 13.3 Hz, 1H), 4.38-4.14 (m, 2H), 3.61-3.50 (m, 2H), 3.32 (br s, 4H), 2.80 (br d, J=13.8 Hz, 4H), 2.67-2.53 (m, 7H), 2.28 (br s, 4H), 2.17-2.07 (m, 4H), 1.80 (br d, J=11.5 Hz, 2H), 1.27 (br d, J=11.5 Hz, 2H). MS m/z: 764.3 $[M+H]^+$.

Example 13
13
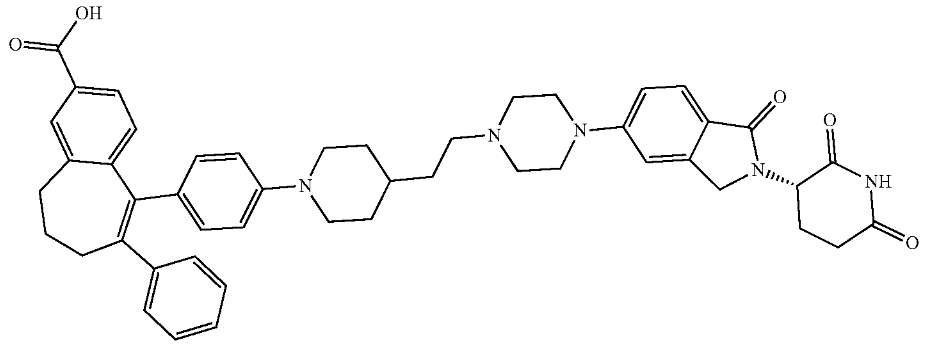
Synthetic Route:

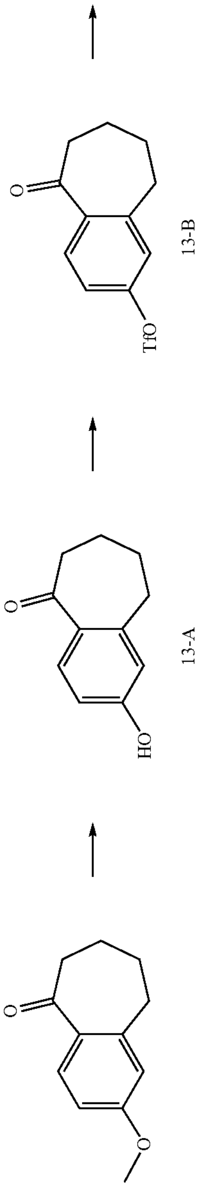
13-A
13-B

-continued
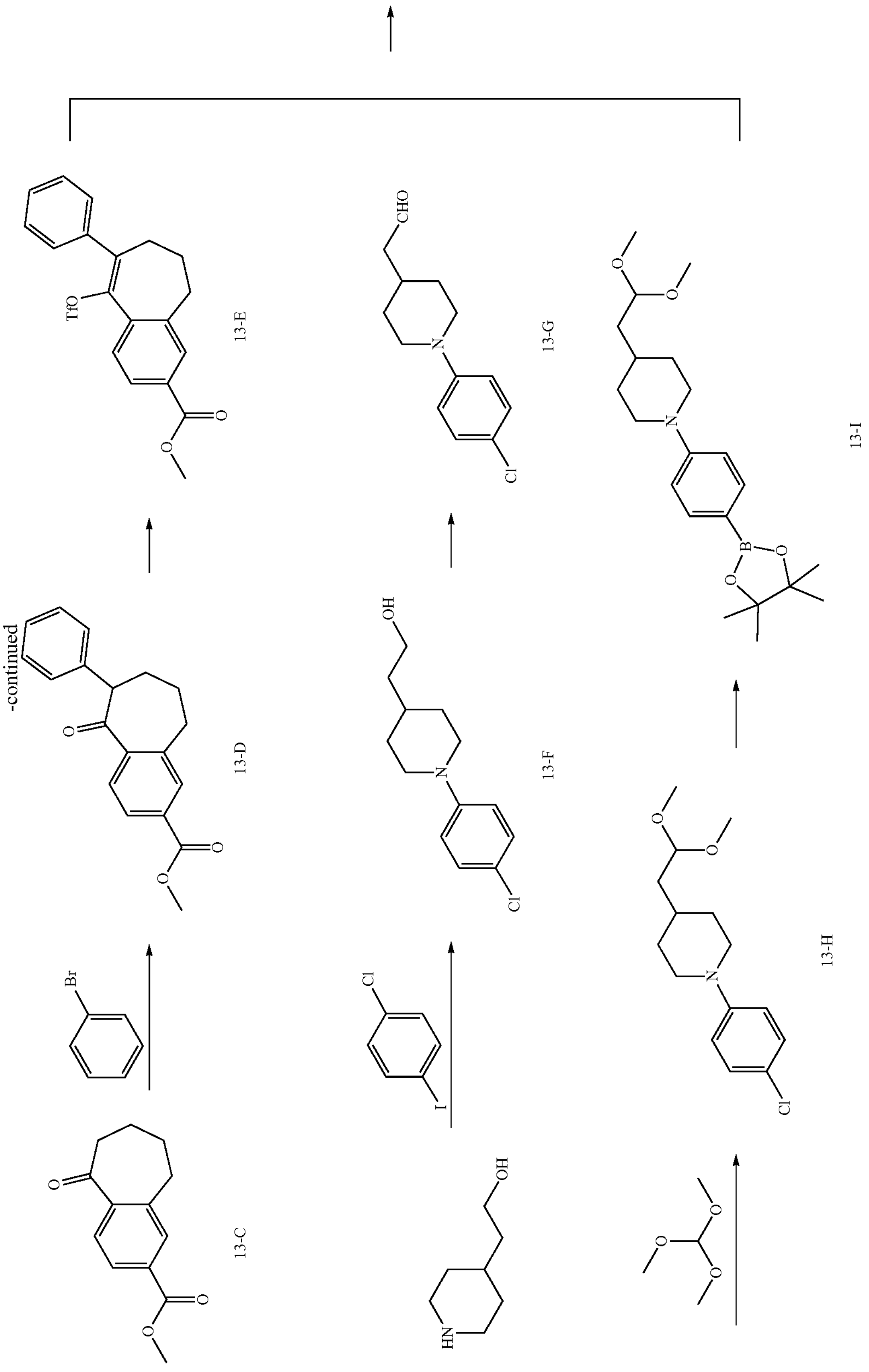
13-C
13-D
13-E
13-F
13-G
13-H
13-I

-continued
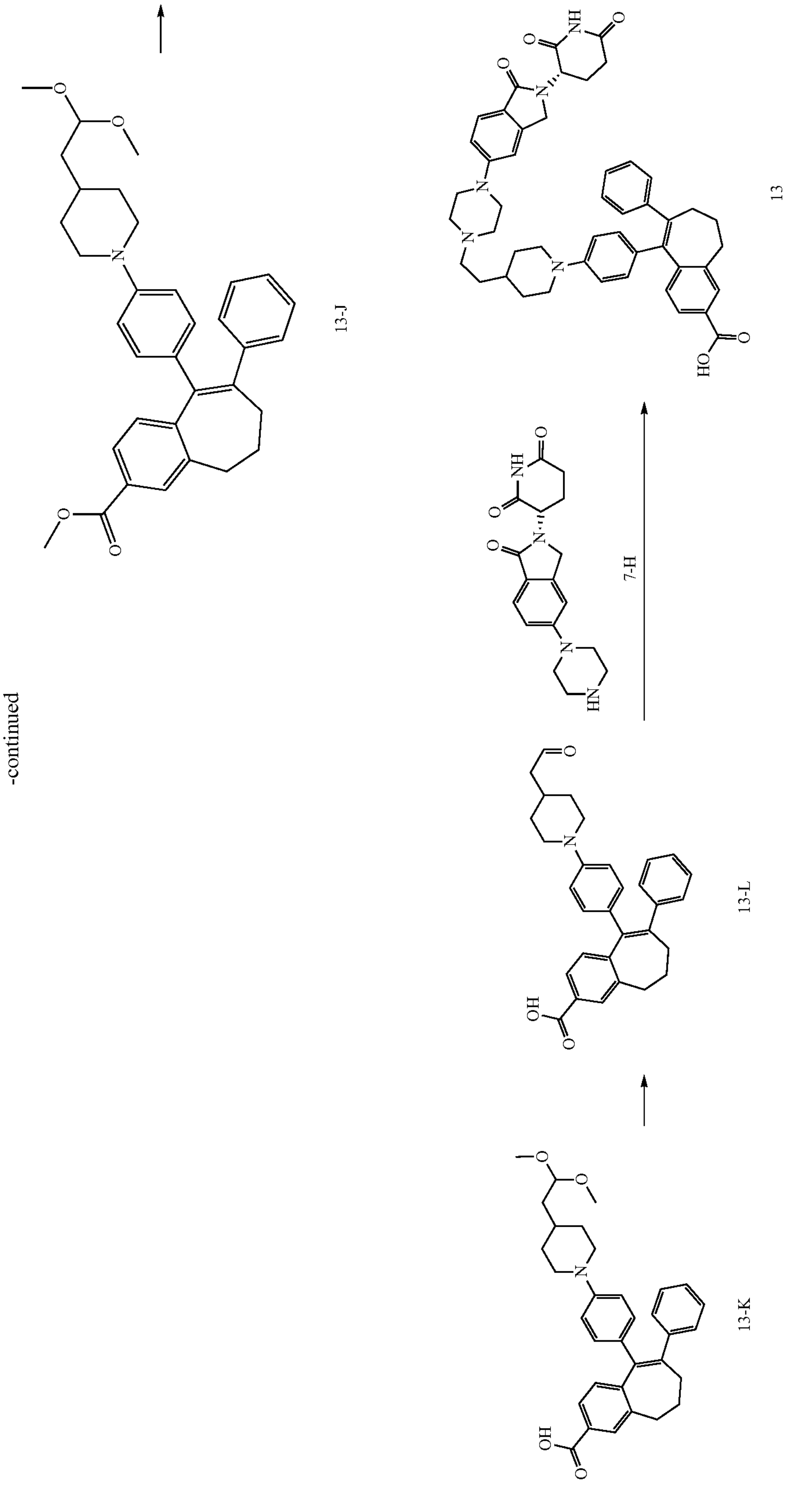
13-J
13-K
13-L
13

Step 1: Synthesis of Compound 13-A

Anhydrous toluene (140 mL) was added to a three-necked flask, and aluminum trichloride (8.41 g) was slowly added with stirring, followed by the addition of 2-methoxybenz-cycloheptan-5-one (5 g). The mixture was stirred at 90° C. for 1 h. The reaction solution was cooled to room temperature, poured into crushed ice (300 g) slowly, stirred for 20 min, and filtered. The filter cake was rinsed with water (75 mL) and isopropyl ether (75 mL), and concentrated by a rotary evaporator to give compound 13-A. MS m/z: 176.8 $[M+H]^+$.

Step 2: Synthesis of Compound 13-B

Compound 13-A (4.2 g) was dissolved in anhydrous dichloromethane (80 mL), and 2,6-dimethylpyridine (5.11 g) was added. Trifluoromethanesulfonic anhydride (13.45 g) was added at 0° C. under nitrogen atmosphere, and the mixture was stirred at 0° C. for 1 h under nitrogen atmosphere. The mixture was stirred at 25° C. for 47 h. The reaction solution was concentrated by a rotary evaporator to give a crude product. The crude product was separated by column chromatography (petroleum ether/ethyl acetate=3:1) and then separated by TLC (petroleum ether/ethyl acetate=3:1) to give compound 13-B. MS m/z: 308.9 $[M+H]^+$.

Step 3: Synthesis of Compound 13-C

Compound 13-B (1 g) was dissolved in anhydrous N,N-dimethylformamide (10 mL), and methanol (10 mL), N,N-diisopropylethylamine (1.61 g) and [1,1-bis(diphenylphosphino)ferrocene]palladium chloride (118.68 mg) were added. The mixture was stirred under carbon monoxide atmosphere at 45 PSI, 75° C. for 48 h. The reaction solution was filtered through diatomite, and the filtrate was concentrated by a rotary evaporator to give a crude product. The crude product was separated by column chromatography (petroleum ether/ethyl acetate=3:1) to give compound 13-C. MS m/z: 218.9 $[M+H]^+$.

$^1$H NMR (400 MHz, $CDCl_3$) δ=7.95 (dd, J=1.6, 7.9 Hz, 1H), 7.89 (s, 1H), 7.74 (d, J=8.0 Hz, 1H), 3.94 (s, 3H), 3.01-2.95 (m, 2H), 2.78-2.72 (m, 2H), 1.95-1.87 (m, 2H), 1.86-1.79 (m, 2H).

Step 4: Synthesis of Compound 13-D

Compound 13-C (0.54 g), bromobenzene (505.02 mg), sodium tert-butoxide (475.55 mg), 2-dicyclohexylphosphine-2,4,6-triisopropylbiphenyl (235.90 mg), and palladium acetate (55.55 mg) were mixed with toluene solution (5 mL) and stirred. The mixture was placed in a microwave tube, purged with nitrogen, and then subjected to a microwave reaction at 120° C. for 1 h. The reaction solution was filtered and subjected to rotary evaporation at reduced pressure to give a crude product. The crude product was purified by column chromatography (0-5%, ethyl acetate/petroleum ether) to give compound 13-D. MS m/z: 294.9 $[M+H]^+$.

$^1$H NMR (400 MHz, $CDCl_3$) δ=7.98-7.93 (m, 2H), 7.64 (d, J=8.3 Hz, 1H), 7.39-7.33 (m, 2H), 7.32-7.27 (m, 2H), 7.26 (d, J=1.8 Hz, 1H), 4.09-4.02 (m, 1H), 3.96 (s, 3H), 3.19-3.03 (m, 2H), 2.26-2.10 (m, 3H), 1.96-1.82 (m, 1H).

Step 5: Synthesis of Compound 13-E

Sodium hydride (298.94 mg, purity: 60%) was dissolved in 2-methyltetrahydrofuran (15 mL), and 1,8-diazabicyclo [5.4.0]undec-7-ene (15.16 mg) was added. A solution of 13-D (1 g) and N-phenylbis(trifluoromethanesulfonyl)imide (2.43 g) in 2-methyltetrahydrofuran (5 mL) was slowly added dropwise at 20° C. under nitrogen atmosphere, and the mixture was stirred at 20° C. for 12 h under nitrogen atmosphere. The reaction solution was cooled to 0° C., and 1 M diluted hydrochloric acid (8 mL) was slowly added dropwise. The phases were separated, and the organic phase was washed once with saturated brine (10 mL), dried over anhydrous sodium sulfate, filtered, and concentrated by a rotary evaporator to give a crude product. The crude product was separated by column chromatography (petroleum ether/ethyl acetate=5:1) to give compound 13-E.

Step 6: Synthesis of Compound 13-F

4-Piperidinoethanol (17 g), 1-chloro-4-iodobenzene (31.38 g) and L-prolyl amide (6.06 g) were dissolved in dimethyl sulfoxide (300 mL), and potassium carbonate (36.37 g) and cuprous iodide (5.01 g) were added. The mixture was stirred at 90° C. for 12 h under nitrogen atmosphere. After the completion of the reaction, water (300 mL) was added, and the mixture was stirred for 0.5 h and extracted with ethyl acetate (300 mL×4). The organic phase was washed with saturated brine (300 mL×3), dried over anhydrous sodium sulfate, filtered, and concentrated to give a crude product. The crude product was purified by column chromatography (0-15%, ethyl acetate/petroleum ether) to give compound 13-F.

$^1$H NMR (400 MHz, DMSO-$d_6$) δ=7.23-7.14 (m, 2H), 6.91 (br d, J=7.0 Hz, 2H), 3.68-3.59 (m, 2H), 3.51-3.42 (m, 2H), 3.34 (s, 1H), 2.61 (br t, J=12.2 Hz, 2H), 1.71 (br d, J=12.5 Hz, 2H), 1.59-1.46 (m, 1H), 1.38 (q, J=6.5 Hz, 2H), 1.26-1.14 (m, 2H).

Step 7: Synthesis of Compound 13-G

Dimethyl sulfoxide (26.07 g) was dissolved in dichloromethane (400 mL), the mixture was cooled to −78° C., and oxalyl chloride (31.77 g) was slowly added dropwise thereto. The mixture was stirred at −78° C. for 0.5 h, a solution of compound 13-F (20 g) in dichloromethane (400 mL) was then added dropwise, and the mixture was stirred at −78° C. for 0.5 h. Triethylamine (50.65 g) was finally added, and the mixture was stirred at 25° C. for 11 h. After the completion of the reaction, dichloromethane (800 mL) was added to dilute the reaction solution, and the organic phase was washed with saturated ammonium chloride solution (800 mL), water (800 mL) and saturated brine (800 mL) in sequence, dried over anhydrous sodium sulfate, filtered, and concentrated at reduced pressure to give compound 13-G.

$^1$H NMR (400 MHz, DMSO-$d_6$) δ=9.70 (t, J=1.8 Hz, 1H), 7.40-7.25 (m, 2H), 7.23-6.87 (m, 2H), 3.62 (br d, J=12.5 Hz, 2H), 3.07-2.72 (m, 2H), 2.46-2.41 (m, 2H), 2.12-1.95 (m, 1H), 1.83-1.70 (m, 2H), 1.53-1.29 (m, 2H).

Step 8: Synthesis of Compound 13-H

Compound 13-G (26 g) and trimethyl orthoformate (58.03 g) were dissolved in methanol (260 mL), and p-toluenesulfonic acid monohydrate (10.40 g) was added. The mixture was stirred at 25° C. for 12 h under nitrogen atmosphere. The mixture was adjusted to pH 7-8 with saturated sodium carbonate solution, water (260 mL) was added, and the mixture was then extracted with dichloromethane (260 mL×3). The organic phase was washed with saturated brine (260 mL×2), dried over anhydrous sodium sulfate, filtered, and concentrated by a rotary evaporator to give compound 13-H.

$^1$H NMR (400 MHz, DMSO-$d_6$) δ=7.24-7.16 (m, 2H), 6.92 (d, J=9.0 Hz, 2H), 4.47 (t, J=5.5 Hz, 1H), 3.64 (br d, J=12.5 Hz, 2H), 3.23 (s, 6H), 2.67-2.57 (m, 2H), 1.74 (br d, J=12.5 Hz, 2H), 1.49 (br d, J=4.8 Hz, 3H), 1.31-1.18 (m, 2H).

Step 9: Synthesis of Compound 13-I

Compound 13-H (3.4 g) and 2-di-tert-butylphosphine-2',4',6'-triisopropylbiphenyl (2.28 g) were dissolved in dioxane (100 mL), and bis(pinacolato)diboron (3.96 g) and potassium acetate (3.53 g) were added. The mixture was stirred for 5 min, and tris(dibenzylideneacetone)dipalladium (2.19 g) was added. The mixture was stirred at 125° C. for 12 h under $N_2$ atmosphere. Ethyl acetate (100) was added for dilution, and the mixture was filtered through diatomite and distilled at reduced pressure to give a crude product. The crude product was purified by column chromatography (0-5%, ethyl acetate/petroleum ether) to give compound 13-I.

$^1$H NMR (400 MHz, DMSO-$d_6$) δ=7.52-7.45 (m, 2H), 6.86 (d, J=8.8 Hz, 2H), 4.46 (t, J=5.6 Hz, 1H), 3.76 (br d, J=12.8 Hz, 2H), 3.21 (s, 6H), 2.68 (br t, J=12.4 Hz, 2H), 1.72 (br d, J=11.5 Hz, 2H), 1.54 (br s, 1H), 1.49-1.42 (m, 2H), 1.25 (s, 12H), 1.24-1.20 (m, 2H).

Step 10: Synthesis of Compound 13-J

Compounds 13-E (200 mg) and 13-I (176.03 mg) were dissolved in dioxane (6 mL) and water (2 mL), and potassium carbonate (194.47 mg) and [1,1-bis(diphenylphosphino)ferrocene]palladium chloride (34.32 mg) were added. The mixture was stirred at 90° C. for 2 h under $N_2$ atmosphere. After the completion of the reaction, the reaction solution was added to water (20 mL) and extracted with ethyl acetate (20 mL×3). The organic phase was washed with saturated brine (20 mL), dried over anhydrous sodium sulfate, filtered, and concentrated to give compound 13-J. MS m/z: 526.2 [M+H]$^+$.

Step 11: Synthesis of Compound 13-K

A solution of sodium hydroxide (57.07 mg) in water (5 mL) was added to a solution of compound 13-J (250 mg) in methanol (5 mL), and the reaction solution was heated to 65° C., stirred and reacted for 2.5 h. After the completion of the reaction, the mixture was adjusted to pH 7 to 8 with diluted hydrochloric acid (1 M) and extracted with dichloromethane (20 mL×3). The organic phase was washed with saturated brine (20 mL), dried over anhydrous sodium sulfate, filtered, and concentrated to give a crude product, which was slurried with petroleum ether (5 mL) and filtered. The filter cake was dried to give compound 13-K. MS m/z: 512.1 [M+H]$^+$.

Step 12: Synthesis of Compound 13-L

Diluted sulfuric acid (1 M, 5.91 mL) was added to a solution of compound 13-K (240 mg) in tetrahydrofuran (6 mL), and the reaction solution was heated to 60° C., stirred and reacted for 1 h. After the completion of the reaction, the reaction solution was cooled to room temperature, and slowly added to water (30 mL). The mixture was stirred at 20° C. for 10 min and filtered, and the filter cake was dried to give compound 13-L. MS m/z: 466.1 [M+H]$^+$.

Step 13: Synthesis of Compound 13

Trifluoroacetate of 7-H (176.73 mg), sodium acetate (54.62 mg), and magnesium sulfate (200.36 mg) were added in sequence to a solution of compound 13-L (155 mg) in dichloromethane (5 mL) and methanol (1 mL). After the reaction solution was stirred at 20° C. for 30 min, sodium triacetoxyborohydride (211.68 mg) was added, and the mixture was stirred at 20° C. for another 11.5 h. After the completion of the reaction, diluted hydrochloric acid (1 M, 1 mL) was added dropwise to the reaction solution. After being stirred for 10 min, the mixture was adjusted to pH 7 to 8 with saturated sodium bicarbonate (20 mL), extracted with dichloromethane (20 mL×3), washed with saturated brine (20 mL), dried over anhydrous sodium sulfate, filtered, and subjected to rotary evaporation at reduced pressure to give a crude product, which was purified by column chromatography (0-2%, methanol/dichloromethane) to give compound 13. MS m/z: 778.3 [M+H]$^+$.

$^1$H NMR (400 MHz, $CDCl_3$) δ=7.96 (d, J=1.3 Hz, 1H), 7.85-7.71 (m, 2H), 7.21-7.15 (m, 4H), 7.15-7.09 (m, 1H), 7.03-6.95 (m, 2H), 6.90 (s, 1H), 6.78-6.58 (m, 4H), 5.21 (dd, J=5.1, 13.2 Hz, 1H), 4.46-4.36 (m, 1H), 4.30-4.22 (m, 1H), 3.65-3.49 (m, 2H), 3.44 (br s, 4H), 2.95-2.83 (m, 7H), 2.61 (br s, 4H), 2.38-2.27 (m, 4H), 2.25-2.09 (m, 4H), 1.78 (br d, J=11.0 Hz, 2H), 1.60 (br d, J=8.0 Hz, 2H), 1.50-1.20 (m, 2H).

Example 14

14

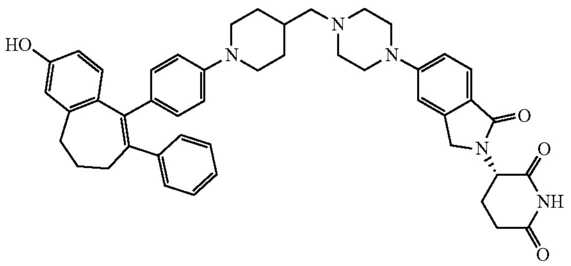

Synthetic Route:

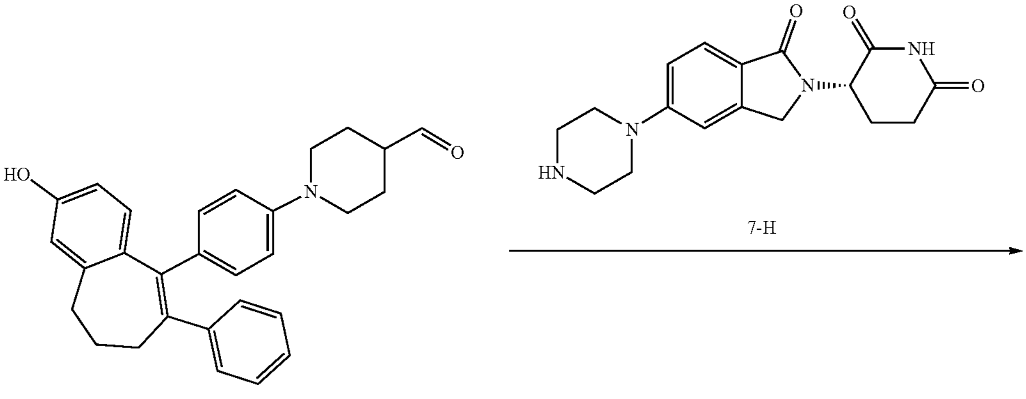

7-H

2-G

-continued

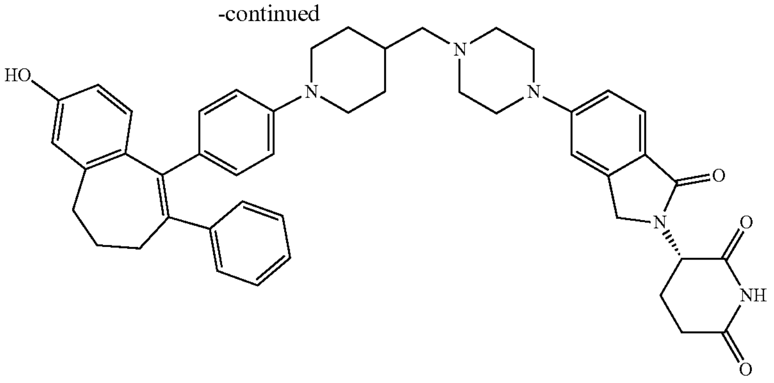

14

Step 1: Synthesis of Compound 14

Trifluoroacetate of 7-H (1.33 g), sodium acetate (449.33 mg), and magnesium sulfate (1.65 g) were added in sequence to a solution of compound 2-G (1.16 g) in dichloromethane (25 mL) and methanol (5 mL). After the reaction solution was stirred at 20° C. for 30 min, sodium triacetoxyborohydride (1.74 g) was added, and the mixture was stirred at 20° C. for another 3.5 h. After the completion of the reaction, diluted hydrochloric acid (1 M, 10 mL) was added dropwise to the reaction solution. After being stirred for 10 min, the mixture was adjusted to pH 7 to 8 with saturated sodium bicarbonate (30 mL), extracted with dichloromethane (50 mL×3), washed with saturated brine (20 mL), dried over anhydrous sodium sulfate, filtered, and subjected to rotary evaporation at reduced pressure to give a crude product, which was purified by column chromatography (methanol: 0-5%, methanol/dichloromethane) to give compound 14. MS m/z: 736.3 $[M+H]^+$.

$^1H$ NMR (400 MHz, $CDCl_3$) δ=8.16 (br s, 1H), 7.74 (br d, J=8.3 Hz, 1H), 7.21-7.06 (m, 5H), 6.99 (br d, J=8.5 Hz, 1H), 6.88 (br s, 1H), 6.78 (br d, J=7.5 Hz, 4H), 6.65 (br d, J=8.3 Hz, 2H), 6.56 (br d, J=8.3 Hz, 1H), 5.34-5.05 (m, 1H), 4.50-4.15 (m, 2H), 3.62 (br d, J=11.5 Hz, 2H), 3.33 (br s, 4H), 2.99-2.79 (m, 2H), 2.74 (br s, 2H), 2.68-2.54 (m, 6H), 2.39-2.11 (m, 8H), 1.86 (br d, J=11.3 Hz, 2H), 1.70 (br s, 2H), 1.37-1.26 (m, 2H).

Example 15

15

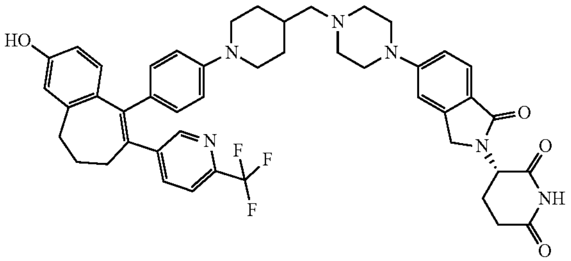

Synthetic Route:

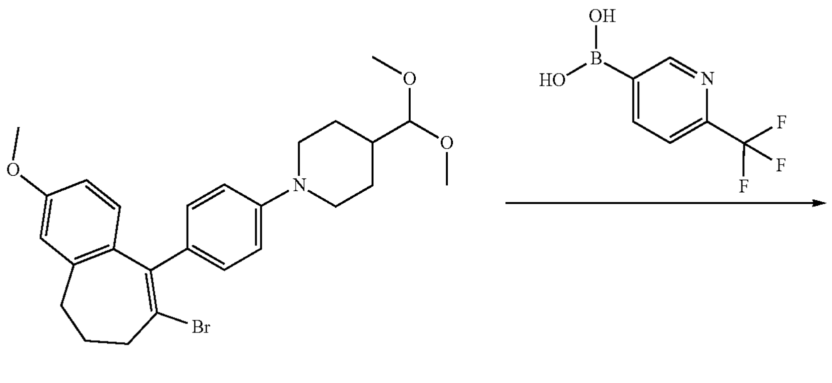

19-B

-continued

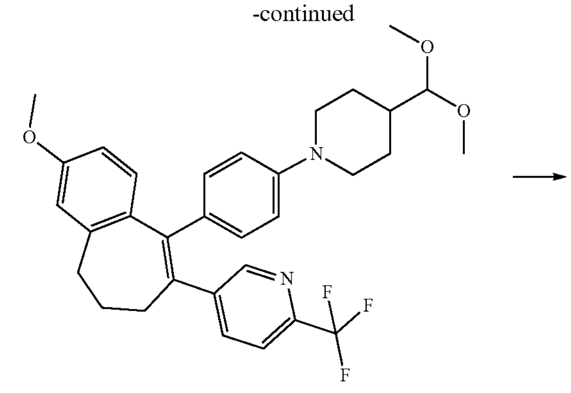

15-A

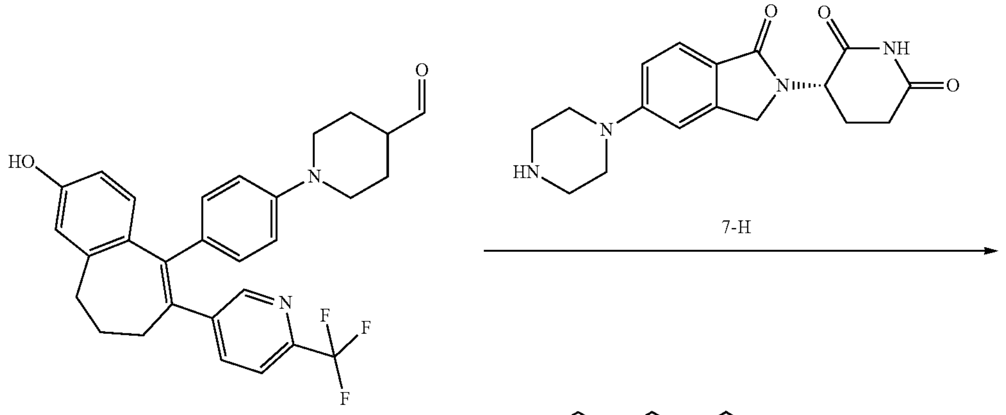

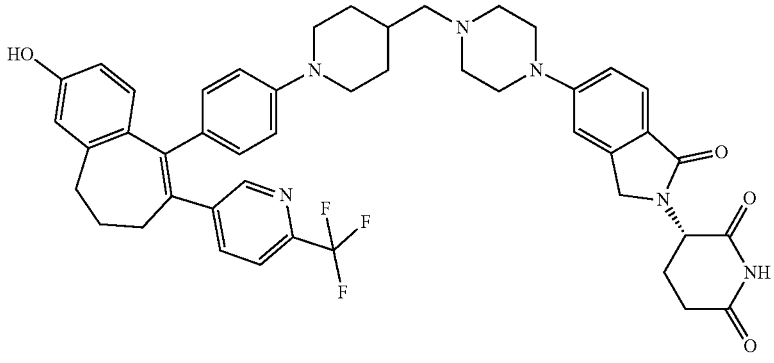

15

Step 1: Synthesis of Compound 15-A

Compound 19-B (100 mg) and 2-(trifluoromethyl)pyridine-5-boronic acid (51.02 mg) were dissolved in dioxane (5 mL) and water (1 mL), and potassium carbonate (65.37 mg) and tetrakis(triphenylphosphine)palladium (23.76 mg) were added. The mixture was stirred at 100° C. for 12 h under $N_2$ atmosphere. After the completion of the reaction, the reaction solution was added to water (50 mL) and extracted with ethyl acetate (20 mL×3). The organic phase was washed with saturated brine (20 mL), dried over anhydrous sodium sulfate, filtered, and concentrated to give compound 15-A. MS m/z: 553.1 $[M+H]^+$.

Step 2: Synthesis of Compound 15-B

Boron tribromide (453.33 mg) was added to a solution of compound 15-A (100 mg) in dichloromethane (20 mL) at 0° C. under nitrogen atmosphere, and the reaction solution was heated to 20° C., stirred and reacted for 1.5 h. After the completion of the reaction, the reaction solution was added slowly to water (30 mL) and extracted with dichloromethane (20 mL×3). The organic phase was washed with saturated brine (20 mL), dried over anhydrous magnesium sulfate, filtered, and concentrated to give compound 15-B. MS m/z: 493.0 $[M+H]^+$.

Step 3: Synthesis of Compound 15

Trifluoroacetate of 7-H (79.04 mg), sodium acetate (26.65 mg), and magnesium sulfate (97.76 mg) were added in sequence to a solution of compound 15-B (80 mg) in dichloromethane (25 mL) and methanol (5 mL). After the reaction solution was stirred at 20° C. for 30 min, sodium triacetoxyborohydride (103.27 mg) was added, and the mixture was stirred at 20° C. for another 11.5 h. After the completion of the reaction, diluted hydrochloric acid (1 M, 10 mL) was added dropwise to the reaction solution. After being stirred for 10 min, the mixture was adjusted to pH 7 to 8 with saturated sodium bicarbonate (30 mL), extracted with dichloromethane (50 mL×3), washed with saturated brine (20 mL), dried over anhydrous magnesium sulfate, filtered, and subjected to rotary evaporation at reduced pressure to give a crude product, which was purified by flash silica gel column chromatography (methanol: 0-5%, methanol/dichloromethane) to give compound 15. MS m/z: 805.2 $[M+H]^+$.

$^1H$ NMR (400 MHz, DMSO-$d_6$) δ=10.94 (br s, 1H), 9.49 (br s, 1H), 8.42 (s, 1H), 7.86 (br d, J=8.4 Hz, 1H), 7.73 (d, J=8.1 Hz, 1H), 7.51 (d, J=8.5 Hz, 1H), 7.06-7.04 (m, 2H), 6.76-6.63 (m, 5H), 6.62-6.55 (m, 2H), 5.04 (dd, J=4.9, 13.3 Hz, 1H), 4.35-4.18 (m, 2H), 3.64 (br d, J=11.9 Hz, 2H), 3.30 (br s, 4H), 2.96-2.84 (m, 1H), 2.76-2.55 (m, 6H), 2.42-2.26 (m 6H), 2.20 (br d, J=6.9 Hz, 2H), 2.10-1.90 (m, 4H), 1.78 (br d, J=11.3 Hz, 2H), 1.16 (br d, J=12.9 Hz, 2H).

Example 16

16

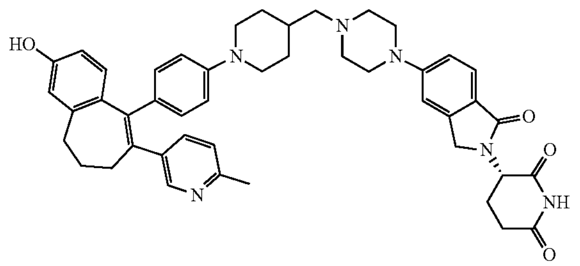

Synthetic Route:

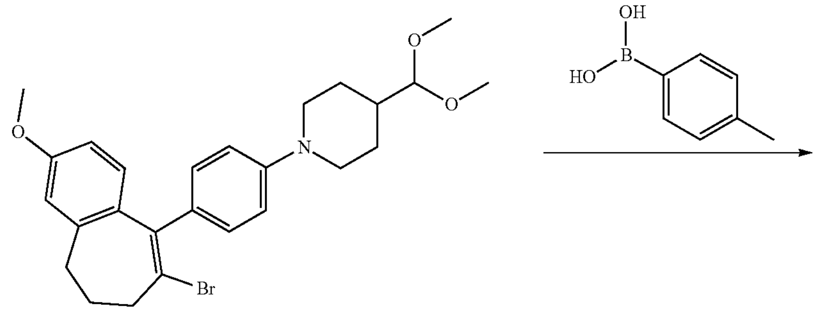

19-B

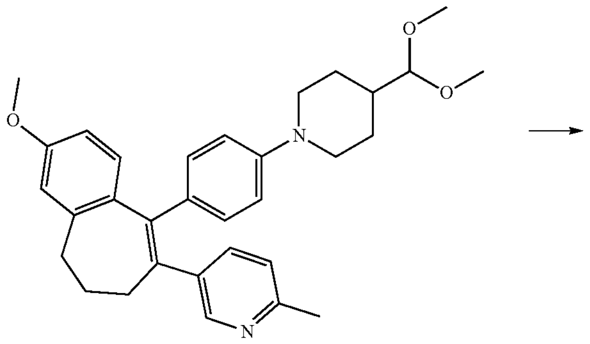

16-A

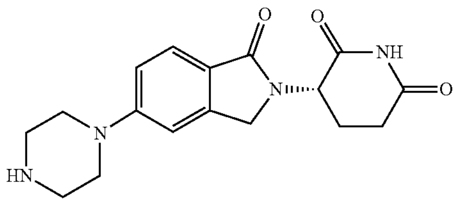

7-H

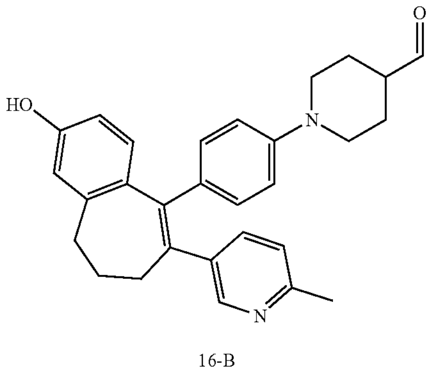

16-B

-continued

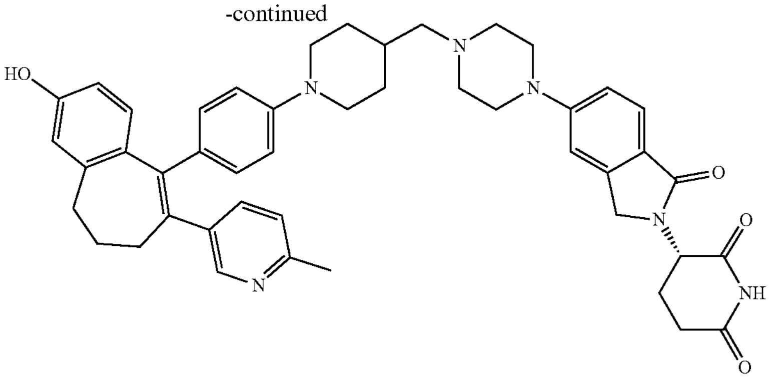

16

Step 1: Synthesis of Compound 16-A

Compound 19-B (0.3 g), 6-dimethylpyridineboronic acid (101.35 mg), and tetrakis(triphenylphosphine)palladium (71.27 mg) were dissolved in dioxane (4 mL), sodium carbonate (196.10 mg) and water (1 mL) were added, and the mixture was stirred and reacted at 100° C. for 1 h. 10 mL of ethyl acetate was added for dilution, the mixture was filtered through diatomite, and the phases were separated. The organic layer was washed with saturated brine (10 mL), dried over anhydrous sodium sulfate, filtered, and concentrated at reduced pressure to give a crude product. The crude product was purified by column chromatography (ethyl acetate: 0-50%, ethyl acetate/petroleum ether) to give compound 16-A. MS m/z: 499.1 [M+H]*.

Step 2: Synthesis of Compound 16-B

Compound 16-A (0.214 g) was dissolved in dichloromethane (10 mL), boron tribromide (1.08 g) was slowly added dropwise at 0° C., and the mixture was reacted for 1 h. The mixture was adjusted to pH 6-7 with saturated sodium bicarbonate solution and concentrated at reduced pressure to give 16-B. MS m/z: 439.2 $[M+H]^+$ Step 3: Synthesis of Compound 16

Compound 16-B (0.188 g), trifluoroacetate of 7-H (189.64 mg), and sodium acetate (80.17 mg) were dissolved in dichloromethane (10 mL), and 2 mL of methanol was added for assisted dissolution. After the mixture was clear, magnesium sulfate (258.00 mg) was added, and the mixture was stirred at 20° C. for 30 min. Sodium triacetoxyborohydride (272.56 mg) was added to the reaction solution, and the mixture was stirred at 20° C. for another 2 h. 2 drops of 1 M diluted hydrochloric acid were added, and the mixture was extracted with dichloromethane (20 mL×3). The organic phases were combined, washed once with saturated brine (10 mL), dried over anhydrous sodium sulfate, and concentrated by a rotary evaporator to give a crude product. The crude product was purified by column chromatography (methanol: 0-10%, methanol/dichloromethane) to give compound 16. MS m/z: 751.3 $[M+H]^+$.

$^1$H NMR (400 MHz, DMSO-$d_6$) δ=11.97 (br s, 1H), 10.95 (s, 1H), 9.42 (s, 1H), 8.13 (s, 1H), 7.53 (br s, 1H), 7.47 (br d, J=7.8 Hz, 1H), 7.09 (br d, J=8.0 Hz, 2H), 6.72-6.66 (m, 5H), 6.57 (s, 2H), 5.05 (br dd, J=4.9, 13.2 Hz, 1H), 4.40-4.16 (m, 2H), 3.64 (br d, J=9.8 Hz, 2H), 3.28 (s, 4H), 2.96-2.86 (m, 1H), 2.68-2.56 (m, 6H), 2.37-2.33 (m, 4H), 2.26-2.22 (m, 4H), 2.07-1.98 (m, 4H), 1.91 (s, 3H), 1.84-1.76 (m, 2H), 1.24-1.15 (m, 2H).

Example 17

17

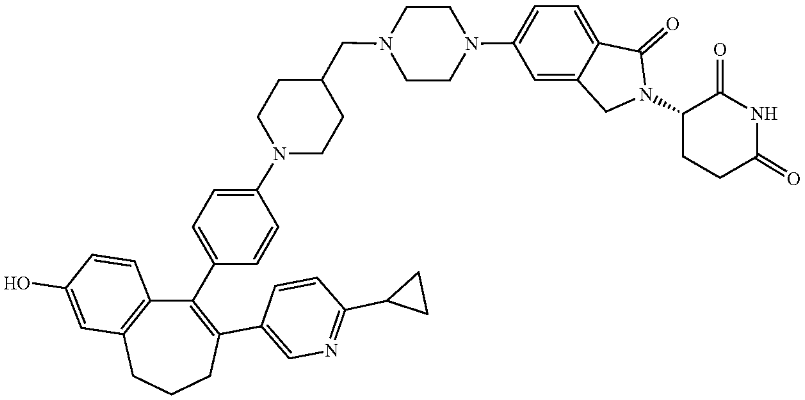

Synthetic Route:
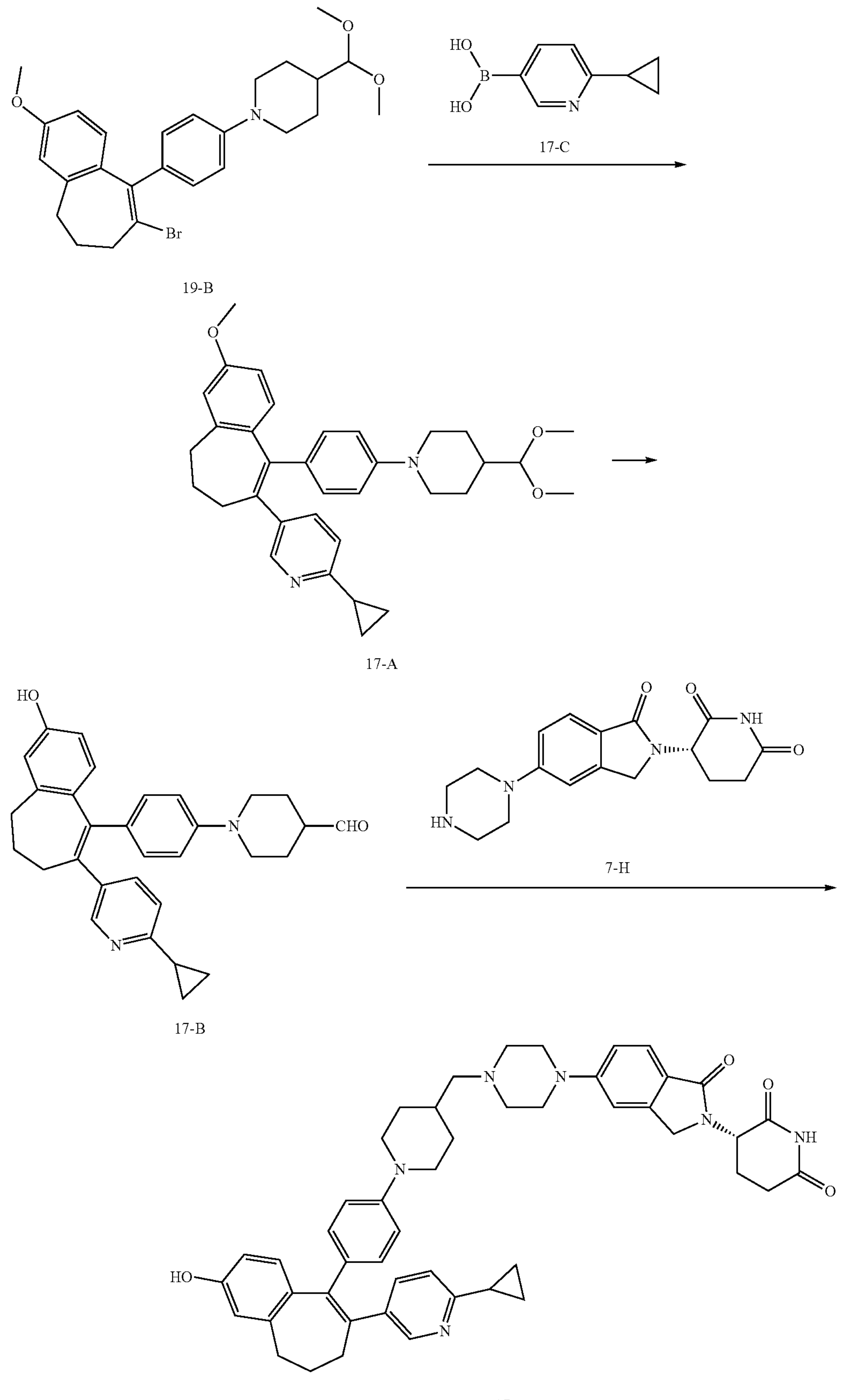
17

Step 1: Synthesis of Compound 17-A

Compounds 19-B (0.23 g) and 17-C (92.47 mg) were dissolved in dioxane (30 mL) and water (10 mL), followed by the addition of tetrakis(triphenylphosphine)palladium (54.64 mg) and sodium carbonate (150.34 mg). The mixture was reacted at 90° C. for 12 h under nitrogen atmosphere. After the completion of the reaction, the system was filtered, and the filtrate was extracted with water (20 mL×2) and ethyl acetate (20 mL×2), and dried over anhydrous sodium sulfate. The organic phase was concentrated at reduced pressure to give 17-A. MS m/z: 525.1 $[M+H]^+$.

Step 2: Synthesis of Compound 17-B

Compound 17-A (0.2 g) was dissolved in dichloromethane (40 mL), and $BBr_3$ (763.95 mg) was added at −60° C. The mixture was reacted at −60° C. to 25° C. for 2 h under nitrogen atmosphere. After the completion of the reaction, the system was quenched with water and extracted with dichloromethane (20 mL×2), and the product was in an aqueous phase. The pH of the aqueous phase was adjusted to be neutral, and the aqueous phase was concentrated at reduced pressure to give 17-B. MS m/z: 465.2 $[M+H]^+$.

Step 3: Synthesis of Compound 17

Compound 17-B (170 mg) and trifluoroacetate of 7-H (242.81 mg) were dissolved in dichloromethane (15 mL) and methanol (5 mL). Sodium acetate (60.03 mg) and anhydrous magnesium sulfate (220.22 mg) were added. After the mixture was stirred for 30 min, sodium triacetoxyborohydride (232.65 mg) was added, and the mixture was reacted at 25° C. for 12 h under nitrogen atmosphere. After the completion of the reaction, the system was filtered, the filtrate was extracted with water (20 mL) and dichloromethane (10 mL), and an aqueous phase was left. The aqueous phase was adjusted to pH=7 and concentrated at reduced pressure to give a crude product. The crude product was purified by column chromatography (methanol: 0-15%, methanol/dichloromethane) to give compound 17. MS m/z: 777.5 $[M+H]^+$.

$^1H$ NMR (400 MHz, DMSO-$d_6$) δ=10.95 (s, 1H), 9.42 (s, 1H), 8.10 (s, 1H), 7.70-7.53 (m, 2H), 7.41 (dd, J=2.3, 8.0 Hz, 1H), 7.34-7.31 (m, 1H), 7.10 (br d, J=8.0 Hz, 2H), 6.69 (br s, 4H), 6.56 (s, 2H), 5.05 (br dd, J=5.1, 13.2 Hz, 1H), 4.43-4.29 (m, 1H), 4.28-4.18 (m, 1H), 4.12 (br s, 3H), 3.67-3.60 (m, 4H), 3.17 (s, 5H), 2.90 (br s, 2H), 2.64 (br d, J=12.5 Hz, 4H), 2.22 (br d, J=6.3 Hz, 2H), 2.06-1.96 (m, 4H), 1.91 (s, 3H), 1.88-1.77 (m, 2H), 1.24 (br s, 1H), 0.91-0.80 (m, 4H).

Example 18

18

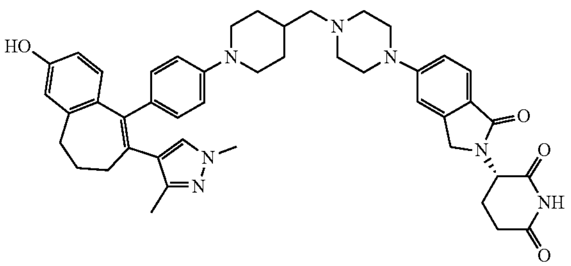

Synthetic Route:

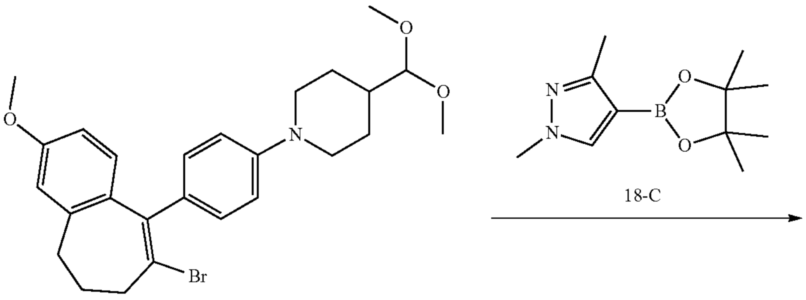

18-C

19-B

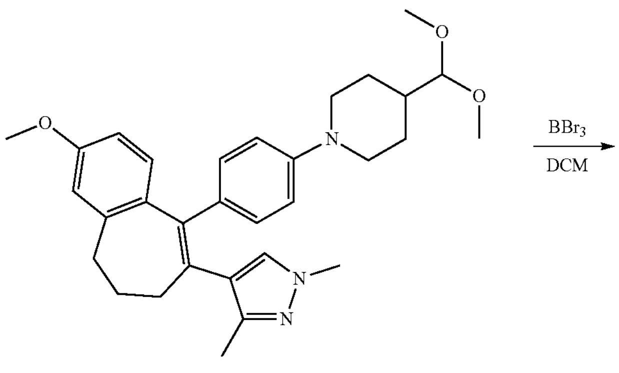

18-A

-continued

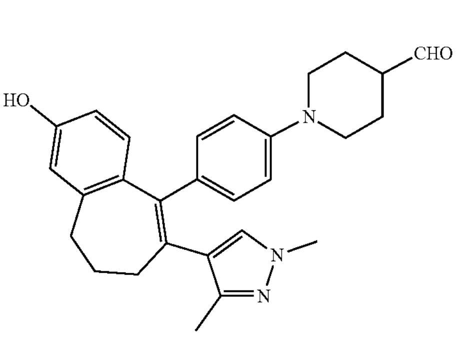

18-B

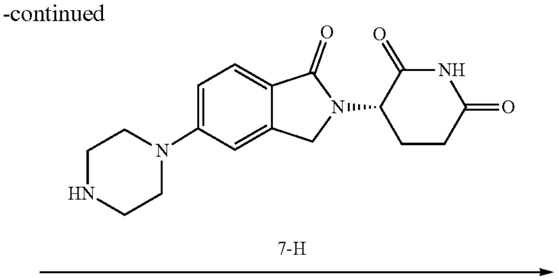

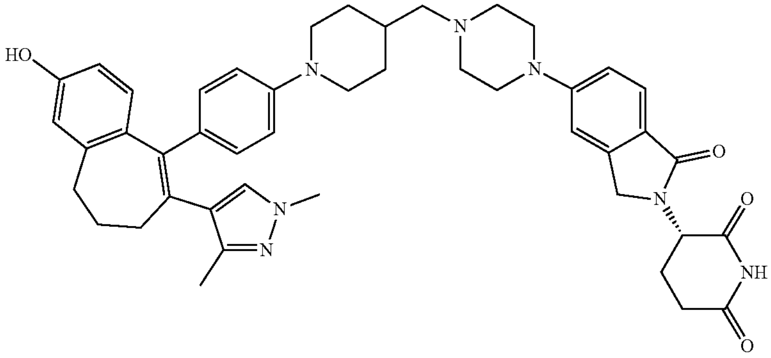

18

Step 1: Synthesis of Compound 18-A

Compounds 19-B (0.23 g) and 18-C (126.01 mg) were dissolved in dioxane (20 mL) and water (10 mL), followed by the addition of tetrakis(triphenylphosphine)palladium (54.64 mg) and sodium carbonate (150.34 mg). The mixture was reacted at 100° C. for 12 h under nitrogen atmosphere. After the completion of the reaction, the system was filtered, and the filtrate was extracted with water (20 mL×2) and ethyl acetate (20 mL×2), and dried over anhydrous sodium sulfate. The organic phase was concentrated at reduced pressure to give 18-A. MS m/z: 502.1 $[M+H]^+$.

Step 2: Synthesis of Compound 18-B

Compound 18-A (0.2 g) was dissolved in dichloromethane (15 mL), and boron tribromide (799.02 mg) was added at −60° C. The mixture was reacted at −60° C. to 25° C. for 2 h under nitrogen atmosphere. The system was quenched with 3 mL of water, the pH was adjusted to be neutral, and the system was dried over anhydrous sodium sulfate and concentrated at reduced pressure to give 18-B. MS m/z: 441.8 $[M+H]^+$.

Step 3: Synthesis of Compound 18

Compound 18-B (170 mg) and trifluoroacetate of 7-H (255.48 mg) were dissolved in dichloromethane (15 mL) and methanol (5 mL). Sodium acetate (63.16 mg) and anhydrous magnesium sulfate (231.71 mg) were added. After the mixture was stirred for 30 min, sodium triacetoxyborohydride (244.79 mg) was added, and the mixture was reacted at 25° C. for 12 h under nitrogen atmosphere. The system was filtered, water (5 mL) was added to the filtrate, and the mixture was adjusted to pH=7, dried over anhydrous sodium sulfate, and concentrated at reduced pressure to give a crude product. The crude product was purified by column chromatography (methanol %: 0-10%, methanol/dichloromethane) to give a crude product, which was purified by column chromatography (methanol %: 0-15%, methanol/dichloromethane) and then purified by thin layer chromatography (methanol %: 10%, methanol/dichloromethane) to give compound 18. MS m/z: 754.2 $[M+H]^+$.

$^1H$ NMR (400 MHz, DMSO-$d_6$) δ=10.95 (s, 1H), 9.31 (s, 1H), 7.57-7.48 (m, 2H), 7.15-7.02 (m, 2H), 6.78-6.47 (m, 7H), 5.05 (dd, J=5.1, 13.2 Hz, 1H), 4.39-4.15 (m, 2H), 3.69 (s, 3H) 3.64 (br d, J=13.1 Hz, 2H), 3.28-3.21 (m, 4H), 3.00-2.81 (m, 1H), 2.64-2.53 (m, 6H), 2.50-2.34 (m, 4H), 2.22 (br d, J=6.5 Hz, 2H), 2.13-2.08 (m, 2H), 2.03-1.94 (m, 2H), 1.80 (br d, J=11.8 Hz, 2H), 1.51 (s, 3H), 1.19 (br d, J=11.0 Hz, 2H).

Example 19

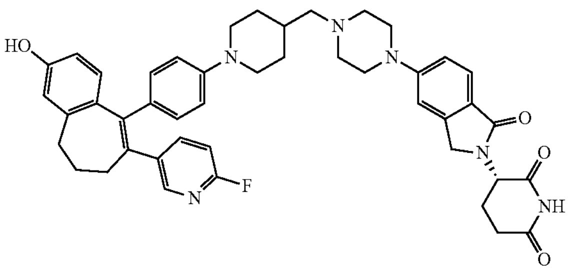

Synthetic Route:
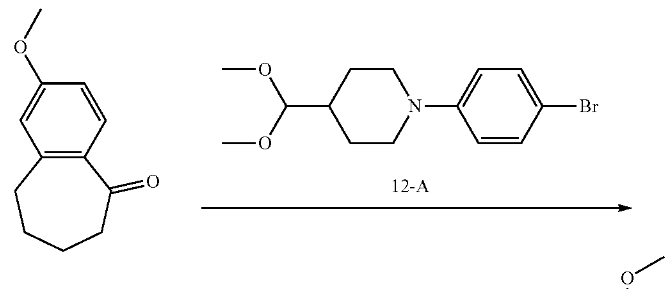
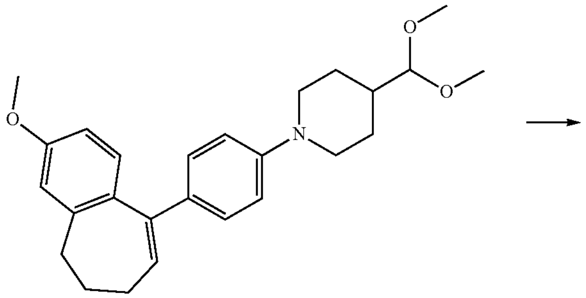
19-A
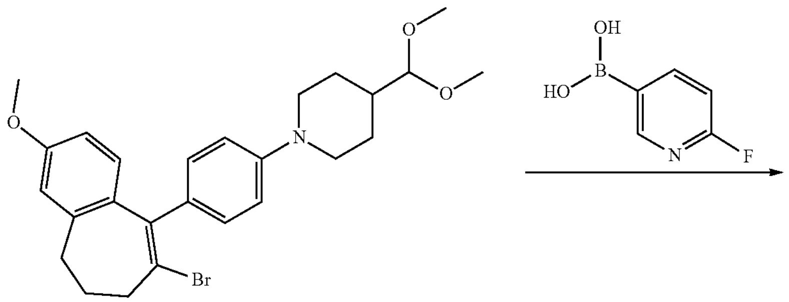
19-B
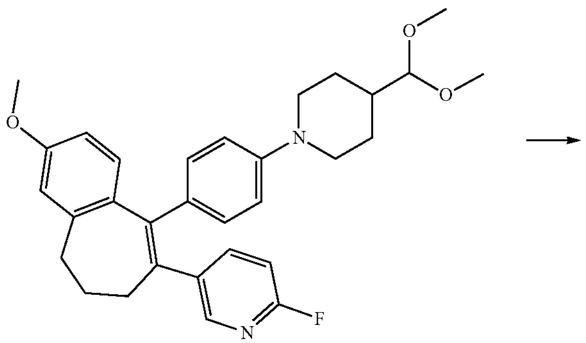
19-C

-continued

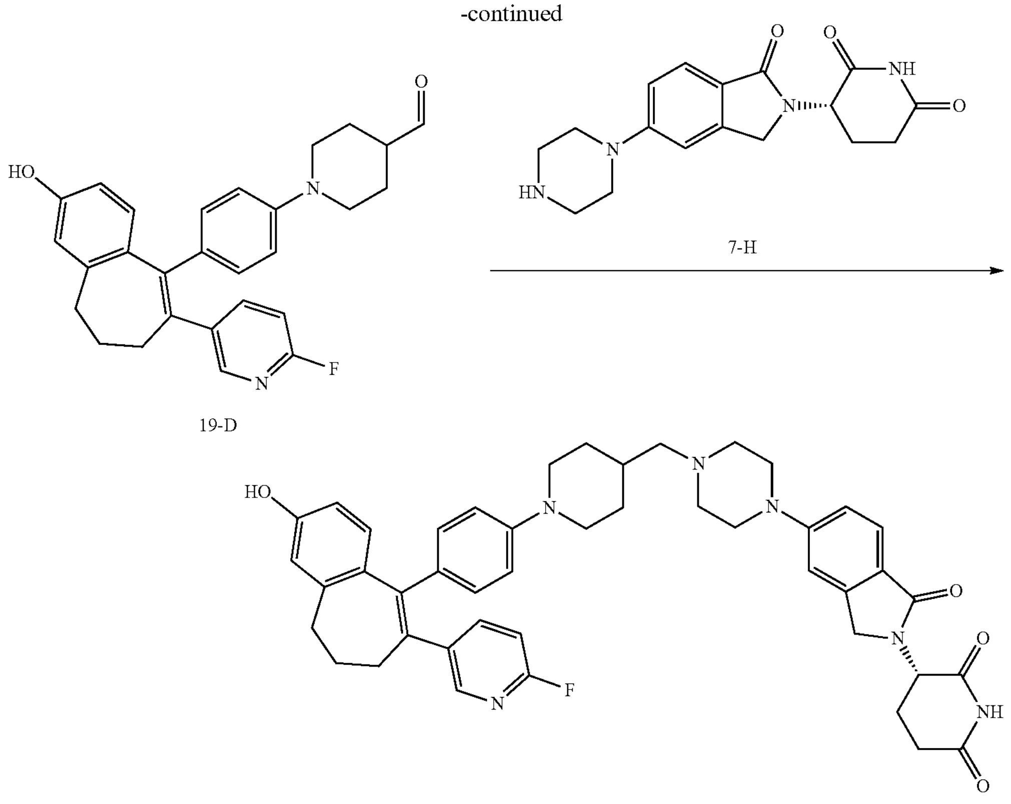

19-D

19

Step 1: Synthesis of Compound 19-A

Compound 2-methoxy-6,7,8,9-tetrahydro-5H-benzo[7]annulen-5-one (3 g) was dissolved in tetrahydrofuran (15 mL). The prepared 2-methoxy-6,7,8,9-tetrahydro-5H-benzo[7]annulen-5-one (5 mL) solution and diisobutylaluminum hydride toluene solution (1 M, 1.91 mL) was slowly added dropwise to a system containing magnesium chips (1.28 g) and tetrahydrofuran (5 mL) at 20° C. under $N_2$ atmosphere. The remaining 2-methoxy-6,7,8,9-tetrahydro-5H-benzo[7]annulen-5-one solution was slowly added dropwise at a controlled temperature of below 50° C. After addition, the mixture was stirred at 20° C. for 1 h, heated to 60° C., stirred for 1 h to prepare the corresponding Grignard reagent, and cooled to −5° C. 12-A (1.45 g) was dissolved in THF (15 mL), and the mixture was slowly added dropwise to the above Grignard reagent. The mixture was stirred at 20° C. for 12 h, quenched with water (30 mL), and filtered. 1 M diluted hydrochloric acid was added to the filtrate to adjust the pH to 5-6, the mixture was extracted with EA (30 mL×3), and the organic phase was washed with saturated brine (30 mL), dried over anhydrous sodium sulfate, filtered, and concentrated at reduced pressure to give a crude product. The crude product was purified by column chromatography (ethyl acetate: 0-5%, ethyl acetate/petroleum ether) to give compound 19-A. MS m/z: 408.6 $[M+H]^+$.

Step 2: Synthesis of Compound 19-B

Compound 19-A (0.7 g) was dissolved in tetrahydrofuran (5 mL), pyridinium tribromide (604.26 mg) was added, and the mixture was stirred at 20° C. for 24 h and concentrated at reduced pressure. Water (10 mL) and dichloromethane (10 mL) were added, and the mixture was stirred for 1 h. The phases were separated, and the aqueous phase was extracted with dichloromethane (10 mL×2). The organic phases were combined, washed with 10% aqueous sodium hydroxide solution (10 mL) and saturated brine (10 mL), dried over anhydrous sodium sulfate, filtered, and concentrated at reduced pressure to give a crude product. The crude product was purified by column chromatography (ethyl acetate: 0-7%, ethyl acetate/petroleum ether) to give compound 19-B. MS m/z: 488.0 $[M+H]^+$.

Step 3: Synthesis of Compound 19-C

Compound 19-B (250 mg), 2-fluoropyridine-5-boronic acid (94.14 mg), and tetrakis(triphenylphosphine)palladium (59.39 mg) were dissolved in dioxane (10 mL), sodium carbonate (163.42 mg) and water (2 mL) were added, and the mixture was stirred and reacted at 100° C. for 12 h. 10 mL of ethyl acetate was added for dilution, the mixture was filtered through diatomite, and the phases were separated. The organic layer was washed with saturated brine (10 mL), dried over anhydrous sodium sulfate, filtered, and concentrated at reduced pressure to give a crude product. The crude product was purified by column chromatography (ethyl acetate: 0-30%, ethyl acetate/petroleum ether) to give compound 19-C. MS m/z: 503.2 $[M+H]^+$.

$^1H$ NMR (400 MHz, DMSO-$d_6$) δ=7.96-7.88 (m, 1H), 7.83-7.73 (m, 1H), 7.07-6.95 (m, 1H), 6.92-6.87 (m, 1H), 6.77-6.62 (m, 6H), 4.10-4.03 (m, 1H), 3.77 (s, 3H), 3.69-3.59 (m, 2H), 3.26 (s, 6H), 2.75 (br t, J=6.5 Hz, 2H), 2.57 (br s, 2H), 2.29-2.23 (m, 1H), 2.29-2.23 (m, 2H), 2.08 (br t, J=7.0 Hz, 2H), 1.67 (br d, J=10.3 Hz, 2H), 1.32-1.17 (m, 2H).

Step 4: Synthesis of Compound 19-D

Compound 19-C (230 mg) was dissolved in dichloromethane (25 mL), and boron tribromide (1.15 g) was added. The mixture was stirred at −60° C. to 20° C. for 4 h under nitrogen atmosphere. The reaction solution was slowly added to water (50 mL), the phases were separated, and the aqueous phase was extracted with dichloromethane (20 mL×3). The organic phases were combined, and the organic layer was washed with saturated brine (20 mL), dried over anhydrous sodium sulfate, filtered, and concentrated at reduced pressure to give 19-D. MS m/z: 442.8 $[M+H]^+$.

Step 5: Synthesis of Compound 19

Compound 19-D (290.78 mg) and trifluoroacetate of compound 7-H (319.76 mg) were dissolved in a solution of methanol (10 mL) and dichloromethane (2 mL), and sodium acetate (112.48 mg) and magnesium sulfate (412.63 mg) were added. The mixture was stirred at 20° C. for 30 min. Sodium triacetoxyborohydride (435.92 mg) was added to the reaction solution, and the mixture was stirred at 20° C. for another 11.5 h. 1 M diluted hydrochloric acid (5 mL) was added and stirred for 30 min to quench the reaction. The mixture was adjusted to pH 7 with saturated sodium bicarbonate solution and extracted with dichloromethane (100 mL×3). The organic phases were combined, washed with saturated brine (20 mL×2), dried over anhydrous sodium sulfate, filtered, and concentrated at reduced pressure to give a crude product. The crude product was purified by column chromatography (methanol: 0-10%, methanol/dichloromethane) to give compound 19. MS m/z: 755.4 $[M+H]^+$.

$^1H$ NMR (400 MHz, DMSO-$d_6$) δ=11.01-10.89 (m, 1H), 7.95-7.86 (m, 1H), 7.80-7.71 (m, 1H), 7.52 (d, J=8.8 Hz, 1H), 7.10-7.00 (m, 3H), 6.76-6.52 (m, 8H), 5.05 (dd, J=5.1, 13.3 Hz, 1H), 4.39-4.14 (m, 2H), 3.63 (br d, J=12.0 Hz, 2H), 3.33 (br s, 6H), 2.96-2.84 (m, 1H), 2.73-2.56 (m, 6H), 2.44-2.28 (m, 2H), 2.27-2.15 (m, 4H), 2.12-2.02 (m, 2H), 2.01-1.86 (m, 3H), 1.83-1.73 (m, 2H), 1.72-1.62 (m, 1H).

Example 20

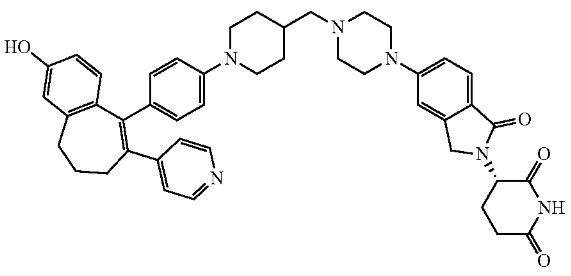

Synthetic Route:

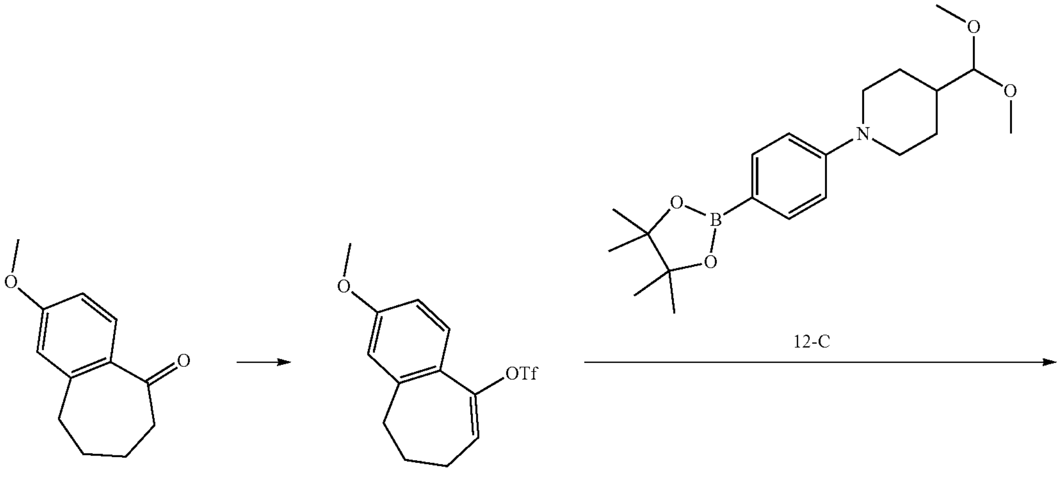

20-A

12-C

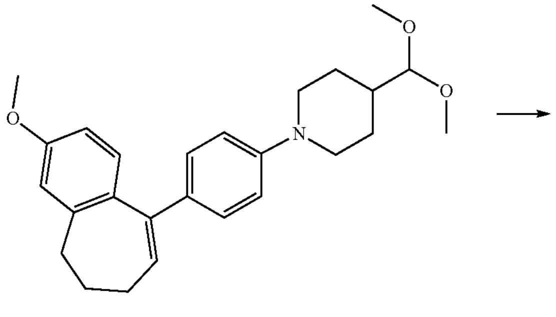

19-A

-continued

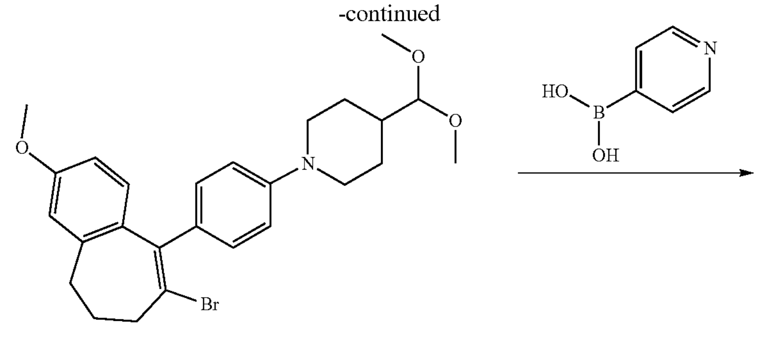

19-B

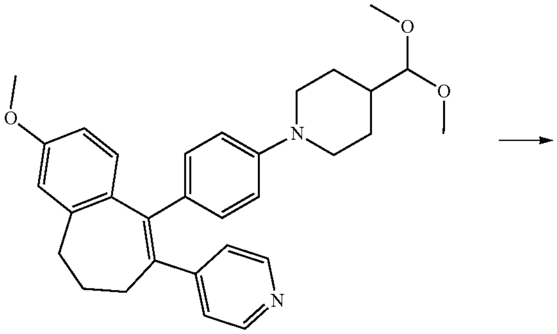

20-B

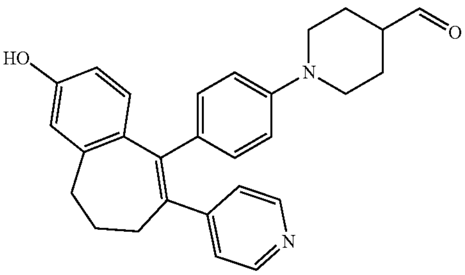

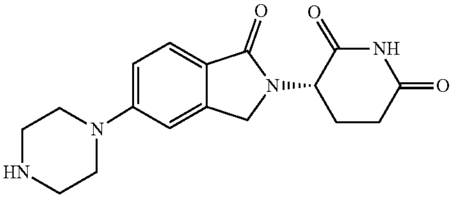

7-H

20-C

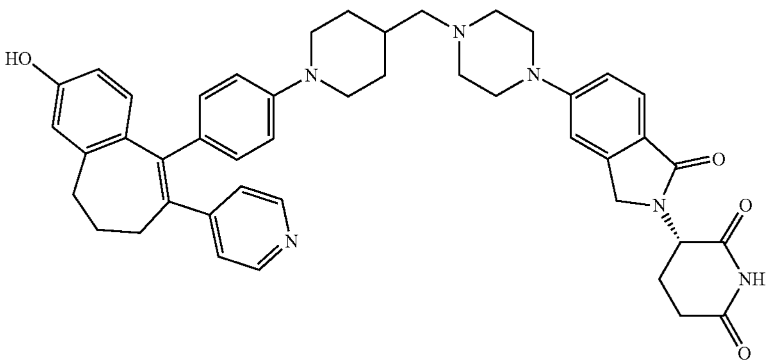

20

Step 1: Synthesis of Compound 20-A

Pyridine (6.24 g) was added to a solution of compound 2-methoxy-6,7,8,9-tetrahydro-5H-benzo[7]annulen-5-one (10.00 g) in dichloromethane (150 mL), trifluoromethanesulfonic anhydride (22.25 g) was slowly added dropwise at 0° C., and the mixture was stirred at 25° C. for 5 h. After the completion of the reaction, the reaction solution was poured into 200 mL of water and extracted with dichloromethane (200 mL×3). The organic phase was washed with saturated sodium bicarbonate solution (80 mL×1), dried over anhydrous sodium sulfate, filtered, and concentrated to give crude product 20-A.

Step 2: Synthesis of Compound 19-A

12-C (7.4 g), [1,1-bis(diphenylphosphino)ferrocene]palladium dichloride (1.50 g), and potassium carbonate (8.49 g) were added to a solution of compound 20-A (9.90 g) in 1,4-dioxane (80 mL) and water (20 mL), and the mixture was purged with nitrogen for 3 times and reacted at 90° C. for 1 h. After the completion of the reaction, the reaction solution was cooled to room temperature and filtered through diatomite, the filter cake was washed with ethyl acetate (20 mL×6), and the organic phase was concentrated at reduced pressure to give a crude product. The crude product was purified by column chromatography (ethyl acetate %: 0-5%, ethyl acetate/petroleum ether) to give compound 19-A. MS m/z: 408.1 $[M+H]^+$.

$^1$H NMR (400 MHz, DMSO-$d_6$) δ=7.05 (d, J=8.5 Hz, 2H), 6.92-6.81 (m, 4H), 6.80-6.74 (m, 1H), 6.24 (t, J=7.3 Hz, 1H), 4.12-4.06 (m, 1H), 3.77 (s, 3H), 3.71 (br d, J=12.5 Hz, 2H), 3.27 (s, 6H), 2.67-2.55 (m, 3H), 2.09 (quin, J=6.9 Hz, 2H), 1.85 (q, J=7.0 Hz, 2H), 1.70 (br d, J=9.0 Hz, 3H), 1.39-1.22 (m, 3H).

Step 3: Synthesis of Compound 19-B

Pyridinium tribromide (5.10 g) was added to a solution of compound 19-A (5.00 g) in tetrahydrofuran (100 mL), and the mixture was stirred at 25° C. for 12 h. After the completion of the reaction, 100 mL of water was added to the reaction solution, and the mixture was stirred for 30 min and extracted with dichloromethane (80 mL×3). The organic phase was washed with saturated sodium carbonate solution (100 mL×1), dried over anhydrous sodium sulfate, filtered, and concentrated to give a crude product. The crude product was purified by column chromatography (ethyl acetate %: 0-7%, ethyl acetate/petroleum ether) to give compound 19-B. MS m/z: 486.0 $[M+H]^+$.

$^1$H NMR (400 MHz, $CDCl_3$) δ=7.13 (d, J=8.5 Hz, 2H), 6.86 (d, J=8.5 Hz, 2H), 6.78-6.74 (m, 2H), 6.64 (dd, J=2.8, 8.5 Hz, 1H), 4.09 (d, J=7.3 Hz, 1H), 3.80 (s, 3H), 3.75 (br d, J=12.3 Hz, 2H), 3.37 (s, 6H), 2.77-2.70 (m, 3H), 2.69 (br d, J=2.0 Hz, 1H), 2.56 (t, J=6.9 Hz, 2H), 2.32-2.24 (m, 2H), 1.85 (br d, J=12.8 Hz, 2H), 1.78-1.70 (m, 1H), 1.44 (dq, J=3.8, 12.3 Hz, 2H).

Step 4: Synthesis of Compound 20-B

4-Pyridineboronic acid (50.54 mg), tetrakis(triphenylphosphine)palladium (95.02 mg), and sodium carbonate (130.73 mg) were added to a solution of compound 19-B (0.20 g) in 1,4-dioxane (10 mL) and water (2 mL), and the mixture was purged with nitrogen for 3 times and reacted at 100° C. for 2 h. After the completion of the reaction, the reaction solution was cooled to room temperature, 10 mL of water was added to the reaction solution, and the mixture was extracted with ethyl acetate (20 mL×2). The organic phase was dried over anhydrous sodium sulfate, filtered, and concentrated to give crude product 20-B. MS m/z: 485.1 $[M+H]^+$.

Step 5: Synthesis of Compound 20-C

Boron tribromide (1.03 g) was added to a solution of compound 20-B (199 mg) in dichloromethane (15 mL) at 0° C., and the reaction solution was stirred at 20° C. for 1 h. After the completion of the reaction, the reaction solution was added to 50 mL of water, and the mixture was adjusted to pH 7 with sodium carbonate solid and extracted with dichloromethane (20 mL×3). The organic phase was dried over anhydrous sodium sulfate, filtered, and concentrated at reduced pressure to give crude compound 20-C. MS m/z: 425.1 $[M+H]^+$.

Step 6: Synthesis of Compound 20

Sodium acetate (67.24 mg) and magnesium sulfate (246.68 mg) were added to a solution of compound 20-C (174 mg) and trifluoroacetate of compound 7-H (235.71 mg) in dichloromethane (10 mL) and methanol (2 mL), and the reaction solution was stirred at 20° C. for 30 min. Sodium triacetoxyborohydride (260.60 mg) was added to the reaction solution, and the mixture was stirred at 20° C. for another 12 h. 1 mL of water was added to the reaction solution, and the mixture was stirred for 10 min and concentrated at reduced pressure to give a crude product, which was purified by column chromatography (methanol %: 0-5%, methanol/dichloromethane) to give compound 20. MS m/z: 737.2 $[M+H]^+$.

$^1$H NMR (400 MHz, DMSO-$d_6$) δ=10.95 (br s, 1H), 9.47 (s, 1H), 8.33 (d, J=5.8 Hz, 2H), 7.53 (d, J=8.5 Hz, 1H), 7.13-7.03 (m, 4H), 6.73-6.66 (m, 5H), 6.59 (s, 2H), 5.05 (dd, J=4.9, 13.2 Hz, 1H), 4.37-4.30 (m, 1H), 4.24-4.17 (m, 1H), 3.64 (br d, J=12.5 Hz, 2H), 3.30 (br d, J=5.5 Hz, 6H), 3.00-2.80 (m, 1H), 2.70-2.53 (m, 8H), 2.40-2.32 (m, 2H), 2.28-2.19 (m, 4H), 2.06-1.94 (m, 3H), 1.81-1.65 (m, 3H).

Example 21

21

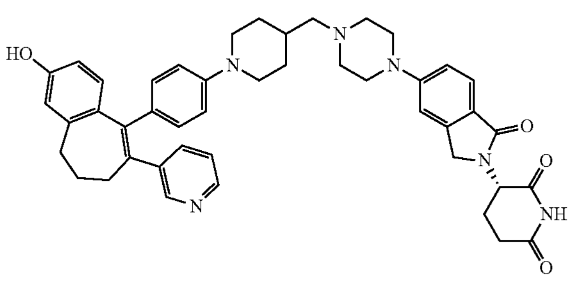

Synthetic Route:

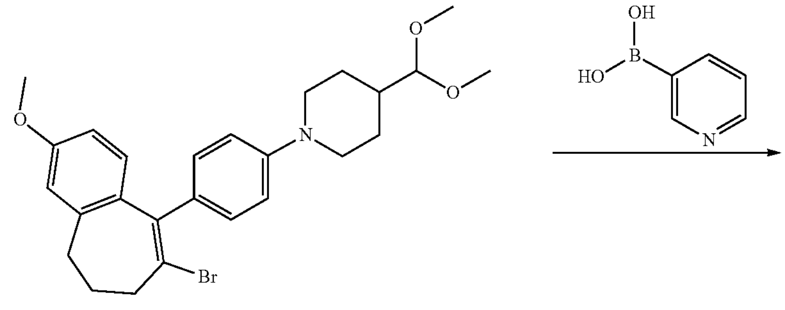

19-B

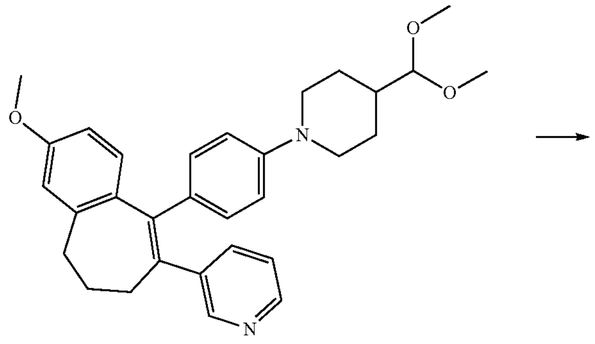

21-C

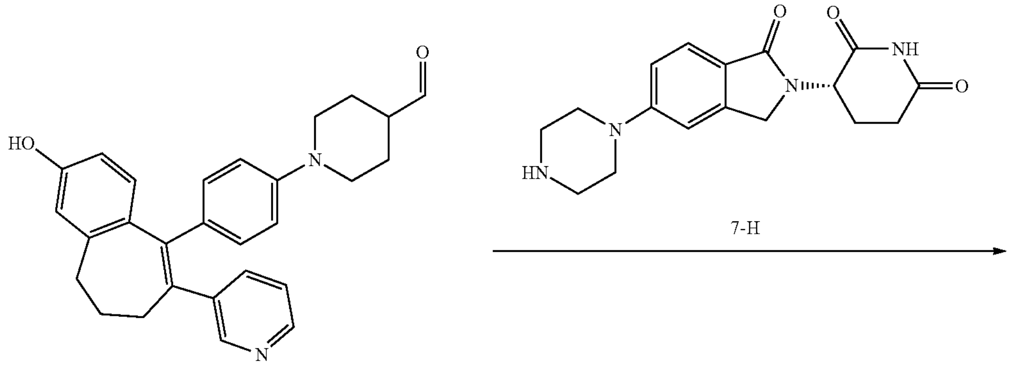

7-H

21-D

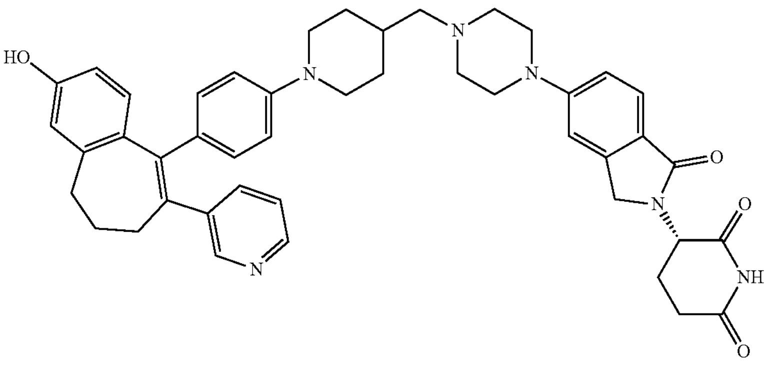

21

Step 1: Synthesis of Compound 21-C

Compound 19-B (300 mg), 3-pyridineboronic acid (98.55 mg), and tetrakis(triphenylphosphine)palladium (71.27 mg) were dissolved in dioxane (8 mL), sodium carbonate (196.10 mg) and water (2 mL) were added, and the mixture was stirred and reacted at 100° C. for 12 h. 10 mL of ethyl acetate was added for dilution, the mixture was filtered through diatomite, and the phases were separated. The organic layer was washed with saturated brine (10 mL), dried over anhydrous sodium sulfate, filtered, and concentrated at reduced pressure to give a crude product. The crude product was purified by column chromatography (ethyl acetate: 0-7%, ethyl acetate/petroleum ether) to give compound 21-C. MS m/z: 485.0 $[M+H]^+$.

$^1H$ NMR (400 MHz, DMSO-$d_6$) δ=7.68-7.50 (m, 3H), 7.27-7.19 (m, 1H), 6.94-6.86 (m, 1H), 6.78-6.60 (m, 6H), 4.08-4.03 (m, 1H), 3.77 (s, 3H), 3.62 (br d, J=11.8 Hz, 2H), 3.25 (s, 6H), 2.80-2.70 (m, 2H), 2.55 (br s, 2H), 2.26 (br t, J=6.8 Hz, 2H), 2.14-2.01 (m, 2H), 1.73-1.59 (m, 3H), 1.33-1.18 (m, 2H).

Step 2: Synthesis of Compound 21-D

Compound 21-C (250 mg) was dissolved in dichloromethane (25 mL), and boron tribromide (1.29 g) was added. The mixture was stirred at −60° C. to 20° C. for 12 h under nitrogen atmosphere. The reaction solution was slowly added to 50 mL of water, the mixture was adjusted to pH 6-7 with saturated sodium bicarbonate solution, and the phases were separated. The aqueous phase was extracted with dichloromethane/methanol=4/1 (20 mL×3), and the organic phases were combined, dried over anhydrous sodium sulfate, filtered, and concentrated at reduced pressure to give 21-D. MS m/z: 425.1 $[M+H]^+$.

Step 3: Synthesis of Compound 21

Compound 21-D (280 mg) and trifluoroacetate of compound 7-H (291.78 mg) were dissolved in a solution of methanol (10 mL) and dichloromethane (2 mL), and sodium acetate (108.21 mg) and magnesium sulfate (396.95 mg) were added. The mixture was stirred at 20° C. for 30 min. Sodium triacetoxyborohydride (419.35 mg) was added to the reaction solution, and the mixture was stirred at 20° C. for another 11.5 h. 1 M diluted hydrochloric acid (1 mL) was added and stirred for 30 min to quench the reaction, and the mixture was concentrated at reduced pressure to give a crude product. The crude product was purified by column chromatography (methanol: 0-10%, methanol/dichloromethane) to give compound 21. MS m/z: 737.2 $[M+H]^+$.

$^1H$ NMR (400 MHz, DMSO-$d_6$) δ=10.95 (s, 1H), 9.43 (s, 1H), 8.36-8.17 (m, 2H), 7.67-7.45 (m, 2H), 7.28-7.19 (m, 1H), 7.10-7.01 (m, 2H), 6.73-6.52 (m, 7H), 5.05 (dd, J=5.0, 13.3 Hz, 1H), 4.39-4.13 (m, 2H), 3.61 (br d, J=11.8 Hz, 2H), 3.28 (brs, 4H), 2.97-2.83 (m, 1H), 2.76-2.54 (m, 6H), 2.50-2.45 (m, 4H), 2.42-2.30 (m, 2H), 2.29-2.14 (m, 4H), 2.12-2.01 (m, 2H), 1.77 (br d, J=12.0 Hz, 2H), 1.27-1.06 (m, 2H).

22

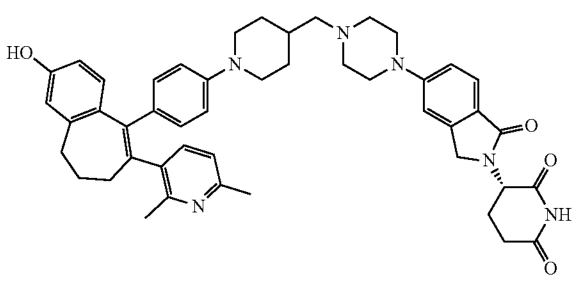

Synthetic Route:

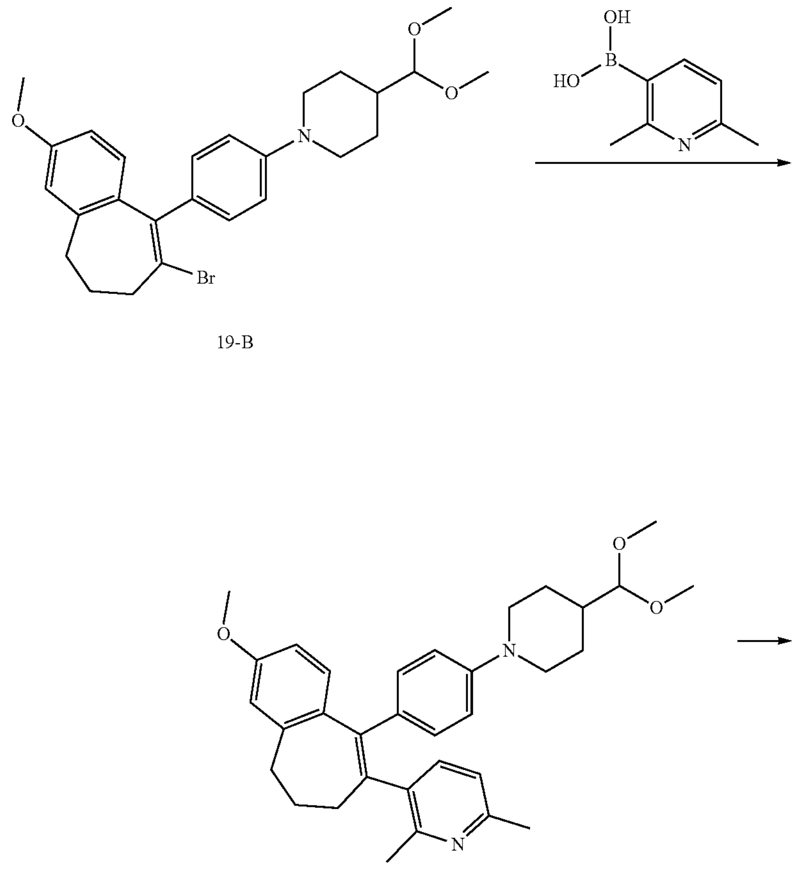

19-B

22-A

-continued

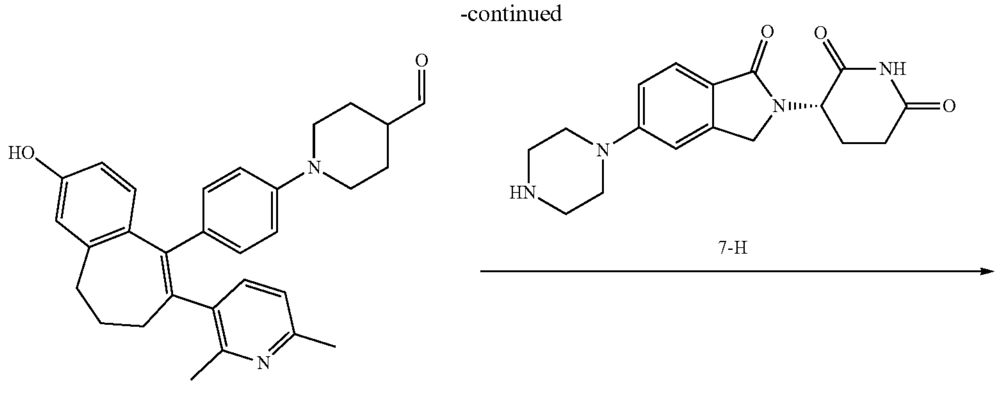

22-B

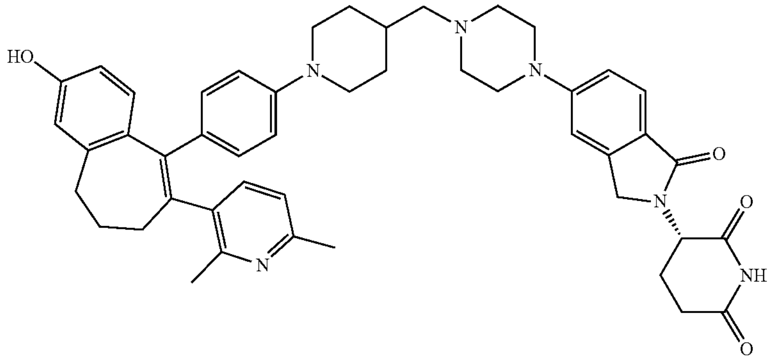

22

Step 1: Synthesis of Compound 22-A

Compound 19-B (300 mg), 2,6-dimethylpyridine-3-boronic acid (111.73 mg), and tetrakis(triphenylphosphine) palladium (71.27 mg) were dissolved in dioxane (4 mL), sodium carbonate (196.10 mg) and water (1 mL) were added, and the mixture was stirred and reacted at 100° C. for 1 h. 10 mL of ethyl acetate was added for dilution, the mixture was filtered through diatomite, and the phases were separated. The organic layer was washed with saturated brine (10 mL), dried over anhydrous sodium sulfate, filtered, and concentrated at reduced pressure to give crude compound 22-A. MS m/z: 513.1 $[M+H]^+$.

Step 2: Synthesis of Compound 22-B

Compound 22-A (550 mg) was dissolved in dichloromethane (10 mL), and boron tribromide (2.69 g) was added. The mixture was stirred at 0° C. for 1 h under nitrogen atmosphere. The reaction solution was adjusted to pH 7 with saturated sodium bicarbonate solution and concentrated by a rotary evaporator to give crude compound 22-B. MS m/z: 453.1 $[M+H]^+$.

Step 3: Synthesis of Compound 22

22-B (0.4 g), trifluoroacetate of 7-H (390.99 mg), and sodium acetate (165.30 mg) were dissolved in dichloromethane (4 mL), and 2 mL of methanol was added for assisted dissolution. After the mixture was clear, magnesium sulfate (851.07 mg) was added, and the mixture was stirred at 20° C. for 30 min. Sodium triacetoxyborohydride (561.94 mg) was added, and the mixture was stirred at 20° C. for 2 h. 2 drops of 1 M diluted hydrochloric acid were added to quench the reaction, and the mixture was extracted with dichloromethane (20 mL×3). The organic phases were combined, washed once with saturated brine (10 mL), dried over anhydrous sodium sulfate, and concentrated by a rotary evaporator to give a crude product. The crude product was purified by column chromatography (methanol: 0-10%, methanol/dichloromethane) to give compound 22. MS m/z: 765.3 $[M+H]^+$.

$^1H$ NMR (400 MHz, $CD_3OD$) δ=7.67-7.64 (d, J=8.0 Hz, 1H), 7.44-7.40 (m, 1H), 7.13-7.08 (m, 2H), 7.02-6.98 (d, J=8.0 Hz, 1H), 6.75-6.73 (m, 1H), 6.72-6.67 (m, 5H), 6.62-6.58 (m, 1H), 5.15-5.08 (m, 1H), 4.45-4.38 (m, 2H), 3.66-3.56 (m, 2H), 3.39 (s, 4H), 2.98-2.87 (m, 1H), 2.84-2.80 (m, 2H), 2.69-2.58 (m, 6H), 2.51-2.41 (m, 5H), 2.38-2.25 (m, 7H), 2.23-2.18 (m, 4H), 1.93-1.85 (m, 2H), 1.38-1.33 (m, 2H).

23

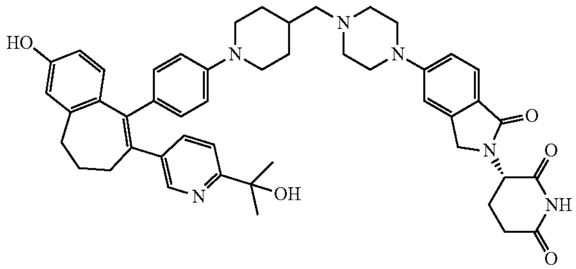

Synthetic Route:

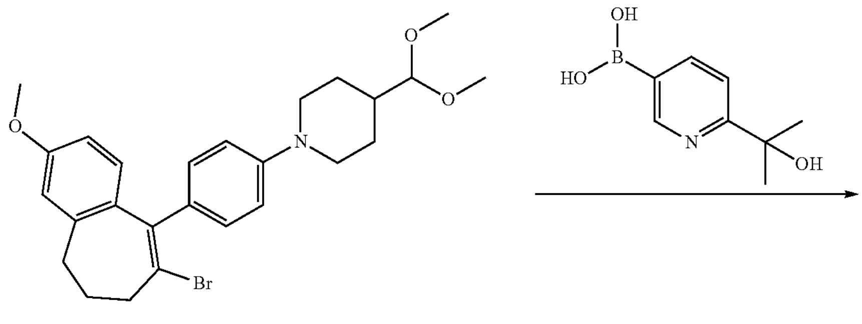

19-B

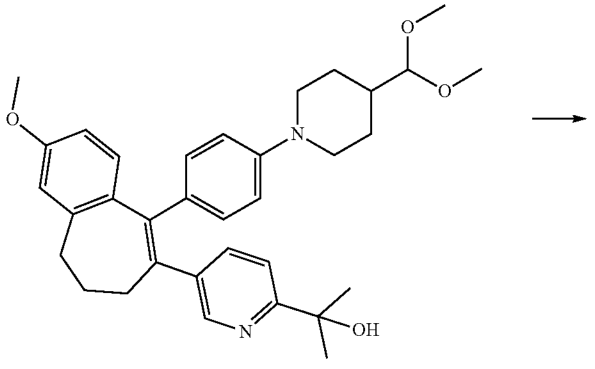

23-C

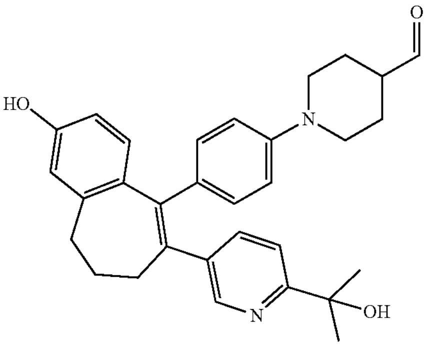

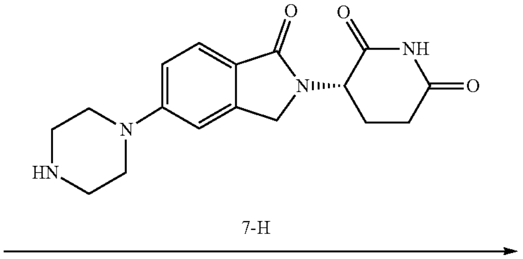

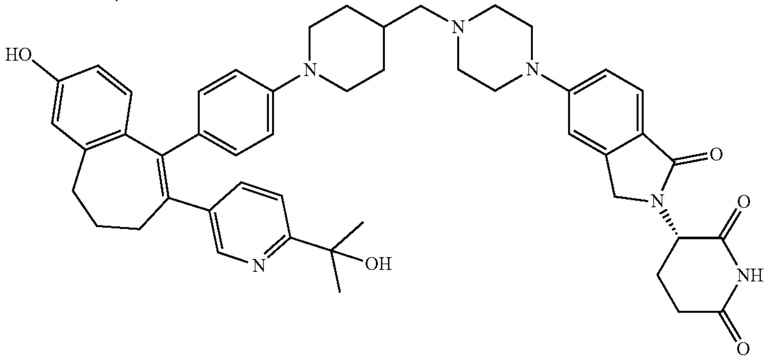

23

Step 1: Synthesis of Compound 23-C

Compound 19-B (0.5 g), (6-(2-hydroxypropan-2-yl)pyridin-3-yl)boronic acid (744.17 mg), and tetrakis(triphenylphosphine)palladium (237.55 mg) were dissolved in dioxane (10 mL), sodium carbonate (326.83 mg) and water (2 mL) were added, and the mixture was stirred and reacted at 100° C. for 12 h. The reaction solution was cooled to room temperature and concentrated at reduced pressure to give a crude product. The crude product was purified by column chromatography (ethyl acetate: 0-30%, ethyl acetate/petroleum ether) to give compound 23-C. MS m/z: 543.1 $[M+H]^+$.

$^1H$ NMR (400 MHz) δ=8.29 (d, J=1.5 Hz, 1H), 7.47 (dd, J=2.1, 8.2 Hz, 1H), 7.14 (d, J=8.3 Hz, 1H), 6.83 (d, J=8.5 Hz, 1H), 6.81 (d, J=2.5 Hz, 1H), 6.75 (d, J=8.8 Hz, 2H), 6.69 (dd, J=2.8, 8.5 Hz, 1H), 6.65 (br d, J=8.8 Hz, 2H), 4.99 (br s, 1H), 4.06 (d, J=7.3 Hz, 1H), 3.83 (s, 3H), 3.64 (br d, J=12.3 Hz, 2H), 3.36 (s, 6H), 2.77 (t, J=6.9 Hz, 2H), 2.67-2.56 (m, 2H), 2.41-2.32 (m, 2H), 2.15 (quin, J=6.9 Hz, 2H), 1.82 (br d, J=12.5 Hz, 2H), 1.77-1.57 (m, 3H), 1.50 (s, 6H).

Step 2: Synthesis of Compound 23-D

Compound 23-C (420 mg) was dissolved in dichloromethane (40 mL), and boron tribromide (1.94 g) was added. The mixture was stirred at −60° C. to 20° C. for 3 h under nitrogen atmosphere. The reaction solution was slowly added to 50 mL of water, the mixture was adjusted to pH 6-7 with saturated sodium bicarbonate solution, and the phases were separated. The aqueous phase was extracted with dichloromethane/methanol=4/1 (20 mL×3), and the organic phases were combined, dried over anhydrous sodium sulfate, filtered, and concentrated at reduced pressure to give 23-D. MS m/z: 483.2 $[M+H]^+$.

Step 3: Synthesis of Compound 23

Compound 23-D (490 mg) and trifluoroacetate of compound 7-H (449.16 mg) were dissolved in a solution of methanol (10 mL) and dichloromethane (2 mL), and sodium acetate (166.57 mg) and magnesium sulfate (611.06 mg) were added. The mixture was stirred at 20° C. for 30 min. Sodium triacetoxyborohydride (645.55 mg) was added to the reaction solution, and the mixture was stirred at 20° C. for another 11.5 h. 1 M diluted hydrochloric acid (1 mL) was added and stirred for 30 min to quench the reaction, and the mixture was concentrated at reduced pressure to give a crude product. The crude product was purified by column chromatography (methanol: 0-10%, methanol/dichloromethane) to give compound 23. MS m/z: 795.3 $[M+H]^+$.

$^1H$ NMR (400 MHz, DMSO-$d_6$) δ=10.94 (s, 1H), 9.42 (br s, 1H), 8.17 (d, J=1.5 Hz, 1H), 7.56-7.50 (m, 2H), 7.46 (d, J=8.3 Hz, 1H), 7.08-7.02 (m, 2H), 6.72-6.65 (m, 5H), 6.60-6.53 (m, 2H), 5.04 (dd, J=5.0, 13.1 Hz, 1H), 4.36-4.17 (m, 2H), 3.61 (br d, J=12.0 Hz, 2H), 3.28 (br s, 4H), 3.17 (d, J=4.0 Hz, 2H), 2.95-2.84 (m, 1H), 2.73-2.53 (m, 6H), 2.45-2.30 (m, 2H), 2.26 (br t, J=6.3 Hz, 2H), 2.20 (br d, J=6.5 Hz, 2H), 2.11-1.91 (m, 4H), 1.77 (br d, J=11.5 Hz, 2H), 1.67 (br d, J=3.8 Hz, 1H), 1.37 (s, 6H), 1.22-1.11 (m, 2H).

Example 24

24

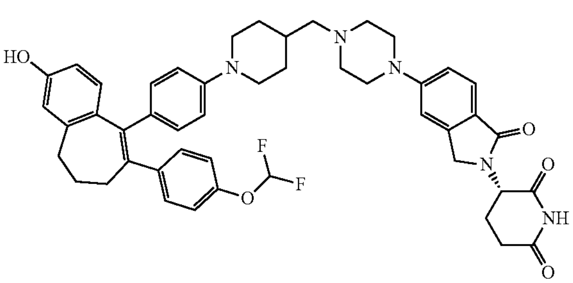

Synthetic Route:

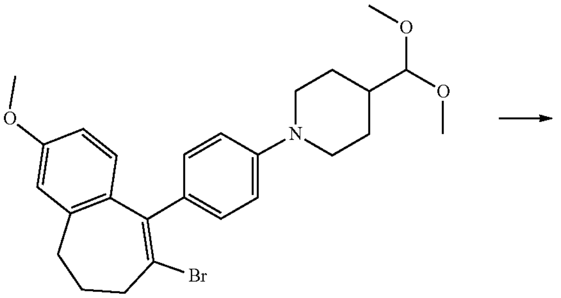

19-B

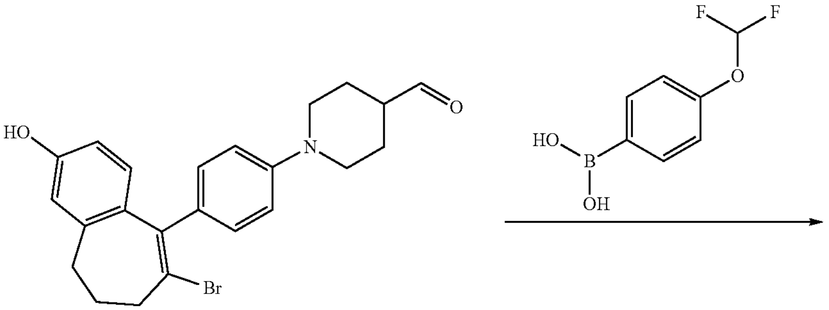

24-A

-continued

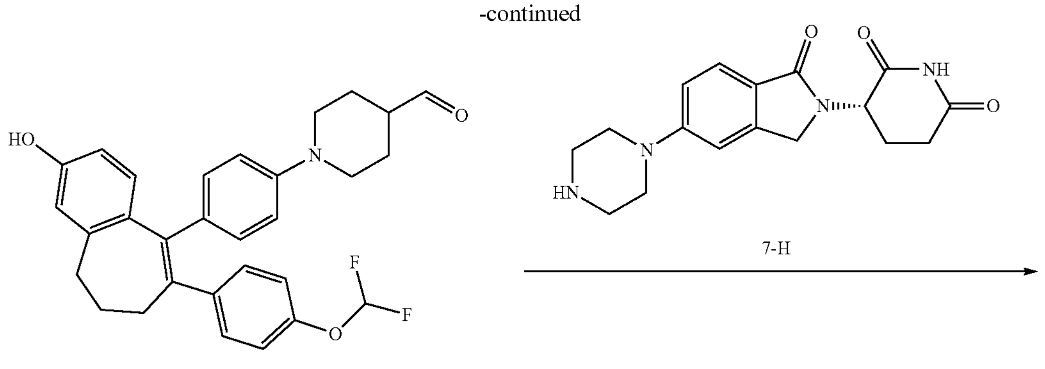

24-B

7-H

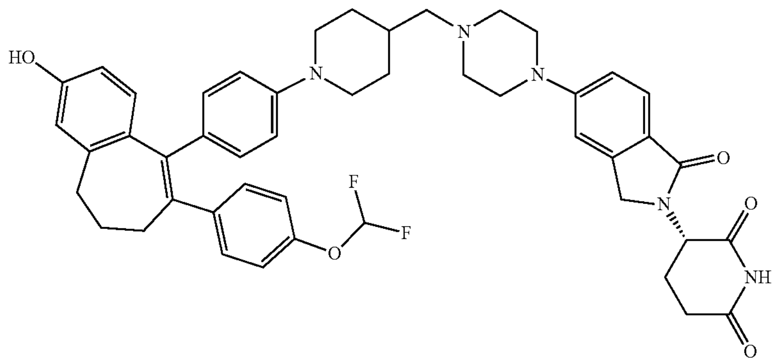

24

Step 1: Synthesis of Compound 24-A

Boron tribromide (772.51 mg) was added to a solution of compound 19-B (300 mg) in dichloromethane (20 mL) at 0° C., and the reaction solution was stirred at 25° C. for 12 h. After the completion of the reaction, the reaction solution was added to 50 mL of water, and the mixture was adjusted to pH 7 with sodium carbonate solid and extracted with dichloromethane (20 mL×3). The organic phase was dried over anhydrous sodium sulfate, filtered, and concentrated at reduced pressure to give crude compound 24-A. MS m/z: 445.7 $[M+H+H_2O]^+$.

Step 2: Synthesis of Compound 24-B 4-(Difluoromethoxy)phenylboronic acid (88.16 mg), tetrakis(triphenylphosphine)palladium (108.42 mg), and sodium carbonate (149.16 mg) were added to a solution of compound 24-A (0.20 g) in 1,4-dioxane (10 mL) and water (2 mL), and the mixture was purged with nitrogen for 3 times and reacted at 100° C. for 2 h. After the completion of the reaction, the reaction solution was cooled to room temperature and concentrated to give a crude product, which was purified by column chromatography (ethyl acetate: 0-25%, ethyl acetate/petroleum ether) to give compound 24-B. MS m/z: 490.0 $[M+H]^+$.

Step 3: Synthesis of Compound 24

Sodium acetate (67.03 mg) and magnesium sulfate (245.88 mg) were added to a solution of compound 24-B (200 mg) and trifluoroacetate of compound 7-H (180.73 mg) in dichloromethane (10 mL) and methanol (2 mL), and the reaction solution was stirred at 20° C. for 30 min. Sodium triacetoxyborohydride (259.76 mg) was added to the reaction solution, and the mixture was stirred at 20° C. for another 12 h. 1 mL of water was added to the reaction solution, and the mixture was stirred for 10 min and concentrated at reduced pressure to give a crude product, which was purified by column chromatography (methanol %: 0-6%, methanol/dichloromethane) to give compound 24. MS m/z: 802.3 $[M+H]^+$.

$^1$H NMR (400 MHz, DMSO-$d_6$) δ=10.96 (s, 1H), 9.39 (s, 1H), 7.52 (d, J=8.6 Hz, 1H), 7.39-6.95 (m, 7H), 6.72-6.63 (m, 5H), 6.60-6.52 (m, 2H), 5.05 (dd, J=5.1, 13.3 Hz, 1H), 4.39-4.15 (m, 2H), 3.62 (br d, J=12.0 Hz, 2H), 3.30 (br d, J=12.9 Hz, 6H), 2.98-2.84 (m, 1H), 2.70-2.52 (m, 8H), 2.45-2.16 (m, 6H), 2.10-1.92 (m, 3H), 1.84-1.61 (m, 3H).

Example 25

25

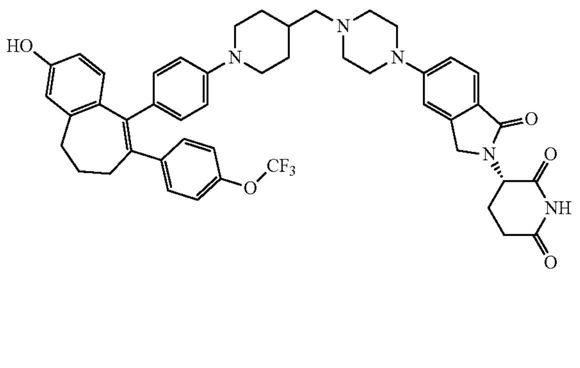

Synthetic Route:
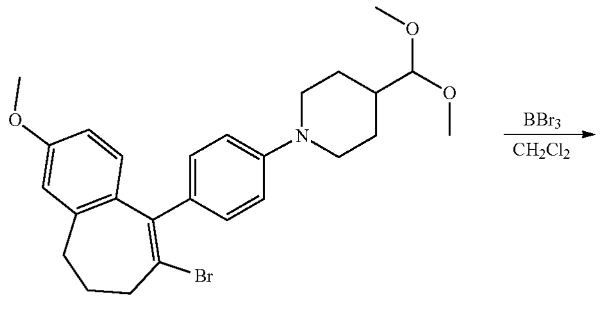
19-B
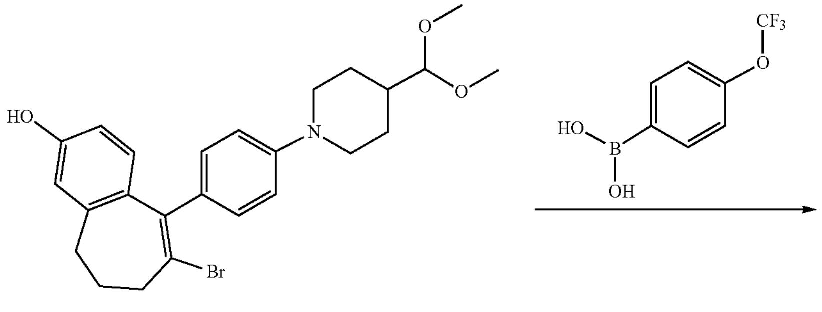
25-A
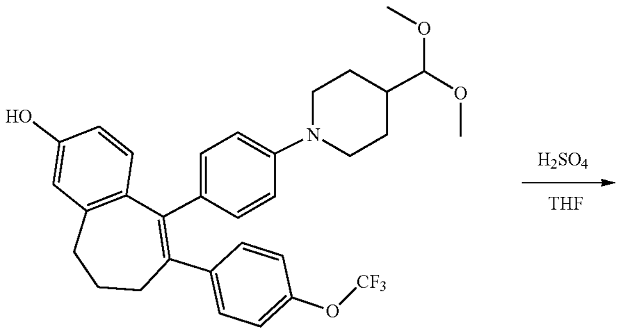
25-B
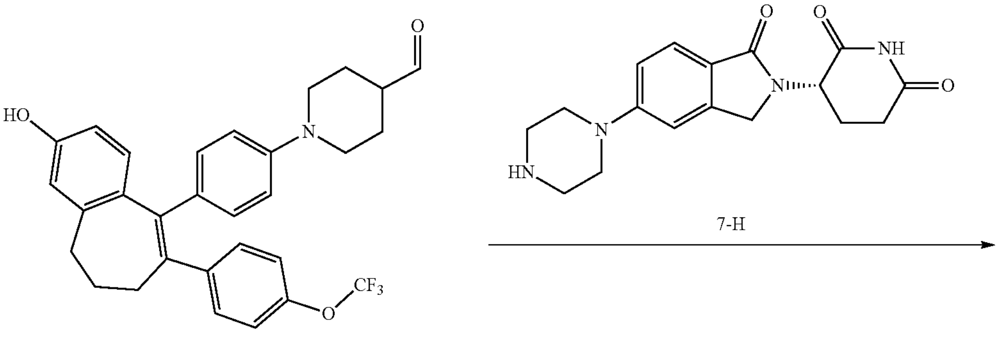
7-H
25-C -continued

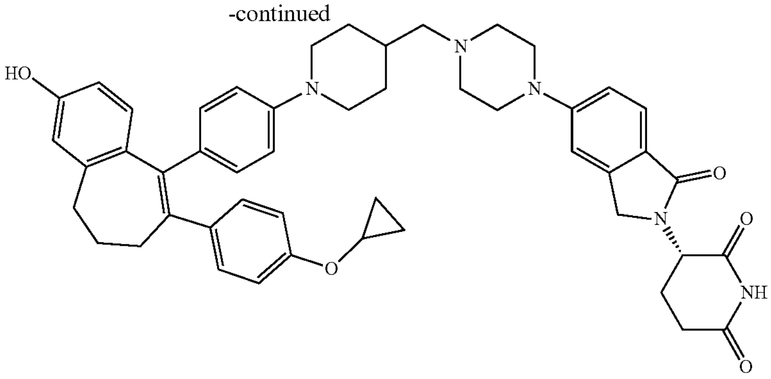

26

Step 1: Synthesis of Compound 25-A

Boron tribromide (1.03 g) was added to a solution of compound 19-B (200 mg) in dichloromethane (5 mL) at 0° C., and the reaction solution was stirred at 0° C. for 1 h. After the completion of the reaction, the reaction solution was added to 10 mL of water, and the mixture was adjusted to pH 7 with sodium carbonate solid and extracted with dichloromethane:methanol=4:1 (10 mL×3). The organic phase was dried over anhydrous sodium sulfate, filtered, and concentrated at reduced pressure to give crude compound 25-A. MS m/z: 473.1 $[M+H]^+$.

Step 2: Synthesis of Compound 25-B

4-Trifluoromethoxyphenylboronic acid (82.82 mg), tetrakis(triphenylphosphine)palladium (46.48 mg), and sodium carbonate (127.88 mg) were added to a solution of compound 25-A (190 mg) in 1,4-dioxane (4 mL) and water (1 mL), and the mixture was purged with nitrogen for 3 times and reacted at 100° C. for 1 h. After the completion of the reaction, the reaction solution was cooled to room temperature, diluted with 10 mL of ethyl acetate, and filtered through diatomite, and the filtrate was washed with 10 mL of saturated brine, dried over anhydrous sodium sulfate, and concentrated to give crude compound 25-B. MS m/z: 554.1 $[M+H]^+$.

Step 3: Synthesis of Compound 25-C

25-B (200 mg) was dissolved in THF (5 mL), $H_2SO_4$ (1 M, 4.34 mL) was added, and the mixture was stirred at 60° C. for 0.5 h. After the completion of the reaction, the mixture was adjusted to pH 7-8 with saturated sodium bicarbonate and extracted with dichloromethane:acetonitrile=4:1 (20 mL×3) to give an organic phase, which was washed with 10 mL of saturated brine and concentrated by a rotary evaporator to give compound 25-C. MS m/z: 508.1 $[M+H]^+$.

Step 4: Synthesis of Compound 25

Sodium acetate (73.70 mg) and magnesium sulfate (379.46 mg) were added to a solution of compound 25-C (200 mg) and trifluoroacetate of compound 7-H (174.33 mg) in dichloromethane (4 mL) and methanol (2 mL), and the reaction solution was stirred at 20° C. for 30 min. Sodium triacetoxyborohydride (250.55 mg) was added to the reaction solution, and the mixture was stirred at 20° C. for another 2 h. 2 drops of 1 M diluted hydrochloric acid were added, and the mixture was extracted with dichloromethane (20 mL×3). The organic phases were combined, washed once with saturated brine (10 mL), dried over anhydrous sodium sulfate, and concentrated by a rotary evaporator to give a crude product. The crude product was purified by column chromatography (methanol %: 0-4%, methanol/dichloromethane) to give compound 25. MS m/z: 820.3 $[M+H]^+$.

$^1H$ NMR (400 MHz, DMSO-d6) δ=10.96 (s, 1H), 9.41 (s, 1H), 7.51 (d, J=8.8 Hz, 1H), 7.5 (d, J=8.0 Hz, 2H), 7.16 (d, J=8.0 Hz, 2H), 7.10-7.04 (m, 2H), 6.73-6.62 (m, 5H), 6.59-6.54 (m, 2H), 5.05 (dd, J=5.0, 13.1 Hz, 1H), 4.38-4.16 (m, 2H), 3.66-3.57 (m, 2H), 3.30-3.25 (m, 4H), 2.95-2.86 (m, 1H), 2.73-2.55 (m, 6H), 2.51-2.44 (m, 4H), 2.41-2.32 (m, 2H), 2.29-2.15 (m, 4H), 2.11-2.01 (m, 2H), 1.78 (br d, 2H), 1.25-1.12 (m, 2H).

Example 26

26

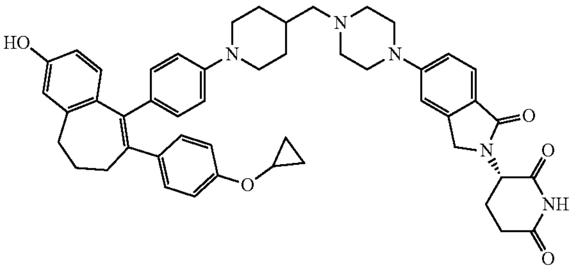

Synthetic Route:

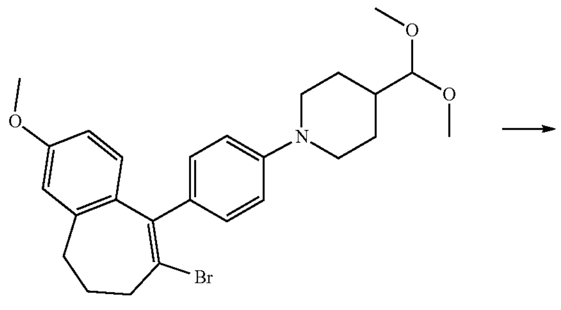

19-B

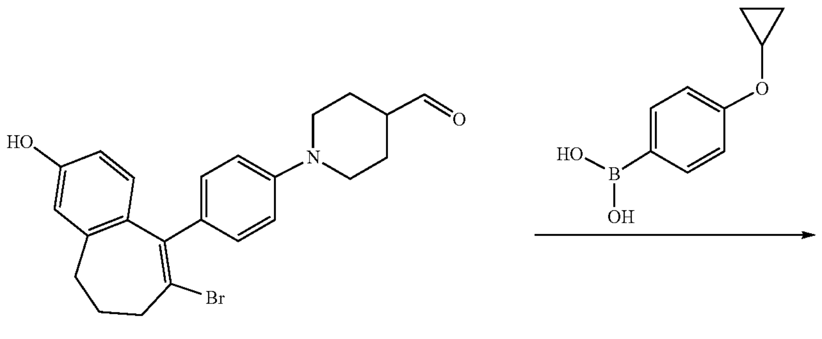

24-A

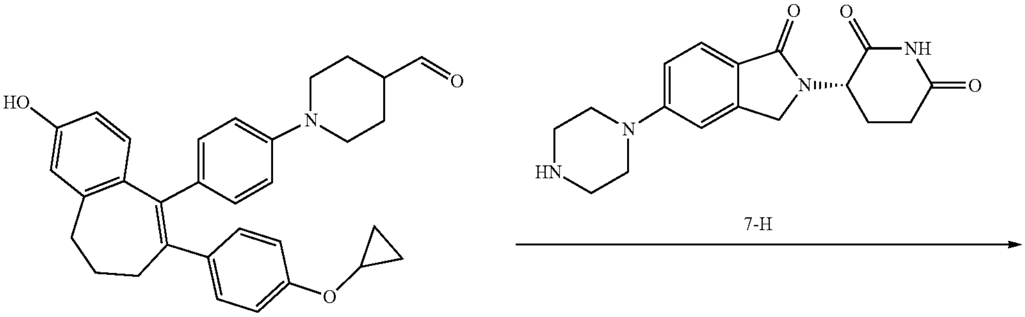

7-H

26-A

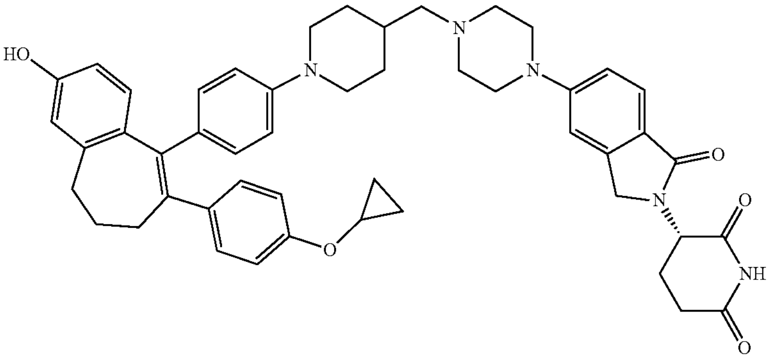

26

Step 1: Synthesis of Compound 24-A

Boron tribromide (1.55 g) was added to a solution of compound 19-B (300 mg) in dichloromethane (20 mL) at 0° C., and the reaction solution was stirred at 0° C. for 1 h. After the completion of the reaction, the reaction solution was added to 10 mL of water, and the mixture was adjusted to pH 7 with sodium carbonate solid and extracted with dichloromethane (20 mL×3). The organic phase was dried over anhydrous sodium sulfate, filtered, and concentrated at reduced pressure to give crude compound 24-A. MS m/z: 445.9 $[M+H+H_2O]^+$.

Step 2: Synthesis of Compound 26-A

4-Cyclopropyloxyphenylboronic acid (108.55 mg), tetrakis(triphenylphosphine)palladium (70.47 mg), and sodium carbonate (193.91 mg) were added to a solution of compound 24-A (0.26 g) in 1,4-dioxane (4 mL) and water (1 mL), and the mixture was purged with nitrogen for 3 times and reacted at 100° C. for 1 h. After the completion of the reaction, the reaction solution was cooled to room temperature, diluted with 10 mL of ethyl acetate, and filtered through diatomite, and the filtrate was washed with 10 mL of saturated brine, dried over anhydrous sodium sulfate, and concentrated to give a crude product, which was purified by column chromatography (ethyl acetate %: 0-25%, ethyl acetate/petroleum ether) to give compound 26-A. MS m/z: 498.0 $[M+H+H_2O]^+$.

Step 3: Synthesis of Compound 26

Sodium acetate (68.41 mg) and magnesium sulfate (250.98 mg) were added to a solution of compound 26-A (200 mg) and trifluoroacetate of compound 7-H (184.48 mg) in dichloromethane (10 mL) and methanol (2 mL), and the reaction solution was stirred at 20° C. for 30 min. Sodium triacetoxyborohydride (265.14 mg) was added to the reaction solution, and the mixture was stirred at 20° C. for another 12 h. 1 mL of water was added to the reaction solution, and the mixture was stirred for 10 min and concentrated at reduced pressure to give a crude product, which was purified by column chromatography (methanol %: 0-3%, methanol/dichloromethane) to give compound 26. MS m/z: 792.3 $[M+H]^+$.

$^1$H NMR (400 MHz, DMSO-$d_6$) δ=10.96 (s, 1H), 9.34 (s, 1H), 7.53 (d, J=8.5 Hz, 1H), 7.09-6.53 (m, 14H), 5.06 (dd, J=5.0, 13.1 Hz, 1H), 4.37-4.17 (m, 2H), 3.77 (td, J=3.0, 5.8 Hz, 1H), 3.61 (br d, J=11.8 Hz, 2H), 3.34-3.22 (m, 6H), 2.99-2.83 (m, 1H), 2.73-2.52 (m, 8H), 2.46-2.17 (m, 6H), 2.06-1.94 (m, 3H), 1.78 (br d, J=11.8 Hz, 2H), 0.79-0.70 (m, 2H), 0.62 (br s, 2H).

Bioassays

Experimental Example 1: MCF-7 ERα Degradation Experiment

Objective:

Compounds were tested for their ability to degrade ERα receptors under experimental conditions.

Materials:

Phenol red-free MEM medium was purchased from Wisent, fetal bovine serum was purchased from Biosera, and Human Total ERα/NR3A1 ELISA kits were purchased from R&D. MCF-7 cell line was purchased from the Cell Bank of Type Culture Collection Committee of the Chinese Academy of Sciences. Nivo5 multi-marker analyzer (PerkinElmer).

Procedure:

Day One:

1. MCF-7 cells were resuspended in medium (phenol red-free MEM+5% Charcoal Dextran Stripped FBS+1% PS), seeded in a 96-well clear cell culture plate, and incubated overnight in a carbon dioxide incubator;
2. ELISA plate was coated with stripes, Human Total ERα Capture Antibody was diluted with 1×PBS, and the plate was incubated at 25° C. overnight.

Day Two:

1. Cell administration: The compounds to be tested were diluted to the $8^{th}$ concentration. The concentration of the compound was 20 μM, and the compound was diluted successively to the $8^{th}$ concentration of 0.256 nM at 4 μM. Two duplicate wells were set. The compound was transferred to the intermediate plate and then to the cell plate to give a final DMSO concentration of 0.5% per well, and the plate was incubated at 37° C. for 4 h;
2. preparation of standard curve solution: 110 ng/mL of standard curve stock solution was 6-fold diluted with buffer #8 to give a solution with a concentration of 18.3 ng/mL. Then, 8-point gradient dilution was performed using buffer #3 with a final concentration of 200 pg/mL to 1.56 pg/mL;
3. the ELISA plate was washed 3 times with a washing solution (1×PBS containing 0.05% Tween);
4. 300 μL of blocking solution (1×PBS containing 1% BSA) was added to each well, and the plate was incubated at 25° C. for 2 h;
5. 1×PBS was pre-cooled. After the incubation of the compound, the supernatant was removed, the plate was washed with pre-cooled 1×PBS, the cell lysate was added, and the cells were lysed on ice for 15 min;
6. the blocking solution was removed from the ELISA plate, the plate was washed, and step 3 was repeated;
7. after the cells were lysed, in the cell plate, the cell lysate was 6-fold diluted with 150 μL of buffer #8 per well, the mixture was pipetted and mixed well, and 100 μL of solution per well was transferred to the ELISA plate;
8. at the same time, 100 μL of Standard per well was transferred to the ELISA plate and incubated overnight at 25° C.

Day Three:

1. The supernatant was removed, and the plate was washed 3 times with a washing solution;
2. Human Total ERα Detection Antibody stock solution (14.4 g/mL) was 36-fold diluted with buffer #1 (1×PBS containing 1% BSA), and the final concentration of Detection Antibody was 400 ng/mL. 100 μL/well of the solution was transferred to the ELISA plate, and the plate was incubated at 25° C. for 2 h;
3. the plate was washed with buffer #1;
4. Streptavidin-HRP A was 200-fold diluted with buffer #1 (1×PBS containing 1% BSA), 100 μL/well of the solution was transferred to the ELISA plate, and the plate was incubated at 25° C. for 20 min;
5. the plate was washed with buffer #1;
6. 100 μL of Substrate Solution per well (1:1 mixture of reagent A ($H_2O_2$) and reagent B (tetramethylbenzidine)) was added to the ELISA plate, and the plate was incubated at 25° C. for 20 min;
7. 50 Lt/well of stop solution was added and the OD450 absorbance was read on a plate reader.

Data Analysis:

The ERα concentration value at the corresponding point was calculated according to the OD450 reading value and the standard curve of the original data of the sample, the concentration value was converted to the inhibition rate using an equation (Sample−Min)/(Max−Min)×100%, and the $DC_{50}$ value was obtained by curve fitting according to a four-parameter equation y=(A−D)/[1+(x/C)]^D. The degradation of ERα by the compounds of the present application is provided in Table 1.

Max well: positive control wells were read at 100 nM FUL-treated cell wells.

Min well: negative control wells were read at 0.5% DMSO-treated cell wells.

The experimental results are shown in Table 1.

TABLE 1

| Degradation of ERα by compounds $DC_{50}$ | |
|---|---|
| Compound No. | $DC_{50}$(nM) |
| 1 | 0.84 |
| 2 | 2.69 |
| 3 | 5.8 |
| 4 | 1.5 |
| 5 | 1.8 |
| 6 | 1.0 |
| 7 | 8.0 |
| 8 | 8.3 |
| 9 | 0.4 |
| 10 | 5.7 |
| 11 | 1.0 |
| 12 | 4.73 |
| 13 | 4.47 |
| 14 | 1.1 |
| 15 | 1.7 |
| 16 | 7.7 |
| 17 | 9.4 |
| 18 | 4.6 |
| 19 | 2.1 |
| 20 | 0.9 |
| 21 | 1.9 |
| 22 | 2.4 |
| 23 | 1.4 |
| 24 | 0.7 |
| 25 | 5.7 |
| 26 | 1.7 |

Conclusion: the compounds of the present application have a good ability to degrade ERα.

The invention claimed is:

1. A compound of formula (IV), an isomer thereof or a pharmaceutically acceptable salt thereof, (IV)

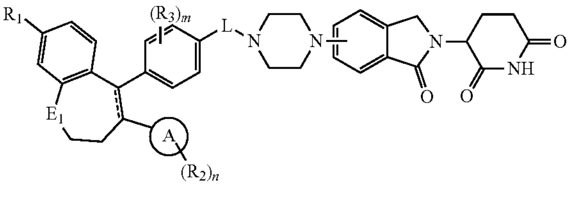

wherein, $R_1$ is selected from the group consisting of OH, $C_{1-3}$ alkoxy, and COOH;

each $R_2$ is independently selected from the group consisting of halogen, OH, CN, $NH_2$, $C_{1-3}$ alkyl, $C_{1-3}$ alkoxy, $C_{3-6}$ cycloalkyl, and —O—$C_{3-6}$ cycloalkyl, wherein the $C_{1-3}$ alkyl, $C_{1-3}$ alkoxy, $C_{3-6}$ cycloalkyl, and —O—$C_{3-6}$ cycloalkyl are each independently optionally substituted with 1, 2, or 3 $R_a$;

each $R_a$ is independently selected from the group consisting of halogen, CN, and OH;

each $R_3$ is independently selected from halogen;

m and n are each independently selected from the group consisting of 0, 1, 2, and 3;

$E_1$ is selected from the group consisting of O and $CH_2$;

L is selected from $C_{1-6}$ alkylene, wherein 1 to 3 methylenes are optionally substituted by O, NH, $C_{3-6}$ cycloalkyl, or 4- to 6-membered heterocycloalkyl;

 is selected from the group consisting of a single bond and a double bond;

ring A is selected from the group consisting of phenyl and 5- to 6-membered heteroaryl.

2. The compound, the isomer thereof or the pharmaceutically acceptable salt thereof according to claim 1, wherein $R_1$ is selected from the group consisting of OH, $CH_3O$—, and COOH.

3. The compound, the isomer thereof or the pharmaceutically acceptable salt thereof according to claim 1, wherein $R_2$ is independently selected from the group consisting of F, Cl, Br, I, OH, CN, $NH_2$, $CH_3$, ethyl, isopropyl, methoxy, ethoxy, isopropoxy, cyclopropyl, and —O-cyclopropyl, wherein the $CH_3$, ethyl, isopropyl, methoxy, ethoxy, isopropoxy, cyclopropyl, and —O-cyclopropyl are optionally independently substituted with 1, 2, or 3 $R_a$, each $R_a$ being independently selected from the group consisting of F, Cl, Br, I, and OH; or, $R_2$ is independently selected from the group consisting of F, Cl, OH, $CH_3$, isopropyl, methoxy, cyclopropyl, and —O-cyclopropyl, wherein the $CH_3$, isopropyl, methoxy, cyclopropyl, and —O-cyclopropyl are optionally independently substituted with 1, 2, or 3 $R_a$, each $R_a$ being independently selected from the group consisting of F and OH; or, $R_2$ is independently selected from the group consisting of F, Cl, Br, I, OH, CN, $NH_2$, $CH_3$, $CF_3$, cyclopropyl,

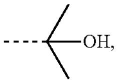

—$OCHF_2$, —$OCF_3$, and —O-cyclopropyl.

4. The compound, the isomer thereof or the pharmaceutically acceptable salt thereof according to claim 1, wherein L is selected from the group consisting of $C_{1-6}$ alkylene, —O—$C_{1-5}$ alkylene, —$C_{3-6}$ cycloalkyl-, —$C_{3-6}$ cycloalkyl-$C_{1-3}$ alkylene, -4- to -6-membered heterocycloalkyl-, and -4- to -6-membered heterocycloalkyl-$C_{1-3}$ alkylene; or, L is selected from the group consisting of $C_{4-6}$ alkylene, —O—$C_{3-5}$ alkylene, -cyclohexyl-, -cyclohexyl-$C_{1-3}$ alkylene, -6-membered heterocycloalkyl-, and -6-membered heterocycloalkyl-$C_{1-3}$ alkylene; or, L is selected from the group consisting of —O—$C_{3-5}$ alkylene and -piperidinyl-$C_{1-3}$ alkylene; or, L is selected from the group consisting of

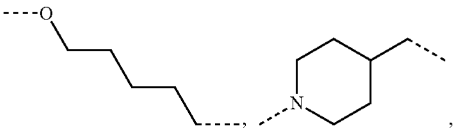

, and

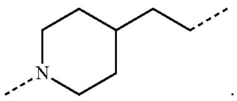

.

5. The compound, the isomer thereof or the pharmaceutically acceptable salt thereof according to claim 1, wherein L is selected from $C_{1-6}$ alkylene, wherein 1 to 3 methylenes are optionally substituted by O, NH, cyclohexyl, or 6-membered heterocycloalkyl; or, L is selected from $C_{1-6}$ alkylene, wherein 1 to 3 methylenes are optionally substituted by O, NH, cyclohexyl, or piperidinyl; or, L is selected from the group consisting of

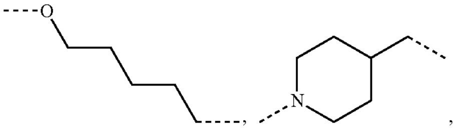

, and

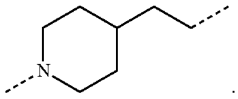

.

6. The compound, the isomer thereof or the pharmaceutically acceptable salt thereof according to claim 1, wherein ring A is selected from the group consisting of phenyl, pyridinyl, and pyrazolyl; or, ring A is selected from the group consisting of phenyl,

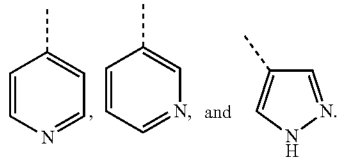

7. The compound, the isomer thereof or the pharmaceutically acceptable salt thereof according to claim 1, wherein the structural unit

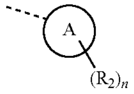

is selected from the group consisting of

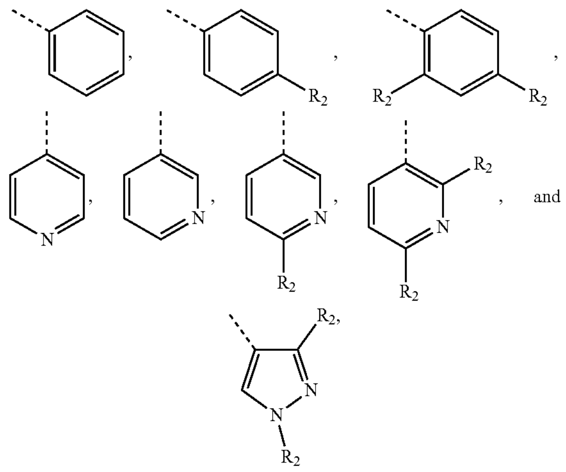

wherein each $R_2$ is independently selected from the group consisting of F, Cl, Br, I, OH, CN, $NH_2$, $CH_3$, ethyl, isopropyl, methoxy, ethoxy, isopropoxy, cyclopropyl, and —O-cyclopropyl, wherein the $CH_3$, ethyl, isopropyl, methoxy, ethoxy, isopropoxy, cyclopropyl, and —O-cyclopropyl are optionally independently substituted with 1, 2, or 3 $R_a$, each $R_a$ being independently selected from the group consisting of F, Cl, Br, I, and OH; or, the structural unit

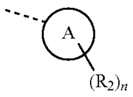

is selected from the group consisting of

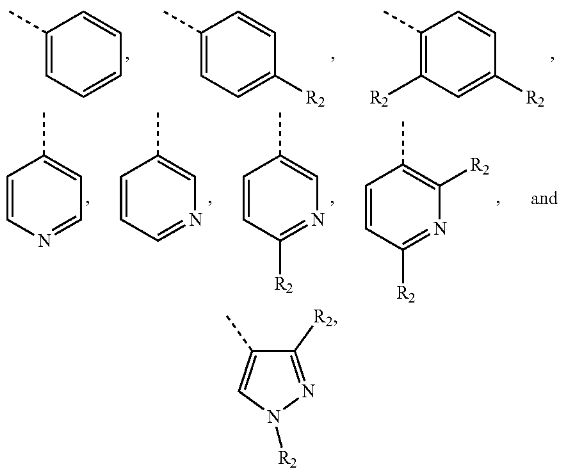

wherein each $R_2$ is independently selected from the group consisting of F, Cl, OH, $CH_3$, isopropyl, methoxy, cyclopropyl, and —O-cyclopropyl, wherein the $CH_3$, isopropyl, methoxy, cyclopropyl, and —O-cyclopropyl are optionally independently substituted with 1, 2, or 3 $R_a$, each $R_a$ being independently selected from the group consisting of F and OH; or, the structural unit

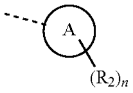

is selected from the group consisting of

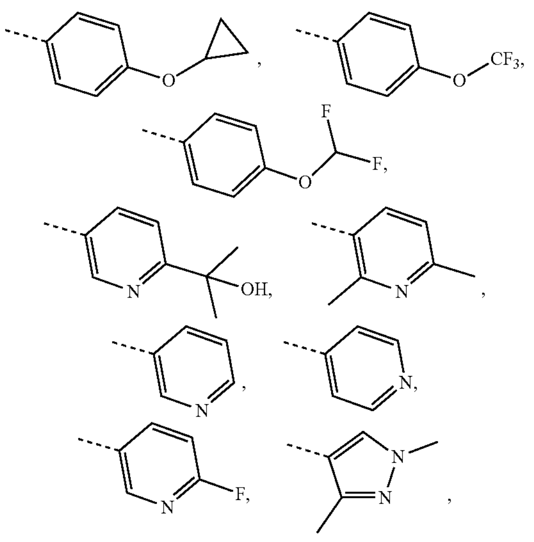

-continued

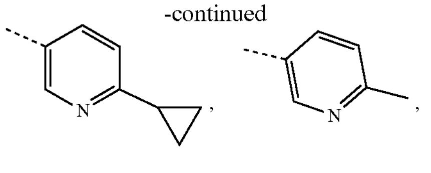

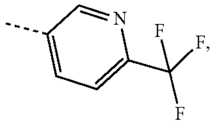

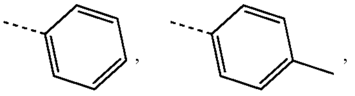

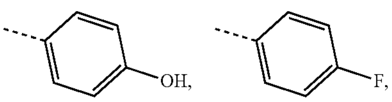

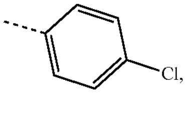

and

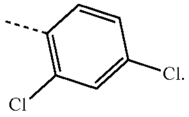

8. A compound of formula (I), an isomer thereof or a pharmaceutically acceptable salt thereof, (I)

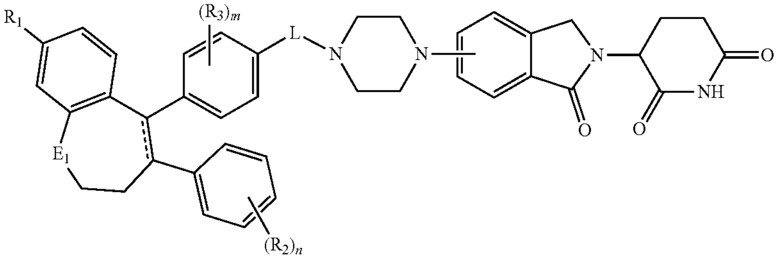

wherein, $R_1$ is selected from the group consisting of OH, $C_{1-3}$ alkoxy, and COOH;

each $R_2$ is independently selected from the group consisting of halogen, OH, CN, $NH_2$, $C_{1-3}$ alkyl, and $C_{1-3}$ alkoxy, wherein the $C_{1-3}$ alkyl and $C_{1-3}$ alkoxy are optionally substituted with 1, 2, or 3 halogens;

each $R_3$ is independently selected from halogen;

m and n are each independently selected from the group consisting of 0, 1, 2, and 3;

$E_1$ is selected from the group consisting of O and $CH_2$;

L is selected from $C_{1-6}$ alkylene, wherein 1 to 3 methylenes are optionally substituted by O, NH, $C_{3-6}$ cycloalkyl, or 4- to 6-membered heterocycloalkyl;

is selected from the group consisting of a single bond and a double bond;

the "hetero" of the "4- to 6-membered heterocycloalkyl" comprises 1, 2, or 3 heteroatoms or heteroatom groups independently selected from the group consisting of O, S, NH, and N.

9. The compound, the isomer thereof or the pharmaceutically acceptable salt thereof according to claim 1, wherein the compound is selected from a compound of formula (IV-1)

(IV-1)

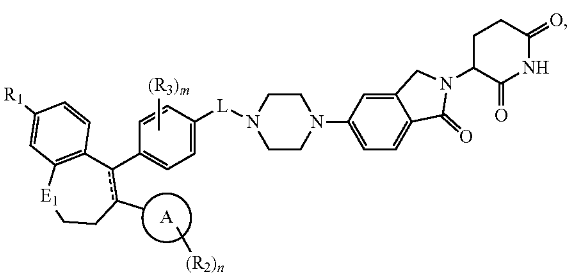

wherein $R_1$, $R_2$, $R_3$, L, $E_1$, ring A, , m, and n are as defined in claim 1;

or the compound is selected from a compound of formula (IV-2), (IV-2)

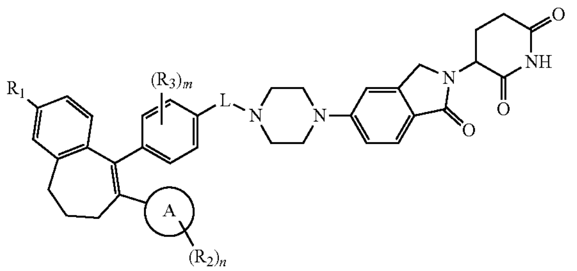

wherein $R_1$, $R_2$, $R_3$, L, ring A, m, and n are as defined in claim 1;

or the compound is selected from a compound of formula (IV-3), (IV-3)

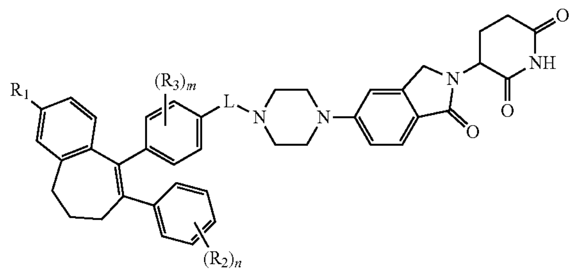

wherein $R_1$, $R_2$, $R_3$, L, m, and n are as defined in claim 1; or the compound is selected from a compound of formula (IV-4), (IV-4)

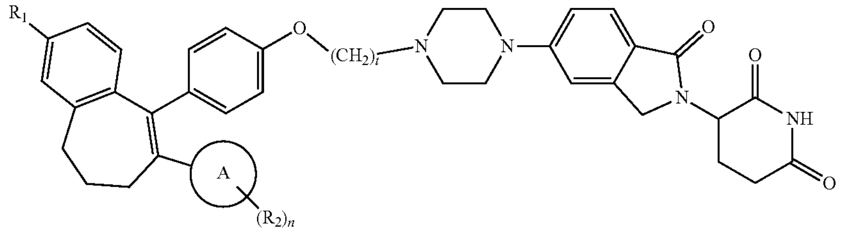

wherein, t is selected from the group consisting of 1, 2, 3, 4, and 5;

$R_1$, $R_2$, ring A, and n are as defined in claim 1;

or the compound is selected from a compound of formula (IV-5), (IV-5)

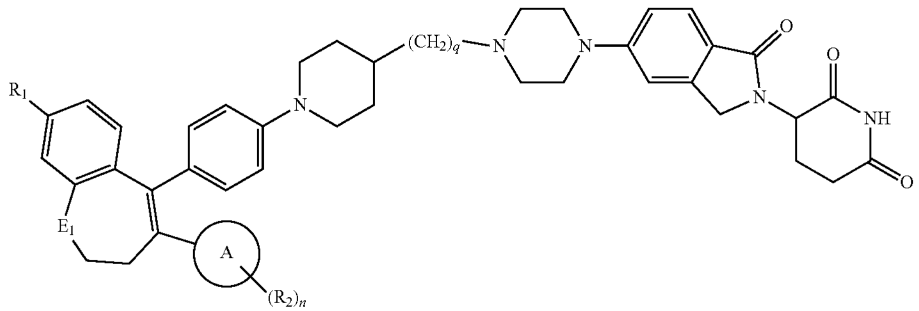

wherein, q is selected from the group consisting of 1 and 2;

$R_1$, $R_2$, $E_1$, ring A, and n are as defined in claim 1;

or the compound is selected from a compound of formula (IV-6), (IV-6)

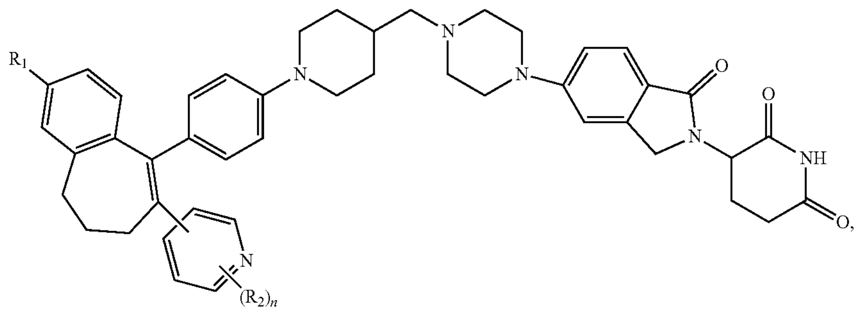

wherein $R_1$, $R_2$, and n are as defined in claim 1.

10. The compound, the isomer thereof or the pharmaceutically acceptable salt thereof according to claim 1, wherein the compound is selected from a compound of formula (IV-5'), (IV-5')

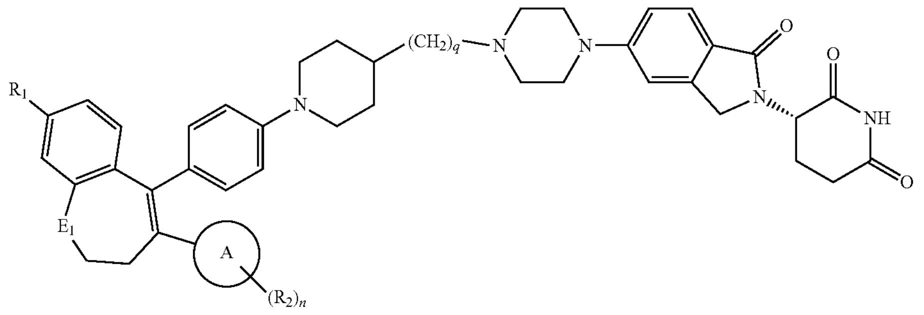

wherein, q is selected from the group consisting of 1 and 2;

$R_1$, $R_2$, $E_1$, ring A, and n are as defined in claim 1;

or the compound is selected from a compound of formula (IV-6'), (IV-6')

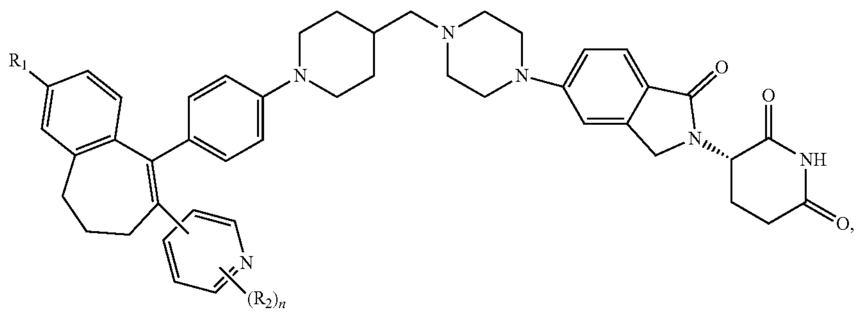

wherein $R_1$, $R_2$, and n are as defined in claim 1.

11. A compound of a formula below or a pharmaceutically acceptable salt thereof, selected from the group consisting of:

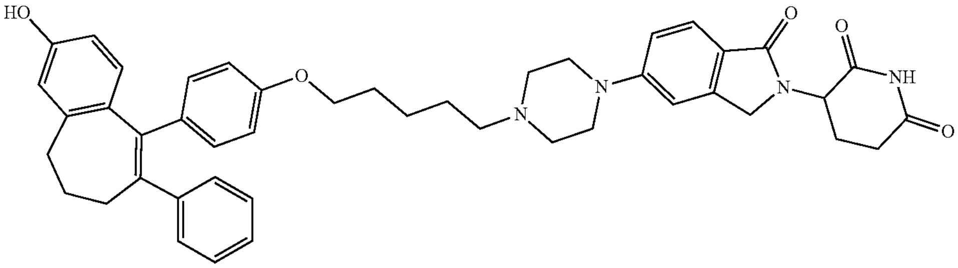
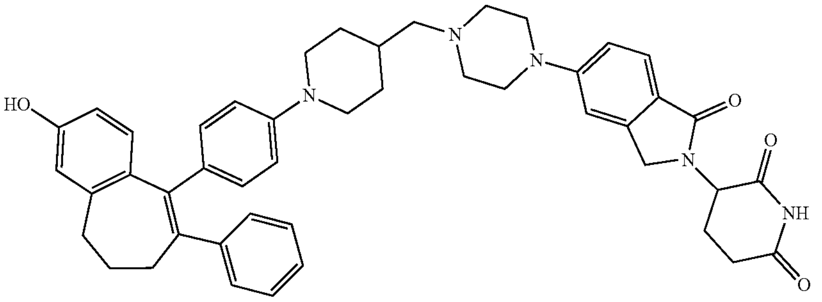
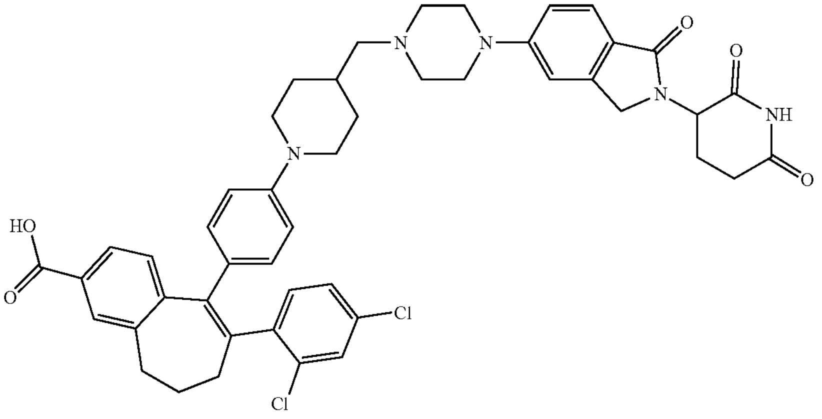
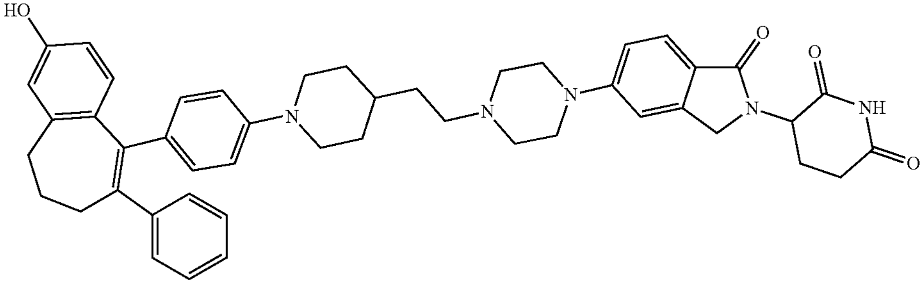
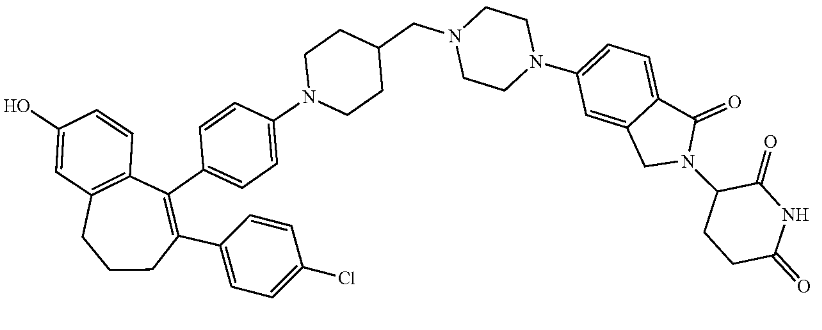

-continued
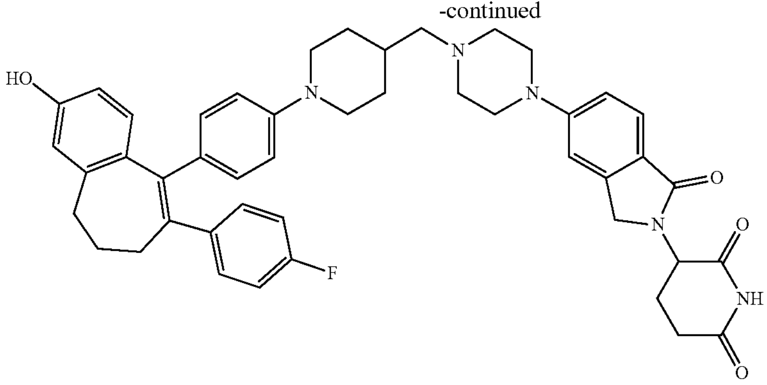
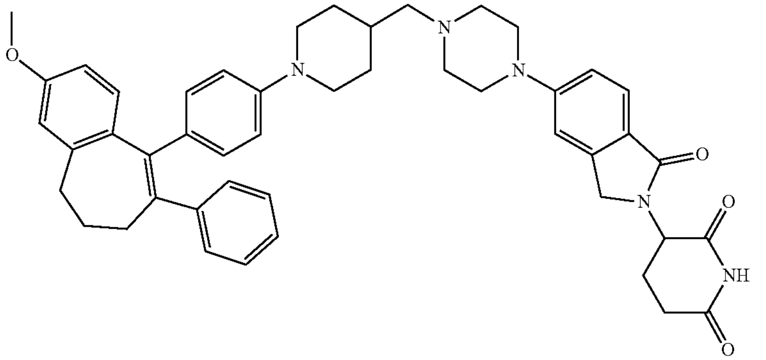
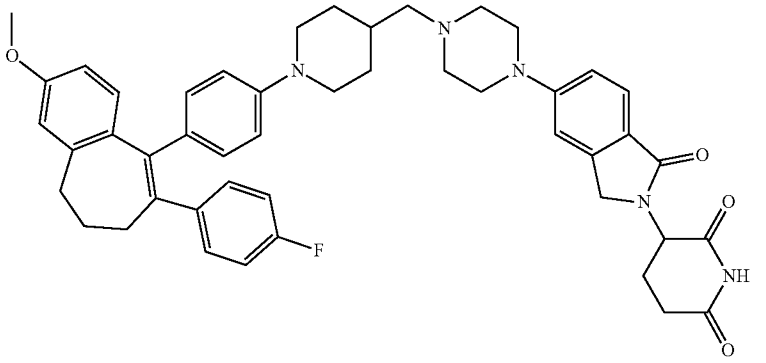
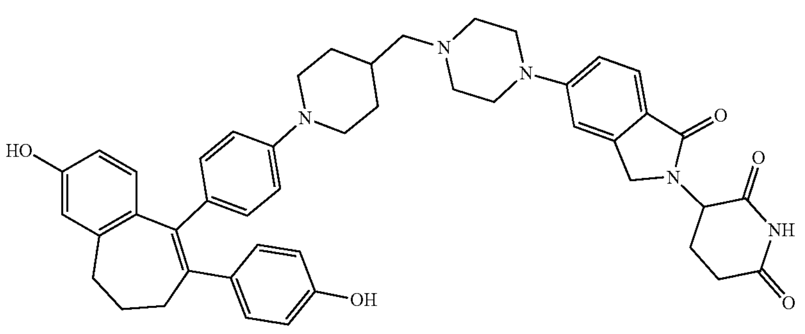

-continued
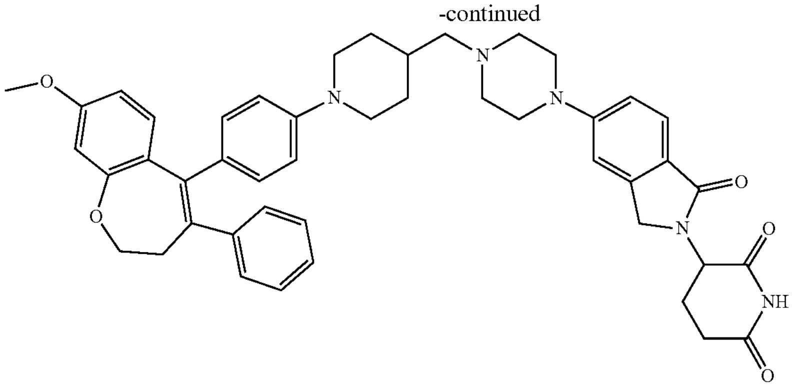
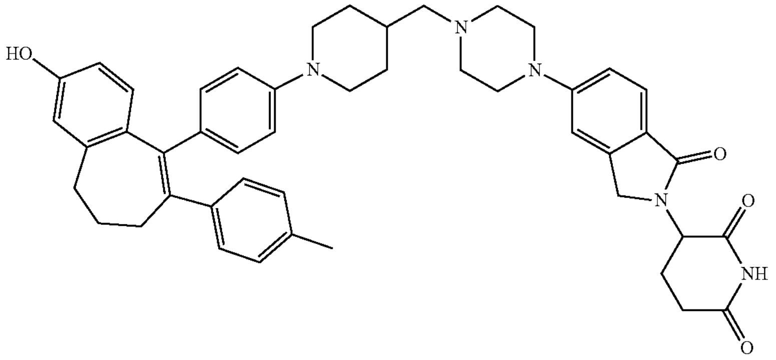
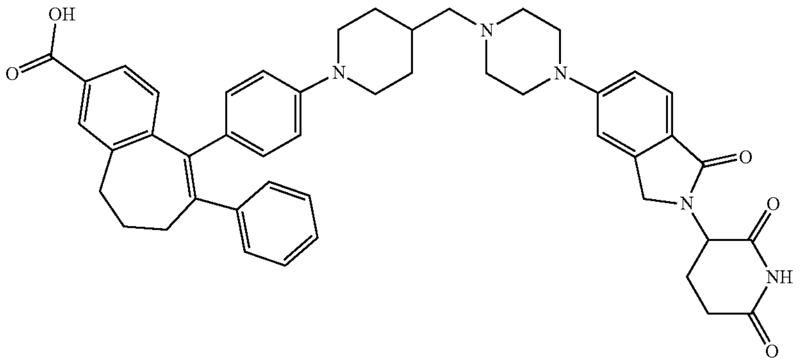
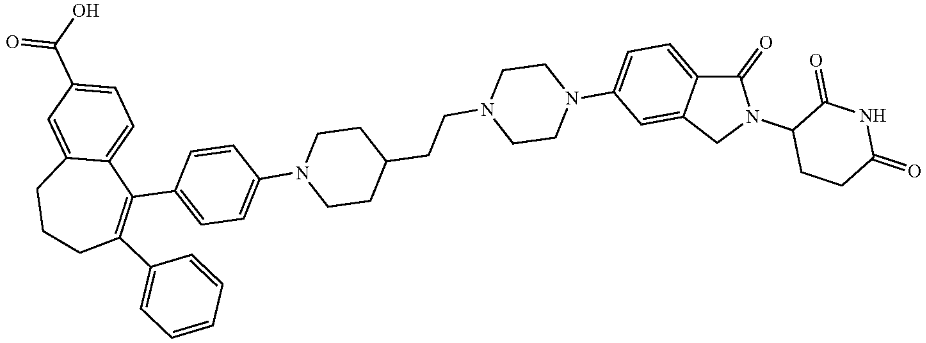

-continued
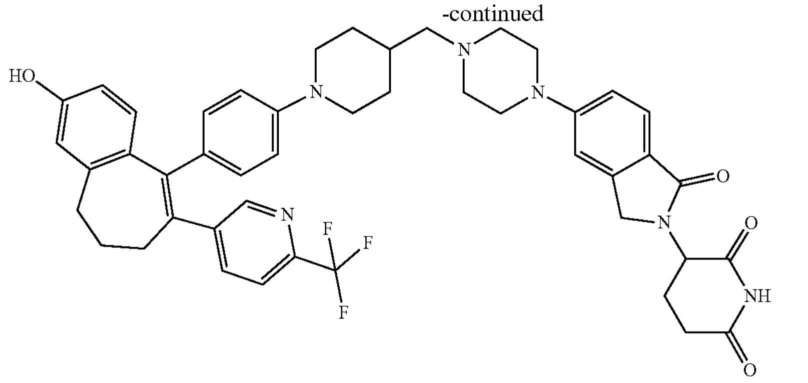
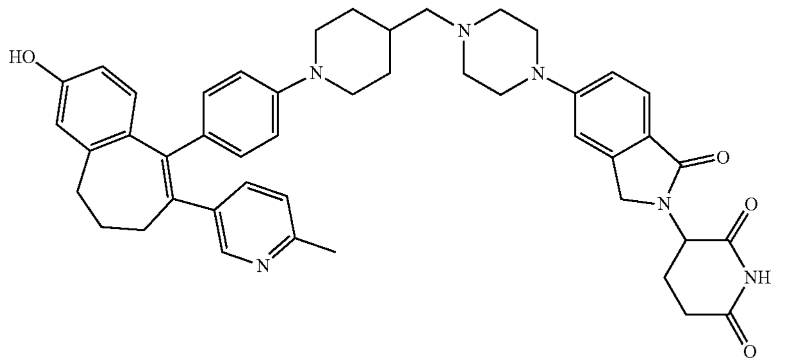
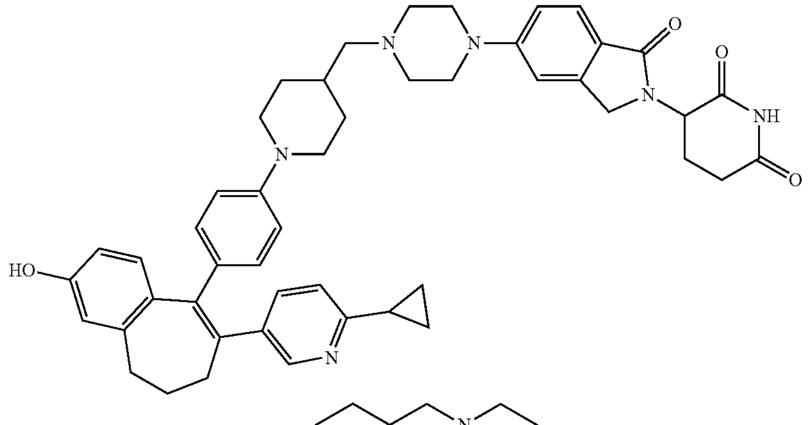
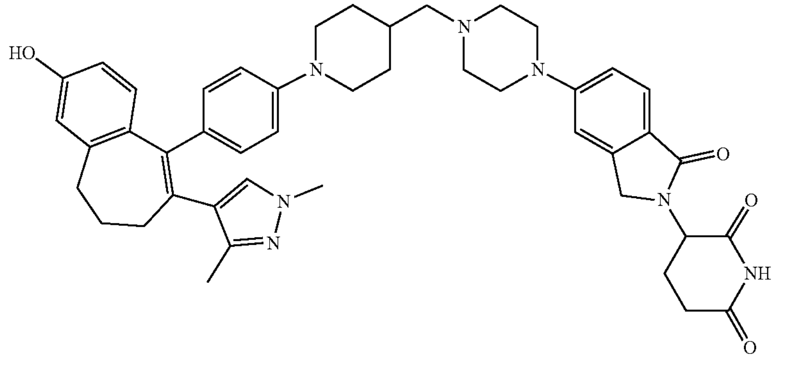

-continued
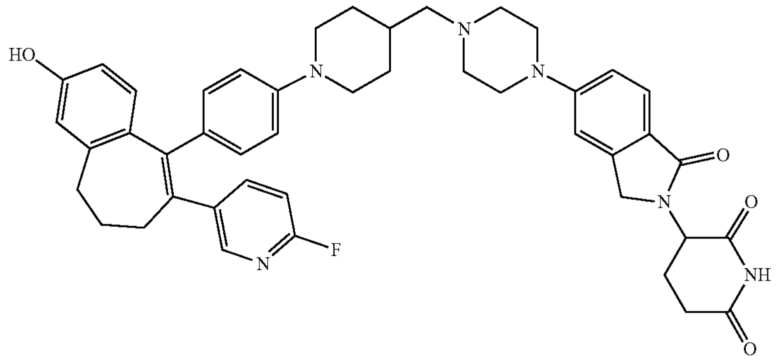
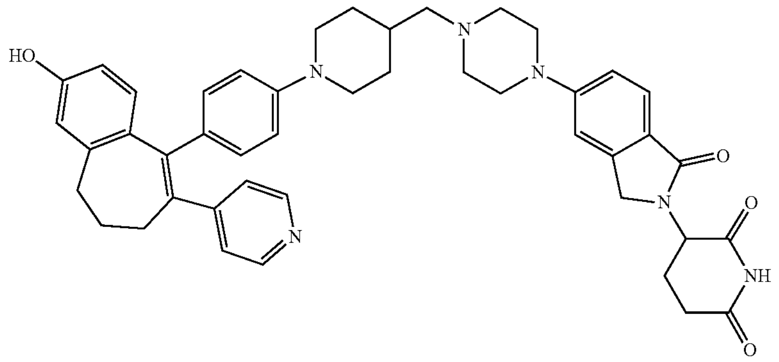
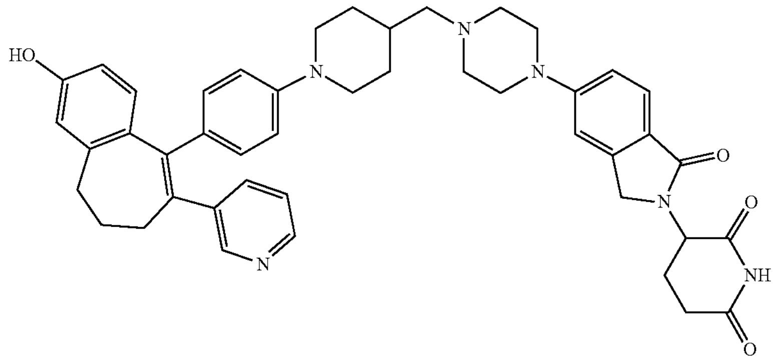
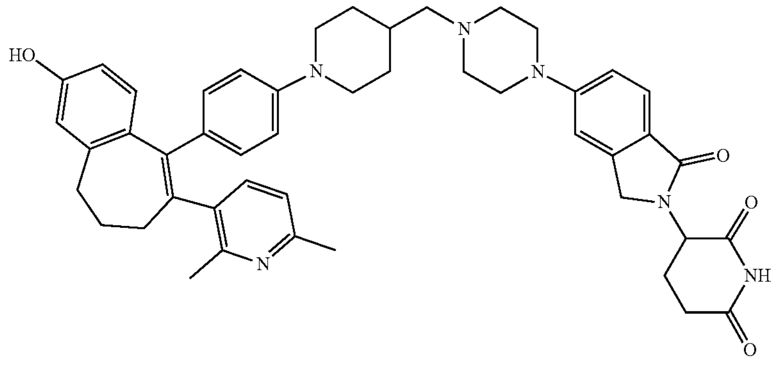

-continued
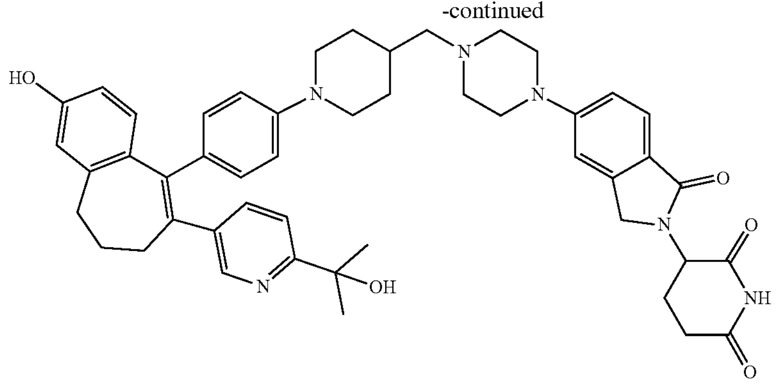
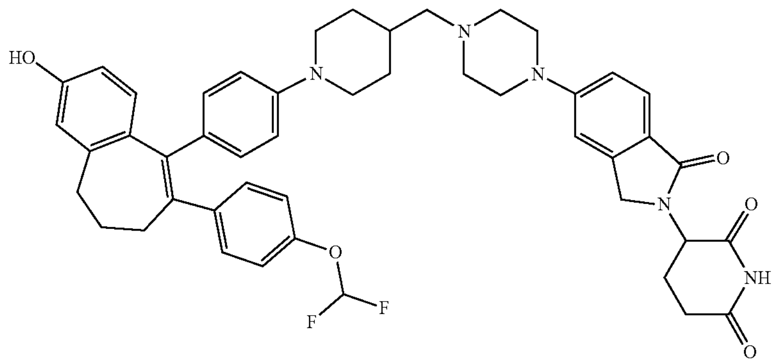
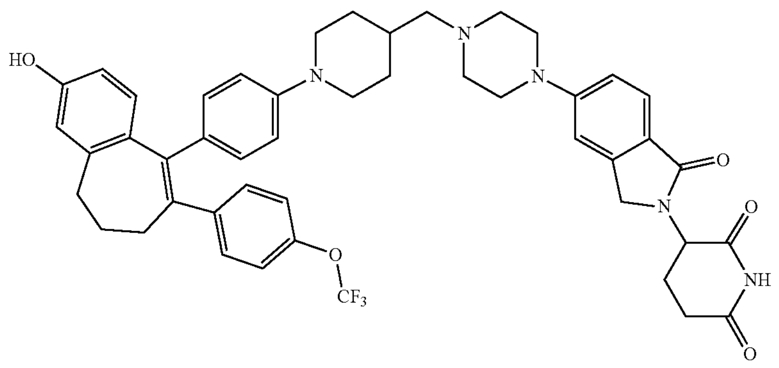
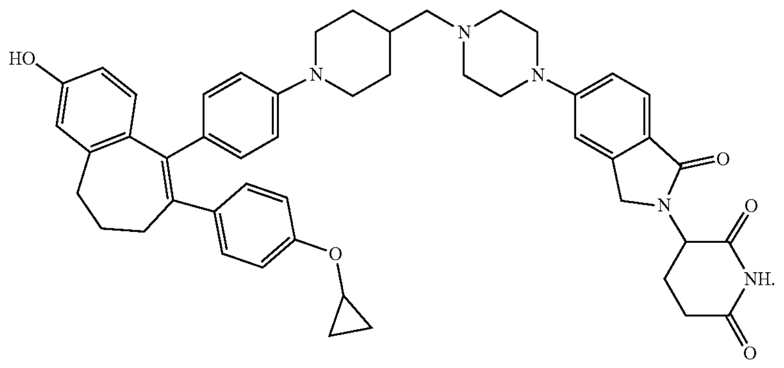

12. The compound or the pharmaceutically acceptable salt thereof according to claim 11, wherein the compound is selected from the group consisting of:
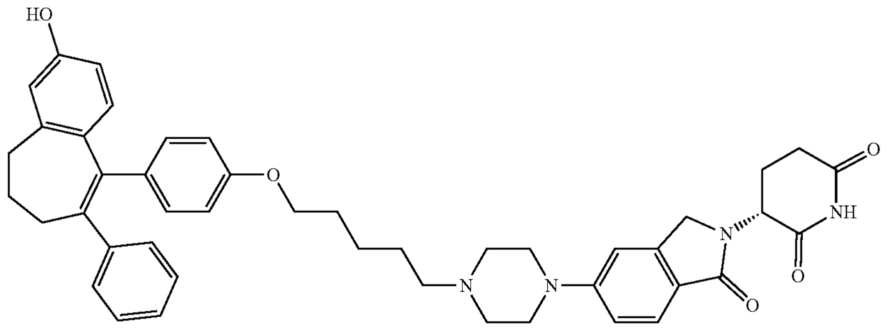
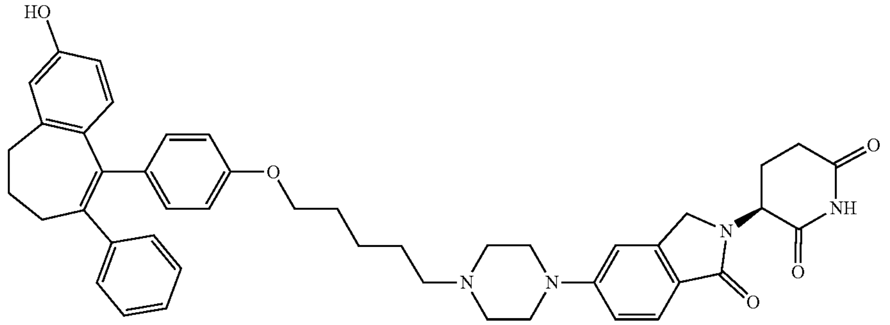
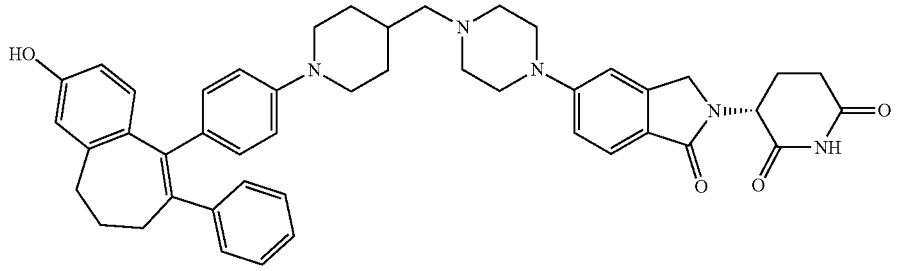
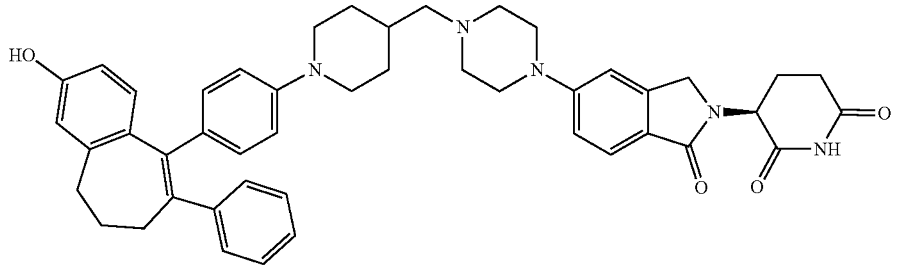
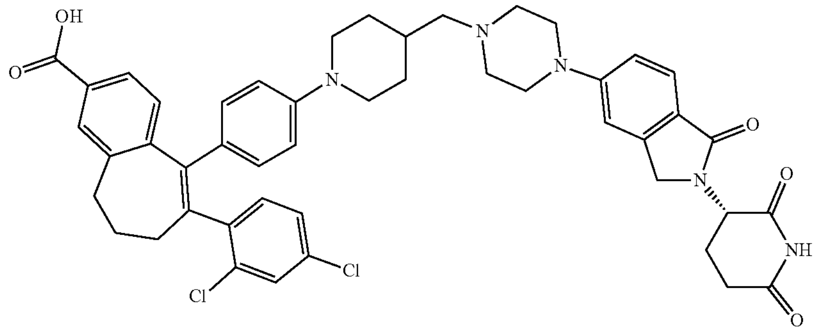

-continued
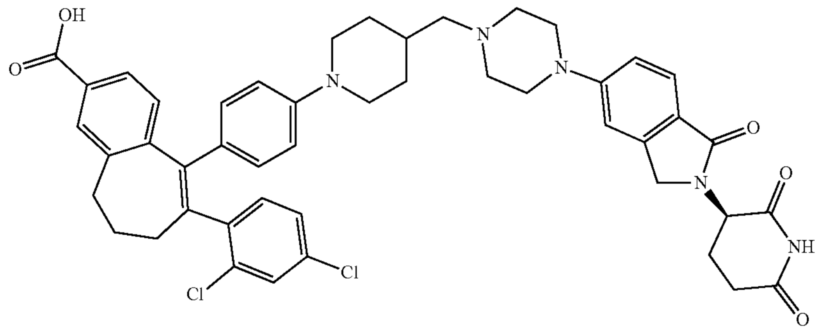
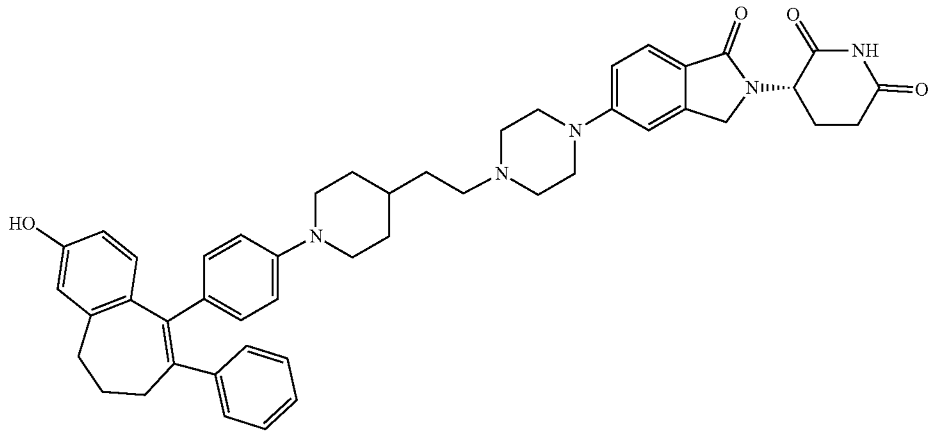
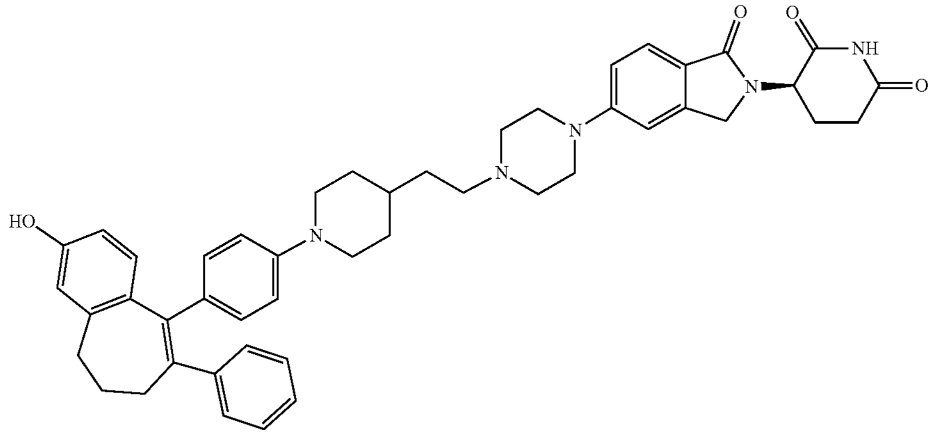
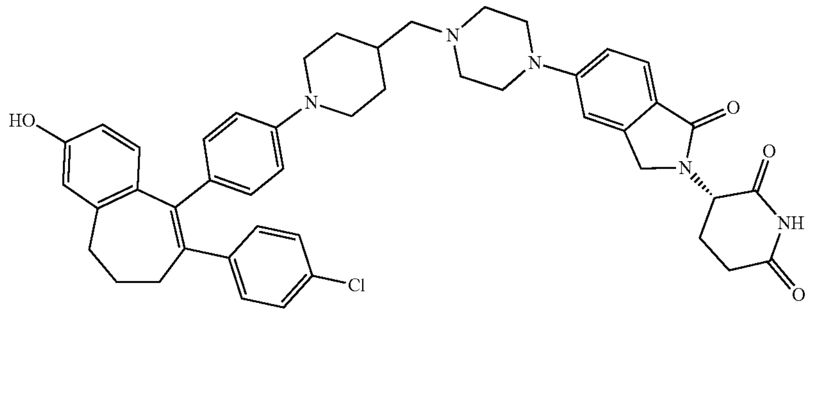

-continued
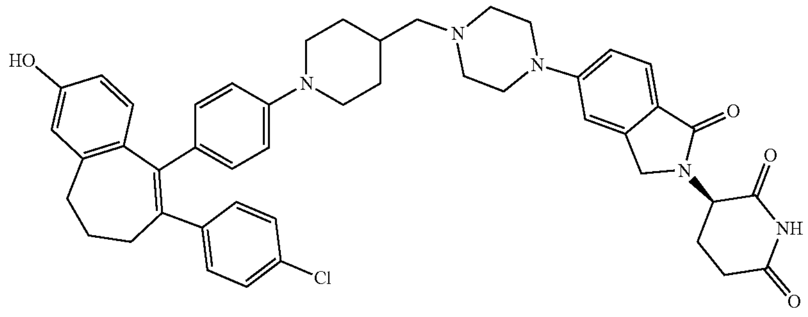
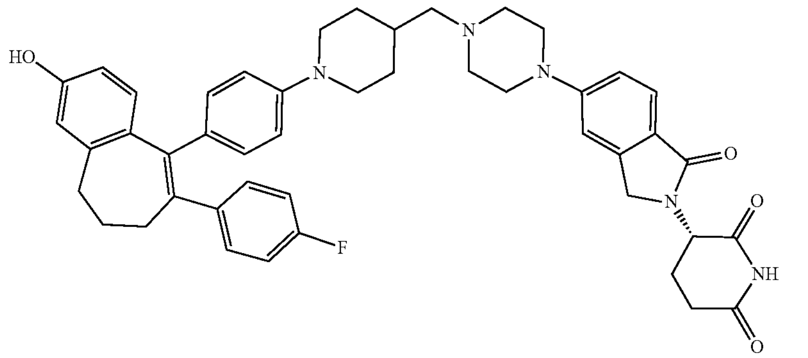
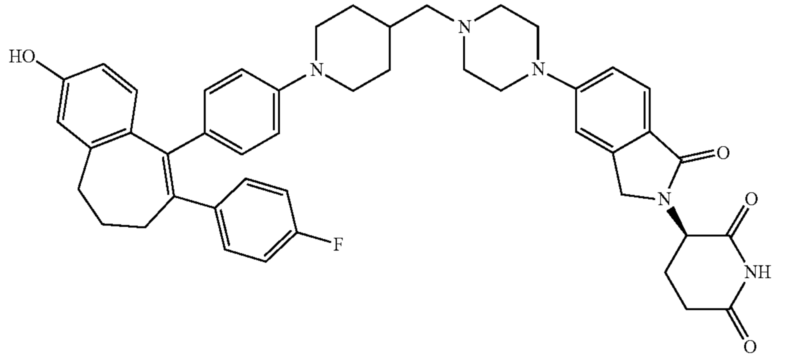
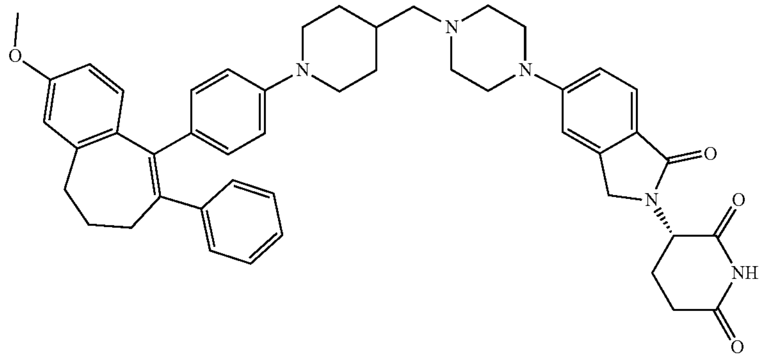

-continued
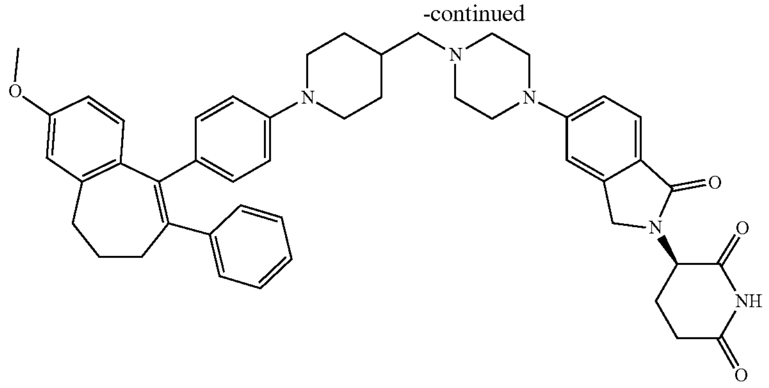
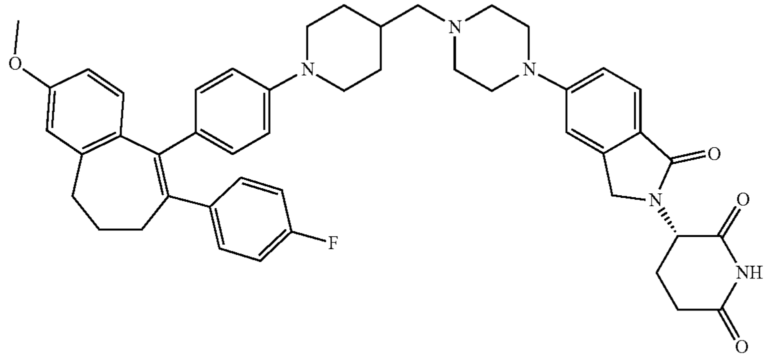
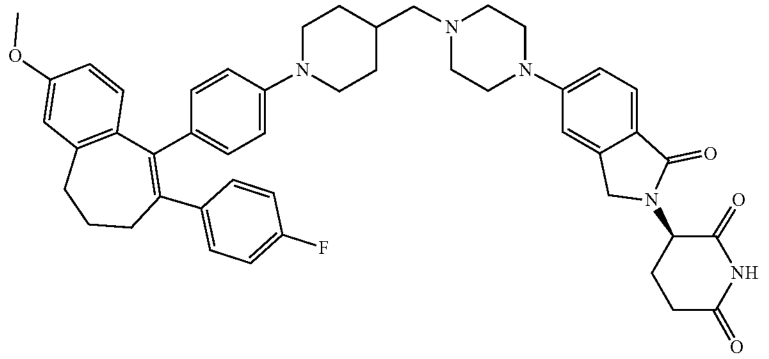
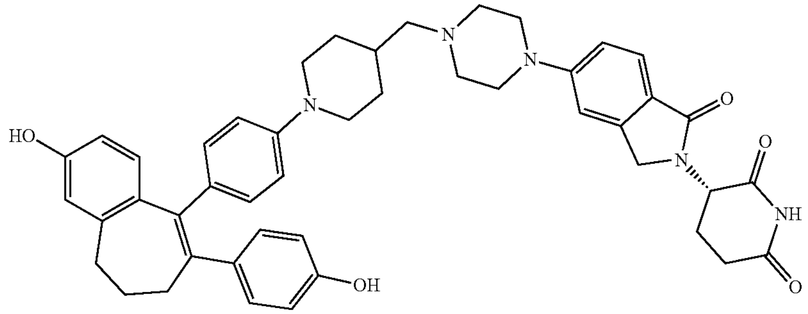
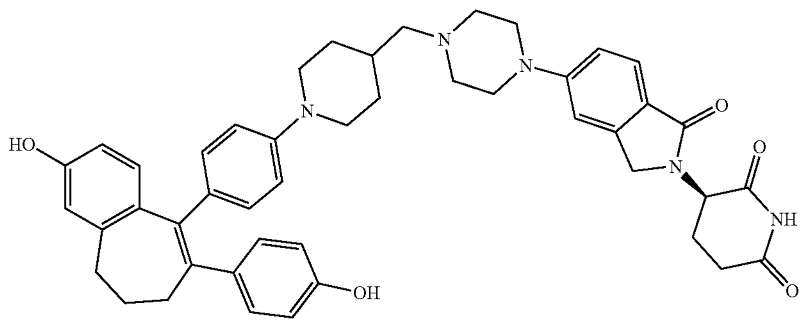

-continued
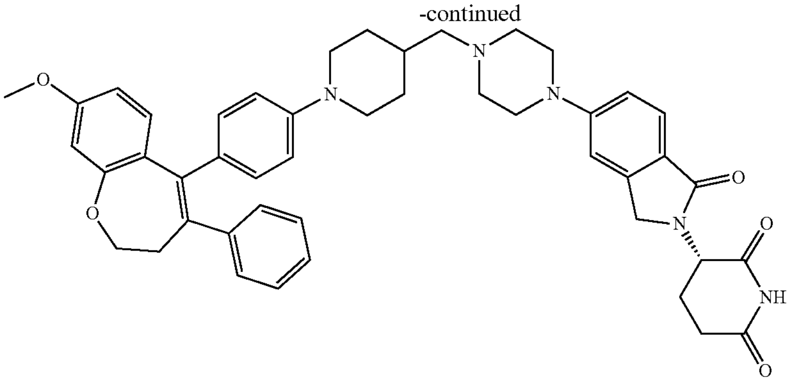
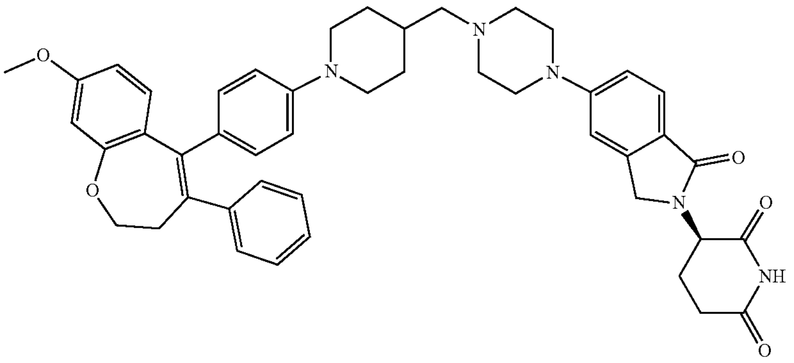
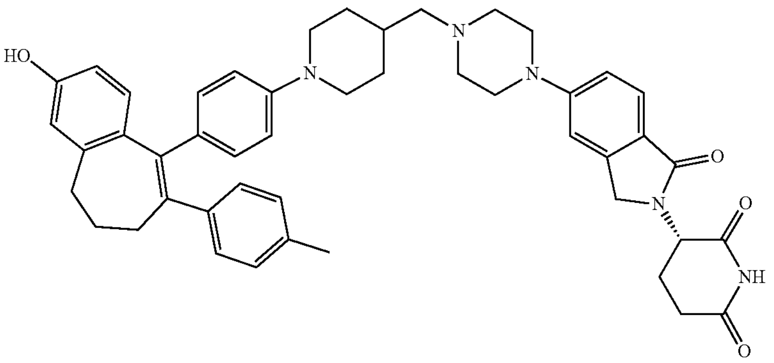
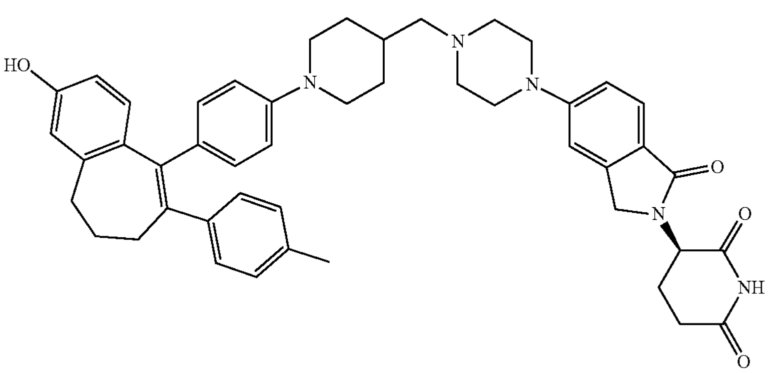

-continued
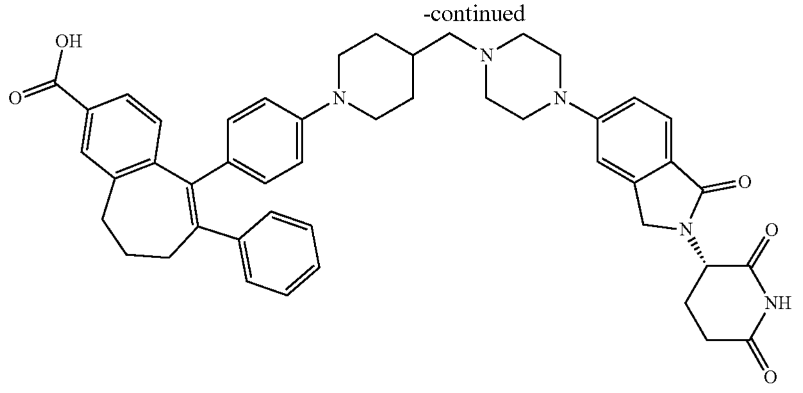
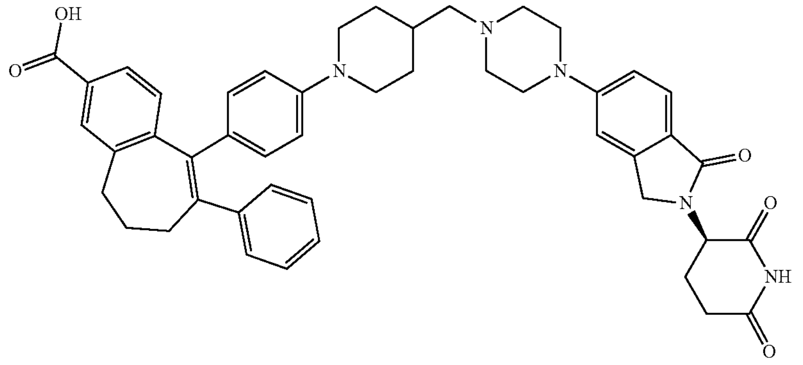
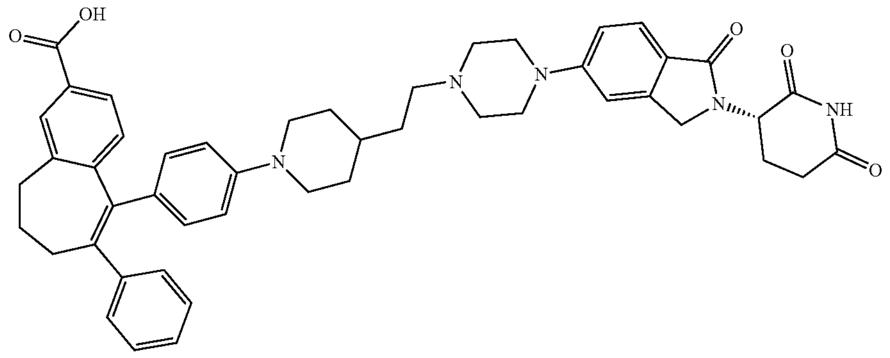
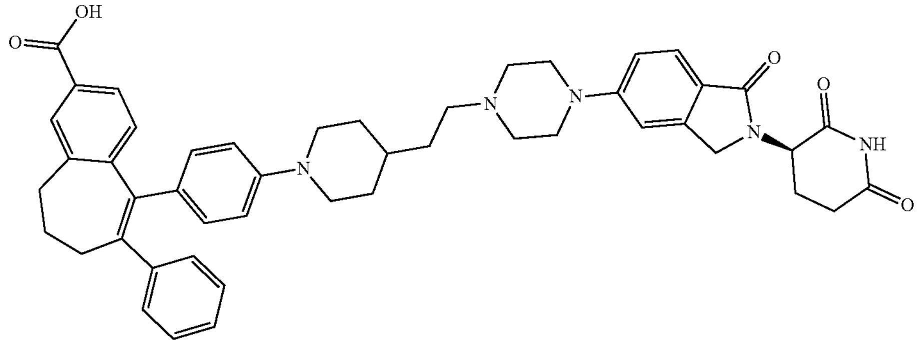

-continued
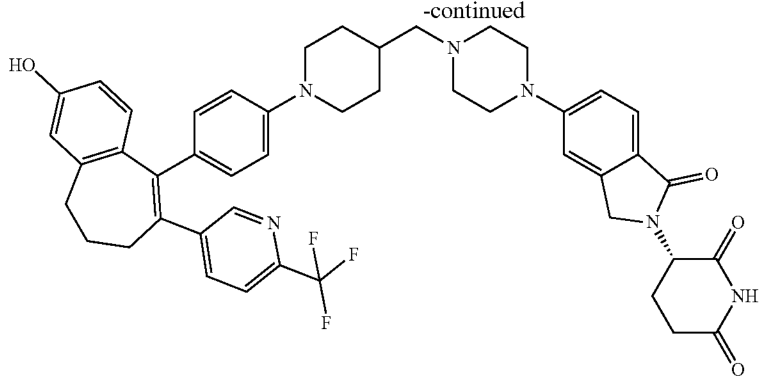
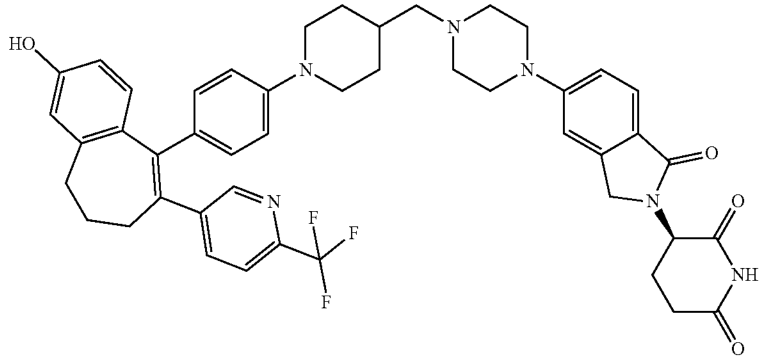
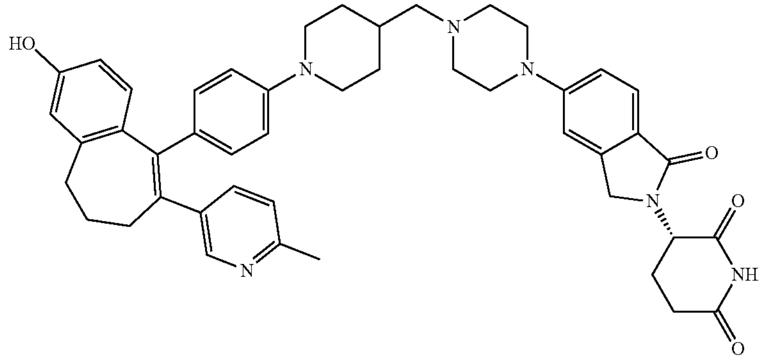
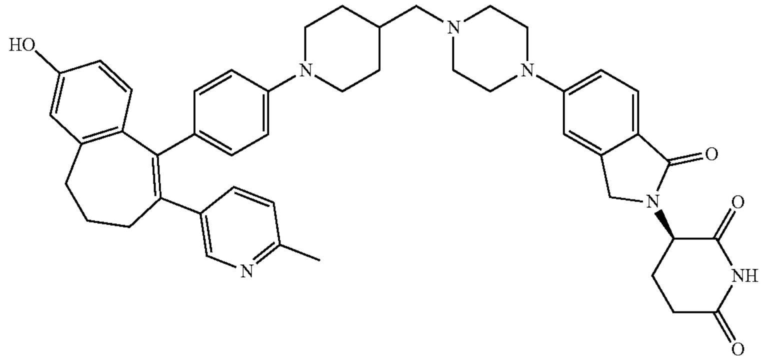

-continued
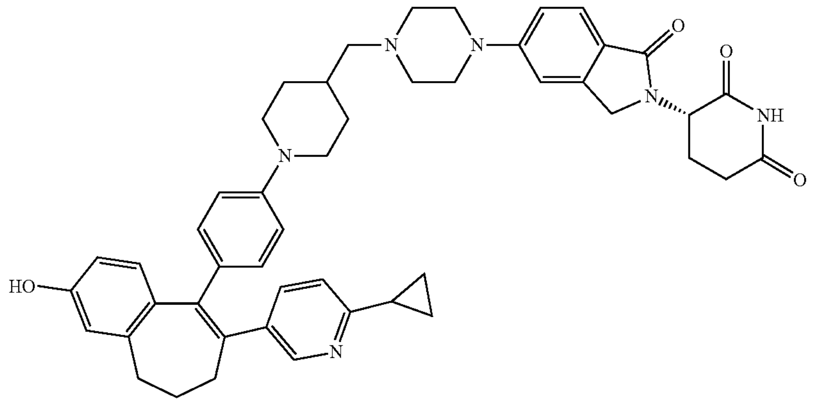
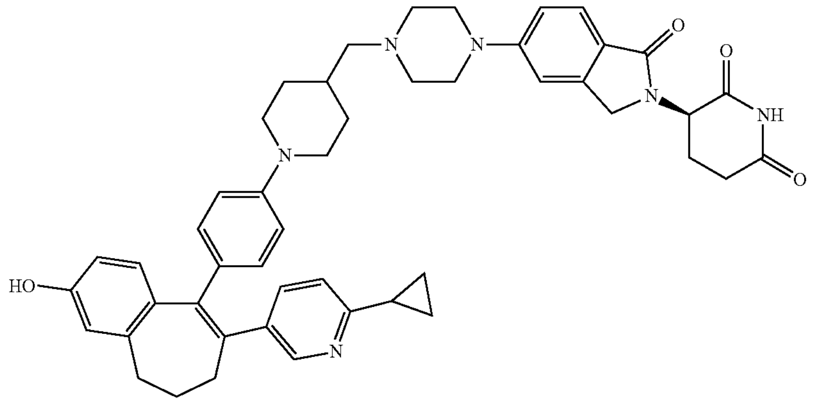
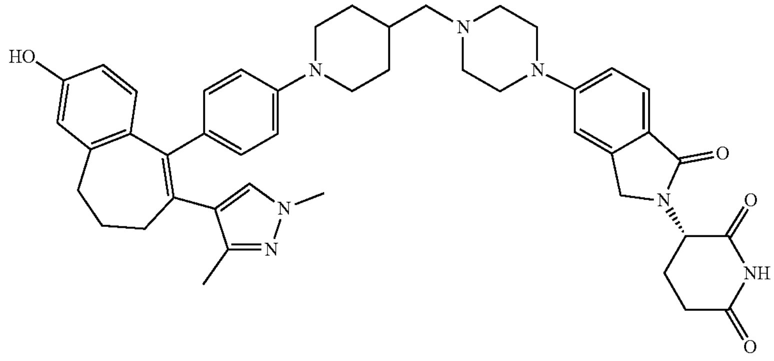
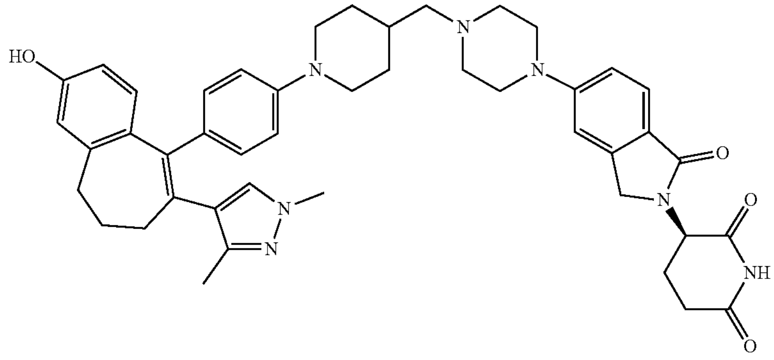

-continued
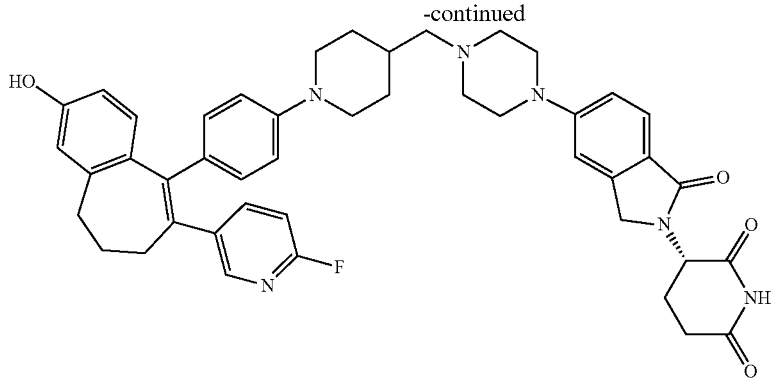
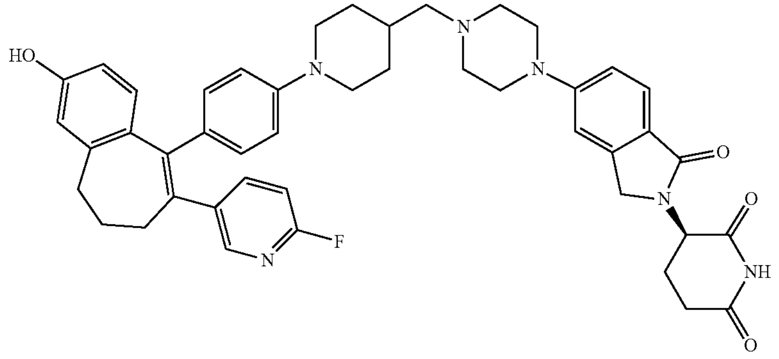
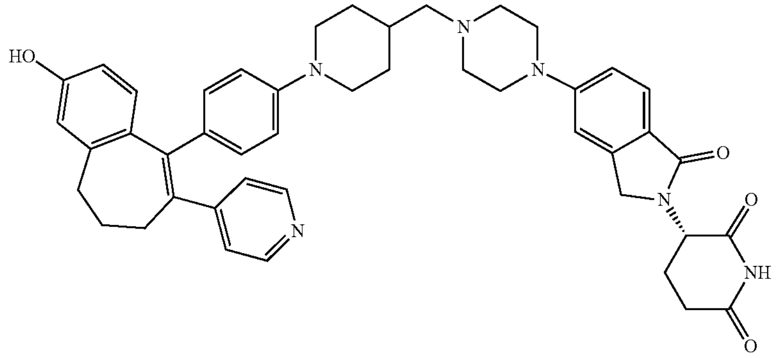
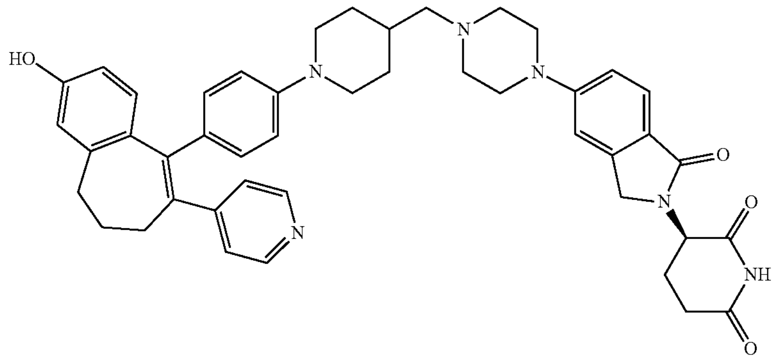

-continued
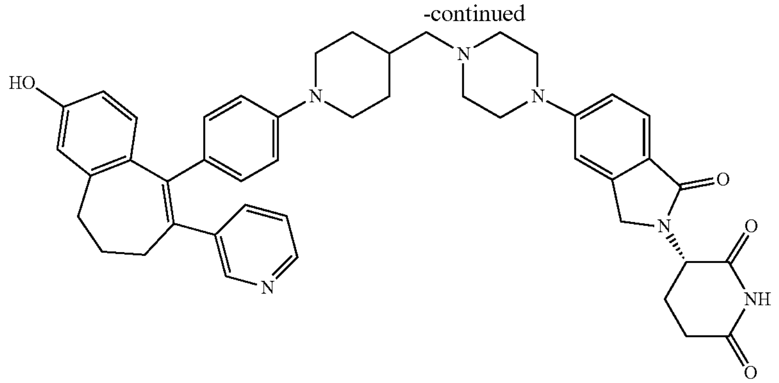
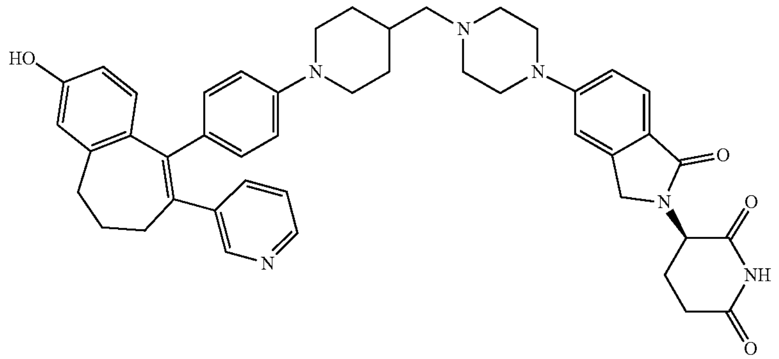
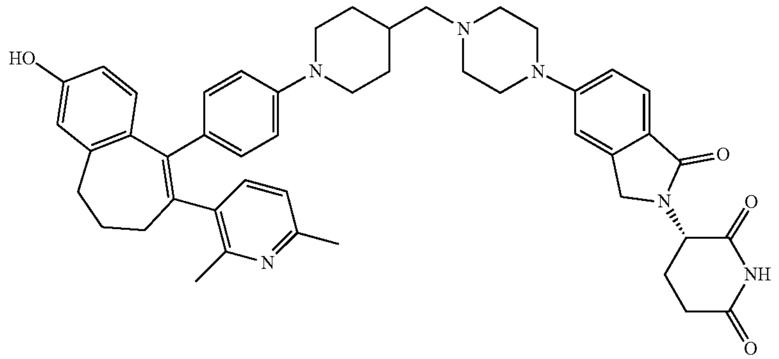
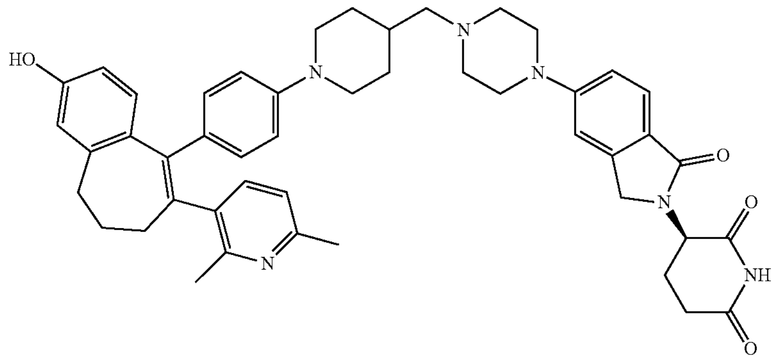

-continued
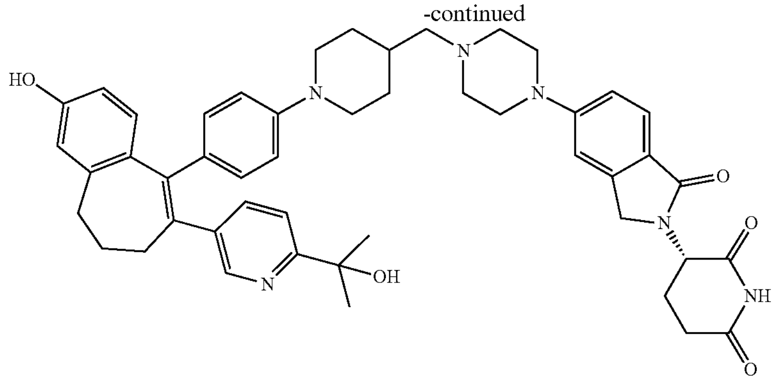
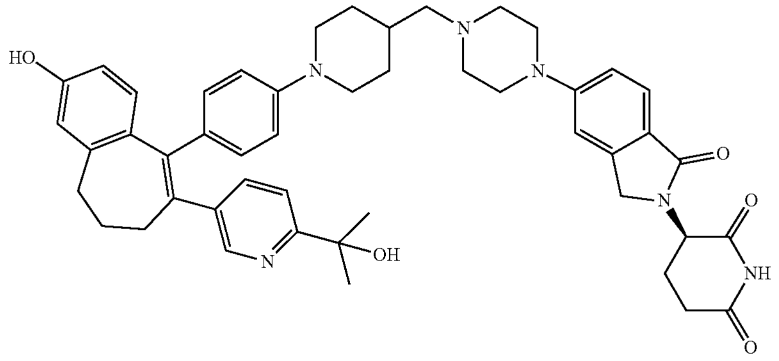
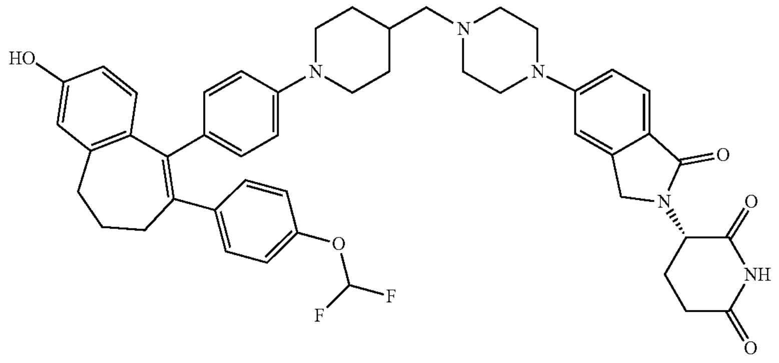
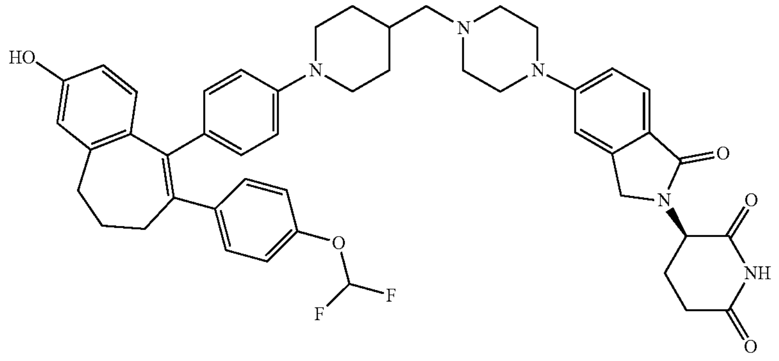

-continued

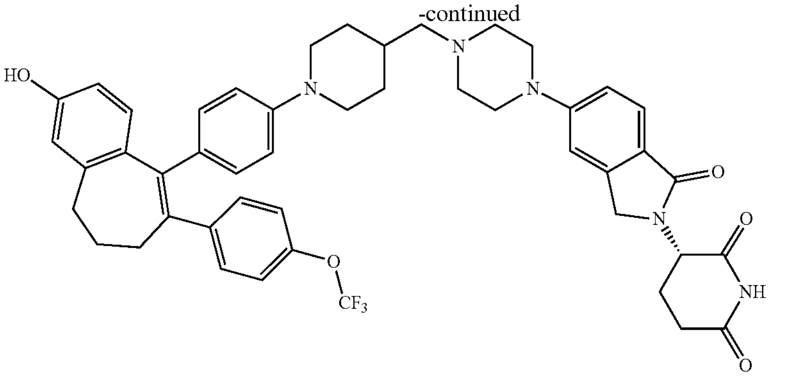

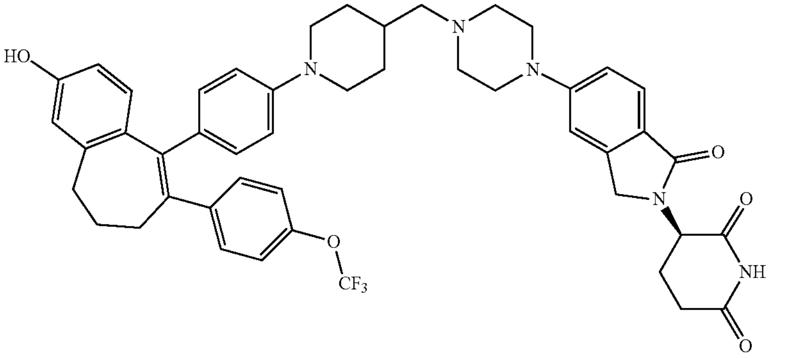

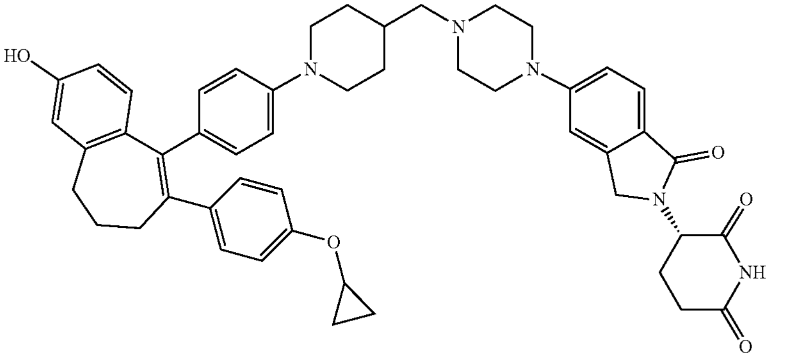

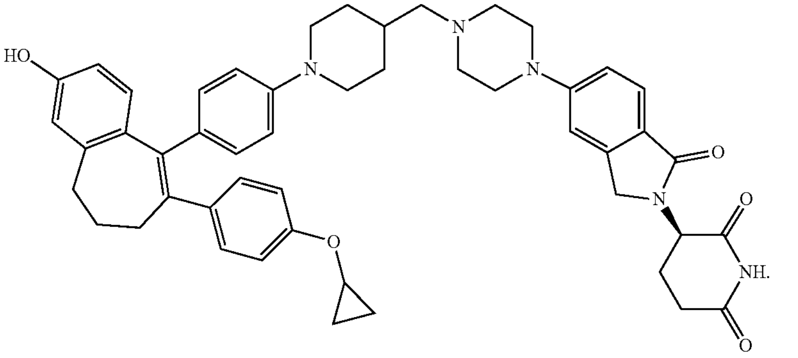

13. A pharmaceutical composition comprising a therapeutically effective amount of the compound, the isomer thereof or the pharmaceutically acceptable salt thereof according to claim 1 and a pharmaceutically acceptable carrier.

14. A method for treating a disease related to estrogen receptor proteolysis-targeting chimera, comprising administering to a mammal in need of such treatment a therapeutically effective amount of the compound, the isomer thereof, or the pharmaceutically acceptable salt thereof according to claim 1, wherein the disease related to the estrogen receptor proteolysis-targeting chimera is selected from the group consisting of breast cancer, endometrial cancer, ovarian cancer, uterine cancer, prostate cancer, endometriosis, lung cancer, and esophageal cancer.

15. The compound, the isomer thereof or the pharmaceutically acceptable salt thereof according to claim 1, wherein $R_2$ is independently selected from the group consisting of F, Cl, Br, I, OH, CN, $NH_2$, $CH_3$, $CF_3$, cyclopropyl,

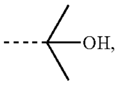

—$OCHF_2$, —$OCF_3$, and —O-cyclopropyl; L is selected from the group consisting of

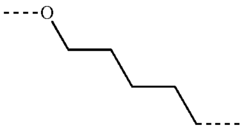

,

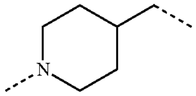

, and

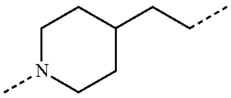

;

ring A is selected from the group consisting of phenyl,

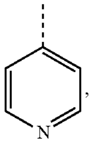

,

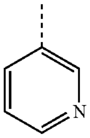

, and

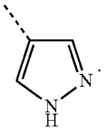

.

16. A pharmaceutical composition comprising a therapeutically effective amount of the compound, the isomer thereof or the pharmaceutically acceptable salt thereof according to claim 8 and a pharmaceutically acceptable carrier.

17. A pharmaceutical composition comprising a therapeutically effective amount of the compound, the isomer thereof or the pharmaceutically acceptable salt thereof according to claim 11 and a pharmaceutically acceptable carrier.

18. A method for treating a disease related to estrogen receptor proteolysis-targeting chimera, comprising administering to a mammal in need of such treatment a therapeutically effective amount of the compound, the isomer thereof, or the pharmaceutically acceptable salt thereof according to claim 8, wherein the disease related to the estrogen receptor proteolysis-targeting chimera is selected from the group consisting of breast cancer, endometrial cancer, ovarian cancer, uterine cancer, prostate cancer, endometriosis, lung cancer, and esophageal cancer.

19. A method for treating a disease related to estrogen receptor proteolysis-targeting chimera, comprising administering to a mammal in need of such treatment a therapeutically effective amount of the compound, the isomer thereof, or the pharmaceutically acceptable salt thereof according to claim 11, wherein the disease related to the estrogen receptor proteolysis-targeting chimera is selected from the group consisting of breast cancer, endometrial cancer, ovarian cancer, uterine cancer, prostate cancer, endometriosis, lung cancer, and esophageal cancer.

* * * * *